(12) United States Patent
Omura et al.

(10) Patent No.: US 7,371,548 B2
(45) Date of Patent: *May 13, 2008

(54) AVERMECTIN AGLYCON SYNTHASE GENES

(75) Inventors: Satoshi Omura, Tokyo (JP); Haruo Ikeda, Kanagawa (JP)

(73) Assignee: The Kitasato Institute, Tokyo (JP)

( * ) Notice: Subject to any disclaimer, the term of this patent is extended or adjusted under 35 U.S.C. 154(b) by 194 days.

This patent is subject to a terminal disclaimer.

(21) Appl. No.: 11/005,196

(22) Filed: Dec. 7, 2004

(65) Prior Publication Data

US 2005/0158749 A1 Jul. 21, 2005

Related U.S. Application Data

(63) Continuation of application No. 09/914,286, filed as application No. PCT/JP00/01041 on Feb. 23, 2000, now Pat. No. 6,864,073.

(30) Foreign Application Priority Data

Feb. 24, 1999 (JP) ................................. 11-46961

(51) Int. Cl.
*C12N 9/00* (2006.01)
*C12N 1/20* (2006.01)
*C07H 21/04* (2006.01)

(52) U.S. Cl. .............. 435/183; 435/252.3; 435/252.35; 435/320.1; 536/23.2

(58) Field of Classification Search ...................... None
See application file for complete search history.

(56) References Cited

U.S. PATENT DOCUMENTS 5,252,474 A 10/1993 Gewain et al.

FOREIGN PATENT DOCUMENTS

| EP | 391594 | 10/1990 |
|---|---|---|
| EP | 0445460 | 9/1991 |
| EP | 791655 | 8/1997 |
| EP | 791656 | 8/1997 |
| WO | WO 00/01827 | 1/2000 |
| WO | WO 01/09155 | 2/2001 |

OTHER PUBLICATIONS

Bevitt et al. "6-deoxyerythronolide-B synthase 2 from *Saccharopolyspora erythraea*" XP-001005944 Eur. J. Biochem. 204:39-49 (1992).

Cortes et al. "An unusually large multifunctional polypeptide in the erythromycin-producing polyketide synthase of *Saccharopolyspora erythraea*" XP-002035889 Nature 348:176-178 (1990).

(Continued)

*Primary Examiner*—Nashaat T. Nashed
(74) *Attorney, Agent, or Firm*—Nixon & Vanderhye P.C.

(57) ABSTRACT

The present invention relates to an isolated DNA which comprises a DNA sequence encoding avermectin aglycon synthase domains that corresponds to multifunctional enzyme proteins involved in the biosynthesis of a polyketide compound, or its mutants having avermectin aglycon synthase activity, particularly functional modules and submodules in the DNA sequence derived from *Streptomyces avermitilis*, a polypeptide or mutants thereof encoded by the DNA or the mutants, a vector containing the DNA or the mutants, a host cell transformed with the DNA, the mutants thereof, or the vector, and a method for producing avermectin.

16 Claims, 3 Drawing Sheets

OTHER PUBLICATIONS

Database Accession No. AB032367 XP-0022769974 (1999).
Database Accession No. L09654 XP-002276973 (1993).
Database Accession No. AF079138 XP-002276971 (1998).
Database Accession No. AF082100 XP-002276972 ((1998).
Donadio et al. "Modular organization of genes required for complex polyketide biosynthesis" XP-002035890 Science 252:675-679 (1991).
Ikeda et al. "Cloning of the gene encoding avermectin B 5-*O*-methyltransferase in avermectin-producing *Streptomyces avermitilis*" Gene 206:175-180 (1998).
Ikeda et al. "Avermectin Biosynthesis" XP002941702 Chem. Rev. 97:2591-2609 (1997).
Ikeda et al. "Organization of the biosynthetic gene cluster for the polyketide anthelmintic macrolide avermectin in *Streptornyces avermitilis*", PNAS 96:9509-9514 (1999).
Ikeda "Genetic analysis of biosynthesis of polyketide anthelmintic macrolide avermectin in *Streptomyces avermitilis*" XP-001180664 Actinomycetol. 13:94-112 (1999).
Ikeda et al. "Control of avermectin biosynthesis in *Streptomyces avermitilis*" XP-009029162 J. Antibiotics 48:549-562 (1995).
Kue et al. "A gene cluster for macrolide anti-biotic biosynthesis in *Streptomyces venezuelac:* Architecture of metabolic diversity" PNAS 95:12111-12116 (1998).
MacNeil et al. "Correlation of the avermectin polyketide synthase genes to the avermectin structure", Ann. Acad. Sci. 721:123-132 (1994).

MacNeil et al. "Complex organization of the *Streptomyces avernitilis* genes encoding the avermectin polyketide synthase" Gene 115:119-125 (1992).
MacNeil et al. "Deletion analysis of the avermectin biosynthetic genes of *Streptomyces avermitilis* by gene cluster displacement" XP009008304 J. Bacteriol. 175:2552-2563 (1993).
Marsden et al. "Engineering broader specific- ity into an antibiotic-producing polyketide synthase" Sci. 279:199-202 (1998).
Motamedi et al. "The biosynthetic gene cluster for the macrolactone ring of the immunosuppressant FK506" XP-000906738 Eur. J. Biochem. 256:528-534 (1998).
Omura et al. "Selective production of specific components of avermectins in *Sterptomyces avermitilis*" XP-009029161 J. Antibiotics 44:560-563 (1991).
Pang et al. "Production of 6,8a-seco-6,8a-deoxy derivatives of avermectins by a mutant strain of *Streptomyces avermitilis*" XP-009029187 J. Antibiotics 48:59-66 (1995).
Swan et al. "Characterisation of a *Streptomyces antibioticus* gene encoding a type I polyketide synthase which has an unusual coding sequence" XP-002087278 Mol. Gen. Genet. 242:358-362 (1994).
European Search Report for European Appln. No. 00905297.8 dated May 14, 2004.
Search Report dated May 14, 2004 for European Appln. No. 00905297.8.
Supplementary Partial European Search Report dated Apr. 15, 2003.

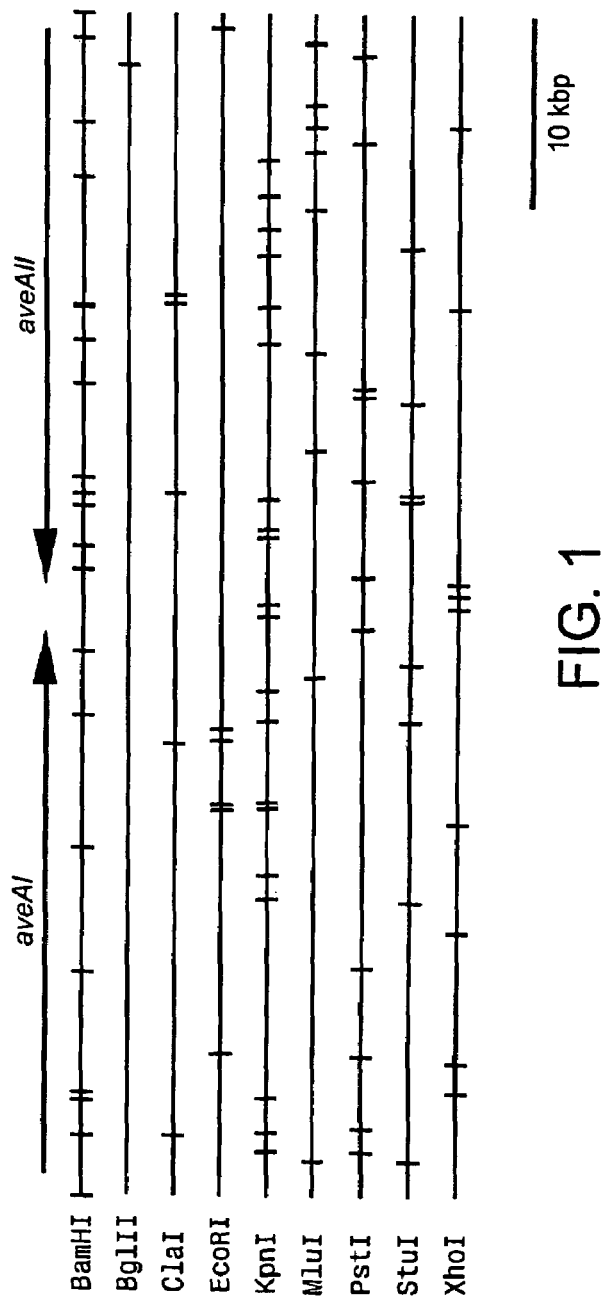
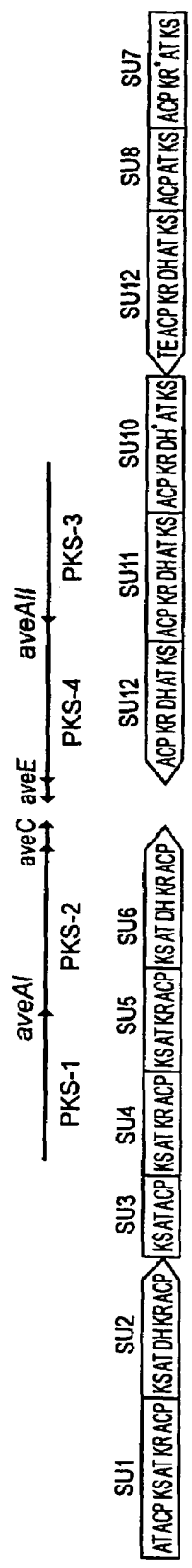
FIG. 1
FIG. 2A

SEQUENCE LISTING

<160> NUMBER OF SEQ ID NOS: 16

<210> SEQ ID NO 1
<211> LENGTH: 30690
<212> TYPE: DNA
<213> ORGANISM: Streptomyces avermitilis
<220> FEATURE:
<221> NAME/KEY: CDS
<222> LOCATION: (1)..(11916)
<220> FEATURE:
<221> NAME/KEY: CDS
<222> LOCATION: (11971)..(30687)

<400> SEQUENCE: 1

```
gtg cag agg atg gac ggc ggg gaa gaa ccc cgc cct gcg gca ggg gag        48
Val Gln Arg Met Asp Gly Gly Glu Glu Pro Arg Pro Ala Ala Gly Glu
 1               5                  10                  15 gtc ctc gga gtg gcc gac gag gcg gac ggc ggc gtc gtc ttc gtt ttt        96
Val Leu Gly Val Ala Asp Glu Ala Asp Gly Gly Val Val Phe Val Phe
             20                  25                  30 ccc ggg cag ggc ccg caa tgg ccg ggc atg gga agg gaa ctt ctc gac       144
Pro Gly Gln Gly Pro Gln Trp Pro Gly Met Gly Arg Glu Leu Leu Asp
         35                  40                  45 gct tcc gac gtc ttc cgg gag agc gtc cgc gcc tgc gaa gcc gcg ttc       192
Ala Ser Asp Val Phe Arg Glu Ser Val Arg Ala Cys Glu Ala Ala Phe
     50                  55                  60 gcg ccc tac gtc gac tgg tcg gtg gag cag gtg ttg cgg gac tcg ccg       240
Ala Pro Tyr Val Asp Trp Ser Val Glu Gln Val Leu Arg Asp Ser Pro
 65                  70                  75                  80 gac gct ccc ggg ctg gac cgg gtg gac gtc gtc cag ccg acc ctg ttc       288
Asp Ala Pro Gly Leu Asp Arg Val Asp Val Val Gln Pro Thr Leu Phe
                 85                  90                  95 gcc gtc atg atc tcc ctg gcc gcc ctc tgg cgc tcg caa ggg gtc gag       336
Ala Val Met Ile Ser Leu Ala Ala Leu Trp Arg Ser Gln Gly Val Glu
            100                 105                 110 ccg tgc gcg gtg ctg gga cac agc ctg ggc gag atc gcg gca gcc cac       384
Pro Cys Ala Val Leu Gly His Ser Leu Gly Glu Ile Ala Ala Ala His
        115                 120                 125 gtc tcg gga ggc ctg tcc ctg gcc gac gcc gca cgc gtg gtg acg ctt       432
Val Ser Gly Gly Leu Ser Leu Ala Asp Ala Ala Arg Val Val Thr Leu
    130                 135                 140 tgg agc cag gca cag acc acc ctt gcc ggg acc ggc gcg ctc gtc tcc       480
Trp Ser Gln Ala Gln Thr Thr Leu Ala Gly Thr Gly Ala Leu Val Ser
145                 150                 155                 160 gtc gcc gcc acg ccg gat gag ctc ctg ccc cga atc gct ccg tgg acc       528
Val Ala Ala Thr Pro Asp Glu Leu Leu Pro Arg Ile Ala Pro Trp Thr
                165                 170                 175 gag gac aac ccg gcg cgg ctc gcc gtc gca gcc gtc aac gga ccc cgg       576
Glu Asp Asn Pro Ala Arg Leu Ala Val Ala Ala Val Asn Gly Pro Arg
```

```
                        180               185               190
agc aca gtc gtt tcc ggt gcc cgc gag gcc gtc gcg gac ctg gtg gcc      624
Ser Thr Val Val Ser Gly Ala Arg Glu Ala Val Ala Asp Leu Val Ala
        195               200               205 gac ctc acc gcc gcg cag gtg cgc acg cgc atg atc ccg gtg gac gtt      672
Asp Leu Thr Ala Ala Gln Val Arg Thr Arg Met Ile Pro Val Asp Val
210               215               220 ccc gcc cac tcc ccc ctg atg tac gcc atc gag gaa cgg gtc gtc agc      720
Pro Ala His Ser Pro Leu Met Tyr Ala Ile Glu Glu Arg Val Val Ser
225               230               235               240 ggc ctg ctg ccc atc acc cca cgc ccc tcc cgc atc ccc ttc cac tcc      768
Gly Leu Leu Pro Ile Thr Pro Arg Pro Ser Arg Ile Pro Phe His Ser
                245               250               255 tcg gtg acc ggc ggc cgc ctc gac acc cgc gag cta gac gcg gcg tac      816
Ser Val Thr Gly Gly Arg Leu Asp Thr Arg Glu Leu Asp Ala Ala Tyr
            260               265               270 tgg tac cgc aac atg tcg agc acg gtc cgg ttc gag ccc gcc gcc cgg      864
Trp Tyr Arg Asn Met Ser Ser Thr Val Arg Phe Glu Pro Ala Ala Arg
        275               280               285 ctg ctt ctg cag cag ggg ccc aag acg ttc gtc gag atg agc ccg cac      912
Leu Leu Leu Gln Gln Gly Pro Lys Thr Phe Val Glu Met Ser Pro His
    290               295               300 ccg gtg ctg acc atg ggc ctg cag gag ctc gcc ccg gac ctg ggc gac      960
Pro Val Leu Thr Met Gly Leu Gln Glu Leu Ala Pro Asp Leu Gly Asp
305               310               315               320 acc acc ggc acc gcc gac acc gtg atc atg ggc acg ctg cgc cgc ggc     1008
Thr Thr Gly Thr Ala Asp Thr Val Ile Met Gly Thr Leu Arg Arg Gly
                325               330               335 cag ggc acc ctg gac cac ttc ctg acg tct ctc gcc caa cta cgg ggg     1056
Gln Gly Thr Leu Asp His Phe Leu Thr Ser Leu Ala Gln Leu Arg Gly
            340               345               350 cat ggt gag acg tcg gcg acc acc gtc ctc tcg gca cgc ctg acc gcg     1104
His Gly Glu Thr Ser Ala Thr Thr Val Leu Ser Ala Arg Leu Thr Ala
        355               360               365 ctg tcc ccc acg cag cag cag tcg ctg ctc ctg gac ctg gtg cgc gcc     1152
Leu Ser Pro Thr Gln Gln Gln Ser Leu Leu Leu Asp Leu Val Arg Ala
    370               375               380 cac acc atg gcg gtg ctg aac gac gac gga aac gag cgc acc gcg tcg     1200
His Thr Met Ala Val Leu Asn Asp Asp Gly Asn Glu Arg Thr Ala Ser
385               390               395               400 gat gcc ggc cca tcg gcg agt ttc gcc cac ctc ggc ttc gac tcc gtc     1248
Asp Ala Gly Pro Ser Ala Ser Phe Ala His Leu Gly Phe Asp Ser Val
                405               410               415 atg ggt gtc gaa ctg cgc aac cgc ctc agc aag gcc acg ggc ctg cgg     1296
Met Gly Val Glu Leu Arg Asn Arg Leu Ser Lys Ala Thr Gly Leu Arg
            420               425               430 ttg ccc gtg acg ctc atc ttc gac cac acc acg ccg gcc gcg gtc gcc     1344
Leu Pro Val Thr Leu Ile Phe Asp His Thr Thr Pro Ala Ala Val Ala
        435               440               445 gcg cgc ctt cgg acc gcg gcg ctc ggc cac ctc gac gag gac acc gcg     1392
Ala Arg Leu Arg Thr Ala Ala Leu Gly His Leu Asp Glu Asp Thr Ala
    450               455               460 ccc gta ccg gac tca ccc agc ggc cac gga ggc acg gca gcg gcg gac     1440
Pro Val Pro Asp Ser Pro Ser Gly His Gly Gly Thr Ala Ala Ala Asp
465               470               475               480 gac ccg atc gcc atc atc ggc atg gca tgc cgt ttc ccg ggc gga gtc     1488
Asp Pro Ile Ala Ile Ile Gly Met Ala Cys Arg Phe Pro Gly Gly Val
                485               490               495 cgg tcc ccg aag gac ctg tgg gag ctg gcc gcc tcg ggc gga gac gcc     1536
```

```
Arg Ser Pro Lys Asp Leu Trp Glu Leu Ala Ala Ser Gly Gly Asp Ala
            500                 505                 510 atc ggg ccg ttc ccc acc gac cgc gga tgg ccc acg gaa cag cgt cac       1584
Ile Gly Pro Phe Pro Thr Asp Arg Gly Trp Pro Thr Glu Gln Arg His
        515                 520                 525 gcc cag gac ccc acg cag ccc ggc acg ttc tat ccg cag gga ggc ggg       1632
Ala Gln Asp Pro Thr Gln Pro Gly Thr Phe Tyr Pro Gln Gly Gly Gly
530                 535                 540 ttc ctt cac gac gcg gcg cac ttc gac gcc ggc ttc ttc gga atc agt       1680
Phe Leu His Asp Ala Ala His Phe Asp Ala Gly Phe Phe Gly Ile Ser
545                 550                 555                 560 cca cgt gag gca ctg gcg atg gat ccg cag cag cgg ctg ctg ctg gag       1728
Pro Arg Glu Ala Leu Ala Met Asp Pro Gln Gln Arg Leu Leu Leu Glu
                565                 570                 575 acg tcc tgg gag gcg ttc gag cgg gcg gga atc gat ccg ctg tcg gta       1776
Thr Ser Trp Glu Ala Phe Glu Arg Ala Gly Ile Asp Pro Leu Ser Val
            580                 585                 590 cgc ggg tcc cgt acg ggc gtc ttc gcg ggc gcc ctc tcc ttc gac tac       1824
Arg Gly Ser Arg Thr Gly Val Phe Ala Gly Ala Leu Ser Phe Asp Tyr
        595                 600                 605 ggc ccg cgt atg gac acc gcg tcg tcg gag ggc gcc gcg gac gtg gag       1872
Gly Pro Arg Met Asp Thr Ala Ser Ser Glu Gly Ala Ala Asp Val Glu
    610                 615                 620 ggc cac atc ctc acc ggt acc acg ggc agc gtc ctg tcg ggc cgt atc       1920
Gly His Ile Leu Thr Gly Thr Thr Gly Ser Val Leu Ser Gly Arg Ile
625                 630                 635                 640 gcc tac agc ttc ggg ctg gaa ggg ccg gcg atc acc gtg gac acg ggg       1968
Ala Tyr Ser Phe Gly Leu Glu Gly Pro Ala Ile Thr Val Asp Thr Gly
                645                 650                 655 tgc tcg gca tcg ctc gtg acg ctg cat ctg gcg tgc cag tcg ctg cgg       2016
Cys Ser Ala Ser Leu Val Thr Leu His Leu Ala Cys Gln Ser Leu Arg
            660                 665                 670 tcg ggt gag tgc acg ctc gcg ctg gcc ggc ggc gtc tcg gtc atg tcc       2064
Ser Gly Glu Cys Thr Leu Ala Leu Ala Gly Gly Val Ser Val Met Ser
        675                 680                 685 acc ctc ggc atg ttc atc gag ttc tcc cgg cag cgc ggg ctg tcg gtg       2112
Thr Leu Gly Met Phe Ile Glu Phe Ser Arg Gln Arg Gly Leu Ser Val
    690                 695                 700 gac ggc agg tgc aag gcg tac tcg gct gca gcc gac ggc acc ggc tgg       2160
Asp Gly Arg Cys Lys Ala Tyr Ser Ala Ala Ala Asp Gly Thr Gly Trp
705                 710                 715                 720 ggc gag ggc gtc ggg atg ctg ttg gtg gag cgg ttg tcg gat gcg gtg       2208
Gly Glu Gly Val Gly Met Leu Leu Val Glu Arg Leu Ser Asp Ala Val
                725                 730                 735 cgg ctg ggg cat cgg gtg ctg gcg gtg gta cgc ggc agt gcg gtc aac       2256
Arg Leu Gly His Arg Val Leu Ala Val Val Arg Gly Ser Ala Val Asn
            740                 745                 750 cag gac ggt gcg tcg aat ggg ctg acg gcg ccg aac ggt ccg gct cag       2304
Gln Asp Gly Ala Ser Asn Gly Leu Thr Ala Pro Asn Gly Pro Ala Gln
        755                 760                 765 gag cgg gtg atc cgg cag gcg ttg gcg aac gcg ggg ttg tcc gtg gcg       2352
Glu Arg Val Ile Arg Gln Ala Leu Ala Asn Ala Gly Leu Ser Val Ala
    770                 775                 780 gat gtg gat gtg gtg gag ggg cac ggg acg ggc acg acg ctg ggt gat       2400
Asp Val Asp Val Val Glu Gly His Gly Thr Gly Thr Thr Leu Gly Asp
785                 790                 795                 800 ccg atc gag gca cag gcg ttg ctc gcc acg tac ggg cag cgg gcc ggt       2448
Pro Ile Glu Ala Gln Ala Leu Leu Ala Thr Tyr Gly Gln Arg Ala Gly
                805                 810                 815
```

```
                                                       -continued gac agg ccg ctg tgg ctg ggg tct ctg aag tcc aac atc ggg cac acc       2496
Asp Arg Pro Leu Trp Leu Gly Ser Leu Lys Ser Asn Ile Gly His Thr
        820                 825                 830 atg gct gcc gcg ggt gtg ggt ggg gtc atc aag atg gtg atg gcg ttg       2544
Met Ala Ala Ala Gly Val Gly Gly Val Ile Lys Met Val Met Ala Leu
835                 840                 845 cgg gag ggg gtg ttg ccg cgg acg ttg cat gtg gat aag ccg tcg ccg       2592
Arg Glu Gly Val Leu Pro Arg Thr Leu His Val Asp Lys Pro Ser Pro
    850                 855                 860 cag gtg gac tgg tcc gcg ggg gcg gtg cgg ctg ctg acg gag gcg gtg       2640
Gln Val Asp Trp Ser Ala Gly Ala Val Arg Leu Leu Thr Glu Ala Val
865                 870                 875                 880 ccg tgg ccg ggg gac gcg gca ggg cgg ttg cgg cgg gcg gga gtg tcg       2688
Pro Trp Pro Gly Asp Ala Ala Gly Arg Leu Arg Arg Ala Gly Val Ser
                885                 890                 895 tcg ttc ggg atc ggc ggc acg aat gcg cat gtg att ttg gag gag gcg       2736
Ser Phe Gly Ile Gly Gly Thr Asn Ala His Val Ile Leu Glu Glu Ala
            900                 905                 910 ccg gcg gcg ggg ggc tgt gtt gcc ggg ggt ggg gtg ttg gag ggt gct       2784
Pro Ala Ala Gly Gly Cys Val Ala Gly Gly Gly Val Leu Glu Gly Ala
        915                 920                 925 ccg ggt ctt gcc att tcg gtg gct gag tcg gtg gcc gct cca gtg gct       2832
Pro Gly Leu Ala Ile Ser Val Ala Glu Ser Val Ala Ala Pro Val Ala
    930                 935                 940 gtg tct gcg ccg gtg gct gag tcg gtg ccg gtg ccg gtg ccg gtg ccg       2880
Val Ser Ala Pro Val Ala Glu Ser Val Pro Val Pro Val Pro Val Pro
945                 950                 955                 960 gtt cct gtg ccg gtg tcg gct agg tct gag gct ggg ttg cgg gcg cag       2928
Val Pro Val Pro Val Ser Ala Arg Ser Glu Ala Gly Leu Arg Ala Gln
                965                 970                 975 gcg gag gcg ttg cgt cag tac gtg gca gtc cgg ccg gac gtt tcg ctt       2976
Ala Glu Ala Leu Arg Gln Tyr Val Ala Val Arg Pro Asp Val Ser Leu
            980                 985                 990 gcc gat gtg ggt gcg ggt ctg gcc tgt ggg cgg gct gtg ctg gag cat       3024
Ala Asp Val Gly Ala Gly Leu Ala Cys Gly Arg Ala Val Leu Glu His
        995                 1000                1005 cgt gcg gtc gtc ctg gcc gcg gac cgt gag gag ctg gtg caa ggg ttg       3072
Arg Ala Val Val Leu Ala Ala Asp Arg Glu Glu Leu Val Gln Gly Leu
    1010                1015                1020 ggg gcg ctg gcg gcg ggt gag ccg gat cgg cgg gtg acc acg ggt cat       3120
Gly Ala Leu Ala Ala Gly Glu Pro Asp Arg Arg Val Thr Thr Gly His
1025                1030                1035                1040 gcg ccg ggt ggt gac cgg ggc ggt gtc gtc ttc gtg ttt ccc gga cag       3168
Ala Pro Gly Gly Asp Arg Gly Gly Val Val Phe Val Phe Pro Gly Gln
                1045                1050                1055 ggt ggg cag tgg gcc ggg atg ggt gtg cgt ctg ctc gcc tcc tct ccg       3216
Gly Gly Gln Trp Ala Gly Met Gly Val Arg Leu Leu Ala Ser Ser Pro
            1060                1065                1070 gtg ttc gcc cgg cgg atg cag gcg tgc gag gag gct ctg gcg ccg tgg       3264
Val Phe Ala Arg Arg Met Gln Ala Cys Glu Glu Ala Leu Ala Pro Trp
        1075                1080                1085 gtg gac tgg tct gtg gtg gac atc ctg cgc cgg gac gcg ggg gat gcg       3312
Val Asp Trp Ser Val Val Asp Ile Leu Arg Arg Asp Ala Gly Asp Ala
    1090                1095                1100 gtg tgg gag cgg gcc gat gtg gtc cag cct gtg ctg ttc agc gtc atg       3360
Val Trp Glu Arg Ala Asp Val Val Gln Pro Val Leu Phe Ser Val Met
1105                1110                1115                1120 gtg tct ttg gct gct ctg tgg cgt tcc tac ggt atc gaa ccc gac gcg       3408
Val Ser Leu Ala Ala Leu Trp Arg Ser Tyr Gly Ile Glu Pro Asp Ala
                1125                1130                1135
```

-continued

| | |
|---|---|
| gtc ctt ggc cat tcc cag ggc gag atc gcg gcc gcg cat gtg tgt ggg<br>Val Leu Gly His Ser Gln Gly Glu Ile Ala Ala Ala His Val Cys Gly<br>                1140                      1145                    1150 | 3456 |
| gcg ctg agc ctg aag gac gcg gcg aag act gtt gcg ctg cgc agc cgg<br>Ala Leu Ser Leu Lys Asp Ala Ala Lys Thr Val Ala Leu Arg Ser Arg<br>1155                      1160                    1165 | 3504 |
| gcg ctg gcc gct gtg cgg ggc cgg ggc atg gcc tca gtc ccg ctg<br>Ala Leu Ala Ala Val Arg Gly Arg Gly Gly Met Ala Ser Val Pro Leu<br>                1170                      1175                    1180 | 3552 |
| cct gcc cag gag gtg gag cag ctc att ggt gag cgg tgg gcg ggg cgg<br>Pro Ala Gln Glu Val Glu Gln Leu Ile Gly Glu Arg Trp Ala Gly Arg<br>1185                      1190                    1195                    1200 | 3600 |
| ttg tgg gtg gcg gcg gtc aac ggc ccc cgc tcc acc gcc gtc tcg ggg<br>Leu Trp Val Ala Ala Val Asn Gly Pro Arg Ser Thr Ala Val Ser Gly<br>                1205                      1210                    1215 | 3648 |
| gat gcc gag gcg gtg gac gag gtg ctg gcg tac tgt gcc ggc acc ggg<br>Asp Ala Glu Ala Val Asp Glu Val Leu Ala Tyr Cys Ala Gly Thr Gly<br>1220                      1225                    1230 | 3696 |
| gtg cgg gcc cgg cgg atc ccg gtc gac tat gcc tcg cac tgc ccc cat<br>Val Arg Ala Arg Arg Ile Pro Val Asp Tyr Ala Ser His Cys Pro His<br>                1235                      1240                    1245 | 3744 |
| gtg cag ccc ctg cgg gag gag ttg ctg gag ctg ctg ggg gac atc agc<br>Val Gln Pro Leu Arg Glu Glu Leu Leu Glu Leu Leu Gly Asp Ile Ser<br>1250                      1255                    1260 | 3792 |
| ccg cag ccg tcc ggc gtg ccg ttc ttc tcc acg gtg gag ggc acc tgg<br>Pro Gln Pro Ser Gly Val Pro Phe Phe Ser Thr Val Glu Gly Thr Trp<br>1265                      1270                    1275                    1280 | 3840 |
| ctg gac acc aca acc ctg gac gcc gcc tac tgg tac cgc aac ctg cac<br>Leu Asp Thr Thr Thr Leu Asp Ala Ala Tyr Trp Tyr Arg Asn Leu His<br>                1285                      1290                    1295 | 3888 |
| cag ccg gtc cgt ttc agc gat gcc gtc cag gcc ctg gcg gat gac gga<br>Gln Pro Val Arg Phe Ser Asp Ala Val Gln Ala Leu Ala Asp Asp Gly<br>1300                      1305                    1310 | 3936 |
| cac cgc gtc ttc gtc gaa gtc agc ccc cac ccc acc ctc gtc ccc gcc<br>His Arg Val Phe Val Glu Val Ser Pro His Pro Thr Leu Val Pro Ala<br>                1315                      1320                    1325 | 3984 |
| atc gaa gac acc acc gaa gac acc gcc gaa gac gtc acc gcg atc ggc<br>Ile Glu Asp Thr Thr Glu Asp Thr Ala Glu Asp Val Thr Ala Ile Gly<br>1330                      1335                    1340 | 4032 |
| agc ctc cgc cgc ggc gac aac gac acc cgc cgc ttc ctc acc gcc ctc<br>Ser Leu Arg Arg Gly Asp Asn Asp Thr Arg Arg Phe Leu Thr Ala Leu<br>1345                      1350                    1355                    1360 | 4080 |
| gcc cac acc cat acc acc ggc atc ggc aca ccc acc acc tgg cac cac<br>Ala His Thr His Thr Thr Gly Ile Gly Thr Pro Thr Thr Trp His His<br>                1365                      1370                    1375 | 4128 |
| cac tac acc cac cac cac acc cac ccc cac ccc cac acg cac ctc gac<br>His Tyr Thr His His His Thr His Pro His Pro His Thr His Leu Asp<br>1380                      1385                    1390 | 4176 |
| ctg ccc acc tac ccc ttc caa cac cag cac tac tgg ctc gag agc tca<br>Leu Pro Thr Tyr Pro Phe Gln His Gln His Tyr Trp Leu Glu Ser Ser<br>                1395                      1400                    1405 | 4224 |
| cag ccg ggt gcc gga tcc ggt tcg ggt gcc ggt gcc ggt tcg ggt gcc<br>Gln Pro Gly Ala Gly Ser Gly Ser Gly Ala Gly Ala Gly Ser Gly Ala<br>1410                      1415                    1420 | 4272 |
| ggt tcc ggg cgg gca ggg act gcg ggc ggg acg gca gag gtg gag tcg<br>Gly Ser Gly Arg Ala Gly Thr Ala Gly Gly Thr Ala Glu Val Glu Ser<br>1425                      1430                    1435                    1440 | 4320 |
| cgg ttc tgg gac gcg gtg gcc cgc cag gac ctg gaa acg gtc gcg acc<br>Arg Phe Trp Asp Ala Val Ala Arg Gln Asp Leu Glu Thr Val Ala Thr | 4368 |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 1445 |     |     |     | 1450 |     |     |     | 1455 |     |     |      |
| aca | ctc | gcc | gtg | ccc | ccc | tcc | gcc | ggc | ctg | gac | acg | gtg | gtg | ccc | gca | 4416 |
| Thr | Leu | Ala | Val | Pro | Pro | Ser | Ala | Gly | Leu | Asp | Thr | Val | Val | Pro | Ala |      |
|     |     |     |     | 1460 |     |     |     |     | 1465 |     |     |     | 1470 |     |     |      |
| ctc | tcc | gcc | tgg | cac | cgc | cac | caa | cac | gac | caa | gcc | cgc | atc | aac | acc | 4464 |
| Leu | Ser | Ala | Trp | His | Arg | His | Gln | His | Asp | Gln | Ala | Arg | Ile | Asn | Thr |      |
|     |     |     | 1475 |     |     |     |     | 1480 |     |     |     |     | 1485 |     |     |      |
| tgg | acc | tac | cag | gaa | acc | tgg | aaa | ccc | ctc | acc | ctc | ccc | acc | acc | cac | 4512 |
| Trp | Thr | Tyr | Gln | Glu | Thr | Trp | Lys | Pro | Leu | Thr | Leu | Pro | Thr | Thr | His |      |
|     | 1490 |     |     |     |     | 1495 |     |     |     |     | 1500 |     |     |     |     |      |
| caa | ccc | cac | caa | acc | tgg | ctc | atc | gcc | atc | ccc | gaa | acc | cag | acc | cac | 4560 |
| Gln | Pro | His | Gln | Thr | Trp | Leu | Ile | Ala | Ile | Pro | Glu | Thr | Gln | Thr | His |      |
| 1505 |     |     |     |     | 1510 |     |     |     |     | 1515 |     |     |     |     | 1520 |      |
| cac | ccc | cac | atc | acc | aac | atc | ctc | acc | aac | ctc | cac | cac | cac | ggc | atc | 4608 |
| His | Pro | His | Ile | Thr | Asn | Ile | Leu | Thr | Asn | Leu | His | His | His | Gly | Ile |      |
|     |     |     |     | 1525 |     |     |     |     | 1530 |     |     |     |     | 1535 |     |      |
| acc | ccc | atc | ccc | ctc | acc | ctc | aac | cac | acc | cac | acc | aac | ccc | caa | cac | 4656 |
| Thr | Pro | Ile | Pro | Leu | Thr | Leu | Asn | His | Thr | His | Thr | Asn | Pro | Gln | His |      |
|     |     |     | 1540 |     |     |     |     | 1545 |     |     |     |     | 1550 |     |     |      |
| ctc | cac | cac | acc | ctc | cac | cac | acc | cga | caa | caa | gcc | caa | aac | cac | acc | 4704 |
| Leu | His | His | Thr | Leu | His | His | Thr | Arg | Gln | Gln | Ala | Gln | Asn | His | Thr |      |
|     |     | 1555 |     |     |     |     | 1560 |     |     |     |     | 1565 |     |     |     |      |
| acc | gga | gcc | atc | acc | ggc | ctg | ctc | tcc | ctc | ctc | gcc | ctc | gac | gaa | aca | 4752 |
| Thr | Gly | Ala | Ile | Thr | Gly | Leu | Leu | Ser | Leu | Leu | Ala | Leu | Asp | Glu | Thr |      |
|     | 1570 |     |     |     |     | 1575 |     |     |     |     | 1580 |     |     |     |     |      |
| ccc | cac | ccc | cac | cac | ccc | cac | aca | ccc | acc | ggc | acc | ctc | ctc | aac | ctc | 4800 |
| Pro | His | Pro | His | His | Pro | His | Thr | Pro | Thr | Gly | Thr | Leu | Leu | Asn | Leu |      |
| 1585 |     |     |     |     | 1590 |     |     |     |     | 1595 |     |     |     |     | 1600 |      |
| acc | ctc | acc | caa | acc | cac | acc | caa | acc | cac | cca | cca | acc | ccc | ctc | tgg | 4848 |
| Thr | Leu | Thr | Gln | Thr | His | Thr | Gln | Thr | His | Pro | Pro | Thr | Pro | Leu | Trp |      |
|     |     |     |     | 1605 |     |     |     |     | 1610 |     |     |     |     | 1615 |     |      |
| tac | gcc | acc | acc | aac | gcc | acc | acc | acc | cac | ccc | aac | gac | ccc | ctc | aca | 4896 |
| Tyr | Ala | Thr | Thr | Asn | Ala | Thr | Thr | Thr | His | Pro | Asn | Asp | Pro | Leu | Thr |      |
|     |     |     | 1620 |     |     |     |     | 1625 |     |     |     |     | 1630 |     |     |      |
| cac | ccc | acc | caa | gcc | caa | acc | tgg | gga | ctc | gcc | cgc | acc | acc | ctc | ctc | 4944 |
| His | Pro | Thr | Gln | Ala | Gln | Thr | Trp | Gly | Leu | Ala | Arg | Thr | Thr | Leu | Leu |      |
|     |     | 1635 |     |     |     |     | 1640 |     |     |     |     | 1645 |     |     |     |      |
| gaa | cac | ccc | acc | cac | acc | gcc | gga | atc | atc | gac | ctc | ccc | acc | acc | ccc | 4992 |
| Glu | His | Pro | Thr | His | Thr | Ala | Gly | Ile | Ile | Asp | Leu | Pro | Thr | Thr | Pro |      |
|     | 1650 |     |     |     |     | 1655 |     |     |     |     | 1660 |     |     |     |     |      |
| acc | ccc | cac | acc | ctc | cag | cac | ctc | acc | caa | acc | ctc | acc | caa | ccc | cac | 5040 |
| Thr | Pro | His | Thr | Leu | Gln | His | Leu | Thr | Gln | Thr | Leu | Thr | Gln | Pro | His |      |
| 1665 |     |     |     |     | 1670 |     |     |     |     | 1675 |     |     |     |     | 1680 |      |
| cac | caa | acc | caa | ctc | gcc | atc | cgc | acc | acc | ggc | acc | cac | acc | cgc | cgc | 5088 |
| His | Gln | Thr | Gln | Leu | Ala | Ile | Arg | Thr | Thr | Gly | Thr | His | Thr | Arg | Arg |      |
|     |     |     |     | 1685 |     |     |     |     | 1690 |     |     |     |     | 1695 |     |      |
| ctc | acc | ccc | acc | acc | ctc | acc | ccc | aca | cac | caa | cca | ccc | acc | ccc | acc | 5136 |
| Leu | Thr | Pro | Thr | Thr | Leu | Thr | Pro | Thr | His | Gln | Pro | Pro | Thr | Pro | Thr |      |
|     |     |     | 1700 |     |     |     |     | 1705 |     |     |     |     | 1710 |     |     |      |
| ccc | cac | gga | acc | acc | ctc | atc | acc | ggc | gga | acc | ggc | gcc | ctc | gcc | acc | 5184 |
| Pro | His | Gly | Thr | Thr | Leu | Ile | Thr | Gly | Gly | Thr | Gly | Ala | Leu | Ala | Thr |      |
|     |     | 1715 |     |     |     |     | 1720 |     |     |     |     | 1725 |     |     |     |      |
| cac | ctc | acc | cac | cac | ctc | acc | acc | cac | caa | ccc | acc | caa | cac | ctc | ctc | 5232 |
| His | Leu | Thr | His | His | Leu | Thr | Thr | His | Gln | Pro | Thr | Gln | His | Leu | Leu |      |
|     | 1730 |     |     |     |     | 1735 |     |     |     |     | 1740 |     |     |     |     |      |
| ctc | acc | agc | cga | acc | ggc | ccc | cac | acc | ccc | cac | gca | caa | cac | ctc | acc | 5280 |
| Leu | Thr | Ser | Arg | Thr | Gly | Pro | His | Thr | Pro | His | Ala | Gln | His | Leu | Thr |      |
| 1745 |     |     |     |     | 1750 |     |     |     |     | 1755 |     |     |     |     | 1760 |      |
| acc | caa | ctc | caa | caa | aaa | ggc | atc | cac | ctc | acc | atc | acc | acc | tgc | gac | 5328 |

```
                Thr Gln Leu Gln Gln Lys Gly Ile His Leu Thr Ile Thr Thr Cys Asp
                                1765                1770                1775 acc agc aac cca gac caa ctc caa caa ctc ctc aac acc atc ccc cca          5376
Thr Ser Asn Pro Asp Gln Leu Gln Gln Leu Leu Asn Thr Ile Pro Pro
            1780                1785                1790 caa cac ccc ctc acc acc gtc atc cac acc gca ggc atc ctc gac gac          5424
Gln His Pro Leu Thr Thr Val Ile His Thr Ala Gly Ile Leu Asp Asp
            1795                1800                1805 gcc acc ctc acc aac ctc acc ccc acc caa ctc aac aac gtc ctc cgc          5472
Ala Thr Leu Thr Asn Leu Thr Pro Thr Gln Leu Asn Asn Val Leu Arg
        1810                1815                1820 gcc aaa gcc cac agc gcc cac ctc ctc cac caa ctc acc caa cac acc          5520
Ala Lys Ala His Ser Ala His Leu Leu His Gln Leu Thr Gln His Thr
1825            1830                1835                1840 ccc ctc acc gcc ttc gtc ctc tac tcc tcc gcc gcc gcc acc ttc ggc          5568
Pro Leu Thr Ala Phe Val Leu Tyr Ser Ser Ala Ala Ala Thr Phe Gly
                1845                1850                1855 gca ccc ggc caa gcc aac tac gcc gca gcc aac gcc tac ctc gac gcc          5616
Ala Pro Gly Gln Ala Asn Tyr Ala Ala Ala Asn Ala Tyr Leu Asp Ala
            1860                1865                1870 ctc gcc cac cac cgc cac acc cac cac ctc ccc gcc acc agc atc gcc          5664
Leu Ala His His Arg His Thr His His Leu Pro Ala Thr Ser Ile Ala
        1875                1880                1885 tgg ggc acc tgg caa gga aac gga ctc gct gat tcg gac aag gcc cgc          5712
Trp Gly Thr Trp Gln Gly Asn Gly Leu Ala Asp Ser Asp Lys Ala Arg
    1890                1895                1900 gca tat ctc gac cgc cgc ggg ttt cga ccc atg tca ccc gag ttg gcc          5760
Ala Tyr Leu Asp Arg Arg Gly Phe Arg Pro Met Ser Pro Glu Leu Ala
1905                1910                1915                1920 acg gca gcg gtc acg cag gcg atc gcg gac acc gaa cgg ccg tat gtc          5808
Thr Ala Ala Val Thr Gln Ala Ile Ala Asp Thr Glu Arg Pro Tyr Val
                1925                1930                1935 gtc atc gcc gac atc gac tgg agc aag atc gaa cac acc tct cag acc          5856
Val Ile Ala Asp Ile Asp Trp Ser Lys Ile Glu His Thr Ser Gln Thr
            1940                1945                1950 agc gac ctg gtg agc gcg gcc cgg gaa agg gag cca gct gtc cag cgc          5904
Ser Asp Leu Val Ser Ala Ala Arg Glu Arg Glu Pro Ala Val Gln Arg
        1955                1960                1965 ccc act cca ccg gcg gag ttg cac aaa acg ctg gcc cat cag acg tcg          5952
Pro Thr Pro Pro Ala Glu Leu His Lys Thr Leu Ala His Gln Thr Ser
    1970                1975                1980 gcc gac caa cgg gcc gca ttg ctc gag ctc gta cga gac cat gtg gcg          6000
Ala Asp Gln Arg Ala Ala Leu Leu Glu Leu Val Arg Asp His Val Ala
1985                1990                1995                2000 gca gtg ctc cgg cac gcg gac ccg aaa gcc atc gcg ccc gac cag tcg          6048
Ala Val Leu Arg His Ala Asp Pro Lys Ala Ile Ala Pro Asp Gln Ser
                2005                2010                2015 ttc cgt gca ctc ggc ttc gat tca ctc acg gcc gtc gag ttc cga aac          6096
Phe Arg Ala Leu Gly Phe Asp Ser Leu Thr Ala Val Glu Phe Arg Asn
            2020                2025                2030 ctg ctg atc aag gca aca gga ctc cgc ctt cct gtc tcg ctg gtc ttc          6144
Leu Leu Ile Lys Ala Thr Gly Leu Arg Leu Pro Val Ser Leu Val Phe
        2035                2040                2045 gac cac ccg acc cct gcc aaa ctc gcc gta cac ctg cag aac caa ctg          6192
Asp His Pro Thr Pro Ala Lys Leu Ala Val His Leu Gln Asn Gln Leu
    2050                2055                2060 cgg ggc aca gca gcg gag tcg gct cct tca gcg gca gcc gtt acc gcc          6240
Arg Gly Thr Ala Ala Glu Ser Ala Pro Ser Ala Ala Ala Val Thr Ala
2065                2070                2075                2080
```

-continued

| | |
|---|---|
| gag gct tct gtc acc gag ccg atc gcc atc gtt ggc atg gcc tgt cgt<br>Glu Ala Ser Val Thr Glu Pro Ile Ala Ile Val Gly Met Ala Cys Arg<br>                2085                     2090              2095 | 6288 |
| ttc ccc ggc gga gtg acc tcg gcg gac gac ttc tgg gat ctg atc tcc<br>Phe Pro Gly Gly Val Thr Ser Ala Asp Asp Phe Trp Asp Leu Ile Ser<br>                2100                     2105              2110 | 6336 |
| tcc gag cag gac gcg atc gga gga ttc ccc acc gac cgc ggc tgg gac<br>Ser Glu Gln Asp Ala Ile Gly Gly Phe Pro Thr Asp Arg Gly Trp Asp<br>                2115                     2120              2125 | 6384 |
| ctg gac acg ctc tac gac ccc gac ccc gac cac ccc ggc acc tgc tac<br>Leu Asp Thr Leu Tyr Asp Pro Asp Pro Asp His Pro Gly Thr Cys Tyr<br>                2130                     2135              2140 | 6432 |
| acc cga aac ggc gga ttc ctc tac gac gca ggc cac ttc gac gcc gaa<br>Thr Arg Asn Gly Gly Phe Leu Tyr Asp Ala Gly His Phe Asp Ala Glu<br>2145                     2150                     2155                   2160 | 6480 |
| ttc ttc ggc atc agc ccc cgc gaa gcc ctc gcc atg gac ccc cag caa<br>Phe Phe Gly Ile Ser Pro Arg Glu Ala Leu Ala Met Asp Pro Gln Gln<br>                2165                     2170              2175 | 6528 |
| cga ctc ctc ctc gaa acc gcc tgg gaa acc atc gaa cac gcc ggc atc<br>Arg Leu Leu Leu Glu Thr Ala Trp Glu Thr Ile Glu His Ala Gly Ile<br>                2180                     2185              2190 | 6576 |
| aac ccc cac acc ctc cac ggc acc ccc acc gga gtc ttc acc ggc acc<br>Asn Pro His Thr Leu His Gly Thr Pro Thr Gly Val Phe Thr Gly Thr<br>                2195                     2200              2205 | 6624 |
| aac gga cag gac tac gca ctt cgc gtg cac aac gcg ggc cag tca acc<br>Asn Gly Gln Asp Tyr Ala Leu Arg Val His Asn Ala Gly Gln Ser Thr<br>                2210                     2215              2220 | 6672 |
| gat ggt ttc gca ctg acc gga acc gcc ggc agc gtc atc tcc ggt cgt<br>Asp Gly Phe Ala Leu Thr Gly Thr Ala Gly Ser Val Ile Ser Gly Arg<br>2225                     2230                     2235                   2240 | 6720 |
| atc tcg tac acg ttt ggt ttt gag ggt cct gcg gtg tcg gtg gac acg<br>Ile Ser Tyr Thr Phe Gly Phe Glu Gly Pro Ala Val Ser Val Asp Thr<br>                2245                     2250              2255 | 6768 |
| gct tgt tcc tcg tcg ttg gtg gct ttg cat ctg gcc tgt cag gcg ttg<br>Ala Cys Ser Ser Ser Leu Val Ala Leu His Leu Ala Cys Gln Ala Leu<br>                2260                     2265              2270 | 6816 |
| cgt gcg ggt gag tgc tcg atg gcg ctt gcc ggg ggt gtg acg gtg atg<br>Arg Ala Gly Glu Cys Ser Met Ala Leu Ala Gly Gly Val Thr Val Met<br>                2275                     2280              2285 | 6864 |
| tcg tct ccg ggt gcc ttc gtg gag ttt tcg cgg cag cgg ggt ctg gcc<br>Ser Ser Pro Gly Ala Phe Val Glu Phe Ser Arg Gln Arg Gly Leu Ala<br>                2290                     2295              2300 | 6912 |
| gcg gac ggg cat tgc aag gcg ttc tcg gcg gcg gcg gac ggg acc ggc<br>Ala Asp Gly His Cys Lys Ala Phe Ser Ala Ala Ala Asp Gly Thr Gly<br>2305                     2310                     2315                   2320 | 6960 |
| tgg ggt gag ggt gtg ggg atg ctg ctg gtg gag cgg ctc tcc gac gcc<br>Trp Gly Glu Gly Val Gly Met Leu Leu Val Glu Arg Leu Ser Asp Ala<br>                2325                     2330              2335 | 7008 |
| cat cgc aac ggt cac cgt gtc ctg gcc gtg gtg cgt ggc agt gcg gtc<br>His Arg Asn Gly His Arg Val Leu Ala Val Val Arg Gly Ser Ala Val<br>                2340                     2345              2350 | 7056 |
| aac cag gac ggt gcg agc aac ggt ctg acc gcg ccc aac ggg ccg tcc<br>Asn Gln Asp Gly Ala Ser Asn Gly Leu Thr Ala Pro Asn Gly Pro Ser<br>                2355                     2360              2365 | 7104 |
| cag cag cgt gtc atc cgc cag gcc ctc gcc aac gcc ggc ttg tcg gcc<br>Gln Gln Arg Val Ile Arg Gln Ala Leu Ala Asn Ala Gly Leu Ser Ala<br>                2370                     2375              2380 | 7152 |
| ggt gat gtc gac gcg gtg gag gcc cac ggc acc ggc acc act ttg ggc<br>Gly Asp Val Asp Ala Val Glu Ala His Gly Thr Gly Thr Thr Leu Gly<br>2385                     2390                     2395                   2400 | 7200 |

-continued

| | |
|---|---|
| gac ccg atc gag gcc cag gcc ctc ctc gcg acc tac gga cag gac cgt<br>Asp Pro Ile Glu Ala Gln Ala Leu Leu Ala Thr Tyr Gly Gln Asp Arg<br>                        2405                              2410                        2415 | 7248 |
| gcc ggc gag ggg ccg ctg tgg ctg ggc tcg gtc aag tcc aat gtc ggt<br>Ala Gly Glu Gly Pro Leu Trp Leu Gly Ser Val Lys Ser Asn Val Gly<br>                        2420                              2425                        2430 | 7296 |
| cac aca cag gct gcc gcg ggc gtc gcc ggg gtg atc aag atg gtg atg<br>His Thr Gln Ala Ala Ala Gly Val Ala Gly Val Ile Lys Met Val Met<br>                        2435                              2440                        2445 | 7344 |
| gcg ctg cgg cat ggt ctg ctg ccg cgg acg ttg cat gtg gat gag ccg<br>Ala Leu Arg His Gly Leu Leu Pro Arg Thr Leu His Val Asp Glu Pro<br>                        2450                              2455                        2460 | 7392 |
| tcg ccg cat gtg gac tgg tcc gcg ggt gcg gtg cag ctg ctg acg gag<br>Ser Pro His Val Asp Trp Ser Ala Gly Ala Val Gln Leu Leu Thr Glu<br>2465                            2470                              2475                        2480 | 7440 |
| acg gtg ccc tgg ccc ggc ggg gag ggg cgg cta cgg cgg gca gga gtg<br>Thr Val Pro Trp Pro Gly Gly Glu Gly Arg Leu Arg Arg Ala Gly Val<br>                        2485                              2490                        2495 | 7488 |
| tca tca ttc ggc gtc agc ggc acc aac gcc cac gtc atc ctc gaa gaa<br>Ser Ser Phe Gly Val Ser Gly Thr Asn Ala His Val Ile Leu Glu Glu<br>                        2500                              2505                        2510 | 7536 |
| gca ccc gcc gac gac gtt ccg ggg gga cca ccc gcc ggc gag ggt gac<br>Ala Pro Ala Asp Asp Val Pro Gly Gly Pro Pro Ala Gly Glu Gly Asp<br>                        2515                              2520                        2525 | 7584 |
| gcg ggc agc gac gat gag gct gct gcc ggc agt cct ggg gtg tgg ccg<br>Ala Gly Ser Asp Asp Glu Ala Ala Ala Gly Ser Pro Gly Val Trp Pro<br>                        2530                              2535                        2540 | 7632 |
| tgg ctg gtg tcg gcc aag tcg cag ccg gcc ctg cgc gcc cag gcc cag<br>Trp Leu Val Ser Ala Lys Ser Gln Pro Ala Leu Arg Ala Gln Ala Gln<br>2545                            2550                              2555                        2560 | 7680 |
| gcc ctg cac gcc cac ctc acc gac cac ccc ggc ctc gac ctc gcg gat<br>Ala Leu His Ala His Leu Thr Asp His Pro Gly Leu Asp Leu Ala Asp<br>                        2565                              2570                        2575 | 7728 |
| gtc gga tac acc ctc gcc cac gcc cgc gcc gtg ttc gac cac cgc gcc<br>Val Gly Tyr Thr Leu Ala His Ala Arg Ala Val Phe Asp His Arg Ala<br>                        2580                              2585                        2590 | 7776 |
| acc ctc atc gcc gcg gac cgc gac acg ttc ctg caa gca ctc cag gca<br>Thr Leu Ile Ala Ala Asp Arg Asp Thr Phe Leu Gln Ala Leu Gln Ala<br>                        2595                              2600                        2605 | 7824 |
| ctc gcc gca ggc gag ccc cac ccc gcc gtc atc cac agc agc gcc ccg<br>Leu Ala Ala Gly Glu Pro His Pro Ala Val Ile His Ser Ser Ala Pro<br>                        2610                              2615                        2620 | 7872 |
| ggc ggg acc ggg acc ggg gag gcc gca gga aag acc gca ttc atc tgc<br>Gly Gly Thr Gly Thr Gly Glu Ala Ala Gly Lys Thr Ala Phe Ile Cys<br>2625                            2630                              2635                        2640 | 7920 |
| tcc gga cag ggc acc caa cgc ccc ggc atg gcc cac ggc ctc tac cac<br>Ser Gly Gln Gly Thr Gln Arg Pro Gly Met Ala His Gly Leu Tyr His<br>                        2645                              2650                        2655 | 7968 |
| acc cac ccc gtc ttc gcc gcc gca ctc aac gac atc tgc acc cac ctc<br>Thr His Pro Val Phe Ala Ala Ala Leu Asn Asp Ile Cys Thr His Leu<br>                        2660                              2665                        2670 | 8016 |
| gac ccc cac ctc gac cac ccc ctc ctc ccc ctc ctc acc caa aac gac<br>Asp Pro His Leu Asp His Pro Leu Leu Pro Leu Leu Thr Gln Asn Asp<br>                        2675                              2680                        2685 | 8064 |
| aac gac aac gag gac gcg gcc gca ctg ctc cag cag acc cgc tac gcc<br>Asn Asp Asn Glu Asp Ala Ala Ala Leu Leu Gln Gln Thr Arg Tyr Ala<br>                        2690                              2695                        2700 | 8112 |
| cag ccc gcc ctc ttc gcc ttc cag gtc gcc ctc cac cgc ctc ctc acc<br>Gln Pro Ala Leu Phe Ala Phe Gln Val Ala Leu His Arg Leu Leu Thr | 8160 |

|  |  |
|---|---|
| gac ggc tac cac atc acc ccc cac tac tac gcc gga cac tcc ctc ggc<br>Asp Gly Tyr His Ile Thr Pro His Tyr Tyr Ala Gly His Ser Leu Gly<br>                        2725                        2730                        2735 | 8208 |
| gaa atc acc gcc gcc cac ctc gcc ggc atc ctc acc ctc acc gac gcc<br>Glu Ile Thr Ala Ala His Leu Ala Gly Ile Leu Thr Leu Thr Asp Ala<br>                        2740                        2745                        2750 | 8256 |
| acc acc ctc atc acc caa cgc gcc acc ctc atg caa acc atg ccc ccc<br>Thr Thr Leu Ile Thr Gln Arg Ala Thr Leu Met Gln Thr Met Pro Pro<br>                        2755                        2760                        2765 | 8304 |
| ggc acc atg acc acc ctc cac acc acc ccc cac cac atc acc cac cac<br>Gly Thr Met Thr Thr Leu His Thr Thr Pro His His Ile Thr His His<br>                        2770                        2775                        2780 | 8352 |
| ctc acc gcc cac gaa aac gac ctc gcc atc gcc gcc atc aac acc ccc<br>Leu Thr Ala His Glu Asn Asp Leu Ala Ile Ala Ala Ile Asn Thr Pro<br>2785                        2790                        2795                        2800 | 8400 |
| acc tcc ctc gtc atc agc ggc acc ccc cac acc gtc caa cac atc acc<br>Thr Ser Leu Val Ile Ser Gly Thr Pro His Thr Val Gln His Ile Thr<br>                        2805                        2810                        2815 | 8448 |
| acc ctc tgc caa caa caa ggc atc aaa acc aaa acc ctc ccc acc aac<br>Thr Leu Cys Gln Gln Gln Gly Ile Lys Thr Lys Thr Leu Pro Thr Asn<br>                        2820                        2825                        2830 | 8496 |
| cac gcc ttc cac tcc ccc cac acc aac ccc atc ctc aac caa ctc cac<br>His Ala Phe His Ser Pro His Thr Asn Pro Ile Leu Asn Gln Leu His<br>                        2835                        2840                        2845 | 8544 |
| cag cac acc caa acc ctc acc tac cac cca ccc cac acc ccc ctc atc<br>Gln His Thr Gln Thr Leu Thr Tyr His Pro Pro His Thr Pro Leu Ile<br>                        2850                        2855                        2860 | 8592 |
| acc gcc aac acc cca ccc gac caa ctc ctc acc ccc cac tac tgg acc<br>Thr Ala Asn Thr Pro Pro Asp Gln Leu Leu Thr Pro His Tyr Trp Thr<br>2865                        2870                        2875                        2880 | 8640 |
| caa caa gcc cgc aac acc gtc gac tac gcc acc acc acc caa acc ctc<br>Gln Gln Ala Arg Asn Thr Val Asp Tyr Ala Thr Thr Thr Gln Thr Leu<br>                        2885                        2890                        2895 | 8688 |
| cac caa cac ggc gtc acc acc tac atc gaa ctc gga ccc gac aac acc<br>His Gln His Gly Val Thr Thr Tyr Ile Glu Leu Gly Pro Asp Asn Thr<br>                        2900                        2905                        2910 | 8736 |
| ctc acc acc ctc acc cac cac aac ctc ccc aac ccc ccc acc acc acc<br>Leu Thr Thr Leu Thr His His Asn Leu Pro Asn Pro Pro Thr Thr Thr<br>                        2915                        2920                        2925 | 8784 |
| ctc acc ctc acc cac ccc cac cac cac ccc caa acc cac ctc ctc acc<br>Leu Thr Leu Thr His Pro His His His Pro Gln Thr His Leu Leu Thr<br>                        2930                        2935                        2940 | 8832 |
| aac ctc gcc aaa acc acc acc acc tgg cac ccc cac cac tac acc cac<br>Asn Leu Ala Lys Thr Thr Thr Thr Trp His Pro His His Tyr Thr His<br>2945                        2950                        2955                        2960 | 8880 |
| cac gac aac caa ccc cac acc cac acc cac ctc gac ctc ccc acc tac<br>His Asp Asn Gln Pro His Thr His Thr His Leu Asp Leu Pro Thr Tyr<br>                        2965                        2970                        2975 | 8928 |
| ccc ttc caa cac cac cac tac tgg ctc gaa agc aca cag ccc ggt gcc<br>Pro Phe Gln His His His Tyr Trp Leu Glu Ser Thr Gln Pro Gly Ala<br>                        2980                        2985                        2990 | 8976 |
| ggc aac gtg tca gca gcc gga ctc gac ccc acc gaa cac ccc cta ctc<br>Gly Asn Val Ser Ala Ala Gly Leu Asp Pro Thr Glu His Pro Leu Leu<br>                        2995                        3000                        3005 | 9024 |
| ggc gcc aca ttg gaa ctg gcg act gac ggt gga gcg ctt ctt gca ggg<br>Gly Ala Thr Leu Glu Leu Ala Thr Asp Gly Gly Ala Leu Leu Ala Gly<br>                        3010                        3015                        3020 | 9072 |
| cgc ttg tct ttg agg tcg cat ccg tgg ctg gct gac cat gcc gtc ggc | 9120 |

```
Arg Leu Ser Leu Arg Ser His Pro Trp Leu Ala Asp His Ala Val Gly
3025                3030                3035                3040 ggc acg gtg ctg ctg tcg ggc gcc acc ttc ctc gaa ctc gcc ctt cat   9168
Gly Thr Val Leu Leu Ser Gly Ala Thr Phe Leu Glu Leu Ala Leu His
        3045                3050                3055 gcg ggc aca tac gtg ggc tgc gac cga gtg gat gag ctg acg ctg cat   9216
Ala Gly Thr Tyr Val Gly Cys Asp Arg Val Asp Glu Leu Thr Leu His
    3060                3065                3070 gcg ccg ctg gtg gtt cct gtg gat ggg ggt gtg agt gtg cag gtt ggg   9264
Ala Pro Leu Val Val Pro Val Asp Gly Gly Val Ser Val Gln Val Gly
    3075                3080                3085 gtt gcg gct gcg gat ggg gag ggg cgg cgt ttg gtg agt gtg tat gcg   9312
Val Ala Ala Ala Asp Gly Glu Gly Arg Arg Leu Val Ser Val Tyr Ala
3090                3095                3100 cgg ggt ggg agt gct tgt ggt ggg ggt ggt gcg tcg ggt ggg gtg tgg   9360
Arg Gly Gly Ser Ala Cys Gly Gly Gly Gly Ala Ser Gly Gly Val Trp
3105                3110                3115                3120 acg tgt cat gcc tcg ggg gtg ctg gtt gag gct gct gct ggt ggt gtg   9408
Thr Cys His Ala Ser Gly Val Leu Val Glu Ala Ala Ala Gly Gly Val
        3125                3130                3135 gtg gtg gat ggt ctg gcg ggg gtg tgg ccg ccg cgg ggt gcg gtg gcg   9456
Val Val Asp Gly Leu Ala Gly Val Trp Pro Pro Arg Gly Ala Val Ala
    3140                3145                3150 gtg gat gtc gat ggt gtc cgt gac cgt ttg gct ggg gct ggt tgt gtt   9504
Val Asp Val Asp Gly Val Arg Asp Arg Leu Ala Gly Ala Gly Cys Val
    3155                3160                3165 ttg ggg ccg gtg ttt tcg ggg ctg cgt gcg gtg tgg cgt gat ggg ggg   9552
Leu Gly Pro Val Phe Ser Gly Leu Arg Ala Val Trp Arg Asp Gly Gly
3170                3175                3180 gat ttg ctg gct gag gtg tgt ctg ccg gag gag gcg tgg ggt gat gcg   9600
Asp Leu Leu Ala Glu Val Cys Leu Pro Glu Glu Ala Trp Gly Asp Ala
3185                3190                3195                3200 gct ggt ttt ggg ctg cat ccg gcg ttg ctg gat ggt gtg gtc cag ccg   9648
Ala Gly Phe Gly Leu His Pro Ala Leu Leu Asp Gly Val Val Gln Pro
        3205                3210                3215 ttg tcg gtg ttg ctt ccg ggt ggg acg ggg ttt ggg gag ggg gcg ggg   9696
Leu Ser Val Leu Leu Pro Gly Gly Thr Gly Phe Gly Glu Gly Ala Gly
    3220                3225                3230 ttc ggg gag ggt gtt cgg gtg ccg gct gtg tgg ggt ggt gtg tcg ctt   9744
Phe Gly Glu Gly Val Arg Val Pro Ala Val Trp Gly Gly Val Ser Leu
    3235                3240                3245 cac cgg gcg ggt gtg acc ggt gtg cgg gtg cgt gtg tcg gct gtc ggg   9792
His Arg Ala Gly Val Thr Gly Val Arg Val Arg Val Ser Ala Val Gly
3250                3255                3260 cgg ggc ggc ggg cgt gag gcg gtg tcg gtc gtg gtc ggg gat gag gcg   9840
Arg Gly Gly Gly Arg Glu Ala Val Ser Val Val Val Gly Asp Glu Ala
3265                3270                3275                3280 ggt gtg ccg gtg gcg tcg gtc gat cgt ctt gag ttg cgg cct gtg gat   9888
Gly Val Pro Val Ala Ser Val Asp Arg Leu Glu Leu Arg Pro Val Asp
        3285                3290                3295 atg ggt cag ttg cgt gct gtc tcg gtt tcg gcg ggg cgg cgg ggt tcg   9936
Met Gly Gln Leu Arg Ala Val Ser Val Ser Ala Gly Arg Arg Gly Ser
    3300                3305                3310 ctg tat gcg gtg cag tgg gct gag gtg ggt cct gtg ccg gtg tgt ggg   9984
Leu Tyr Ala Val Gln Trp Ala Glu Val Gly Pro Val Pro Val Cys Gly
    3315                3320                3325 cag gcg tgg gcg tgg cac gag gac gtg ggt gag agc ggt ggt ggg cct   10032
Gln Ala Trp Ala Trp His Glu Asp Val Gly Glu Ser Gly Gly Gly Pro
3330                3335                3340
```

| | |
|---|---|
| gtg ccg ggg gtg gtg gtg ttg cgg tgc ccg gat gcc ggt gcc ggt ggc<br>Val Pro Gly Val Val Val Leu Arg Cys Pro Asp Ala Gly Ala Gly Gly<br>3345                       3350                        3355                     3360 | 10080 |
| ggt ggc ggt ggc ggt ggt ggc ggt ggt gtg ggt gag gtt gtt ggt ggg<br>Gly Gly Gly Gly Gly Gly Gly Gly Gly Val Gly Glu Val Val Gly Gly<br>               3365                        3370                     3375 | 10128 |
| gtg ttg ggt gtg gtg cag ggg tgg ctg ggg ctg gag cgg ttt gcg ggt<br>Val Leu Gly Val Val Gln Gly Trp Leu Gly Leu Glu Arg Phe Ala Gly<br>         3380                       3385                     3390 | 10176 |
| tcg cgg ctg gtg gtg gtg acc cgg ggt gcg gtg gtg gcc ggc ccg gag<br>Ser Arg Leu Val Val Val Thr Arg Gly Ala Val Val Ala Gly Pro Glu<br>         3395                       3400                     3405 | 10224 |
| gac ggc ccg gtg gat gtg gtg ggt gcg tcg gtg tgg ggg ctg gtg cgt<br>Asp Gly Pro Val Asp Val Val Gly Ala Ser Val Trp Gly Leu Val Arg<br>         3410                       3415                     3420 | 10272 |
| tcg gcg cag gct gag cat ccg gac cgg ttt gtc ctc ctc gac ctc gac<br>Ser Ala Gln Ala Glu His Pro Asp Arg Phe Val Leu Leu Asp Leu Asp<br>3425                       3430                        3435                     3440 | 10320 |
| acc gac acc ggc acc gac ctc gac acc ggt gct ggt gct ggt tgg ggc<br>Thr Asp Thr Gly Thr Asp Leu Asp Thr Gly Ala Gly Ala Gly Trp Gly<br>                       3445                       3450                     3455 | 10368 |
| gtg gat ggt ggg cgt gtg gcg gcg gtg gtg gcg tgt ggt gag ccg cag<br>Val Asp Gly Gly Arg Val Ala Ala Val Val Ala Cys Gly Glu Pro Gln<br>         3460                       3465                     3470 | 10416 |
| ttg gcg gtg cgt ggg gag cgg ttg ctg gcc gca cgc ctg aaa cga ctt<br>Leu Ala Val Arg Gly Glu Arg Leu Leu Ala Ala Arg Leu Lys Arg Leu<br>         3475                       3480                     3485 | 10464 |
| gag tca tcc ggt gat gtt cca gcc cag cgg tcc ggt gac aca cga gcc<br>Glu Ser Ser Gly Asp Val Pro Ala Gln Arg Ser Gly Asp Thr Arg Ala<br>         3490                       3495                     3500 | 10512 |
| cgg cgg tcc gac gtg cct gcc cag cgc tcc ggt ggc gtg cct gct cgg<br>Arg Arg Ser Asp Val Pro Ala Gln Arg Ser Gly Gly Val Pro Ala Arg<br>3505                       3510                        3515                     3520 | 10560 |
| cgg tcg gtt gat gta tcg ggt cgg gag gtg ttg ccg tgg ttg tcg ggt<br>Arg Ser Val Asp Val Ser Gly Arg Glu Val Leu Pro Trp Leu Ser Gly<br>                       3525                       3530                     3535 | 10608 |
| ggg tcg gtg ttg gtg acg ggt ggg acg ggt gtg ctg ggt gcg gcg gtg<br>Gly Ser Val Leu Val Thr Gly Gly Thr Gly Val Leu Gly Ala Ala Val<br>                       3540                       3545                     3550 | 10656 |
| gcg cgg cat ctg gct ggt gtg tgt ggg gtg cgg gat ctg ctg ttg gtg<br>Ala Arg His Leu Ala Gly Val Cys Gly Val Arg Asp Leu Leu Leu Val<br>                       3555                       3560                     3565 | 10704 |
| agc cgg cgt ggt ccg gat gct ccg ggt gcg gag ggt ctg cgg gcg gag<br>Ser Arg Arg Gly Pro Asp Ala Pro Gly Ala Glu Gly Leu Arg Ala Glu<br>         3570                       3575                     3580 | 10752 |
| ctg gcc gcg ttg ggg gcg gag gtg cgg att gtt gcg tgt gat gtg ggg<br>Leu Ala Ala Leu Gly Ala Glu Val Arg Ile Val Ala Cys Asp Val Gly<br>3585                       3590                        3595                     3600 | 10800 |
| gag cgg cgg gag gtg gtc cgg ctg ctg gag ggt gtt cct gcc ggg tgt<br>Glu Arg Arg Glu Val Val Arg Leu Leu Glu Gly Val Pro Ala Gly Cys<br>                       3605                       3610                     3615 | 10848 |
| ccg ctg acg ggt gtc gtg cat gcg gct ggt gtg ctg gac gat gcg acg<br>Pro Leu Thr Gly Val Val His Ala Ala Gly Val Leu Asp Asp Ala Thr<br>                       3620                       3625                     3630 | 10896 |
| atc gcc tct ctc acg ccc gag cgg ctg ggc acg gtg ttc gcg gcc aag<br>Ile Ala Ser Leu Thr Pro Glu Arg Leu Gly Thr Val Phe Ala Ala Lys<br>         3635                       3640                     3645 | 10944 |
| gtg gat gcc gct ctt ttg ctg gat gag ctg acg cgg ggt atg gag ctg<br>Val Asp Ala Ala Leu Leu Leu Asp Glu Leu Thr Arg Gly Met Glu Leu<br>         3650                       3655                     3660 | 10992 |

```
tcg gcg ttc gtg ctg ttc tcc tcg gcc gcg ggg atc ctg ggg tcg gcc    11040
Ser Ala Phe Val Leu Phe Ser Ser Ala Ala Gly Ile Leu Gly Ser Ala
3665            3670                3675                3680 ggg cag ggc aac tac gcc gcg gcc aat gcc gct ctg gac gcg ctg gcg    11088
Gly Gln Gly Asn Tyr Ala Ala Ala Asn Ala Ala Leu Asp Ala Leu Ala
            3685                3690                3695 tac cgg cgg cgg gcg gcg ggt ctg ccg ggg gtg tcg ctg gcg tgg ggg    11136
Tyr Arg Arg Arg Ala Ala Gly Leu Pro Gly Val Ser Leu Ala Trp Gly
3700                3705                3710 ctg tgg gaa gag gcc agc ggg atg acc ggg cac ctg gcc ggc acc gac    11184
Leu Trp Glu Glu Ala Ser Gly Met Thr Gly His Leu Ala Gly Thr Asp
        3715                3720                3725 cac cgg cgc atc atc cgt tcc ggt ctg cat ccc atg tcg acc ccg gac    11232
His Arg Arg Ile Ile Arg Ser Gly Leu His Pro Met Ser Thr Pro Asp
3730                3735                3740 gca ctg gcc ctc ttc gat gcg gcc ctg gct ctg gac cgg ccg gtc ctg    11280
Ala Leu Ala Leu Phe Asp Ala Ala Leu Ala Leu Asp Arg Pro Val Leu
3745            3750                3755                3760 ctg ccc gcc gac ctg cgt ccc gcc ccg ccc ctg ccg ccc ctg ctg cag    11328
Leu Pro Ala Asp Leu Arg Pro Ala Pro Pro Leu Pro Pro Leu Leu Gln
                3765                3770                3775 gac ctc ctg ccc gcc acc cgc cgc cgc acc acc cgc acc acc act acc    11376
Asp Leu Leu Pro Ala Thr Arg Arg Arg Thr Thr Arg Thr Thr Thr Thr
            3780                3785                3790 ggt ggt gcg gac aac ggc gcc cag ctg cac gcc cgg ctg gcc ggc cag    11424
Gly Gly Ala Asp Asn Gly Ala Gln Leu His Ala Arg Leu Ala Gly Gln
3795                3800                3805 aca cac gaa caa cag cac acc acc ctc ctc gcc ctg gtc cgc tcc cac    11472
Thr His Glu Gln Gln His Thr Thr Leu Leu Ala Leu Val Arg Ser His
        3810                3815                3820 atc gcc acc gtc ctg ggc cac acc acc ccc gac acc atc ccc ccc gac    11520
Ile Ala Thr Val Leu Gly His Thr Thr Pro Asp Thr Ile Pro Pro Asp
3825            3830                3835                3840 cgc gcg ttc cgc gac ctc ggc ttc gac tcc ctc acc gcc gtc gaa cta    11568
Arg Ala Phe Arg Asp Leu Gly Phe Asp Ser Leu Thr Ala Val Glu Leu
                3845                3850                3855 cgc aac cgg ctc tcc cgc acc acc gga ctc cgc ctc ccc acc acc ctc    11616
Arg Asn Arg Leu Ser Arg Thr Thr Gly Leu Arg Leu Pro Thr Thr Leu
            3860                3865                3870 gcc ttc gac cac ccc aac ccc acc acc ctc acc cac cac ctc cac aca    11664
Ala Phe Asp His Pro Asn Pro Thr Thr Leu Thr His His Leu His Thr
3875                3880                3885 caa ctc cag cca caa ccg gac aac gct gtc gcc ccc gtg ttg gcg gag    11712
Gln Leu Gln Pro Gln Pro Asp Asn Ala Val Ala Pro Val Leu Ala Glu
        3890                3895                3900 ctc gac aaa ctc gaa tcc gcc ctc tcc gcc ctc gac aaa acc gac agc    11760
Leu Asp Lys Leu Glu Ser Ala Leu Ser Ala Leu Asp Lys Thr Asp Ser
3905            3910                3915                3920 gcc agc gaa aga gtc acc ctg cgg ctg aag tca ctc atg ttg agg tgg    11808
Ala Ser Glu Arg Val Thr Leu Arg Leu Lys Ser Leu Met Leu Arg Trp
                3925                3930                3935 aac gca ccc cag cat ccg aca gcc gaa agc gct gat gac gac gag aag    11856
Asn Ala Pro Gln His Pro Thr Ala Glu Ser Ala Asp Asp Asp Glu Lys
            3940                3945                3950 ttc aca tcg gca aca gag gct gag att ttc aaa ttc att gac aac gac    11904
Phe Thr Ser Ala Thr Glu Ala Glu Ile Phe Lys Phe Ile Asp Asn Asp
3955                3960                3965 ctc ggc ctg tcc tgaaccggac gcctgccact ccgcccgtat ccgctgggcc       11956
Leu Gly Leu Ser
```

-continued

```
        3970
ctgctaggac gtga atg caa ttg gcg aat gaa gcg aag ctc ctg gaa tac        12006
            Met Gln Leu Ala Asn Glu Ala Lys Leu Leu Glu Tyr
                 3975                 3980
ctc aag cgc gtc act gcg gac ctg gac cgc act cgc cgt cgc ctg tac        12054
Leu Lys Arg Val Thr Ala Asp Leu Asp Arg Thr Arg Arg Arg Leu Tyr
3985                 3990                 3995                 4000
gag gtg gtc gag cgt gag cag gag ccg atc gcg att gtg ggg atg gcg        12102
Glu Val Val Glu Arg Glu Gln Glu Pro Ile Ala Ile Val Gly Met Ala
             4005                 4010                 4015
tgt cgt tac cca ggc ggg gcg acg tca ccc acg cga ctg tgg cat ctc        12150
Cys Arg Tyr Pro Gly Gly Ala Thr Ser Pro Thr Arg Leu Trp His Leu
             4020                 4025                 4030
gtc aag tcc cag acg gac gct atc ggg gag ttc ccg acc gac cgt gga        12198
Val Lys Ser Gln Thr Asp Ala Ile Gly Glu Phe Pro Thr Asp Arg Gly
             4035                 4040                 4045
tgg aac ctg gag cag ctc tac gac ccg gac ccc gac cgc tca gga acc        12246
Trp Asn Leu Glu Gln Leu Tyr Asp Pro Asp Pro Asp Arg Ser Gly Thr
             4050                 4055                 4060
agt tac acg cgc agc gga ggg ttt ctc tat gac gcg ggc gac ttc gac        12294
Ser Tyr Thr Arg Ser Gly Gly Phe Leu Tyr Asp Ala Gly Asp Phe Asp
4065                 4070                 4075                 4080
gcc gcg ttc ttc gag ttg tca ccg cgt gag gcg ctg gca atg gac ccg        12342
Ala Ala Phe Phe Glu Leu Ser Pro Arg Glu Ala Leu Ala Met Asp Pro
             4085                 4090                 4095
cag cag cgc ctg ctg ctc gaa acc act tgg gaa acg ttc gaa cag ggc        12390
Gln Gln Arg Leu Leu Leu Glu Thr Thr Trp Glu Thr Phe Glu Gln Gly
             4100                 4105                 4110
gga atc gac ccg agg tcc atg cgc gga agc cgg acc ggg gtt ttc gtg        12438
Gly Ile Asp Pro Arg Ser Met Arg Gly Ser Arg Thr Gly Val Phe Val
             4115                 4120                 4125
ggg atc aat ccg gag gac tac acc acc gga tac aca cat cag ccc tca        12486
Gly Ile Asn Pro Glu Asp Tyr Thr Thr Gly Tyr Thr His Gln Pro Ser
             4130                 4135                 4140
aac gca gtc gag ggc tac ctg ctc act ggc agc gcg gca agc att gcg        12534
Asn Ala Val Glu Gly Tyr Leu Leu Thr Gly Ser Ala Ala Ser Ile Ala
4145                 4150                 4155                 4160
tca ggc cgt atc tcc tac aac ttc ggg ctc gaa ggc cct gcg atc act        12582
Ser Gly Arg Ile Ser Tyr Asn Phe Gly Leu Glu Gly Pro Ala Ile Thr
             4165                 4170                 4175
atc gac acc gcg tgt tcc tcg ctc gtc gcc ctg cat ctg gcc tgc        12630
Ile Asp Thr Ala Cys Ser Ser Leu Val Ala Leu His Leu Ala Cys
             4180                 4185                 4190
caa gcg ctc cgg tcc ggt gaa tgc acc atg gcg ctc gca ggc ggc gcc        12678
Gln Ala Leu Arg Ser Gly Glu Cys Thr Met Ala Leu Ala Gly Gly Ala
             4195                 4200                 4205
tcc gtc atg gcc act ccc ttc gtc ttc acc gag ttc tct cgc cag cgg        12726
Ser Val Met Ala Thr Pro Phe Val Phe Thr Glu Phe Ser Arg Gln Arg
             4210                 4215                 4220
ggc ctg gcc gca gac ggc cgg tgc aag gcg ttt tcg gcg gcg gcg gac        12774
Gly Leu Ala Ala Asp Gly Arg Cys Lys Ala Phe Ser Ala Ala Ala Asp
4225                 4230                 4235                 4240
ggg acc ggc tgg tcc gag ggt gtg ggg atg ctg ctg gtg gag cgg ctc        12822
Gly Thr Gly Trp Ser Glu Gly Val Gly Met Leu Leu Val Glu Arg Leu
             4245                 4250                 4255
tcc gac gcc cgc cgc aac ggt cac cgt gtc ctg gcc gtc gtc cgc ggc        12870
Ser Asp Ala Arg Arg Asn Gly His Arg Val Leu Ala Val Val Arg Gly
             4260                 4265                 4270
agc gcc gtc aac cag gac ggc gca agc aac ggc ctg acc gca ccc aac        12918
```

```
Ser Ala Val Asn Gln Asp Gly Ala Ser Asn Gly Leu Thr Ala Pro Asn
        4275                4280                4285 ggt cgt tca caa gtc aag gtc atc cgc cag gct ttg gcc aac gca cac   12966
Gly Arg Ser Gln Val Lys Val Ile Arg Gln Ala Leu Ala Asn Ala His
    4290                4295                4300 ctc tcc cct gcc gat gtc gat gcg gtg gag gcc cac ggc acg ggg acc   13014
Leu Ser Pro Ala Asp Val Asp Ala Val Glu Ala His Gly Thr Gly Thr
4305                4310                4315                4320 acc ctg ggc gac ccg atc gag gct caa gcc ctc gtc gaa gcc tac ggt   13062
Thr Leu Gly Asp Pro Ile Glu Ala Gln Ala Leu Val Glu Ala Tyr Gly
        4325                4330                4335 cag gac cgc ccc aac ggc cgc ccc ctc tgg ctc gga acc ctc aag tcc   13110
Gln Asp Arg Pro Asn Gly Arg Pro Leu Trp Leu Gly Thr Leu Lys Ser
    4340                4345                4350 aac atc ggg cac tcc atg gcc gct gcg ggt gtg ggc ggg gtc atc aag   13158
Asn Ile Gly His Ser Met Ala Ala Ala Gly Val Gly Gly Val Ile Lys
4355                4360                4365 atg gtg atg gcg ctg cgg aat ggt ctg ctg ccg cgg acg ttg cat gtg   13206
Met Val Met Ala Leu Arg Asn Gly Leu Leu Pro Arg Thr Leu His Val
        4370                4375                4380 gat gag ccg tcg ccg cat gtg gac tgg tcc gcg ggt gcg gtg cag ctg   13254
Asp Glu Pro Ser Pro His Val Asp Trp Ser Ala Gly Ala Val Gln Leu
4385                4390                4395                4400 ctg acg gag acg gtg ccc tgg ccc ggg gag ggg cgg cta cgg cgg       13302
Leu Thr Glu Thr Val Pro Trp Pro Gly Gly Glu Gly Arg Leu Arg Arg
        4405                4410                4415 gca gga gtg tca tca ttc ggc gtc agc ggc acc aac gcc cac gtc atc   13350
Ala Gly Val Ser Ser Phe Gly Val Ser Gly Thr Asn Ala His Val Ile
    4420                4425                4430 ctc gag gaa gca ccc gcc cac aac atc ccg tca gac aca ccc gcc gac   13398
Leu Glu Glu Ala Pro Ala His Asn Ile Pro Ser Asp Thr Pro Ala Asp
4435                4440                4445 gac gtc ccg gga gaa tca gcc gcc gac gag gat gcc ggt agt ggc gat   13446
Asp Val Pro Gly Glu Ser Ala Ala Asp Glu Asp Ala Gly Ser Gly Asp
        4450                4455                4460 gag gct gct gcc ggc agt cca ggg gtg tgg ccg tgg ctg gtg tcg gcc   13494
Glu Ala Ala Ala Gly Ser Pro Gly Val Trp Pro Trp Leu Val Ser Ala
4465                4470                4475                4480 aag tcg cag ccg gcc ctg cgc gcc cag gcc cag gcc ctg cac gcc cac   13542
Lys Ser Gln Pro Ala Leu Arg Ala Gln Ala Gln Ala Leu His Ala His
        4485                4490                4495 ctc acc gac cac ccc ggc ctc gac ctc gcc gac gtc ggg tac acc ctc   13590
Leu Thr Asp His Pro Gly Leu Asp Leu Ala Asp Val Gly Tyr Thr Leu
    4500                4505                4510 gcc cac gcc cgc gcc gtg ttc gac cac cgc gcc acc ctc atc gcc gcc   13638
Ala His Ala Arg Ala Val Phe Asp His Arg Ala Thr Leu Ile Ala Ala
        4515                4520                4525 gac cgc gac acc ttc ctg caa gca ctc cag gca ctc gcc gca ggc gaa   13686
Asp Arg Asp Thr Phe Leu Gln Ala Leu Gln Ala Leu Ala Ala Gly Glu
4530                4535                4540 ccc cac ccc gcc gtc atc cac agc agc gcc cca ggc ggg acc ggg acc   13734
Pro His Pro Ala Val Ile His Ser Ser Ala Pro Gly Gly Thr Gly Thr
4545                4550                4555                4560 ggg gag gcc gca gga aag acc gca ttc atc tgc tcc gga cag ggc acc   13782
Gly Glu Ala Ala Gly Lys Thr Ala Phe Ile Cys Ser Gly Gln Gly Thr
        4565                4570                4575 caa cgc ccc ggc atg gcc cac ggc ctc tac cac acc cac ccc gtc ttc   13830
Gln Arg Pro Gly Met Ala His Gly Leu Tyr His Thr His Pro Val Phe
    4580                4585                4590
```

```
gcc gcc gca ctc aac gac atc tgc acc cac ctc gac ccc cac ctc gac    13878
Ala Ala Ala Leu Asn Asp Ile Cys Thr His Leu Asp Pro His Leu Asp
        4595                4600                4605 cac ccc ctc ctc ccc ctc ctc acc cag gac ccc aac acc cag gac acc    13926
His Pro Leu Leu Pro Leu Leu Thr Gln Asp Pro Asn Thr Gln Asp Thr
    4610                4615                4620 acc acc ctc gaa gaa gcg gcc gca ctg ctc cag cag acc cgc tac gcc    13974
Thr Thr Leu Glu Glu Ala Ala Ala Leu Leu Gln Gln Thr Arg Tyr Ala
4625                4630                4635                4640 cag ccc gcc ctc ttc gcc ttc cag gtc gcc ctc cac cgc ctc ctc acc    14022
Gln Pro Ala Leu Phe Ala Phe Gln Val Ala Leu His Arg Leu Leu Thr
                4645                4650                4655 gac ggc tac cac atc acc ccc cac tac tac gcc gga cac tcc ctc ggc    14070
Asp Gly Tyr His Ile Thr Pro His Tyr Tyr Ala Gly His Ser Leu Gly
            4660                4665                4670 gaa atc acc gcc gcc cac ctc gcc ggc atc ctc acc ctc acc gac gcc    14118
Glu Ile Thr Ala Ala His Leu Ala Gly Ile Leu Thr Leu Thr Asp Ala
        4675                4680                4685 acc acc ctc atc acc caa cgc gcc acc ctc atg caa acc atg ccc ccc    14166
Thr Thr Leu Ile Thr Gln Arg Ala Thr Leu Met Gln Thr Met Pro Pro
    4690                4695                4700 ggc acc atg acc acc ctc cac acc acc ccc cac cac atc acc cac cac    14214
Gly Thr Met Thr Thr Leu His Thr Thr Pro His His Ile Thr His His
4705                4710                4715                4720 ctc acc gcc cac gaa aac gac ctc gcc atc gcc gcc atc aac acc ccc    14262
Leu Thr Ala His Glu Asn Asp Leu Ala Ile Ala Ala Ile Asn Thr Pro
                4725                4730                4735 acc tcc ctc gtc atc agc ggc acc ccc cac acc gtc caa cac atc acc    14310
Thr Ser Leu Val Ile Ser Gly Thr Pro His Thr Val Gln His Ile Thr
            4740                4745                4750 acc ctc tgc caa caa caa ggc atc aaa acc aaa acc ctc ccc acc aac    14358
Thr Leu Cys Gln Gln Gln Gly Ile Lys Thr Lys Thr Leu Pro Thr Asn
        4755                4760                4765 cac gcc ttc cac tcc ccc cac acc aac ccc atc ctc aac caa ctc cac    14406
His Ala Phe His Ser Pro His Thr Asn Pro Ile Leu Asn Gln Leu His
    4770                4775                4780 cag cac acc caa acc ctc acc tac cac cca ccc cac acc ccc ctc atc    14454
Gln His Thr Gln Thr Leu Thr Tyr His Pro Pro His Thr Pro Leu Ile
4785                4790                4795                4800 acc gcc aac acc cca ccc gac caa ctc ctc acc ccc cac tac tgg acc    14502
Thr Ala Asn Thr Pro Pro Asp Gln Leu Leu Thr Pro His Tyr Trp Thr
                4805                4810                4815 caa caa gcc cgc aac acc gtc gac tac gcc acc acc acc caa acc ctc    14550
Gln Gln Ala Arg Asn Thr Val Asp Tyr Ala Thr Thr Thr Gln Thr Leu
            4820                4825                4830 cac caa cac ggc gtc acc acc tac atc gaa ctc gga ccc gac aac acc    14598
His Gln His Gly Val Thr Thr Tyr Ile Glu Leu Gly Pro Asp Asn Thr
        4835                4840                4845 ctc acc acc ctc acc cac gac aac ctc ccc aac acc ccc acc acc acc    14646
Leu Thr Thr Leu Thr His Asp Asn Leu Pro Asn Thr Pro Thr Thr Thr
    4850                4855                4860 ctc acc ctc acc cac ccc cac cac cac ccc caa acc cac ctc ctc acc    14694
Leu Thr Leu Thr His Pro His His His Pro Gln Thr His Leu Leu Thr
4865                4870                4875                4880 aac ctc gcc aaa acc acc acc acc tgg cac ccc cac cac tac acc cac    14742
Asn Leu Ala Lys Thr Thr Thr Thr Trp His Pro His His Tyr Thr His
                4885                4890                4895 cac cac aac caa ccc cac acc cac acc cac ctc gac ctc ccc acc tac    14790
His His Asn Gln Pro His Thr His Thr His Leu Asp Leu Pro Thr Tyr
            4900                4905                4910
```

| | |
|---|---|
| ccc ttc caa cac cac cac tac tgg ctc caa cca ccc ggc aag ccg agc<br>Pro Phe Gln His His His Tyr Trp Leu Gln Pro Pro Gly Lys Pro Ser<br>         4915                      4920                      4925 | 14838 |
| gac ccg tca ccg agc gaa ggc cgt gag caa gcc acg acc cca tca acc<br>Asp Pro Ser Pro Ser Glu Gly Arg Glu Gln Ala Thr Thr Pro Ser Thr<br>         4930                      4935                      4940 | 14886 |
| ccg ctg cgt gat gtc ctc gtg ggc aag tct ccg cag gag cga gac gaa<br>Pro Leu Arg Asp Val Leu Val Gly Lys Ser Pro Gln Glu Arg Asp Glu<br>4945                      4950                      4955                      4960 | 14934 |
| gag ctg ttg cgc ctg gtg cgc acc cat gcg gcc gct gtg ctg ggc cat<br>Glu Leu Leu Arg Leu Val Arg Thr His Ala Ala Ala Val Leu Gly His<br>                      4965                      4970                      4975 | 14982 |
| gcc act ccc gaa gtg atc gtt ccg aac aag gcc ttc aaa gag ctg ggt<br>Ala Thr Pro Glu Val Ile Val Pro Asn Lys Ala Phe Lys Glu Leu Gly<br>         4980                      4985                      4990 | 15030 |
| ttt gat tct ctc gcc gca att cag ctt cgt aat cga ctg ctt gct gac<br>Phe Asp Ser Leu Ala Ala Ile Gln Leu Arg Asn Arg Leu Leu Ala Asp<br>                      4995                      5000                      5005 | 15078 |
| gtt gac ctg ccg ctt ccg gcc acg ctg atc ttc gat tac ccc act ccg<br>Val Asp Leu Pro Leu Pro Ala Thr Leu Ile Phe Asp Tyr Pro Thr Pro<br>5010                      5015                      5020 | 15126 |
| atg gcg ctt tgc cag ttc ctc cgg gcg gcg atc gtc gga gcg gac aca<br>Met Ala Leu Cys Gln Phe Leu Arg Ala Ala Ile Val Gly Ala Asp Thr<br>5025                      5030                      5035                      5040 | 15174 |
| ggc acg acc act cgt ctg ccg cta act gcg gtc ccc gcc gac gag ccg<br>Gly Thr Thr Thr Arg Leu Pro Leu Thr Ala Val Pro Ala Asp Glu Pro<br>                      5045                      5050                      5055 | 15222 |
| atc gcc atc gtc ggc atg gcc tgt cgg tac ccc ggt gat gta cgg acg<br>Ile Ala Ile Val Gly Met Ala Cys Arg Tyr Pro Gly Asp Val Arg Thr<br>         5060                      5065                      5070 | 15270 |
| gtc gat gat ctc tgg cag gtg gtc agt ggt ggc cat gac gcg atc ggc<br>Val Asp Asp Leu Trp Gln Val Val Ser Gly Gly His Asp Ala Ile Gly<br>                      5075                      5080                      5085 | 15318 |
| gga ttc ccg acg aac cgt ggg tgg gac ctc gac acg ctg tac aac ccg<br>Gly Phe Pro Thr Asn Arg Gly Trp Asp Leu Asp Thr Leu Tyr Asn Pro<br>         5090                      5095                      5100 | 15366 |
| gac ccg gac cac cac gga acc agc tac acc cgg agc ggc gga ttc ctt<br>Asp Pro Asp His His Gly Thr Ser Tyr Thr Arg Ser Gly Gly Phe Leu<br>5105                      5110                      5115                      5120 | 15414 |
| tac gac gca ggc aat ttc gat ccc gac ttc ttc ggt atc agt ccg cgt<br>Tyr Asp Ala Gly Asn Phe Asp Pro Asp Phe Phe Gly Ile Ser Pro Arg<br>                      5125                      5130                      5135 | 15462 |
| gag gca ctg gcg atg gac ccg cag cag cgg ctg ctg ctg gaa aca gcg<br>Glu Ala Leu Ala Met Asp Pro Gln Gln Arg Leu Leu Leu Glu Thr Ala<br>         5140                      5145                      5150 | 15510 |
| tgg gag agc atc gaa cac gcc tgc atc aac ccc gac agc ctc cgt ggc<br>Trp Glu Ser Ile Glu His Ala Cys Ile Asn Pro Asp Ser Leu Arg Gly<br>                      5155                      5160                      5165 | 15558 |
| aca cca acc ggc gtc ttc gcc ggg ctg acc tac cac gac tac gcc gcg<br>Thr Pro Thr Gly Val Phe Ala Gly Leu Thr Tyr His Asp Tyr Ala Ala<br>5170                      5175                      5180 | 15606 |
| cgc ttt ccc aca gct ccg gca ggg ttc gag ggg tat ctc ggg cac gga<br>Arg Phe Pro Thr Ala Pro Ala Gly Phe Glu Gly Tyr Leu Gly His Gly<br>5185                      5190                      5195                      5200 | 15654 |
| agc gca ggc agt atc gcc tcg ggt cgt gtc gcc tac gct ctc ggc ctg<br>Ser Ala Gly Ser Ile Ala Ser Gly Arg Val Ala Tyr Ala Leu Gly Leu<br>                      5205                      5210                      5215 | 15702 |
| gaa ggt ccg gcc ctc aca gtc gac act gcc tgc tct tcg tcc ctg gtc<br>Glu Gly Pro Ala Leu Thr Val Asp Thr Ala Cys Ser Ser Ser Leu Val | 15750 |

-continued

|  |  |  |  |
|---|---|---|---|
| 5220 | 5225 | 5230 | |
| gct ctg cac ctg gcc tgt cag gcg ctg cgg tcc ggc gag tgt tcc atg<br>Ala Leu His Leu Ala Cys Gln Ala Leu Arg Ser Gly Glu Cys Ser Met<br>5235                      5240                      5245 | | | 15798 |
| gcc ctc gcg ggt ggc gtc acg gtg atg tca acc ccg gcc ggg ttc gtg<br>Ala Leu Ala Gly Gly Val Thr Val Met Ser Thr Pro Ala Gly Phe Val<br>5250                      5255                      5260 | | | 15846 |
| gag ttt tcg cgg cag cgg ggc ctg gcc gtg gac ggg cgg tgc aag gcg<br>Glu Phe Ser Arg Gln Arg Gly Leu Ala Val Asp Gly Arg Cys Lys Ala<br>5265                      5270                      5275                      5280 | | | 15894 |
| ttc tcg gca gcg gct gac ggc acc ggc tgg ggt gag ggt gtc gga atg<br>Phe Ser Ala Ala Ala Asp Gly Thr Gly Trp Gly Glu Gly Val Gly Met<br>                  5285                      5290                      5295 | | | 15942 |
| ctg ctg gtg gag cgg ctg tcg gac gcg cgg cgg ctc ggt cac cga atc<br>Leu Leu Val Glu Arg Leu Ser Asp Ala Arg Arg Leu Gly His Arg Ile<br>                  5300                      5305                      5310 | | | 15990 |
| ctc gcg gtg gtg cgt ggc agt gcg gtc aat cag gac ggt gcg agc aac<br>Leu Ala Val Val Arg Gly Ser Ala Val Asn Gln Asp Gly Ala Ser Asn<br>                  5315                      5320                      5325 | | | 16038 |
| ggg ctg acg gcg ccc aac ggg ccg tcc cag gag cgt gtc atc cgc ctg<br>Gly Leu Thr Ala Pro Asn Gly Pro Ser Gln Glu Arg Val Ile Arg Leu<br>5330                      5335                      5340 | | | 16086 |
| gcc ctg gcc aac gcg gac ctg acc ccc gcc gac gtc gat gcg gtg gag<br>Ala Leu Ala Asn Ala Asp Leu Thr Pro Ala Asp Val Asp Ala Val Glu<br>5345                      5350                      5355                      5360 | | | 16134 |
| gcc cac ggc acc ggc acc act ttg ggc gac ccg atc gag gcc cag gcc<br>Ala His Gly Thr Gly Thr Thr Leu Gly Asp Pro Ile Glu Ala Gln Ala<br>                  5365                      5370                      5375 | | | 16182 |
| ctc ctc gcc acc tac gga cag gac cgc ccc ggc aac gaa ccg ctg tgg<br>Leu Leu Ala Thr Tyr Gly Gln Asp Arg Pro Gly Asn Glu Pro Leu Trp<br>                  5380                      5385                      5390 | | | 16230 |
| ctg ggc tcg atg aag tcg aac atc ggc cac gcg cag gct gcc gca ggt<br>Leu Gly Ser Met Lys Ser Asn Ile Gly His Ala Gln Ala Ala Ala Gly<br>                  5395                      5400                      5405 | | | 16278 |
| gtg ggc ggg gtc atc aag atg gtg atg gcg ctg cgg aat ggt ctg ctg<br>Val Gly Gly Val Ile Lys Met Val Met Ala Leu Arg Asn Gly Leu Leu<br>                  5410                      5415                      5420 | | | 16326 |
| ccg cgg acg ttg cat gtg gat gag ccg tcg ccg cat gtg gac tgg tcc<br>Pro Arg Thr Leu His Val Asp Glu Pro Ser Pro His Val Asp Trp Ser<br>5425                      5430                      5435                      5440 | | | 16374 |
| gcg ggg gcg gtg cag ctg ctg acg gag acg gtg ccc tgg ccc ggc ggg<br>Ala Gly Ala Val Gln Leu Leu Thr Glu Thr Val Pro Trp Pro Gly Gly<br>                  5445                      5450                      5455 | | | 16422 |
| gag ggg cgg ctg cgg cgg gca gga gtg tca tcg ttc ggc gtc agc ggc<br>Glu Gly Arg Leu Arg Arg Ala Gly Val Ser Ser Phe Gly Val Ser Gly<br>                  5460                      5465                      5470 | | | 16470 |
| acc aac gcc cac gtc atc ctc gaa gaa gca ccc gcc cac aac atc ccg<br>Thr Asn Ala His Val Ile Leu Glu Glu Ala Pro Ala His Asn Ile Pro<br>                  5475                      5480                      5485 | | | 16518 |
| tca gac aca ccc gcc gac gac gcc ccg gga gaa gca gcc gcc gac gat<br>Ser Asp Thr Pro Ala Asp Asp Ala Pro Gly Glu Ala Ala Ala Asp Asp<br>5490                      5495                      5500 | | | 16566 |
| gtt ccg ggg gaa gcg gcc ggc gac gac gcc ggt acc ggc ggg gaa gcg<br>Val Pro Gly Glu Ala Ala Gly Asp Asp Ala Gly Thr Gly Gly Glu Ala<br>5505                      5510                      5515                      5520 | | | 16614 |
| act ggt cct gct gcc ggc agt cca ggg gtg tgg ccg tgg ctg gtg tcg<br>Thr Gly Pro Ala Ala Gly Ser Pro Gly Val Trp Pro Trp Leu Val Ser<br>                  5525                      5530                      5535 | | | 16662 |
| gcc aag tcg cag ccg gcc ctg cgc gcc cag gcc cag gcc ctg cac gcc | | | 16710 |

```
Ala Lys Ser Gln Pro Ala Leu Arg Ala Gln Ala Gln Ala Leu His Ala
        5540                5545                5550 cac ctc acc gac cac ccc ggc ctc gac ctc gcc gac gtc ggg tac acc    16758
His Leu Thr Asp His Pro Gly Leu Asp Leu Ala Asp Val Gly Tyr Thr
        5555                5560                5565 ctc gcc cac gcc cgc gcc gtg ttc gac cac cgc gcc acc ctc atc gcc    16806
Leu Ala His Ala Arg Ala Val Phe Asp His Arg Ala Thr Leu Ile Ala
    5570                5575                5580 gcc gac cgc gac acc ttc ctg caa gca ctc cag gca ctc gcc gca ggc    16854
Ala Asp Arg Asp Thr Phe Leu Gln Ala Leu Gln Ala Leu Ala Ala Gly
5585                5590                5595                5600 gaa ccc cac ccc gcc gtc atc cac agc agc gcc cca ggc ggg acc ggg    16902
Glu Pro His Pro Ala Val Ile His Ser Ser Ala Pro Gly Gly Thr Gly
            5605                5610                5615 acc ggg gag gcc gca gga aag acc gca ttc atc tgc tcc gga cag ggc    16950
Thr Gly Glu Ala Ala Gly Lys Thr Ala Phe Ile Cys Ser Gly Gln Gly
        5620                5625                5630 acc caa cgc ccc ggc atg gcc cac ggc ctc tac cac acc cac ccc gtc    16998
Thr Gln Arg Pro Gly Met Ala His Gly Leu Tyr His Thr His Pro Val
    5635                5640                5645 ttc gcc gcc gca ctc aac gac atc tgc acc cac ctc gac ccc cac ctc    17046
Phe Ala Ala Ala Leu Asn Asp Ile Cys Thr His Leu Asp Pro His Leu
5650                5655                5660 gac cac ccc ctc ctc ccc ctc ctc acc cag gac ccc aac acc cag gac    17094
Asp His Pro Leu Leu Pro Leu Leu Thr Gln Asp Pro Asn Thr Gln Asp
5665                5670                5675                5680 acc acc acc ctc gaa gaa gcg gcc gca ctg ctc cag cag acc ccg tac    17142
Thr Thr Thr Leu Glu Glu Ala Ala Ala Leu Leu Gln Gln Thr Pro Tyr
            5685                5690                5695 gcc cag ccc gcc ctc ttc gcc ttc cag gtc gcc ctc cac cgc ctc ctc    17190
Ala Gln Pro Ala Leu Phe Ala Phe Gln Val Ala Leu His Arg Leu Leu
        5700                5705                5710 acc gac ggc tac cac atc acc ccc cac tac tac gcc gga cac tcc ctc    17238
Thr Asp Gly Tyr His Ile Thr Pro His Tyr Tyr Ala Gly His Ser Leu
    5715                5720                5725 ggc gaa atc acc gcc gcc cac ctc gcc ggc atc ctc acc ctc acc gac    17286
Gly Glu Ile Thr Ala Ala His Leu Ala Gly Ile Leu Thr Leu Thr Asp
5730                5735                5740 gcc acc acc ctc atc acc caa cgc gcc acc ctc atg caa acc atg ccc    17334
Ala Thr Thr Leu Ile Thr Gln Arg Ala Thr Leu Met Gln Thr Met Pro
5745                5750                5755                5760 ccc ggc acc atg acc acc ctc cac acc acc ccc cac cac atc acc cac    17382
Pro Gly Thr Met Thr Thr Leu His Thr Thr Pro His His Ile Thr His
            5765                5770                5775 cac ctc acc gcc cac gaa aac gac ctc gcc atc gcc gcc atc aac acc    17430
His Leu Thr Ala His Glu Asn Asp Leu Ala Ile Ala Ala Ile Asn Thr
        5780                5785                5790 ccc acc tcc ctc gtc atc agc ggc acc ccc cac acc gtc caa cac atc    17478
Pro Thr Ser Leu Val Ile Ser Gly Thr Pro His Thr Val Gln His Ile
    5795                5800                5805 acc acc ctc tgc caa caa caa ggc atc aaa acc aaa acc ctc ccc acc    17526
Thr Thr Leu Cys Gln Gln Gln Gly Ile Lys Thr Lys Thr Leu Pro Thr
5810                5815                5820 aaa aac gcc ttc cac tcc ccc cac acc aac ccc atc ctc aac caa ctc    17574
Lys Asn Ala Phe His Ser Pro His Thr Asn Pro Ile Leu Asn Gln Leu
5825                5830                5835                5840 cac cag cac acc caa acc ctc acc tac cac cca ccc cac acc ccc ctc    17622
His Gln His Thr Gln Thr Leu Thr Tyr His Pro Pro His Thr Pro Leu
            5845                5850                5855
```

```
atc acc gcc aac acc cca ccc gac caa ctc ctc acc ccc cac tac tgg      17670
Ile Thr Ala Asn Thr Pro Pro Asp Gln Leu Leu Thr Pro His Tyr Trp
            5860                5865                5870 acc caa caa gcc cgc aac acc gtc gac tac gcc acc acc caa acc          17718
Thr Gln Gln Ala Arg Asn Thr Val Asp Tyr Ala Thr Thr Gln Thr
        5875                5880                5885 ctc cac caa cac ggc gtc acc acc tac atc gaa ctc gga ccc gac aac      17766
Leu His Gln His Gly Val Thr Thr Tyr Ile Glu Leu Gly Pro Asp Asn
            5890                5895                5900 acc ctc acc acc ctc acc cac cac aac ctc ccc aac acc ccc acc acc      17814
Thr Leu Thr Thr Leu Thr His His Asn Leu Pro Asn Thr Pro Thr Thr
5905                5910                5915                5920 acc ctc acc ctc acc cac ccc cac cac ccc caa acc cac ctc ctc          17862
Thr Leu Thr Leu Thr His Pro His His Pro Gln Thr His Leu Leu
        5925                5930                5935 acc aac ctc gcc aaa acc acc acc acc tgg cac ccc cac cac tac acc      17910
Thr Asn Leu Ala Lys Thr Thr Thr Thr Trp His Pro His His Tyr Thr
            5940                5945                5950 cac cac cac aac caa ccc cac acc cac acc cac ctc gac ctc ccc acc      17958
His His His Asn Gln Pro His Thr His Thr His Leu Asp Leu Pro Thr
            5955                5960                5965 tac ccc ttc caa cac cag cac tac tgg ctc gaa agc aca cag ccg ggt      18006
Tyr Pro Phe Gln His Gln His Tyr Trp Leu Glu Ser Thr Gln Pro Gly
            5970                5975                5980 gcc gga tcc ggt tcg ggt tcc ggt tcc ggg cgg gca ggg act gcg ggc      18054
Ala Gly Ser Gly Ser Gly Ser Gly Ser Gly Arg Ala Gly Thr Ala Gly
5985                5990                5995                6000 ggg acg gca gag gtg gag tcg cgg ttc tgg gac gcg gtg gcc cgc cag      18102
Gly Thr Ala Glu Val Glu Ser Arg Phe Trp Asp Ala Val Ala Arg Gln
            6005                6010                6015 gac ctg gaa acg gtc gcg acc acg ctc gcc gtg ccc ccc tcc gcc ggc      18150
Asp Leu Glu Thr Val Ala Thr Thr Leu Ala Val Pro Pro Ser Ala Gly
            6020                6025                6030 ctg gac acg gtg gtg ccc gca ctc tcc gcc tgg cac cgc cac caa cac      18198
Leu Asp Thr Val Val Pro Ala Leu Ser Ala Trp His Arg His Gln His
6035                6040                6045 gac caa gcc cgc atc aac acc tgg acc tac cag gaa acc tgg aaa ccc      18246
Asp Gln Ala Arg Ile Asn Thr Trp Thr Tyr Gln Glu Thr Trp Lys Pro
        6050                6055                6060 ctc acc ctc ccc acc acc cac caa ccc cac caa acc tgg ctc atc gcc      18294
Leu Thr Leu Pro Thr Thr His Gln Pro His Gln Thr Trp Leu Ile Ala
6065                6070                6075                6080 atc ccc gaa acc cag acc cac cac ccc cac atc acc aac atc ctc acc      18342
Ile Pro Glu Thr Gln Thr His His Pro His Ile Thr Asn Ile Leu Thr
            6085                6090                6095 aac ctc cac cac cac ggc atc acc ccc atc ccc ctc acc ctc aac cac      18390
Asn Leu His His His Gly Ile Thr Pro Ile Pro Leu Thr Leu Asn His
            6100                6105                6110 acc cac acc aac ccc caa cac ctc cac cac acc cga caa caa gcc caa      18438
Thr His Thr Asn Pro Gln His Leu His His Thr Arg Gln Gln Ala Gln
        6115                6120                6125 aac cac acc acc gga ccc atc acc ggc ctg ctc tcc ctc ctc gcc ctc      18486
Asn His Thr Thr Gly Pro Ile Thr Gly Leu Leu Ser Leu Leu Ala Leu
            6130                6135                6140 gac gaa aca ccc cac ccc cac cac ccc cac aca ccc acc ggc acc ctc      18534
Asp Glu Thr Pro His Pro His His Pro His Thr Pro Thr Gly Thr Leu
6145                6150                6155                6160 ctc aac ctc acc ctc acc caa acc cac acc caa acc cac cca cca acc      18582
Leu Asn Leu Thr Leu Thr Gln Thr His Thr Gln Thr His Pro Pro Thr
        6165                6170                6175
```

```
ccc ctc tgg tac gcc acc acc aac gcc acc acc acc cac ccc aac gac    18630
Pro Leu Trp Tyr Ala Thr Thr Asn Ala Thr Thr Thr His Pro Asn Asp
            6180            6185            6190 ccc ctc aca cac ccc acc caa gcc caa acc tgg gga ctc gcc cgc acc    18678
Pro Leu Thr His Pro Thr Gln Ala Gln Thr Trp Gly Leu Ala Arg Thr
            6195            6200            6205 acc ctc ctc gaa cac ccc acc cac acc gcc gga atc atc gac ctc ccc    18726
Thr Leu Leu Glu His Pro Thr His Thr Ala Gly Ile Ile Asp Leu Pro
        6210            6215            6220 acc acc ccc acc ccc cac acc ctc cac cac ctc acc caa acc ctc acc    18774
Thr Thr Pro Thr Pro His Thr Leu His His Leu Thr Gln Thr Leu Thr
6225            6230            6235            6240 caa ccc cac cac caa acc caa ctc gcc atc cgc acc acc ggc acc cac    18822
Gln Pro His His Gln Thr Gln Leu Ala Ile Arg Thr Thr Gly Thr His
            6245            6250            6255 acc cgc cgc ctc acc ccc acc acc ctc acc ccc aca cac caa cca ccc    18870
Thr Arg Arg Leu Thr Pro Thr Thr Leu Thr Pro Thr His Gln Pro Pro
            6260            6265            6270 acc ccc acc ccc cac gga acc acc ctc atc acc ggc gga acc ggc gcc    18918
Thr Pro Thr Pro His Gly Thr Thr Leu Ile Thr Gly Gly Thr Gly Ala
            6275            6280            6285 ctc gcc acc cac ctc acc cac cac ctc acc acc cac caa ccc acc caa    18966
Leu Ala Thr His Leu Thr His His Leu Thr Thr His Gln Pro Thr Gln
            6290            6295            6300 cac ctc ctc ctc acc agc cga acc ggc ccc cac acc ccc cac gca caa    19014
His Leu Leu Leu Thr Ser Arg Thr Gly Pro His Thr Pro His Ala Gln
6305            6310            6315            6320 cac ctc acc acc caa ctc caa caa aaa ggc atc cac ctc acc atc acc    19062
His Leu Thr Thr Gln Leu Gln Gln Lys Gly Ile His Leu Thr Ile Thr
            6325            6330            6335 acc tgc gac acc agc aac cca gac caa ctc caa caa ctc ctc aac acc    19110
Thr Cys Asp Thr Ser Asn Pro Asp Gln Leu Gln Gln Leu Leu Asn Thr
            6340            6345            6350 atc ccc cca caa cac ccc ctc acc acc gtc atc cac acc gca ggc atc    19158
Ile Pro Pro Gln His Pro Leu Thr Thr Val Ile His Thr Ala Gly Ile
            6355            6360            6365 ctc gac gac gcc acc ctc acc aac ctc acc ccc acc caa ctc aac aac    19206
Leu Asp Asp Ala Thr Leu Thr Asn Leu Thr Pro Thr Gln Leu Asn Asn
        6370            6375            6380 gtc ctc cgc gcc aaa gcc cac agc gcc cac ctc ctc cac caa ctc acc    19254
Val Leu Arg Ala Lys Ala His Ser Ala His Leu Leu His Gln Leu Thr
6385            6390            6395            6400 caa cac acc ccc ctc aac gcc ttc gtc ctc tac tcc tcc gcc gcc gcc    19302
Gln His Thr Pro Leu Asn Ala Phe Val Leu Tyr Ser Ser Ala Ala Ala
            6405            6410            6415 acc ttc ggc gca ccc ggc caa gcc aac tac gcc gca gcc aac gcc tac    19350
Thr Phe Gly Ala Pro Gly Gln Ala Asn Tyr Ala Ala Ala Asn Ala Tyr
            6420            6425            6430 ctc gac gcc ctc gcc cac cac cgc cac acc cac cac ctc ccc gcc acc    19398
Leu Asp Ala Leu Ala His His Arg His Thr His His Leu Pro Ala Thr
            6435            6440            6445 agc atc gcc tgg ggc acc tgg caa gga aac gga ctg gcg act ggt caa    19446
Ser Ile Ala Trp Gly Thr Trp Gln Gly Asn Gly Leu Ala Thr Gly Gln
            6450            6455            6460 gtc agc gaa cat ctc cgc cgc cgc ggg atg ttc gcc atg ccg ccc gag    19494
Val Ser Glu His Leu Arg Arg Arg Gly Met Phe Ala Met Pro Pro Glu
6465            6470            6475            6480 ttg gcg gtc aca gct gtt gac ggc gcg atc gcg agc ggg cgc ccg agt    19542
Leu Ala Val Thr Ala Val Asp Gly Ala Ile Ala Ser Gly Arg Pro Ser
```

```
                    6485                6490                6495
ctc ctc gtc gcc gat atc gac tgg aag aaa ttg gga ccg gtt ctc tcc       19590
Leu Leu Val Ala Asp Ile Asp Trp Lys Lys Leu Gly Pro Val Leu Ser
                    6500                6505                6510 agc aag tcg tcg gtc ttg ctc gag gac ctt ccc cag gca cag gga act       19638
Ser Lys Ser Ser Val Leu Leu Glu Asp Leu Pro Gln Ala Gln Gly Thr
                    6515                6520                6525 gag gag gcg cgc agt acc gtt gag cag acg gag agc aca aac ctc cgg       19686
Glu Glu Ala Arg Ser Thr Val Glu Gln Thr Glu Ser Thr Asn Leu Arg
                    6530                6535                6540 caa ctc ctc atg ggt cgg tca cgt tcc gag cag gaa gaa gag ctg ctc       19734
Gln Leu Leu Met Gly Arg Ser Arg Ser Glu Gln Glu Glu Glu Leu Leu
6545                6550                6555                6560 agc ctc gtc cgc atc cac tcc gcg gca gtg ctc ggg cgc gac gac tcc       19782
Ser Leu Val Arg Ile His Ser Ala Ala Val Leu Gly Arg Asp Asp Ser
                    6565                6570                6575 gag gcc atc ccg ccc ggt cgg ctg ttc agg gat cta ggg ttc gac tcg       19830
Glu Ala Ile Pro Pro Gly Arg Leu Phe Arg Asp Leu Gly Phe Asp Ser
                    6580                6585                6590 ctt gcg gcg gtg gag ctt cgc aac cac ctc gca gca cag acg gag ctg       19878
Leu Ala Ala Val Glu Leu Arg Asn His Leu Ala Ala Gln Thr Glu Leu
                    6595                6600                6605 gct ctg ccg acg act ctc gtc ttc gat tac ccc agc ccc acc aag ctc       19926
Ala Leu Pro Thr Thr Leu Val Phe Asp Tyr Pro Ser Pro Thr Lys Leu
                    6610                6615                6620 gcc caa ttt ctg ctc tcc gag atc gcg gag ttc cag ccc gac aac tca       19974
Ala Gln Phe Leu Leu Ser Glu Ile Ala Glu Phe Gln Pro Asp Asn Ser
6625                6630                6635                6640 act ccg ctt ccg cga ccc cgg gca gag ctc gat gag ccg atc gcc atc       20022
Thr Pro Leu Pro Arg Pro Arg Ala Glu Leu Asp Glu Pro Ile Ala Ile
                    6645                6650                6655 gtt ggc atg gcc tgt cgc ttc ccc ggc gga gtg acc tcg gcg gac gac       20070
Val Gly Met Ala Cys Arg Phe Pro Gly Gly Val Thr Ser Ala Asp Asp
                    6660                6665                6670 ttc tgg gat ctg atc tcc tcc gag cag gac gcg atc ggc gga ttc ccc       20118
Phe Trp Asp Leu Ile Ser Ser Glu Gln Asp Ala Ile Gly Gly Phe Pro
                    6675                6680                6685 acc gac cgc ggc tgg gac ctg gac acg ctc tac gac ccc gac ccc gac       20166
Thr Asp Arg Gly Trp Asp Leu Asp Thr Leu Tyr Asp Pro Asp Pro Asp
                    6690                6695                6700 cac ccc ggc acc tgc tac acc cga aac ggc gga ttc ctc tac gac gca       20214
His Pro Gly Thr Cys Tyr Thr Arg Asn Gly Gly Phe Leu Tyr Asp Ala
6705                6710                6715                6720 ggc cac ttc gac gcc gaa ttc ttc ggc atc agc ccc cgc gaa gcc ctc       20262
Gly His Phe Asp Ala Glu Phe Phe Gly Ile Ser Pro Arg Glu Ala Leu
                    6725                6730                6735 gcc atg gac ccc cag caa cga ctc ctc ctc gaa acc gcc tgg gaa acc       20310
Ala Met Asp Pro Gln Gln Arg Leu Leu Leu Glu Thr Ala Trp Glu Thr
                    6740                6745                6750 atc gaa cac gcc ggc atc aac ccc cac acc ctc cac ggc acc ccc acc       20358
Ile Glu His Ala Gly Ile Asn Pro His Thr Leu His Gly Thr Pro Thr
                    6755                6760                6765 gga gtc ttc acc ggc acc aac gga cag gac cac gcg gca cac atc cgt       20406
Gly Val Phe Thr Gly Thr Asn Gly Gln Asp His Ala Ala His Ile Arg
                    6770                6775                6780 cag gcc ccg agc ggt acc gag gga ttc gtc ctg acc ggg gca gcc acc       20454
Gln Ala Pro Ser Gly Thr Glu Gly Phe Val Leu Thr Gly Ala Ala Thr
6785                6790                6795                6800 agc atc gcc tcc ggc cga atc tcc tac atc ctc ggg ttg gaa ggg cct       20502
```

-continued

```
                Ser Ile Ala Ser Gly Arg Ile Ser Tyr Ile Leu Gly Leu Glu Gly Pro
                                6805                6810                6815 gcg gtc acc ctc gac aca gcg tgt tcc tcc tcg ctc gtc gcc ctg cac        20550
Ala Val Thr Leu Asp Thr Ala Cys Ser Ser Ser Leu Val Ala Leu His
            6820                6825                6830 ctc gcc tgc cag tcc ctc agg tcc ggt gaa tgc acc atg gcc ttg gcc        20598
Leu Ala Cys Gln Ser Leu Arg Ser Gly Glu Cys Thr Met Ala Leu Ala
            6835                6840                6845 ggc ggg gcc acg gtc atg acc acc ccg atc acc ttc acc gaa ttc gcc        20646
Gly Gly Ala Thr Val Met Thr Thr Pro Ile Thr Phe Thr Glu Phe Ala
            6850                6855                6860 cgc caa cgc gga ctc gcc ccc gac ggg cgt tgc aag gcg ttc tcg gcg        20694
Arg Gln Arg Gly Leu Ala Pro Asp Gly Arg Cys Lys Ala Phe Ser Ala
6865                6870                6875                6880 gcg gct gac ggt acc ggc tgg ggt gag ggt gtg ggg atg ctg ctg gtg        20742
Ala Ala Asp Gly Thr Gly Trp Gly Glu Gly Val Gly Met Leu Leu Val
                6885                6890                6895 gag cgg ctc tcc gac gcc cgc cgc aac ggt cac cgt gtc ctg gcc gtg        20790
Glu Arg Leu Ser Asp Ala Arg Arg Asn Gly His Arg Val Leu Ala Val
            6900                6905                6910 gtg cgt ggc agt gcg gtc aac cag gac ggt gcg agc aac ggt ctg acc        20838
Val Arg Gly Ser Ala Val Asn Gln Asp Gly Ala Ser Asn Gly Leu Thr
            6915                6920                6925 gcg ccc aac ggg ccc tcc cag cag cgc gtc atc cgc cag gcc ctc gcc        20886
Ala Pro Asn Gly Pro Ser Gln Gln Arg Val Ile Arg Gln Ala Leu Ala
            6930                6935                6940 aac gcg gac ctg acc ccc gcc gac gtc gat gcg gtg gag gcc cac ggc        20934
Asn Ala Asp Leu Thr Pro Ala Asp Val Asp Ala Val Glu Ala His Gly
6945                6950                6955                6960 acc ggc acc act ttg ggc gac ccg atc gag gcc cag gcc atc ctc gcg        20982
Thr Gly Thr Thr Leu Gly Asp Pro Ile Glu Ala Gln Ala Ile Leu Ala
                6965                6970                6975 acc tac gga cag gac cgt ccc ggc aac ggg ccg ttg tgg ctg ggc tcc        21030
Thr Tyr Gly Gln Asp Arg Pro Gly Asn Gly Pro Leu Trp Leu Gly Ser
            6980                6985                6990 gtc aag tcc aac gtc gga cac aca cag gcc gcg gcg ggc gtg gcc gga        21078
Val Lys Ser Asn Val Gly His Thr Gln Ala Ala Ala Gly Val Ala Gly
            6995                7000                7005 gtg atc aag atg gtg atg gcc ctc cgc cac cgg aca ctc cca ccg act        21126
Val Ile Lys Met Val Met Ala Leu Arg His Arg Thr Leu Pro Pro Thr
            7010                7015                7020 ctc cac gcg gat gag ccg tcg ccg cat gtg gac tgg tcc gcg ggt gcg        21174
Leu His Ala Asp Glu Pro Ser Pro His Val Asp Trp Ser Ala Gly Ala
7025                7030                7035                7040 gtg cag ctg ctg acg gag acg gtg ccc tgg ccc ggc ggg gag ggg cgg        21222
Val Gln Leu Leu Thr Glu Thr Val Pro Trp Pro Gly Gly Glu Gly Arg
                7045                7050                7055 ccg cgg cgg gca gga gtg tca tca ttc ggc gtc agc ggc acc aac gcc        21270
Pro Arg Arg Ala Gly Val Ser Ser Phe Gly Val Ser Gly Thr Asn Ala
            7060                7065                7070 cac gtc atc ctc gaa gaa gca ccc gcc gac gac gtt ccg ggg gga cca        21318
His Val Ile Leu Glu Glu Ala Pro Ala Asp Asp Val Pro Gly Gly Pro
            7075                7080                7085 ccc gcc gac gag gat gcc ggt agt ggc gag gag gct gct gcc ggc agt        21366
Pro Ala Asp Glu Asp Ala Gly Ser Gly Glu Glu Ala Ala Ala Gly Ser
            7090                7095                7100 cct ggg gtg tgg ccg tgg ctg gtg tcg gcc aag tcg cag ccg gcc ctg        21414
Pro Gly Val Trp Pro Trp Leu Val Ser Ala Lys Ser Gln Pro Ala Leu
7105                7110                7115                7120
```

```
cgc gcc cag gcc cag gcc ctg cac gcc cac ctc acc gac cac ccc ggc      21462
Arg Ala Gln Ala Gln Ala Leu His Ala His Leu Thr Asp His Pro Gly
             7125                7130                7135 ctc gac ctc gcc gac gtc gga tac acc ctc gcc cac gcc cgc gcc gtg      21510
Leu Asp Leu Ala Asp Val Gly Tyr Thr Leu Ala His Ala Arg Ala Val
         7140                7145                7150 ttc gac cac cgc gcc acc ctc atc gcc gcc gac cgc gac acc ttc ctg      21558
Phe Asp His Arg Ala Thr Leu Ile Ala Ala Asp Arg Asp Thr Phe Leu
             7155                7160                7165 caa gca ctc cag gca ctc gcc gca ggc gaa ccc cac ccc gcc gtc atc      21606
Gln Ala Leu Gln Ala Leu Ala Ala Gly Glu Pro His Pro Ala Val Ile
         7170                7175                7180 cac agc agc gcc cca ggc ggg acc ggg acc ggg gag gcc gca gga aag      21654
His Ser Ser Ala Pro Gly Gly Thr Gly Thr Gly Glu Ala Ala Gly Lys
7185                7190                7195                7200 acc gca ttc atc tgc tcc gga cag ggc acc caa cgc ccc ggc atg gcc      21702
Thr Ala Phe Ile Cys Ser Gly Gln Gly Thr Gln Arg Pro Gly Met Ala
             7205                7210                7215 cac ggc ctc tac cac acc cac ccc gtc ttc gcc gcc gca ctc aac gac      21750
His Gly Leu Tyr His Thr His Pro Val Phe Ala Ala Ala Leu Asn Asp
         7220                7225                7230 atc tgc acc cac ctc gac ccc cac ctc gac cac ccc ctc ctc ccc ctc      21798
Ile Cys Thr His Leu Asp Pro His Leu Asp His Pro Leu Leu Pro Leu
             7235                7240                7245 ctc acc caa aac gac aac gac aac gac aac gag gac gcg gcc gca ctg      21846
Leu Thr Gln Asn Asp Asn Asp Asn Asp Asn Glu Asp Ala Ala Ala Leu
         7250                7255                7260 ctc cag cag acc ccg tac gcc cag ccc gcc ctc ttc gcc ttc cag gtc      21894
Leu Gln Gln Thr Pro Tyr Ala Gln Pro Ala Leu Phe Ala Phe Gln Val
7265                7270                7275                7280 gcc ctc cac cgc ctc ctc acc gac ggc tac cac atc acc ccc cac tac      21942
Ala Leu His Arg Leu Leu Thr Asp Gly Tyr His Ile Thr Pro His Tyr
             7285                7290                7295 tac gcc gga cac tcc ctc ggc gaa atc acc gcc gcc cac ctc gcc ggc      21990
Tyr Ala Gly His Ser Leu Gly Glu Ile Thr Ala Ala His Leu Ala Gly
         7300                7305                7310 atc ctc acc ctc acc gac gcc acc acc ctc atc acc caa cgc gcc acc      22038
Ile Leu Thr Leu Thr Asp Ala Thr Thr Leu Ile Thr Gln Arg Ala Thr
             7315                7320                7325 ctc atg caa acc atg ccc ccc ggc acc atg acc acc ctc cac acc acc      22086
Leu Met Gln Thr Met Pro Pro Gly Thr Met Thr Thr Leu His Thr Thr
         7330                7335                7340 cca cac cac atc acc cac cac ctc acc gcc cac gaa aac gac ctc gcc      22134
Pro His His Ile Thr His His Leu Thr Ala His Glu Asn Asp Leu Ala
7345                7350                7355                7360 atc gcc gcc atc aac acc ccc acc tcc ctc gtc atc agc ggc acc ccc      22182
Ile Ala Ala Ile Asn Thr Pro Thr Ser Leu Val Ile Ser Gly Thr Pro
             7365                7370                7375 cac acc gtc caa cac atc acc acc ctc tgc caa caa caa ggc atc aaa      22230
His Thr Val Gln His Ile Thr Thr Leu Cys Gln Gln Gln Gly Ile Lys
         7380                7385                7390 acc aaa acc ctc ccc acc aac cac gcc ttc cac tcc ccc cac acc aac      22278
Thr Lys Thr Leu Pro Thr Asn His Ala Phe His Ser Pro His Thr Asn
             7395                7400                7405 ccc atc ctc aac caa ctc cac cag cac acc caa acc ctc acc tac cac      22326
Pro Ile Leu Asn Gln Leu His Gln His Thr Gln Thr Leu Thr Tyr His
         7410                7415                7420 cca ccc cac acc ccc ctc atc acc gcc aac acc cca ccc gac caa ctc      22374
Pro Pro His Thr Pro Leu Ile Thr Ala Asn Thr Pro Pro Asp Gln Leu
7425                7430                7435                7440
```

```
ctc acc ccc cac tac tgg acc caa caa gcc cgc aac acc gtc gac tac      22422
Leu Thr Pro His Tyr Trp Thr Gln Gln Ala Arg Asn Thr Val Asp Tyr
                7445              7450              7455 gcc acc acc acc caa acc ctc cac caa cac ggc gtc acc acc tac atc      22470
Ala Thr Thr Thr Gln Thr Leu His Gln His Gly Val Thr Thr Tyr Ile
        7460              7465              7470 gaa ctc gga ccc gac aac acc ctc acc acc ctc acc cac cac aac ctc      22518
Glu Leu Gly Pro Asp Asn Thr Leu Thr Thr Leu Thr His His Asn Leu
            7475              7480              7485 ccc aac acc ccc acc acc acc ctc acc ctc acc cac ccc cac cac cac      22566
Pro Asn Thr Pro Thr Thr Thr Leu Thr Leu Thr His Pro His His His
        7490              7495              7500 ccc caa acc cac ctc ctc acc aac ctc gcc aaa acc acc acc acc tgg      22614
Pro Gln Thr His Leu Leu Thr Asn Leu Ala Lys Thr Thr Thr Thr Trp
7505              7510              7515              7520 cac ccc cac cac tac acc cac cac cac aac caa ccc cac acc cac acc      22662
His Pro His His Tyr Thr His His His Asn Gln Pro His Thr His Thr
                7525              7530              7535 cac ctc gac ctc ccc acc tac ccc ttc caa cac cac cac tac tgg ctc      22710
His Leu Asp Leu Pro Thr Tyr Pro Phe Gln His His His Tyr Trp Leu
            7540              7545              7550 gaa cta ccc agc gcc caa acc agc ccc ggt caa agg cgt tct cgc cgc      22758
Glu Leu Pro Ser Ala Gln Thr Ser Pro Gly Gln Arg Arg Ser Arg Arg
        7555              7560              7565 tcg gct cca gac acc gcc gag tcg gag ttc tgg gac gcg gtg aac gag      22806
Ser Ala Pro Asp Thr Ala Glu Ser Glu Phe Trp Asp Ala Val Asn Glu
    7570              7575              7580 gaa gac ctc cag agc ctc gcc gaa acc ctc gac atc gac gcc tct gct      22854
Glu Asp Leu Gln Ser Leu Ala Glu Thr Leu Asp Ile Asp Ala Ser Ala
7585              7590              7595              7600 ctg gac acg gtg gtg ccc gca ctc tcc gcc tgg cac cgc cac caa cac      22902
Leu Asp Thr Val Val Pro Ala Leu Ser Ala Trp His Arg His Gln His
                7605              7610              7615 gac caa gcc cgc atc aac acc tgg acc tac cag gaa acc tgg aaa ccc      22950
Asp Gln Ala Arg Ile Asn Thr Trp Thr Tyr Gln Glu Thr Trp Lys Pro
            7620              7625              7630 ctc acc ctc ccc acc acc cac caa ccc cac caa acc tgg ctc atc gcc      22998
Leu Thr Leu Pro Thr Thr His Gln Pro His Gln Thr Trp Leu Ile Ala
        7635              7640              7645 atc ccc gaa acc cag acc cac cac ccc cac atc acc aac atc ctc acc      23046
Ile Pro Glu Thr Gln Thr His His Pro His Ile Thr Asn Ile Leu Thr
    7650              7655              7660 aac ctc cac cac cac ggc atc acc ccc atc ccc ctc act gtc aac cac      23094
Asn Leu His His His Gly Ile Thr Pro Ile Pro Leu Thr Val Asn His
7665              7670              7675              7680 acc cac acc aac ccc caa cac ctc cac cac acc ctc cac cac acc cga      23142
Thr His Thr Asn Pro Gln His Leu His His Thr Leu His His Thr Arg
                7685              7690              7695 caa caa gcc caa aac cac acc acc gga ccc atc acc ggc ctg ctc tcc      23190
Gln Gln Ala Gln Asn His Thr Thr Gly Pro Ile Thr Gly Leu Leu Ser
            7700              7705              7710 ctc ctc gcc ctc gac gaa aca ccc cac ccc cac cac ccc cac aca ccc      23238
Leu Leu Ala Leu Asp Glu Thr Pro His Pro His His Pro His Thr Pro
        7715              7720              7725 acc ggc acc ctc ctc aac ctc acc ctc ccc caa acc cac acc caa acc      23286
Thr Gly Thr Leu Leu Asn Leu Thr Leu Pro Gln Thr His Thr Gln Thr
    7730              7735              7740 cac cca cca acc ccc ctc tgg tac gcc acc acc aac gcc acc acc acc      23334
His Pro Pro Thr Pro Leu Trp Tyr Ala Thr Thr Asn Ala Thr Thr Thr
```

|  |  |
|---|---|
| cac ccc aac gac ccc ctc aca cac ccc acc caa gcc caa acc tgg gga<br>His Pro Asn Asp Pro Leu Thr His Pro Thr Gln Ala Gln Thr Trp Gly<br>              7765                       7770                    7775 | 23382 |
| ctc gcc cgc acc acc ctc ctc gaa cac ccc acc cac acc gcc gga atc<br>Leu Ala Arg Thr Thr Leu Leu Glu His Pro Thr His Thr Ala Gly Ile<br>              7780                       7785                    7790 | 23430 |
| atc gac ctc ccc acc acc ccc acc ccc cac acc ctc cac cac ctc acc<br>Ile Asp Leu Pro Thr Thr Pro Thr Pro His Thr Leu His His Leu Thr<br>              7795                       7800                    7805 | 23478 |
| caa acc ctc acc caa ccc cac cac caa acc caa ctc gcc atc cgc acc<br>Gln Thr Leu Thr Gln Pro His His Gln Thr Gln Leu Ala Ile Arg Thr<br>              7810                       7815                    7820 | 23526 |
| acc ggc acc cac acc cgc cgc ctc acc ccc acc acc ctc acc ccc aca<br>Thr Gly Thr His Thr Arg Arg Leu Thr Pro Thr Thr Leu Thr Pro Thr<br>7825                       7830                       7835                    7840 | 23574 |
| cac caa cca ccc acc ccc acc ccc cac gga acc acc ctc atc acc ggc<br>His Gln Pro Pro Thr Pro Thr Pro His Gly Thr Thr Leu Ile Thr Gly<br>              7845                       7850                    7855 | 23622 |
| gga acc ggc gcc ctc gcc acc cac ctc acc cac cac ctc acc acc cac<br>Gly Thr Gly Ala Leu Ala Thr His Leu Thr His His Leu Thr Thr His<br>              7860                       7865                    7870 | 23670 |
| caa ccc acc caa cac ctc ctc ctc acc agc cga acc ggc ccc cac acc<br>Gln Pro Thr Gln His Leu Leu Leu Thr Ser Arg Thr Gly Pro His Thr<br>              7875                       7880                    7885 | 23718 |
| ccc cac gca caa cac ctc acc acc caa ctc caa caa aaa ggc atc cac<br>Pro His Ala Gln His Leu Thr Thr Gln Leu Gln Gln Lys Gly Ile His<br>              7890                       7895                    7900 | 23766 |
| ctc acc atc acc acc tgc gac acc agc aac cca gac caa ctc caa caa<br>Leu Thr Ile Thr Thr Cys Asp Thr Ser Asn Pro Asp Gln Leu Gln Gln<br>7905                       7910                       7915                    7920 | 23814 |
| ctc ctc aac acc atc ccc cca caa cac ccc ctc acc acc gtc atc cac<br>Leu Leu Asn Thr Ile Pro Pro Gln His Pro Leu Thr Thr Val Ile His<br>              7925                       7930                    7935 | 23862 |
| acc gca ggc gtc aat ctc ttc gcc ccc gtg tcg gaa acc gat gcc gaa<br>Thr Ala Gly Val Asn Leu Phe Ala Pro Val Ser Glu Thr Asp Ala Glu<br>              7940                       7945                    7950 | 23910 |
| tcc ttc tct tcc gtt acg gca gcg aag gca acg ggc gcg gcg att ctg<br>Ser Phe Ser Ser Val Thr Ala Ala Lys Ala Thr Gly Ala Ala Ile Leu<br>              7955                       7960                    7965 | 23958 |
| cat gag ttg ctg ctg gac cat gaa acg ctt gaa cac ttc att ctc ttc<br>His Glu Leu Leu Leu Asp His Glu Thr Leu Glu His Phe Ile Leu Phe<br>              7970                       7975                    7980 | 24006 |
| tcg tcg ggc gcc ggc gct tgg ggc agc ggg aat cag tgc gca tac tcg<br>Ser Ser Gly Ala Gly Ala Trp Gly Ser Gly Asn Gln Cys Ala Tyr Ser<br>7985                       7990                       7995                    8000 | 24054 |
| gcg gcc aac gca tac ctg gac gcg ctc gcg acg cat cgt cag aca cat<br>Ala Ala Asn Ala Tyr Leu Asp Ala Leu Ala Thr His Arg Gln Thr His<br>              8005                       8010                    8015 | 24102 |
| gga ctt ccc ggg gca tcg atc gcc tgg ggc ccc tgg gcc gga aag ggc<br>Gly Leu Pro Gly Ala Ser Ile Ala Trp Gly Pro Trp Ala Gly Lys Gly<br>              8020                       8025                    8030 | 24150 |
| atg tcg gcc ggt gat gcg gct cat ggt tac ctg gaa aag cgc ggc att<br>Met Ser Ala Gly Asp Ala Ala His Gly Tyr Leu Glu Lys Arg Gly Ile<br>              8035                       8040                    8045 | 24198 |
| ctg ccg atg gag cca cgc atg gcg ctc gcg gca ttc cat cgt gcg cgg<br>Leu Pro Met Glu Pro Arg Met Ala Leu Ala Ala Phe His Arg Ala Arg<br>              8050                       8055                    8060 | 24246 |
| gcg cag cgg ccg aat tcc aac ctg atc atc gcg gac atc gac tgg gag | 24294 |

```
Ala Gln Arg Pro Asn Ser Asn Leu Ile Ile Ala Asp Ile Asp Trp Glu
8065                8070                8075                8080 cgc ttc gtc ccc gcc ttc acc gct cga cgc cac agc ccg ctc atc gag    24342
Arg Phe Val Pro Ala Phe Thr Ala Arg Arg His Ser Pro Leu Ile Glu
            8085                8090                8095 gac att ccg gag gtt cgg caa gcg gct cag gag ctg gaa gca gct gcg    24390
Asp Ile Pro Glu Val Arg Gln Ala Ala Gln Glu Leu Glu Ala Ala Ala
        8100                8105                8110 tcg acg gca aag acg acc aca gct cag ccg att gcg acg tct ctc cgt    24438
Ser Thr Ala Lys Thr Thr Thr Ala Gln Pro Ile Ala Thr Ser Leu Arg
            8115                8120                8125 gag cga ttg gcc cga ctg acg tcc tca aag cag aac cag gtg ctg ctc    24486
Glu Arg Leu Ala Arg Leu Thr Ser Ser Lys Gln Asn Gln Val Leu Leu
        8130                8135                8140 ggc ctg att cgg aca ggc atc tgc acc gtt ctc ggc ctt cgt aat ccg    24534
Gly Leu Ile Arg Thr Gly Ile Cys Thr Val Leu Gly Leu Arg Asn Pro
8145                8150                8155                8160 gaa ggc atc gag gac caa cga gcc ttc cgc gac ctc ggc ttc gac tcg    24582
Glu Gly Ile Glu Asp Gln Arg Ala Phe Arg Asp Leu Gly Phe Asp Ser
            8165                8170                8175 ctg acg tcg gct cag ttc agc aag gaa ctc gcc aag gaa acc gga ctg    24630
Leu Thr Ser Ala Gln Phe Ser Lys Glu Leu Ala Lys Glu Thr Gly Leu
        8180                8185                8190 cca ctc ccc ccg tcc ctg gtc ttc gac tat ccc acc ccg cag gaa tgt    24678
Pro Leu Pro Pro Ser Leu Val Phe Asp Tyr Pro Thr Pro Gln Glu Cys
            8195                8200                8205 gct gcc cat ctg cgc aca caa ctc gtc gac cta gac gac gaa gag gac    24726
Ala Ala His Leu Arg Thr Gln Leu Val Asp Leu Asp Asp Glu Glu Asp
        8210                8215                8220 gcg gca ctg tcg aat gct ctc ccg caa gtg gcc cat cgg cgt acc gtc    24774
Ala Ala Leu Ser Asn Ala Leu Pro Gln Val Ala His Arg Arg Thr Val
8225                8230                8235                8240 gag gac gaa ccg atc gcc atc atc ggt atg gca tgt cgc ttc ccc ggc    24822
Glu Asp Glu Pro Ile Ala Ile Ile Gly Met Ala Cys Arg Phe Pro Gly
            8245                8250                8255 ggc gta cgt tct gcc gac gac ctg tgg gaa ttg ctc gct tcg ggt aag    24870
Gly Val Arg Ser Ala Asp Asp Leu Trp Glu Leu Leu Ala Ser Gly Lys
        8260                8265                8270 gac gct atc ggc gtc ttc ccg acc gac cgc ggc tgg gac ctg gac acg    24918
Asp Ala Ile Gly Val Phe Pro Thr Asp Arg Gly Trp Asp Leu Asp Thr
            8275                8280                8285 ctc tac gac ccc gac ccc gac cac ccc ggc acc tgc tac acc cga aac    24966
Leu Tyr Asp Pro Asp Pro Asp His Pro Gly Thr Cys Tyr Thr Arg Asn
        8290                8295                8300 ggc gga ttc ctc tac ggc gca ggc cac ttc gac gcc gaa ttc ttc ggc    25014
Gly Gly Phe Leu Tyr Gly Ala Gly His Phe Asp Ala Glu Phe Phe Gly
8305                8310                8315                8320 atc agc ccc cgc gaa gcc ctc gcc atg gac ccc cag caa cga ctc ctc    25062
Ile Ser Pro Arg Glu Ala Leu Ala Met Asp Pro Gln Gln Arg Leu Leu
            8325                8330                8335 ctc gaa acc gcc tgg gaa acc atc gaa cac gcc ggc atc aac ccc cac    25110
Leu Glu Thr Ala Trp Glu Thr Ile Glu His Ala Gly Ile Asn Pro His
        8340                8345                8350 acc ctc cac ggc acc ccc acc gga gtc ttc gcc gga atc aac gct caa    25158
Thr Leu His Gly Thr Pro Thr Gly Val Phe Ala Gly Ile Asn Ala Gln
        8355                8360                8365 gac cac gcc gcg cat atc cgc caa agc cgt gat gtg gag acc atc gag    25206
Asp His Ala Ala His Ile Arg Gln Ser Arg Asp Val Glu Thr Ile Glu
        8370                8375                8380
```

| | |
|---|---|
| ggc tac gcc ctg acc ggc agt tcg gga agt gtg gcg tcc ggc cgg gtg<br>Gly Tyr Ala Leu Thr Gly Ser Ser Gly Ser Val Ala Ser Gly Arg Val<br>8385                 8390                 8395                 8400 | 25254 |
| gcc tac acg ctc ggg ctc gaa ggc ccc gcg gtg tcg gtg gat acg gcg<br>Ala Tyr Thr Leu Gly Leu Glu Gly Pro Ala Val Ser Val Asp Thr Ala<br>                8405                8410                8415 | 25302 |
| tgt tcg tcg tcg ttg gtg gcg ttg cat tgg gcg gcg cag gcg ttg cgt<br>Cys Ser Ser Ser Leu Val Ala Leu His Trp Ala Ala Gln Ala Leu Arg<br>                8420                8425                8430 | 25350 |
| gcg ggt gag tgt tcg atg gcg ctt gcc ggg ggt gtg acg gtg atg tcg<br>Ala Gly Glu Cys Ser Met Ala Leu Ala Gly Gly Val Thr Val Met Ser<br>8435                 8440                8445 | 25398 |
| tct ccg ggt acg ttt gtg gag ttc tca cgt cag cgg ggt ctg gcc gcg<br>Ser Pro Gly Thr Phe Val Glu Phe Ser Arg Gln Arg Gly Leu Ala Ala<br>            8450                8455                8460 | 25446 |
| gac ggg cgg tgc aag gcc tat tcg gcg gct gct gac ggt acc ggc tgg<br>Asp Gly Arg Cys Lys Ala Tyr Ser Ala Ala Ala Asp Gly Thr Gly Trp<br>8465                 8470                8475                8480 | 25494 |
| gcc gag ggt gtg ggg atg ctg ctg gtg gag cgg ctc tcc gac gcc cgt<br>Ala Glu Gly Val Gly Met Leu Leu Val Glu Arg Leu Ser Asp Ala Arg<br>                8485                8490                8495 | 25542 |
| cgc aac ggt cac cgt gtc ctg gcc gtg gtg cgt ggc agt gcg gtc aac<br>Arg Asn Gly His Arg Val Leu Ala Val Val Arg Gly Ser Ala Val Asn<br>            8500                8505                8510 | 25590 |
| cag gac ggt gcg agc aac ggt ctg acc gcg ccc aac ggg ccc tcc cag<br>Gln Asp Gly Ala Ser Asn Gly Leu Thr Ala Pro Asn Gly Pro Ser Gln<br>                8515                8520                8525 | 25638 |
| cag cgt gtc atc cgt cag gcc ctg gcc aat gcg gga ctg acc ccg gcc<br>Gln Arg Val Ile Arg Gln Ala Leu Ala Asn Ala Gly Leu Thr Pro Ala<br>            8530                8535                8540 | 25686 |
| gat gtc gac gca gtg gag ggc cac ggc acc ggg acc act ctg ggg gac<br>Asp Val Asp Ala Val Glu Gly His Gly Thr Gly Thr Thr Leu Gly Asp<br>8545                 8550                8555                8560 | 25734 |
| ccg atc gag gcc cag gca ctc ctg gcc gcc tac gga caa cac cgc ccc<br>Pro Ile Glu Ala Gln Ala Leu Leu Ala Ala Tyr Gly Gln His Arg Pro<br>                8565                8570                8575 | 25782 |
| cac cac cgc ccc ttg tgg ctg gga tcc ctc aaa tcc aac atc ggg cac<br>His His Arg Pro Leu Trp Leu Gly Ser Leu Lys Ser Asn Ile Gly His<br>            8580                8585                8590 | 25830 |
| gca cag gcc gcc gcg ggc gtg ggc gga gtc atc aag atg gtg atg gcc<br>Ala Gln Ala Ala Ala Gly Val Gly Gly Val Ile Lys Met Val Met Ala<br>                8595                8600                8605 | 25878 |
| ctg cgc aac ggg ctg ctg cca cag acc ctc cac gtg gac gag ccc acc<br>Leu Arg Asn Gly Leu Leu Pro Gln Thr Leu His Val Asp Glu Pro Thr<br>8610                 8615                8620 | 25926 |
| ccc cag gtc gac tgg tcc aca ggc gca gta caa ctc ctg aca caa ccg<br>Pro Gln Val Asp Trp Ser Thr Gly Ala Val Gln Leu Leu Thr Gln Pro<br>8625                 8630                8635                8640 | 25974 |
| gtg ccc tgg ccc gcc gac ccg gcc ggc cgg cca cgc cac gcc ggc gtg<br>Val Pro Trp Pro Ala Asp Pro Ala Gly Arg Pro Arg His Ala Gly Val<br>                8645                8650                8655 | 26022 |
| tca tca ttc ggc gtc agc ggc acc aac gcc cac atc atc ctc gaa gaa<br>Ser Ser Phe Gly Val Ser Gly Thr Asn Ala His Ile Ile Leu Glu Glu<br>            8660                8665                8670 | 26070 |
| gca ccc act ccc cag gac agc gat acc gac gac gaa ccg cct gcc aac<br>Ala Pro Thr Pro Gln Asp Ser Asp Thr Asp Asp Glu Pro Pro Ala Asn<br>                8675                8680                8685 | 26118 |
| gca cca gcc ctg ccc cat ccc ctc cct ctt ccc gtg ccg gtg tcg gcg<br>Ala Pro Ala Leu Pro His Pro Leu Pro Leu Pro Val Pro Val Ser Ala<br>            8690                8695                8700 | 26166 |

| | |
|---|---|
| agg tct gag gcc ggg ttg cgg gcg cag gca cag gcg ttg cgc cag tac<br>Arg Ser Glu Ala Gly Leu Arg Ala Gln Ala Gln Ala Leu Arg Gln Tyr<br>8705              8710                    8715                  8720 | 26214 |
| gtg gca gcc cgc ccg gac atg tca cct gcc gac att ggt gcg ggt ctg<br>Val Ala Ala Arg Pro Asp Met Ser Pro Ala Asp Ile Gly Ala Gly Leu<br>                    8725                    8730                  8735 | 26262 |
| gcc cgc ggc cgg gcc gta ctg gaa cac cgc gcc gtc atc ctg gcc gcg<br>Ala Arg Gly Arg Ala Val Leu Glu His Arg Ala Val Ile Leu Ala Ala<br>                  8740                    8745                  8750 | 26310 |
| gac cgc gag gaa ctg gcg cag gca ctg aca gcc ctg gca gcc ggc gaa<br>Asp Arg Glu Glu Leu Ala Gln Ala Leu Thr Ala Leu Ala Ala Gly Glu<br>            8755                    8760                  8765 | 26358 |
| ccc cac ccc cac atc acc aca ggc cac acc cgg ggc ggt gac cgc ggc<br>Pro His Pro His Ile Thr Thr Gly His Thr Arg Gly Gly Asp Arg Gly<br>                  8770                    8775                  8780 | 26406 |
| ggc gtc gtc ttc gtc ttc ccc gga cag ggc ggc cag tgg gcc ggg atg<br>Gly Val Val Phe Val Phe Pro Gly Gln Gly Gly Gln Trp Ala Gly Met<br>8785              8790                    8795                  8800 | 26454 |
| ggc ctg acc ctg ctc acc tcc tca ccc gtg ttc gcc gaa cac atc gac<br>Gly Leu Thr Leu Leu Thr Ser Ser Pro Val Phe Ala Glu His Ile Asp<br>                    8805                    8810                  8815 | 26502 |
| gca tgc gag aaa gcc ctc acc ccc tgg gtg ccc tgg tcc ctg acc gac<br>Ala Cys Glu Lys Ala Leu Thr Pro Trp Val Pro Trp Ser Leu Thr Asp<br>            8820                    8825                  8830 | 26550 |
| atc ctg cac cgc gac ccc gac gac ccc gca tgg caa caa gcc gac gtg<br>Ile Leu His Arg Asp Pro Asp Asp Pro Ala Trp Gln Gln Ala Asp Val<br>                  8835                    8840                  8845 | 26598 |
| gtc cag ccc gtg ctc ttc agc atc atg gtc tcc ctc gcc gcc ctg tgg<br>Val Gln Pro Val Leu Phe Ser Ile Met Val Ser Leu Ala Ala Leu Trp<br>            8850                    8855                  8860 | 26646 |
| cgc tcc tac ggc atc gaa ccc gac gcg gtc ctc ggc cac tcc cag gga<br>Arg Ser Tyr Gly Ile Glu Pro Asp Ala Val Leu Gly His Ser Gln Gly<br>8865              8870                    8875                  8880 | 26694 |
| gaa atc gcc gcc gcc cac atc tgc ggc gca ctc agc ctg aaa gac gcc<br>Glu Ile Ala Ala Ala His Ile Cys Gly Ala Leu Ser Leu Lys Asp Ala<br>                    8885                    8890                  8895 | 26742 |
| gcc aaa acc gtt gca ctg cgc agc cgc gca ctg gcc gcc gta cga ggc<br>Ala Lys Thr Val Ala Leu Arg Ser Arg Ala Leu Ala Ala Val Arg Gly<br>            8900                    8905                  8910 | 26790 |
| cgg ggc gcc atg gcc tca ctg ccc ctg ccc gcc cag gac gtg cag cag<br>Arg Gly Ala Met Ala Ser Leu Pro Leu Pro Ala Gln Asp Val Gln Gln<br>                  8915                    8920                  8925 | 26838 |
| ctc att tcc gaa cgg tgg gaa ggg cag ttg tgg gtg gca gcc ctc aac<br>Leu Ile Ser Glu Arg Trp Glu Gly Gln Leu Trp Val Ala Ala Leu Asn<br>            8930                    8935                  8940 | 26886 |
| ggc ccc cac tcc acc acc gtc tcc ggc gac acc aag gcg gtg gat gag<br>Gly Pro His Ser Thr Thr Val Ser Gly Asp Thr Lys Ala Val Asp Glu<br>8945              8950                    8955                  8960 | 26934 |
| gtg ctg gcg cac tgc acc gac acc ggc cta cgg gcc aaa cgc atc ccc<br>Val Leu Ala His Cys Thr Asp Thr Gly Leu Arg Ala Lys Arg Ile Pro<br>                    8965                    8970                  8975 | 26982 |
| gtc gac tac gcc tcc cac tgc ccc cac gtc caa ccc ctc cac gac gaa<br>Val Asp Tyr Ala Ser His Cys Pro His Val Gln Pro Leu His Asp Glu<br>            8980                    8985                  8990 | 27030 |
| ctc ctg cac ctg ctg gga gac atc acc ccc cag ccg tcc acc gtg ccg<br>Leu Leu His Leu Leu Gly Asp Ile Thr Pro Gln Pro Ser Thr Val Pro<br>                  8995                    9000                  9005 | 27078 |
| ttc ttc tcc acc gtg gaa ggc acc tgg ctg gac acc aca acc ctg gac<br>Phe Phe Ser Thr Val Glu Gly Thr Trp Leu Asp Thr Thr Thr Leu Asp | 27126 |

-continued

| | |
|---|---|
| gcc gcc tac tgg tac cgc aac ctc cac cag ccc gtc cgc ttc agc cac<br>Ala Ala Tyr Trp Tyr Arg Asn Leu His Gln Pro Val Arg Phe Ser His<br>9025                       9030                      9035                    9040 | 27174 |
| gcc atc cag acc ctg acc gac gac gga cac cgc gcc ttc atc gaa atc<br>Ala Ile Gln Thr Leu Thr Asp Asp Gly His Arg Ala Phe Ile Glu Ile<br>                    9045                    9050                    9055 | 27222 |
| agc ccc cac ccc acc ctc gtc ccc gcc atc gaa gac acc acc gaa aac<br>Ser Pro His Pro Thr Leu Val Pro Ala Ile Glu Asp Thr Thr Glu Asn<br>9060                      9065                    9070 | 27270 |
| acc acc gaa aac atc acc gcg acc ggc agc ctc cgc cgc ggc gac aac<br>Thr Thr Glu Asn Ile Thr Ala Thr Gly Ser Leu Arg Arg Gly Asp Asn<br>                    9075                    9080                    9085 | 27318 |
| gac acc cac cgc ttc ctc acc gcc ctc gcc cac acc cac acc acc ggc<br>Asp Thr His Arg Phe Leu Thr Ala Leu Ala His Thr His Thr Thr Gly<br>9090                      9095                    9100 | 27366 |
| atc ggc aca ccc acc acc tgg cac cac cac tac acc caa acc cac ccc<br>Ile Gly Thr Pro Thr Thr Trp His His His Tyr Thr Gln Thr His Pro<br>9105                      9110                    9115                    9120 | 27414 |
| cac ccc aac ccc cac acc cac ctc gac ctg ccc acc tac ccc ttc caa<br>His Pro Asn Pro His Thr His Leu Asp Leu Pro Thr Tyr Pro Phe Gln<br>                    9125                    9130                    9135 | 27462 |
| cac cag cac tac tgg ctc caa cca ccc acc aca aca acc gac ctc acc<br>His Gln His Tyr Trp Leu Gln Pro Pro Thr Thr Thr Thr Asp Leu Thr<br>9140                      9145                    9150 | 27510 |
| acc acc ggc ctc acc ccc acc cac cac ccc ctc ctc acc gcc aca ctc<br>Thr Thr Gly Leu Thr Pro Thr His His Pro Leu Leu Thr Ala Thr Leu<br>9155                      9160                    9165 | 27558 |
| acc ctc gcc gac aac aac aca caa cta ctc acc ggc cgc ctc tcc cta<br>Thr Leu Ala Asp Asn Asn Thr Gln Leu Leu Thr Gly Arg Leu Ser Leu<br>                    9170                    9175                    9180 | 27606 |
| cgc acc cac ccc tgg ctc acc gac cac acc gtc gcc ggc atg gtc ctc<br>Arg Thr His Pro Trp Leu Thr Asp His Thr Val Ala Gly Met Val Leu<br>9185                      9190                    9195                    9200 | 27654 |
| ctg ccg ggc acc gcg ctc ctc gaa ctc gcc ctc caa gcc ggc gaa cgg<br>Leu Pro Gly Thr Ala Leu Leu Glu Leu Ala Leu Gln Ala Gly Glu Arg<br>                    9205                    9210                    9215 | 27702 |
| gtg gac tgc cct cgg gtg gag gaa ctg acc ctg cac gca ccg ttg gtg<br>Val Asp Cys Pro Arg Val Glu Glu Leu Thr Leu His Ala Pro Leu Val<br>9220                      9225                    9230 | 27750 |
| atc ccg cac acc gag gac gtg acg ttg cag gtc acc gtt cgg gca gcc<br>Ile Pro His Thr Glu Asp Val Thr Leu Gln Val Thr Val Arg Ala Ala<br>                    9235                    9240                    9245 | 27798 |
| gat gag agt ggc cat cgc gcc ctc gcg atc cac tcg tac tcc ggc acc<br>Asp Glu Ser Gly His Arg Ala Leu Ala Ile His Ser Tyr Ser Gly Thr<br>9250                      9255                    9260 | 27846 |
| gcg tcg tcg gcg gac cgg gag tgg acc cgt cac gcc acg ggc ctc ctc<br>Ala Ser Ser Ala Asp Arg Glu Trp Thr Arg His Ala Thr Gly Leu Leu<br>9265                      9270                    9275                    9280 | 27894 |
| aca cac cac gcc gac acc gat cac cgt gcc gac acg cac acg gac gcg<br>Thr His His Ala Asp Thr Asp His Arg Ala Asp Thr His Thr Asp Ala<br>                    9285                    9290                    9295 | 27942 |
| tgc ctt ggc ggg agc tgg ccc ccg ccc ggc gcg cag ccc atc gaa ctg<br>Cys Leu Gly Gly Ser Trp Pro Pro Pro Gly Ala Gln Pro Ile Glu Leu<br>9300                      9305                    9310 | 27990 |
| ggc gac gtc tac ggt cgt atg gcg gcg gac tcg gac atc gcc tac ggg<br>Gly Asp Val Tyr Gly Arg Met Ala Ala Asp Ser Asp Ile Ala Tyr Gly<br>                    9315                    9320                    9325 | 28038 |
| ccg gtc ttc cag ggg ctg cac gcc gcc tgg agg ttc ggc gac gat gtc | 28086 |

```
                Pro Val Phe Gln Gly Leu His Ala Ala Trp Arg Phe Gly Asp Asp Val
                    9330                9335                9340 ctg gcc gag gtg cgt ctg ccg gaa gag gct ctg cgc gat gct ccg gcg        28134
Leu Ala Glu Val Arg Leu Pro Glu Glu Ala Leu Arg Asp Ala Pro Ala
9345                9350                9355                9360 gcg gcc ttc ggt gtt cac ccg gcc ttg ctc gac gcg gcc ctg cac gcc        28182
Ala Ala Phe Gly Val His Pro Ala Leu Leu Asp Ala Ala Leu His Ala
                9365                9370                9375 acg gcg ctc acc ccc cag aac ggg gac ggc tcg acg gag aac gtc gcc        28230
Thr Ala Leu Thr Pro Gln Asn Gly Asp Gly Ser Thr Glu Asn Val Ala
            9380                9385                9390 cag gag agc atg cct gac cgc gca gcc cac cag gcg cga ctg ccg ttc        28278
Gln Glu Ser Met Pro Asp Arg Ala Ala His Gln Ala Arg Leu Pro Phe
        9395                9400                9405 agc tgg agc ggc gtg tcc ctg cac acg gcg ggc agt tcc gtg ttg cgc        28326
Ser Trp Ser Gly Val Ser Leu His Thr Ala Gly Ser Ser Val Leu Arg
    9410                9415                9420 gta cgg ctg tcg cgc agt ccg cag cac ggt aat gcc gtg gcc ctc acc        28374
Val Arg Leu Ser Arg Ser Pro Gln His Gly Asn Ala Val Ala Leu Thr
9425                9430                9435                9440 gcg gcc gac gag gac ggt cgg ccg gtg gtg acg atc gag tcg ctc gcg        28422
Ala Ala Asp Glu Asp Gly Arg Pro Val Val Thr Ile Glu Ser Leu Ala
                9445                9450                9455 ctg cgg ccg gtg tcc acc gag gag ctg cgc gcg gcc gcg gat cgt acg        28470
Leu Arg Pro Val Ser Thr Glu Glu Leu Arg Ala Ala Ala Asp Arg Thr
            9460                9465                9470 ccc gag cac gag tcg ctc ttc cga ctg gac tgg gtt tcc gta cca gtg        28518
Pro Glu His Glu Ser Leu Phe Arg Leu Asp Trp Val Ser Val Pro Val
        9475                9480                9485 ccc gcc aac gcc cct tcg ccc acc gcg gac cgg ccc tgg gcg gtc atc        28566
Pro Ala Asn Ala Pro Ser Pro Thr Ala Asp Arg Pro Trp Ala Val Ile
    9490                9495                9500 ggc gcg ggc ctt ccc cac ctg ccc ggc ctg acg gag cac gag cac gtg        28614
Gly Ala Gly Leu Pro His Leu Pro Gly Leu Thr Glu His Glu His Val
9505                9510                9515                9520 acc gcg tat gac gag ccg gcg gac ctg ctt ctg gct ctg gac cgc ggt        28662
Thr Ala Tyr Asp Glu Pro Ala Asp Leu Leu Leu Ala Leu Asp Arg Gly
                9525                9530                9535 gct ccg ccg ccc ggt gtg ctg gtc gta ggt ggt gtc gcc cac acc gaa        28710
Ala Pro Pro Pro Gly Val Leu Val Val Gly Gly Val Ala His Thr Glu
            9540                9545                9550 gcc cgg gag tat tcc gcc gaa gcc ccc ggg gag cgc ggg acc gag gcc        28758
Ala Arg Glu Tyr Ser Ala Glu Ala Pro Gly Glu Arg Gly Thr Glu Ala
        9555                9560                9565 tgc gag gcc cgg ccg gac gtc gtg cac gtg ggc gtc gtg cac acg gct        28806
Cys Glu Ala Arg Pro Asp Val Val His Val Gly Val Val His Thr Ala
    9570                9575                9580 gcc gtg cac gcg gct gcc gcg cag atg ttg gcc agg ctc cag gcc tgg        28854
Ala Val His Ala Ala Ala Ala Gln Met Leu Ala Arg Leu Gln Ala Trp
9585                9590                9595                9600 ctg ggc gac gag cgc ctc gca gac agc cgg ctg ctc gtc ctg acg tgc        28902
Leu Gly Asp Glu Arg Leu Ala Asp Ser Arg Leu Leu Val Leu Thr Cys
                9605                9610                9615 ggc gcg gtc gcc cgc gcc tcc ggc gac gat gcg acg gac ctg ccc ggg        28950
Gly Ala Val Ala Arg Ala Ser Gly Asp Asp Ala Thr Asp Leu Pro Gly
            9620                9625                9630 gcc gcc gtg tgg ggg ctg gtg cgt tcg gcg cag tcc gag cac ccg gac        28998
Ala Ala Val Trp Gly Leu Val Arg Ser Ala Gln Ser Glu His Pro Asp
        9635                9640                9645
```

| | |
|---|---|
| cgc atc acg ctg ctg gac ttc gag cgg ggc aca gag gcg gag ccc ggt<br>Arg Ile Thr Leu Leu Asp Phe Glu Arg Gly Thr Glu Ala Glu Pro Gly<br>         9650                  9655                  9660 | 29046 |
| cag ctg gcg acg gcg ctg aac tgc ggg gag cgg cag ctt gcc gtc cgc<br>Gln Leu Ala Thr Ala Leu Asn Cys Gly Glu Arg Gln Leu Ala Val Arg<br>9665                  9670                  9675                  9680 | 29094 |
| ccc gga ggg ctg ttc acg cca cgg ctg gtg cgc gcg cca cgt gtc gcc<br>Pro Gly Gly Leu Phe Thr Pro Arg Leu Val Arg Ala Pro Arg Val Ala<br>                  9685                  9690                  9695 | 29142 |
| gac gcc gta ccc gcc gta ccc gcc gtg gcc gta cca tca gcg ggt cac<br>Asp Ala Val Pro Ala Val Pro Ala Val Ala Val Pro Ser Ala Gly His<br>         9700                  9705                  9710 | 29190 |
| gca gcc gta ccg gca gcg ggt ccc ttc ctt ccg ggc gga acg gtg ctg<br>Ala Ala Val Pro Ala Ala Gly Pro Phe Leu Pro Gly Gly Thr Val Leu<br>         9715                  9720                  9725 | 29238 |
| atc acc ggc gga acc ggt gtc ctg ggc cgg ctc gtg gcc cgg cat ctg<br>Ile Thr Gly Gly Thr Gly Val Leu Gly Arg Leu Val Ala Arg His Leu<br>         9730                  9735                  9740 | 29286 |
| gtg gag gcg cac ggc gta cgg cat ctg ttg ctg gcg ggt cgg cgc gga<br>Val Glu Ala His Gly Val Arg His Leu Leu Leu Ala Gly Arg Arg Gly<br>9745                  9750                  9755                  9760 | 29334 |
| ccg gac gcc gag ggt gcg ccg gag ttg cgg gcg gag ctc ggt ggg ctc<br>Pro Asp Ala Glu Gly Ala Pro Glu Leu Arg Ala Glu Leu Gly Gly Leu<br>                  9765                  9770                  9775 | 29382 |
| ggc gcg acg gtg gag gtc gtc gcc tgc gac gcg gcg gac cgg cag cag<br>Gly Ala Thr Val Glu Val Val Ala Cys Asp Ala Ala Asp Arg Gln Gln<br>                  9780                  9785                  9790 | 29430 |
| ctg gcc gac ctg ctg aca cgg atc ccc gac gat cgg ccg ctg acc ggt<br>Leu Ala Asp Leu Leu Thr Arg Ile Pro Asp Asp Arg Pro Leu Thr Gly<br>         9795                  9800                  9805 | 29478 |
| gtc gtg cac agt gcg ggc atc ctg gac gac ggc gtg atc acg tcg ctg<br>Val Val His Ser Ala Gly Ile Leu Asp Asp Gly Val Ile Thr Ser Leu<br>9810                  9815                  9820 | 29526 |
| tcg ccg gag cgg ctc ggg gcc gtc ctc cgg gcc aag gcg gac gct gcg<br>Ser Pro Glu Arg Leu Gly Ala Val Leu Arg Ala Lys Ala Asp Ala Ala<br>9825                  9830                  9835                  9840 | 29574 |
| ctg ctt ctc gac gag ctg acg cgc ggg gca gag ctg tcg gct ttc gtc<br>Leu Leu Leu Asp Glu Leu Thr Arg Gly Ala Glu Leu Ser Ala Phe Val<br>         9845                  9850                  9855 | 29622 |
| atg ttc tcc tcc gcg tcg gcg gtg gtc ggc tcg ccc ggg cag ggc aac<br>Met Phe Ser Ser Ala Ser Ala Val Val Gly Ser Pro Gly Gln Gly Asn<br>                  9860                  9865                  9870 | 29670 |
| tac gcc gcc gcc aac gcc gtc ctc gac ttc ctt gct cat cgc cgc cgc<br>Tyr Ala Ala Ala Asn Ala Val Leu Asp Phe Leu Ala His Arg Arg Arg<br>         9875                  9880                  9885 | 29718 |
| gcc gag ggg ctg ccc gcc gtc tct ctc gcc tgg ggc ctg tgg gaa gag<br>Ala Glu Gly Leu Pro Ala Val Ser Leu Ala Trp Gly Leu Trp Glu Glu<br>         9890                  9895                  9900 | 29766 |
| ggc aca ggg atg acg ggc cac ctc gac gtc gac gac cat gcg cgg atc<br>Gly Thr Gly Met Thr Gly His Leu Asp Val Asp Asp His Ala Arg Ile<br>9905                  9910                  9915                  9920 | 29814 |
| agc cgc gcg gga atg cgg ccg ctg ccg act gcc gag gct ctg gcg ctg<br>Ser Arg Ala Gly Met Arg Pro Leu Pro Thr Ala Glu Ala Leu Ala Leu<br>                  9925                  9930                  9935 | 29862 |
| ttc gac gcg gcc ttg gcc gac ggc gag ccg ttc ctg atg ccg gct cgg<br>Phe Asp Ala Ala Leu Ala Asp Gly Glu Pro Phe Leu Met Pro Ala Arg<br>                  9940                  9945                  9950 | 29910 |
| ctc gac ctc acg gcc gta cgg tct ggt gcc gcg tcc gca ccg gtg ccg<br>Leu Asp Leu Thr Ala Val Arg Ser Gly Ala Ala Ser Ala Pro Val Pro<br>         9955                  9960                  9965 | 29958 |

| | | |
|---|---|---|
| ccg ctg ctg caa ggt ctg ctt cag ctg cct cgg tcc cgc tcg gcc gcc<br>Pro Leu Leu Gln Gly Leu Leu Gln Leu Pro Arg Ser Arg Ser Ala Ala<br>              9970                           9975                       9980 | 30006 |
| gcg gcc ccc ggc cat ggg gcc ccg gcg gcg gac gag gcg gcg gcc tgg<br>Ala Ala Pro Gly His Gly Ala Pro Ala Ala Asp Glu Ala Ala Ala Trp<br>9985                      9990                      9995                   10000 | 30054 |
| cgt gag cgt ctg gcc cgg cag agt gcc ggt gag cgc agg cag gcg ctg<br>Arg Glu Arg Leu Ala Arg Gln Ser Ala Gly Glu Arg Arg Gln Ala Leu<br>            10005                   10010                   10015 | 30102 |
| ctg cgc ctg gtg cgg tcg cat gtc gcg gcg gtg ctc ggc cat agc ggt<br>Leu Arg Leu Val Arg Ser His Val Ala Ala Val Leu Gly His Ser Gly<br>         10020                   10025                   10030 | 30150 |
| gcc gac gga atc gac gca tcg cgg gcg ttc cgc gag ctg ggg ttc gac<br>Ala Asp Gly Ile Asp Ala Ser Arg Ala Phe Arg Glu Leu Gly Phe Asp<br>            10035                   10040                   10045 | 30198 |
| tcg ctc acg gcg gtc gag ctg cgc aac cgt ctc acg gcc gcg acg ggc<br>Ser Leu Thr Ala Val Glu Leu Arg Asn Arg Leu Thr Ala Ala Thr Gly<br>10050                   10055                   10060 | 30246 |
| ctg cgg ctg cgg gcc acg ctg gcc ttc gat ttc ccg acc ccg gca gcg<br>Leu Arg Leu Arg Ala Thr Leu Ala Phe Asp Phe Pro Thr Pro Ala Ala<br>10065                   10070                   10075                   10080 | 30294 |
| ctg gcc gag cac ttg ggc gag cgt ctg ctt ccc gac cag gag gcc acg<br>Leu Ala Glu His Leu Gly Glu Arg Leu Leu Pro Asp Gln Glu Ala Thr<br>            10085                   10090                   10095 | 30342 |
| ggc gag caa gcc ggc gat cag ctc tcc ggc ggc agc gag gag gac gta<br>Gly Glu Gln Ala Gly Asp Gln Leu Ser Gly Gly Ser Glu Glu Asp Val<br>         10100                   10105                   10110 | 30390 |
| cgc agc ctc ctg acg tcc att ccg atc ggc agg ctg cgg gac gcg ggg<br>Arg Ser Leu Leu Thr Ser Ile Pro Ile Gly Arg Leu Arg Asp Ala Gly<br>            10115                   10120                   10125 | 30438 |
| ctc ctc ggg ccc ctg ctc acg ctc gcg gac acg ggc cgc ggc gcc tcg<br>Leu Leu Gly Pro Leu Leu Thr Leu Ala Asp Thr Gly Arg Gly Ala Ser<br>10130                   10135                   10140 | 30486 |
| ggc gcc gcc gca ggt ccg gag gac gcg ccg ccc tcc ggc cag gac aca<br>Gly Ala Ala Ala Gly Pro Glu Asp Ala Pro Pro Ser Gly Gln Asp Thr<br>10145                   10150                   10155                   10160 | 30534 |
| ccg gct ccc gtc tcg atc gac gag atg gac atc gac gac ctg atg gat<br>Pro Ala Pro Val Ser Ile Asp Glu Met Asp Ile Asp Asp Leu Met Asp<br>            10165                   10170                   10175 | 30582 |
| ctg gcg cac ggg cat ggc acc gca ccc gcc cgt gag ccc gcc gac gca<br>Leu Ala His Gly His Gly Thr Ala Pro Ala Arg Glu Pro Ala Asp Ala<br>         10180                   10185                   10190 | 30630 |
| gag gac tcg tcg tca tca cga aac cgg aca cac cac aca cac gaa ggt<br>Glu Asp Ser Ser Ser Ser Arg Asn Arg Thr His His Thr His Glu Gly<br>            10195                   10200                   10205 | 30678 |
| gag aca gcg tga<br>Glu Thr Ala<br>    10210 | 30690 |

```
<210> SEQ ID NO 2
<211> LENGTH: 31422
<212> TYPE: DNA
<213> ORGANISM: Streptomyces avermitilis
<220> FEATURE:
<221> NAME/KEY: CDS
<222> LOCATION: (1)..(14643)
<220> FEATURE:
<221> NAME/KEY: CDS
<222> LOCATION: (14824)..(31419)

<400> SEQUENCE: 2
```

```
atg gct aac gag gaa aag ctc cgc gac tat ctc aag cgc gtt act gcc    48
Met Ala Asn Glu Glu Lys Leu Arg Asp Tyr Leu Lys Arg Val Thr Ala
 1               5                  10                  15 gat ctc ctc aat gtg cgg cgt cga ctt cag cag att gaa tcg ggc gag    96
Asp Leu Leu Asn Val Arg Arg Arg Leu Gln Gln Ile Glu Ser Gly Glu
             20                  25                  30 cag gag ccg att gca att gtg ggg atg gcg tgc cgt ttt ccg ggg ggt   144
Gln Glu Pro Ile Ala Ile Val Gly Met Ala Cys Arg Phe Pro Gly Gly
         35                  40                  45 gtg gag tcg gcg gag gat ttc tgg gag ttg att gcg tcg ggt cgg gat   192
Val Glu Ser Ala Glu Asp Phe Trp Glu Leu Ile Ala Ser Gly Arg Asp
     50                  55                  60 gcg gtg ggg gag ttt ccg gtc gac cgg ggt tgg gac gtg gag gct ttc   240
Ala Val Gly Glu Phe Pro Val Asp Arg Gly Trp Asp Val Glu Ala Phe
 65                  70                  75                  80 tat gat ccg gag ccg ggg cgg gcg ggt tcg tcg tat acg cgc cgg ggc   288
Tyr Asp Pro Glu Pro Gly Arg Ala Gly Ser Ser Tyr Thr Arg Arg Gly
                 85                  90                  95 ggt ttc ctg gag ggt gcg gcg gag ttc gat gcg ggg ttt ttc ggg atc   336
Gly Phe Leu Glu Gly Ala Ala Glu Phe Asp Ala Gly Phe Phe Gly Ile
            100                 105                 110 agt ccg cgt gag gcg ttg gcg atg gat ccg cag cag cgg ttg atg ctg   384
Ser Pro Arg Glu Ala Leu Ala Met Asp Pro Gln Gln Arg Leu Met Leu
        115                 120                 125 gag gtg tcc tgg gag gcg ttg gag cgg gcg ggc atc gac ccc gcc acg   432
Glu Val Ser Trp Glu Ala Leu Glu Arg Ala Gly Ile Asp Pro Ala Thr
    130                 135                 140 ttg cgc ggc agc cgg acg ggc gtc ttc gcc ggc ctc atg tcc cag gac   480
Leu Arg Gly Ser Arg Thr Gly Val Phe Ala Gly Leu Met Ser Gln Asp
145                 150                 155                 160 tac gcg acc cgt ctg ctc tcg gtc ccc gac gac ctg gcc ggc tac ctg   528
Tyr Ala Thr Arg Leu Leu Ser Val Pro Asp Asp Leu Ala Gly Tyr Leu
                165                 170                 175 ggc aac ggc aac gcg gga agc atc ctg tcc gga cgc gtc gcc tac acc   576
Gly Asn Gly Asn Ala Gly Ser Ile Leu Ser Gly Arg Val Ala Tyr Thr
            180                 185                 190 ttc ggc ttc gag ggc ccc gcg gtg acg gtc gac acg gcg tgc tcg tcg   624
Phe Gly Phe Glu Gly Pro Ala Val Thr Val Asp Thr Ala Cys Ser Ser
        195                 200                 205 tcg ctg gtg gca ctg cac ctc gcc tgc cag tca ctg cgc acc ggt gag   672
Ser Leu Val Ala Leu His Leu Ala Cys Gln Ser Leu Arg Thr Gly Glu
    210                 215                 220 tcc tcc ttc gcc ctc gcc gga ggc gtg acg gtc atg tcc acc ccg ggc   720
Ser Ser Phe Ala Leu Ala Gly Gly Val Thr Val Met Ser Thr Pro Gly
225                 230                 235                 240 atg ttc gtg gag ttc tcg cgg cag cgg ggt ctg tcg ccg gac ggc cgg   768
Met Phe Val Glu Phe Ser Arg Gln Arg Gly Leu Ser Pro Asp Gly Arg
                245                 250                 255 tgc aag gcg tac gcg tcg gct gcc gac ggc acc ggc atg tcc gag ggc   816
Cys Lys Ala Tyr Ala Ser Ala Ala Asp Gly Thr Gly Met Ser Glu Gly
            260                 265                 270 gtg ggg att ttg ctg ctg gag cgg ctg tcc gag gct gaa cgt cgt ggt   864
Val Gly Ile Leu Leu Leu Glu Arg Leu Ser Glu Ala Glu Arg Arg Gly
        275                 280                 285 cat cgg gtt ttg gcg gtg gtg cgg ggg agt gcg gtg aat cag gac ggt   912
His Arg Val Leu Ala Val Val Arg Gly Ser Ala Val Asn Gln Asp Gly
    290                 295                 300 gcg tcg aat ggg ttg acg gcg ccg aat ggt ccg tcg cag cag cgg gtg   960
Ala Ser Asn Gly Leu Thr Ala Pro Asn Gly Pro Ser Gln Gln Arg Val
305                 310                 315                 320
```

-continued

| | | |
|---|---|---|
| att cgg cag gcg ttg gcg tgt gcg ggg ttg tct gtg gcg gat gtg gat<br>Ile Arg Gln Ala Leu Ala Cys Ala Gly Leu Ser Val Ala Asp Val Asp<br>325 330 335 | 1008 |
| gtg gtg gag ggg cac ggg acg ggc acg acg ctg ggt gat ccg atc gag<br>Val Val Glu Gly His Gly Thr Gly Thr Thr Leu Gly Asp Pro Ile Glu<br>340 345 350 | 1056 |
| gcg cag gcg ttg ctc gcc acg tac ggg cag cgg gcc ggt gac acg ccg<br>Ala Gln Ala Leu Leu Ala Thr Tyr Gly Gln Arg Ala Gly Asp Thr Pro<br>355 360 365 | 1104 |
| gtg tgg ttg ggg tcg gtg aag tcg aac atc ggg cat gcg cag gct gct<br>Val Trp Leu Gly Ser Val Lys Ser Asn Ile Gly His Ala Gln Ala Ala<br>370 375 380 | 1152 |
| gcg ggt gtg gcg ggt gtg atc aag atg gtg atg gcg ttg cgg gcg ggg<br>Ala Gly Val Ala Gly Val Ile Lys Met Val Met Ala Leu Arg Ala Gly<br>385 390 395 400 | 1200 |
| gtg ttg ccg cgg acg ttg cat gtg gat gag ccg tcg tcg cag gtg gat<br>Val Leu Pro Arg Thr Leu His Val Asp Glu Pro Ser Ser Gln Val Asp<br>405 410 415 | 1248 |
| tgg tcg agt ggg tcg gtt cgt gtg ttg gcg gat gag gtg gag tgg ccg<br>Trp Ser Ser Gly Ser Val Arg Val Leu Ala Asp Glu Val Glu Trp Pro<br>420 425 430 | 1296 |
| ggg gtg gag ggt cgg ctg cgg cgt gcg ggg gtg tct gcg ttc ggg gtg<br>Gly Val Glu Gly Arg Leu Arg Arg Ala Gly Val Ser Ala Phe Gly Val<br>435 440 445 | 1344 |
| agt ggg acg aat gcg cat gtg att ttg gag gag gcg tcg ggg ggc gcg<br>Ser Gly Thr Asn Ala His Val Ile Leu Glu Glu Ala Ser Gly Gly Ala<br>450 455 460 | 1392 |
| ggt ggg ggt gcg ggc cgg ctg cag gag ttg ggt ccg ggg gtg gtg tcg<br>Gly Gly Gly Ala Gly Arg Leu Gln Glu Leu Gly Pro Gly Val Val Ser<br>465 470 475 480 | 1440 |
| ggt tcg ggg gtg gtg ccg tgg gtg gtg tcg gcg cgg tcg gag ttg gcg<br>Gly Ser Gly Val Val Pro Trp Val Val Ser Ala Arg Ser Glu Leu Ala<br>485 490 495 | 1488 |
| ttg cgg ggg cag gcg cgt cgg ttg cgt ggg gtt gtg gcg gtt ggt ggg<br>Leu Arg Gly Gln Ala Arg Arg Leu Arg Gly Val Val Ala Val Gly Gly<br>500 505 510 | 1536 |
| ggt gcg gat ggt gtg ggg gtg agt ccg gct ggg gtc ggg cgg gct ttg<br>Gly Ala Asp Gly Val Gly Val Ser Pro Ala Gly Val Gly Arg Ala Leu<br>515 520 525 | 1584 |
| gtg tcg gag cgg tcg gtg ttc gag cat cgt gcg gtg gtc gtg gcc gag<br>Val Ser Glu Arg Ser Val Phe Glu His Arg Ala Val Val Val Ala Glu<br>530 535 540 | 1632 |
| gac cgc gac gag ttc ctg cac gca ctc gac gca ctg gcc ggc ggc cgc<br>Asp Arg Asp Glu Phe Leu His Ala Leu Asp Ala Leu Ala Gly Gly Arg<br>545 550 555 560 | 1680 |
| ccc gtg ccc ggc gtc gtc gag gga cga acc acc tcg ggc gaa ctc gcc<br>Pro Val Pro Gly Val Val Glu Gly Arg Thr Thr Ser Gly Glu Leu Ala<br>565 570 575 | 1728 |
| gta ctc ttc gcc ggg cag gga acc cag cgc gca ggc atg ggc cgc gaa<br>Val Leu Phe Ala Gly Gln Gly Thr Gln Arg Ala Gly Met Gly Arg Glu<br>580 585 590 | 1776 |
| ctg tac gag gcg tac ccc gtc ttc gcc cag gcc atc gac gag atc tgc<br>Leu Tyr Glu Ala Tyr Pro Val Phe Ala Gln Ala Ile Asp Glu Ile Cys<br>595 600 605 | 1824 |
| gcg gag gcc gac acc gcc cgc acc gac ccc ggt gcc cct ggg ctg cgg<br>Ala Glu Ala Asp Thr Ala Arg Thr Asp Pro Gly Ala Pro Gly Leu Arg<br>610 615 620 | 1872 |
| gac gta ctc ttc gca ccg cag gac tct ccc gaa ggc cgg ctg atc gag<br>Asp Val Leu Phe Ala Pro Gln Asp Ser Pro Glu Gly Arg Leu Ile Glu | 1920 |

```
                625                 630                 635                 640
gac acg ggt ttc gcc cag ccc gcc ctg ttc gcc ttc gag gtg gcg ctg         1968
Asp Thr Gly Phe Ala Gln Pro Ala Leu Phe Ala Phe Glu Val Ala Leu
                    645                 650                 655 ttc cgg ctg ctg gag acc tgg ggt ctg acg ccc gac tac gtc ctc ggc         2016
Phe Arg Leu Leu Glu Thr Trp Gly Leu Thr Pro Asp Tyr Val Leu Gly
            660                 665                 670 cat tcc gtc ggt gaa ctg gcg gcc gcc cat gtc gcc ggg atg ctc tgc         2064
His Ser Val Gly Glu Leu Ala Ala Ala His Val Ala Gly Met Leu Cys
        675                 680                 685 ctt gcc gac gcg gtg gca ctg gtg gtc gca cga ggc cgc ctg atg caa         2112
Leu Ala Asp Ala Val Ala Leu Val Val Ala Arg Gly Arg Leu Met Gln
    690                 695                 700 ggg ctc ccg tcc ggc gga gcc atg gtg gcc atc gag gcg tcc gag gac         2160
Gly Leu Pro Ser Gly Gly Ala Met Val Ala Ile Glu Ala Ser Glu Asp
705                 710                 715                 720 gag atc ctc ccg ctg ccc gac gaa tac gca tcc cgg gtc gcg cac gcc         2208
Glu Ile Leu Pro Leu Pro Asp Glu Tyr Ala Ser Arg Val Ala His Ala
                    725                 730                 735 gcg gtg aac ggg ccg cgg tcg atc gtc ctc tcc ggg gac gag gac gcg         2256
Ala Val Asn Gly Pro Arg Ser Ile Val Leu Ser Gly Asp Glu Asp Ala
                740                 745                 750 gtc ctg gac ctc gcg cag caa tgg gcg gca cga ggc cgc cgc acc cgg         2304
Val Leu Asp Leu Ala Gln Gln Trp Ala Ala Arg Gly Arg Arg Thr Arg
        755                 760                 765 cgg ctg cgg acc agc cac gcc ttc cac tcg ccg cac atg gac gcc atg         2352
Arg Leu Arg Thr Ser His Ala Phe His Ser Pro His Met Asp Ala Met
    770                 775                 780 ttg ggc gac ttc cgc cgc gcg gcc gag cag gtc acc ttc agc gcc ccg         2400
Leu Gly Asp Phe Arg Arg Ala Ala Glu Gln Val Thr Phe Ser Ala Pro
785                 790                 795                 800 cgg att ccc gtc gtc tcc aac gtc acc ggc gcg ccc ctc ccc gcc gag         2448
Arg Ile Pro Val Val Ser Asn Val Thr Gly Ala Pro Leu Pro Ala Glu
                    805                 810                 815 acc atg tgc acc ccg gac tac tgg gtc gaa cac gcc cgc agc acg gtc         2496
Thr Met Cys Thr Pro Asp Tyr Trp Val Glu His Ala Arg Ser Thr Val
                820                 825                 830 cgt ttc gcg gac ggc atc tca tgg ctt cag gaa cag ggc gtc acc acc         2544
Arg Phe Ala Asp Gly Ile Ser Trp Leu Gln Glu Gln Gly Val Thr Thr
        835                 840                 845 tgc ctc gaa atc ggc ccc gac ggc acg ctg tcg gcc ctc gca cag gac         2592
Cys Leu Glu Ile Gly Pro Asp Gly Thr Leu Ser Ala Leu Ala Gln Asp
    850                 855                 860 tcg ctc agt gca ccg gcc cgc gcc atc ccc gcc ctg cgg ccg gac cag         2640
Ser Leu Ser Ala Pro Ala Arg Ala Ile Pro Ala Leu Arg Pro Asp Gln
865                 870                 875                 880 ccg gag gca cgg tcg gtc atg acc gcc ctg gcg gag ttg ttc gtg gct         2688
Pro Glu Ala Arg Ser Val Met Thr Ala Leu Ala Glu Leu Phe Val Ala
                    885                 890                 895 ggg acg gcg gtt gag tgg gcc ggt gtg ttc gag ggg act gct cgc gag         2736
Gly Thr Ala Val Glu Trp Ala Gly Val Phe Glu Gly Thr Ala Arg Glu
                900                 905                 910 gtc ggt gat gga tgc ggg gtg gag ctg ccg acg tat gcg ttt gag cgg         2784
Val Gly Asp Gly Cys Gly Val Glu Leu Pro Thr Tyr Ala Phe Glu Arg
        915                 920                 925 gag cga ttt tgg ctg gac gtg gag gag gga tct gcg gga ggt tcc ggg         2832
Glu Arg Phe Trp Leu Asp Val Glu Glu Gly Ser Ala Gly Gly Ser Gly
    930                 935                 940 gtt tcc ggg atg tgg ggt ggt ccg ttg tgg gag gcg gtc gag tgt ggt         2880
```

```
      Val Ser Gly Met Trp Gly Gly Pro Leu Trp Glu Ala Val Glu Cys Gly
      945                 950                 955                 960 gat gcg ggg gtg gtg gca tcg ctc ctt ggg gtg gat gag ggg gcg tcg       2928
Asp Ala Gly Val Val Ala Ser Leu Leu Gly Val Asp Glu Gly Ala Ser
                    965                 970                 975 ctg ggt gcg gtg gtg tcg gcg ttg ggg gaa tgg ggg cgg gta cgg cac       2976
Leu Gly Ala Val Val Ser Ala Leu Gly Glu Trp Gly Arg Val Arg His
                980                 985                 990 gag cgt gaa gtg gtg gac ggg tgg cgc tat cgg gag gtg tgg cga ccc       3024
Glu Arg Glu Val Val Asp Gly Trp Arg Tyr Arg Glu Val Trp Arg Pro
            995                 1000                1005 gtt tcg ggc ggt ggt gta ggg ggg ctg tcg ggc gcg tgg ctg gtg gtg       3072
Val Ser Gly Gly Gly Val Gly Gly Leu Ser Gly Ala Trp Leu Val Val
        1010                1015                1020 tcc gag ggc gag gcg ggc ccg gtt gat gtg gtg gcg gag ggg ttg gag       3120
Ser Glu Gly Glu Ala Gly Pro Val Asp Val Val Ala Glu Gly Leu Glu
1025                1030                1035                1040 cgg tgt ggg gcg cga gtg gtt cgg gtg gag gtg gaa gcg ggg tgt gtg       3168
Arg Cys Gly Ala Arg Val Val Arg Val Glu Val Glu Ala Gly Cys Val
                    1045                1050                1055 agc agg gaa gtg ttg gcc ggc cac ctg cgt gag gcg gtc gat ggt gag       3216
Ser Arg Glu Val Leu Ala Gly His Leu Arg Glu Ala Val Asp Gly Glu
                1060                1065                1070 gct gtc ggc ggt gtc gtc tcc ctt gtg ggc tgg ggg agt ggc gtc gtg       3264
Ala Val Gly Gly Val Val Ser Leu Val Gly Trp Gly Ser Gly Val Val
            1075                1080                1085 cag gcg gga gtg gcg tct gtg ggg ttg gtg cag gcg ctg ggt gat gtg       3312
Gln Ala Gly Val Ala Ser Val Gly Leu Val Gln Ala Leu Gly Asp Val
        1090                1095                1100 ggc gtg ggg gcg cgg ctg tgg tgt gtg acg ggc ggg gcc gtg tcg gtg       3360
Gly Val Gly Ala Arg Leu Trp Cys Val Thr Gly Gly Ala Val Ser Val
1105                1110                1115                1120 ggg ggc cgg gat gct gtg tgg ggg ccg gcc tcg ggt gtg gtg tgg ggg       3408
Gly Gly Arg Asp Ala Val Trp Gly Pro Ala Ser Gly Val Val Trp Gly
                    1125                1130                1135 ctg ggc cgt gtg gtg ggg gcg gag gca ccg gac cgc tgg ggt ggg ctg       3456
Leu Gly Arg Val Val Gly Ala Glu Ala Pro Asp Arg Trp Gly Gly Leu
                1140                1145                1150 gtt gat gtg ccg gag ctc gtg gat gag cgg gtg gtc gat ggg ttg gta       3504
Val Asp Val Pro Glu Leu Val Asp Glu Arg Val Val Asp Gly Leu Val
            1155                1160                1165 ggt gtg ctg gcg ggt gtg ggg gga ggg ggt gag agt gag ttt gcc gtg       3552
Gly Val Leu Ala Gly Val Gly Gly Gly Gly Glu Ser Glu Phe Ala Val
        1170                1175                1180 cgg tct tcg ggg gcg ttt gtg cgg cgg ttg gtg cgg gcg ccg ttg gag       3600
Arg Ser Ser Gly Ala Phe Val Arg Arg Leu Val Arg Ala Pro Leu Glu
1185                1190                1195                1200 gag gcc gtc gcg gag cgg gag tgg cgg ccc cgc ggc acc gta ctc gtc       3648
Glu Ala Val Ala Glu Arg Glu Trp Arg Pro Arg Gly Thr Val Leu Val
                    1205                1210                1215 acc gga ggc acc ggc gag ttg ggt gcg cac gtc gcc cgg tgg atg gcc       3696
Thr Gly Gly Thr Gly Glu Leu Gly Ala His Val Ala Arg Trp Met Ala
                1220                1225                1230 cgg cgt ggc gcc gaa cac ctg ctg ctg gtg agc cga cgc ggg gag agc       3744
Arg Arg Gly Ala Glu His Leu Leu Leu Val Ser Arg Arg Gly Glu Ser
            1235                1240                1245 gcc cag gga gtc gaa gaa ctc cga gcg gac ttg atg ggc ttg ggc gcg       3792
Ala Gln Gly Val Glu Glu Leu Arg Ala Asp Leu Met Gly Leu Gly Ala
        1250                1255                1260
```

```
cgg gtg tcg gtg gtg gcg tgt gat gcg gcg gac cgt gag gcg ttg gcg      3840
Arg Val Ser Val Val Ala Cys Asp Ala Ala Asp Arg Glu Ala Leu Ala
1265                1270                1275                1280 gag gtg ttg cgg tcg gcc gtt ccg gcg gag tgc ccg ctg ggt gtg gtg      3888
Glu Val Leu Arg Ser Ala Val Pro Ala Glu Cys Pro Leu Gly Val Val
                1285                1290                1295 gtg cat gcc gcg gga gtt gtg gat gac ggg gtg ttg gag ggg ttg tcg      3936
Val His Ala Ala Gly Val Val Asp Asp Gly Val Leu Glu Gly Leu Ser
1300                1305                1310 tcc gag cgt gtc acg ggg gtg ctg cgg gcg aag gcg ctg gcg gcc tgg      3984
Ser Glu Arg Val Thr Gly Val Leu Arg Ala Lys Ala Leu Ala Ala Trp
     1315                1320                1325 aat ctg cat gag ttg acg cgg ggg gcg gat ctt tcg ggg ttc gtg gtg      4032
Asn Leu His Glu Leu Thr Arg Gly Ala Asp Leu Ser Gly Phe Val Val
1330                1335                1340 ttc tcg tcg gct gcg gcg acg ttc ggg ccg gcg gga cag ggg agt tac      4080
Phe Ser Ser Ala Ala Ala Thr Phe Gly Pro Ala Gly Gln Gly Ser Tyr
1345                1350                1355                1360 gcg gcg gcg aac gcg tat gtg gag gca atc gtt cgg cac cgg cgt ggt      4128
Ala Ala Ala Asn Ala Tyr Val Glu Ala Ile Val Arg His Arg Arg Gly
                1365                1370                1375 gag ggc ctg ccg ggg ttg gcg gtg gcg tgg ggt ccg tgg gct ggt ggg      4176
Glu Gly Leu Pro Gly Leu Ala Val Ala Trp Gly Pro Trp Ala Gly Gly
            1380                1385                1390 ggg atg gcg gag ggg gcc gtg ggg cag atg cgg cgt cgg ggt ctg gcg      4224
Gly Met Ala Glu Gly Ala Val Gly Gln Met Arg Arg Arg Gly Leu Ala
        1395                1400                1405 gcg atg acg ccg gag acg gcg ctg gtg gca ctg ggc cag gcg ttg gac      4272
Ala Met Thr Pro Glu Thr Ala Leu Val Ala Leu Gly Gln Ala Leu Asp
1410                1415                1420 cat gac gag acc tgt gtg acg gtc gcc gac atc gac tgg gac cga ttc      4320
His Asp Glu Thr Cys Val Thr Val Ala Asp Ile Asp Trp Asp Arg Phe
1425                1430                1435                1440 acc gcc aac tcc ctc ccc ggc tcc cga ctc tcg ccc ctc atc agc gac      4368
Thr Ala Asn Ser Leu Pro Gly Ser Arg Leu Ser Pro Leu Ile Ser Asp
                1445                1450                1455 atc ccc gaa gca cgc ctc gcc cgg gaa acc acc gga ctc gac acc gcc      4416
Ile Pro Glu Ala Arg Leu Ala Arg Glu Thr Thr Gly Leu Asp Thr Ala
            1460                1465                1470 acc gca tcc ccc gac tcg ttc tcc gca cgg ctc aag gcc atg gac acc      4464
Thr Ala Ser Pro Asp Ser Phe Ser Ala Arg Leu Lys Ala Met Asp Thr
        1475                1480                1485 gcc gag cag gaa cgt gcg ctt ctc gac ctg gtc cgt acg tac gcg gcg      4512
Ala Glu Gln Glu Arg Ala Leu Leu Asp Leu Val Arg Thr Tyr Ala Ala
1490                1495                1500 acc gtg ctc gga cac agc acc ccc acc gcc gta cgc cct gag cga gcc      4560
Thr Val Leu Gly His Ser Thr Pro Thr Ala Val Arg Pro Glu Arg Ala
1505                1510                1515                1520 ttc cgc gac ctg ggc ttc gtc tcc gtg agc gcc gtc gaa ctg cgc aac      4608
Phe Arg Asp Leu Gly Phe Val Ser Val Ser Ala Val Glu Leu Arg Asn
                1525                1530                1535 cgc ctc aac gcc gtc acc ggg ctc ctg ctg ccc acc acg ctg atc ttc      4656
Arg Leu Asn Ala Val Thr Gly Leu Leu Leu Pro Thr Thr Leu Ile Phe
            1540                1545                1550 gac tac ccc act ccc tcc gcg ctg gcc gga tac ctc aag gaa cag ctg      4704
Asp Tyr Pro Thr Pro Ser Ala Leu Ala Gly Tyr Leu Lys Glu Gln Leu
        1555                1560                1565 gag gag ggc gcg ggc ggc cag cgt gac att gct cct ccg gtc ccg gcg      4752
Glu Glu Gly Ala Gly Gly Gln Arg Asp Ile Ala Pro Pro Val Pro Ala
1570                1575                1580
```

-continued

| | |
|---|---|
| tcg cgt gtc gac gtt gac gag ccg att gcg att gtg ggg atg gcg tgc<br>Ser Arg Val Asp Val Asp Glu Pro Ile Ala Ile Val Gly Met Ala Cys<br>1585                    1590                  1595                 1600 | 4800 |
| cgt ttt ccg ggg ggt gtg gag tcg gcg gag gac ttg tgg gaa ctg gtc<br>Arg Phe Pro Gly Gly Val Glu Ser Ala Glu Asp Leu Trp Glu Leu Val<br>                1605                  1610                  1615 | 4848 |
| gcg tcg ggt cgg gat gcg gtg gga gag ttt ccg gtc gac cgg ggt tgg<br>Ala Ser Gly Arg Asp Ala Val Gly Glu Phe Pro Val Asp Arg Gly Trp<br>1620                    1625                  1630 | 4896 |
| gac gtg gag gct ttc tat gat ccg gag ccg ggg cgg gcg ggt tcg tcg<br>Asp Val Glu Ala Phe Tyr Asp Pro Glu Pro Gly Arg Ala Gly Ser Ser<br>                1635                  1640                  1645 | 4944 |
| tat acg cgc cgg ggc ggt ttc ctg gag ggt gcg gcg gag ttc gat gcg<br>Tyr Thr Arg Arg Gly Gly Phe Leu Glu Gly Ala Ala Glu Phe Asp Ala<br>1650                    1655                  1660 | 4992 |
| ggg ttt ttc ggg atc agt ccg cgt gag gcg ttg gcg atg gat ccg cag<br>Gly Phe Phe Gly Ile Ser Pro Arg Glu Ala Leu Ala Met Asp Pro Gln<br>1665                    1670                  1675                 1680 | 5040 |
| cag cgg ttg atg ctg gag gtg tcc tgg gag gcg ttg gag cgg gcg ggc<br>Gln Arg Leu Met Leu Glu Val Ser Trp Glu Ala Leu Glu Arg Ala Gly<br>                1685                  1690                  1695 | 5088 |
| atc gac ccc gcc acg ttg cgc ggg tcc acg acc ggt gtc ttc gcc ggc<br>Ile Asp Pro Ala Thr Leu Arg Gly Ser Thr Thr Gly Val Phe Ala Gly<br>1700                    1705                  1710 | 5136 |
| atg tgc agt cag gac tac gcc gac ctc gtg cgc cgg gcc acc gag gac<br>Met Cys Ser Gln Asp Tyr Ala Asp Leu Val Arg Arg Ala Thr Glu Asp<br>                1715                  1720                  1725 | 5184 |
| ctc gag ggc tac gcc atg acg ggc ctg tcc agc agc gtc aca tcc gga<br>Leu Glu Gly Tyr Ala Met Thr Gly Leu Ser Ser Ser Val Thr Ser Gly<br>1730                    1735                  1740 | 5232 |
| cgc gtc gcc tac acc ctg ggg ctc gag ggt ccg gcg gtg acg gtg gat<br>Arg Val Ala Tyr Thr Leu Gly Leu Glu Gly Pro Ala Val Thr Val Asp<br>1745                    1750                  1755                 1760 | 5280 |
| acg gcg tgt tcg tcg tcg ttg gtg gcg ctg cat ctg gcg tgt cag gcg<br>Thr Ala Cys Ser Ser Ser Leu Val Ala Leu His Leu Ala Cys Gln Ala<br>                1765                  1770                  1775 | 5328 |
| ttg agg tcg ggg gag tgt tcg ctg gcg ttg gcg ggg ggt gtg acg gtg<br>Leu Arg Ser Gly Glu Cys Ser Leu Ala Leu Ala Gly Gly Val Thr Val<br>1780                    1785                  1790 | 5376 |
| atg tcg acg ccg ggt gcg ttt gtg gag ttc tcg cgg cag cgg ggt ctg<br>Met Ser Thr Pro Gly Ala Phe Val Glu Phe Ser Arg Gln Arg Gly Leu<br>                1795                  1800                  1805 | 5424 |
| tcg ccg gac ggc cgg tgc aag gcg tac ggg tcg ggg gcc gat ggg gtc<br>Ser Pro Asp Gly Arg Cys Lys Ala Tyr Gly Ser Gly Ala Asp Gly Val<br>1810                    1815                  1820 | 5472 |
| ggc tgg gcc gag ggt gtg ggt gtg ctg ttg gtg gag cgg ctg tcc gag<br>Gly Trp Ala Glu Gly Val Gly Val Leu Leu Val Glu Arg Leu Ser Glu<br>1825                    1830                  1835                 1840 | 5520 |
| gct gaa cgt cgt ggt cat cgg gtt ttg gcg gtg gtg cgg ggg agt gcg<br>Ala Glu Arg Arg Gly His Arg Val Leu Ala Val Val Arg Gly Ser Ala<br>                1845                  1850                  1855 | 5568 |
| gtg aat cag gac ggt gcg tcg aat ggg ttg acg gcg ccg aat ggt ccg<br>Val Asn Gln Asp Gly Ala Ser Asn Gly Leu Thr Ala Pro Asn Gly Pro<br>1860                    1865                  1870 | 5616 |
| tcg cag cag cgg gtg att cgg cag gcg ttg gcg tgt gcg ggg ttg tcc<br>Ser Gln Gln Arg Val Ile Arg Gln Ala Leu Ala Cys Ala Gly Leu Ser<br>                1875                  1880                  1885 | 5664 |
| gtg gcg gat gtg gat gtg gtg gag ggg cac ggg acg ggt acg acg ttg<br>Val Ala Asp Val Asp Val Val Glu Gly His Gly Thr Gly Thr Thr Leu | 5712 |

-continued

```
           1890                1895                1900
ggt gat ccg atc gag gcg cag gcg ttg ctc gcc act tat ggg cag ggt      5760
Gly Asp Pro Ile Glu Ala Gln Ala Leu Leu Ala Thr Tyr Gly Gln Gly
1905                1910                1915                1920 cgt tcg ggg gag cgg ccg gtg tgg ttg ggg tcg gtg aag tcg aac atc      5808
Arg Ser Gly Glu Arg Pro Val Trp Leu Gly Ser Val Lys Ser Asn Ile
            1925                1930                1935 ggg cat gcg cag gct gct gcg ggt gtg gcg ggt gtg atc aag atg gtg      5856
Gly His Ala Gln Ala Ala Ala Gly Val Ala Gly Val Ile Lys Met Val
        1940                1945                1950 atg gcg ttg cgg gcg ggg gtg ttg ccg cgg acg ttg cat gtg gat gag      5904
Met Ala Leu Arg Ala Gly Val Leu Pro Arg Thr Leu His Val Asp Glu
            1955                1960                1965 ccg tcg tcg cag gtg gat tgg tcg agt ggg tcg gtt cgt gtg ttg gcg      5952
Pro Ser Ser Gln Val Asp Trp Ser Ser Gly Ser Val Arg Val Leu Ala
        1970                1975                1980 gat gag gtg gag tgg ccg ggg gtg gag ggt cgg ctg cgg cgt gcg ggg      6000
Asp Glu Val Glu Trp Pro Gly Val Glu Gly Arg Leu Arg Arg Ala Gly
1985                1990                1995                2000 gtg tct gcg ttc ggg gtg agt ggg acg aat gcg cat gtg att ttg gag      6048
Val Ser Ala Phe Gly Val Ser Gly Thr Asn Ala His Val Ile Leu Glu
            2005                2010                2015 gag gcg tcc ggg ggc gcg gat ggg ggt gcg ggc cgg ctg cag gag ttg      6096
Glu Ala Ser Gly Gly Ala Asp Gly Gly Ala Gly Arg Leu Gln Glu Leu
        2020                2025                2030 ggt ccg ggg gtg gtg tcg ggt tcg ggg gtg gtg ccg tgg gtg gtg tcg      6144
Gly Pro Gly Val Val Ser Gly Ser Gly Val Val Pro Trp Val Val Ser
            2035                2040                2045 gcg cgg tcg gag ttg gcg ttg cgg ggg cag gcg cgt cgg ttg cgt ggg      6192
Ala Arg Ser Glu Leu Ala Leu Arg Gly Gln Ala Arg Arg Leu Arg Gly
        2050                2055                2060 gtt gtg gcg gtt ggt ggg ggt gcg gat ggt gtg ggg gtg agt ccg gct      6240
Val Val Ala Val Gly Gly Gly Ala Asp Gly Val Gly Val Ser Pro Ala
2065                2070                2075                2080 ggg gtc ggg cgg gct ttg gtg tcg gag cgg tcg gtg ttc gag cat cgt      6288
Gly Val Gly Arg Ala Leu Val Ser Glu Arg Ser Val Phe Glu His Arg
            2085                2090                2095 gcg gtg gtc gtg gcc gag gac cgc gac gag ttc ctg cac gca ctc gac      6336
Ala Val Val Val Ala Glu Asp Arg Asp Glu Phe Leu His Ala Leu Asp
        2100                2105                2110 gca ctg gcc gag ggg gca ccc acc gcg ggg gtg gta cag ggt gtg gcc      6384
Ala Leu Ala Glu Gly Ala Pro Thr Ala Gly Val Val Gln Gly Val Ala
            2115                2120                2125 gga ccg gcg gcc gac gga aag atc gcc atg ctg ttc gga gga cag ggc      6432
Gly Pro Ala Ala Asp Gly Lys Ile Ala Met Leu Phe Gly Gly Gln Gly
        2130                2135                2140 acc cac tgg gaa ggc atg gcg cag gaa ctc ctc ggc tcc tca ccg gtc      6480
Thr His Trp Glu Gly Met Ala Gln Glu Leu Leu Gly Ser Ser Pro Val
2145                2150                2155                2160 ttc gcc cag cag atg tcc gac tgc gcc caa gcc ctc gaa ccg tac ctg      6528
Phe Ala Gln Gln Met Ser Asp Cys Ala Gln Ala Leu Glu Pro Tyr Leu
            2165                2170                2175 gac tgg tct ctc ctc gac gtc ctg cgc ggc gca ccg gac gca ccc cct      6576
Asp Trp Ser Leu Leu Asp Val Leu Arg Gly Ala Pro Asp Ala Pro Pro
        2180                2185                2190 ctg caa cgc gtc gat gtc gtc cag ccc gtc ctc ttc gcg gtg atg gtc      6624
Leu Gln Arg Val Asp Val Val Gln Pro Val Leu Phe Ala Val Met Val
            2195                2200                2205 tcg ctg gcg gcg ctc tgg cgc tcg tac ggt gta cac ccg gac gcg gtg      6672
```

```
                Ser Leu Ala Ala Leu Trp Arg Ser Tyr Gly Val His Pro Asp Ala Val
                    2210                2215                2220 gcc ggg cac tcg cag ggc gag atc gca gcg gcc tac gtc gcc ggt gca              6720
Ala Gly His Ser Gln Gly Glu Ile Ala Ala Ala Tyr Val Ala Gly Ala
2225                2230                2235                2240 ctc tcc ctc gac gac gcc gcc cgg gtc acc gcc ctg cgc agc cag gcg              6768
Leu Ser Leu Asp Asp Ala Ala Arg Val Thr Ala Leu Arg Ser Gln Ala
                2245                2250                2255 ctg gcc gca ctg gcc ggg cag ggg gcg atg gca tcg gtc ggt ctg ccg              6816
Leu Ala Ala Leu Ala Gly Gln Gly Ala Met Ala Ser Val Gly Leu Pro
            2260                2265                2270 gtc gag aag ctg gag ccg cgt ctt gcg aca tgg ggc gac cgt ctg gtc              6864
Val Glu Lys Leu Glu Pro Arg Leu Ala Thr Trp Gly Asp Arg Leu Val
        2275                2280                2285 atc gcc gcc gtg aac ggg gcg cgt tcg gcc gtg gtc tcc ggg gag ccg              6912
Ile Ala Ala Val Asn Gly Ala Arg Ser Ala Val Val Ser Gly Glu Pro
    2290                2295                2300 gaa gcg gtc gac gcc ctg gtg gag gag ctg tca cac gaa gac gta ccg              6960
Glu Ala Val Asp Ala Leu Val Glu Glu Leu Ser His Glu Asp Val Pro
2305                2310                2315                2320 gcc cgc agg ctc atg gtc gac tgg gcg tcg cac tcc ccg cag gtc gag              7008
Ala Arg Arg Leu Met Val Asp Trp Ala Ser His Ser Pro Gln Val Glu
                2325                2330                2335 gcg atc cag ggg cgg ctg ctc gaa ctc ctc gcc ccc atc cgc gcg agg              7056
Ala Ile Gln Gly Arg Leu Leu Glu Leu Leu Ala Pro Ile Arg Ala Arg
                2340                2345                2350 acc ggc gac gtg ccc ttc tac tcc acc gtc acc ggc gaa cgc atc gac              7104
Thr Gly Asp Val Pro Phe Tyr Ser Thr Val Thr Gly Glu Arg Ile Asp
            2355                2360                2365 ggc acc gaa ctc gac gcc gac tac tgg tac cgc aac ctg cgc cag gtc              7152
Gly Thr Glu Leu Asp Ala Asp Tyr Trp Tyr Arg Asn Leu Arg Gln Val
        2370                2375                2380 gtc cgc ttc cgg gac gcg aca cag gcg ctg gtc cgc gcc ggc cac acc              7200
Val Arg Phe Arg Asp Ala Thr Gln Ala Leu Val Arg Ala Gly His Thr
    2385                2390                2395                2400 gtc ttc atc gag gcg tgc ccg cat ccg gcc gtc gcg gtc ggt gtg cag              7248
Val Phe Ile Glu Ala Cys Pro His Pro Ala Val Ala Val Gly Val Gln
                2405                2410                2415 gaa acc ctg gac gag atg ggt gac ttg gac agc ctg gtc gtc gga tct              7296
Glu Thr Leu Asp Glu Met Gly Asp Leu Asp Ser Leu Val Val Gly Ser
                2420                2425                2430 ctg cgc cgg ggc gaa ggc ggc ttg cga cgc ttc ctg atg tcc gtg gcc              7344
Leu Arg Arg Gly Glu Gly Gly Leu Arg Arg Phe Leu Met Ser Val Ala
            2435                2440                2445 gag ttg ttc gtg ggt ggg gtg gcg gtt gag tgg tcc ggt gtg ttc ggg              7392
Glu Leu Phe Val Gly Gly Val Ala Val Glu Trp Ser Gly Val Phe Gly
        2450                2455                2460 agt gtt ggt cgc ggg gtc gct ggt ggt tgc ggg gtg gag ctg ccg acg              7440
Ser Val Gly Arg Gly Val Ala Gly Gly Cys Gly Val Glu Leu Pro Thr
2465                2470                2475                2480 tat gcg ttc gag cga gag cgc ttt tgg ctg gat gtg gag ggg gcg ccg              7488
Tyr Ala Phe Glu Arg Glu Arg Phe Trp Leu Asp Val Glu Gly Ala Pro
                2485                2490                2495 cgg ggt tcc ggg gtc tct ggg cag tgg ggt ggt cag ttg tcg gag gcg              7536
Arg Gly Ser Gly Val Ser Gly Gln Trp Gly Gly Gln Leu Ser Glu Ala
            2500                2505                2510 gtg gac acc gtg cgc ggc ggc atg ctg cgc gac tgc ctc gcc gga ctc              7584
Val Asp Thr Val Arg Gly Gly Met Leu Arg Asp Cys Leu Ala Gly Leu
        2515                2520                2525
```

```
gac ccc gcc gca cag gcc gag acc gtg ctg gac ctg gtc ctt acc cat    7632
Asp Pro Ala Ala Gln Ala Glu Thr Val Leu Asp Leu Val Leu Thr His
        2530                2535                2540 gcc gcg gcc gtc ctt gga cac ggc acc gcc gat gcg gtg gtg ccc gag    7680
Ala Ala Ala Val Leu Gly His Gly Thr Ala Asp Ala Val Val Pro Glu
2545                2550                2555                2560 cgc gcc ttc cgc gac ctc ggt ttc gac tcc ctc acc gcc gtc gaa cta    7728
Arg Ala Phe Arg Asp Leu Gly Phe Asp Ser Leu Thr Ala Val Glu Leu
            2565                2570                2575 cgc aac cgc ctc aac acc gcc acg ggc ctg cgc ttc ccg agg acc ctg    7776
Arg Asn Arg Leu Asn Thr Ala Thr Gly Leu Arg Phe Pro Arg Thr Leu
        2580                2585                2590 gtg ttc gac cat ccc cgc ccg gtg gca ctc gcg gca cac atc cac gag    7824
Val Phe Asp His Pro Arg Pro Val Ala Leu Ala Ala His Ile His Glu
    2595                2600                2605 cag ctg agc ggc gga agc ccg acc acc ggc act gcc ctt gcc ctt gcc    7872
Gln Leu Ser Gly Gly Ser Pro Thr Thr Gly Thr Ala Leu Ala Leu Ala
2610                2615                2620 ctt cgg gcc ccg gca ccg cgt gtg gat gtc gac gag ccg att gcc att    7920
Leu Arg Ala Pro Ala Pro Arg Val Asp Val Asp Glu Pro Ile Ala Ile
2625                2630                2635                2640 gtg ggg atg gcg tgc cgt ttt ccg ggg ggt gtg gag tcg gcg gag gat    7968
Val Gly Met Ala Cys Arg Phe Pro Gly Gly Val Glu Ser Ala Glu Asp
            2645                2650                2655 ttc tgg gag ttg atc gcg tcg ggt cgg gat gcg gtg ggg gag ttt ccg    8016
Phe Trp Glu Leu Ile Ala Ser Gly Arg Asp Ala Val Gly Glu Phe Pro
        2660                2665                2670 gtc gac cgg ggt tgg gac gtg gag gct ttc tat gat ccg gag ccg ggg    8064
Val Asp Arg Gly Trp Asp Val Glu Ala Phe Tyr Asp Pro Glu Pro Gly
    2675                2680                2685 cgg gcg ggt acg tcc tac acg cgg tgt ggt ggg ttt ttg cag ggt gcg    8112
Arg Ala Gly Thr Ser Tyr Thr Arg Cys Gly Gly Phe Leu Gln Gly Ala
2690                2695                2700 gcg gag ttc gat gcg ggg ttt ttc ggg atc agt ccg cgt gag gcg ttg    8160
Ala Glu Phe Asp Ala Gly Phe Phe Gly Ile Ser Pro Arg Glu Ala Leu
2705                2710                2715                2720 gcg atg gat ccg cag cag cgg ttg atg ctg gag gtg tcc tgg gag gcg    8208
Ala Met Asp Pro Gln Gln Arg Leu Met Leu Glu Val Ser Trp Glu Ala
            2725                2730                2735 ttg gag cgg gcg ggc atc gac ccc gcc acg ctg cac ggg tcc acg acc    8256
Leu Glu Arg Ala Gly Ile Asp Pro Ala Thr Leu His Gly Ser Thr Thr
        2740                2745                2750 ggt gtc ttc gcc ggc gtc tcg cag cag gac tac gcc gag ctc ctg cgc    8304
Gly Val Phe Ala Gly Val Ser Gln Gln Asp Tyr Ala Glu Leu Leu Arg
    2755                2760                2765 cgc ggc acc cag gac cac gag ggg tac gcg ctc acc ggc gtc tcc aac    8352
Arg Gly Thr Gln Asp His Glu Gly Tyr Ala Leu Thr Gly Val Ser Asn
2770                2775                2780 agc gtc gtc tcc ggg cgg ctt tcc tac acc ttc ggc ttc gag ggt ccg    8400
Ser Val Val Ser Gly Arg Leu Ser Tyr Thr Phe Gly Phe Glu Gly Pro
2785                2790                2795                2800 gcg gtg acg gtg gat acg gcg tgt tcg tcg tcg ttg gtg gcg ctg cat    8448
Ala Val Thr Val Asp Thr Ala Cys Ser Ser Ser Leu Val Ala Leu His
            2805                2810                2815 ctg gcg tgt cag gcg ttg agg tcg ggg gag tgt tcg ctg gcg ttg gcg    8496
Leu Ala Cys Gln Ala Leu Arg Ser Gly Glu Cys Ser Leu Ala Leu Ala
        2820                2825                2830 ggg ggt gtg acg gtg atg tcg acg ccg ggt gcg ttt gtg gag ttc tcg    8544
Gly Gly Val Thr Val Met Ser Thr Pro Gly Ala Phe Val Glu Phe Ser
    2835                2840                2845
```

-continued

| | |
|---|---|
| cgg cag cgg ggt ctg tcg ccg gac ggc cgg tgc aag gcg tac ggg tcg<br>Arg Gln Arg Gly Leu Ser Pro Asp Gly Arg Cys Lys Ala Tyr Gly Ser<br>              2850                     2855                         2860 | 8592 |
| ggg gcc gat ggg gtc ggc tgg gcc gag ggt gtg ggt gtg ctg ttg gtg<br>Gly Ala Asp Gly Val Gly Trp Ala Glu Gly Val Gly Val Leu Leu Val<br>2865                  2870                     2875                     2880 | 8640 |
| gag cgg ctg tcc gag gct gaa cgt cgt ggt cat cgg gtt ttg gcg gtg<br>Glu Arg Leu Ser Glu Ala Glu Arg Arg Gly His Arg Val Leu Ala Val<br>              2885                     2890                     2895 | 8688 |
| gtg cgg ggg agt gcg gtg aat cag gac ggt gcg tcg aat ggg ttg acg<br>Val Arg Gly Ser Ala Val Asn Gln Asp Gly Ala Ser Asn Gly Leu Thr<br>2900                  2905                     2910 | 8736 |
| gcg ccg aat ggt ccg tcg cag cag cgg gtg att cgg cag gcg ttg gcg<br>Ala Pro Asn Gly Pro Ser Gln Gln Arg Val Ile Arg Gln Ala Leu Ala<br>              2915                     2920                     2925 | 8784 |
| tgt gcg ggg ttg tcc gtg gcg gat gtg gat gtg gtg gag ggg cac ggg<br>Cys Ala Gly Leu Ser Val Ala Asp Val Asp Val Val Glu Gly His Gly<br>2930                  2935                     2940 | 8832 |
| acg ggt acg acg ttg ggt gat ccg atc gag gcg cag gcg ttg ctc gcc<br>Thr Gly Thr Thr Leu Gly Asp Pro Ile Glu Ala Gln Ala Leu Leu Ala<br>2945                  2950                     2955                     2960 | 8880 |
| acg tac ggg cag ggt cgt tcg ggg gag cgg ccg gtg tgg ttg ggg tcg<br>Thr Tyr Gly Gln Gly Arg Ser Gly Glu Arg Pro Val Trp Leu Gly Ser<br>              2965                     2970                     2975 | 8928 |
| gtg aag tcg aac atc ggg cat gcg cag gct gcc gcg ggt gtg gcc ggt<br>Val Lys Ser Asn Ile Gly His Ala Gln Ala Ala Ala Gly Val Ala Gly<br>2980                  2985                     2990 | 8976 |
| gtg atc aag atg gtc atg gcc ctg aac cac gaa ctg ttg ccg acc agc<br>Val Ile Lys Met Val Met Ala Leu Asn His Glu Leu Leu Pro Thr Ser<br>              2995                     3000                     3005 | 9024 |
| ctg cac atc gac gaa ccc tcc ccc cac atc gac tgg tcg agc ggc ggc<br>Leu His Ile Asp Glu Pro Ser Pro His Ile Asp Trp Ser Ser Gly Gly<br>3010                  3015                     3020 | 9072 |
| gtc cgg ctt ctc acc gag ccc gta ccg tgg cag cag aac ggc cgg ccc<br>Val Arg Leu Leu Thr Glu Pro Val Pro Trp Gln Gln Asn Gly Arg Pro<br>3025                  3030                     3035                     3040 | 9120 |
| agg cgc gcg ggc gtc tcc gcg ttc gga gtc agc ggg acc aac gcc cac<br>Arg Arg Ala Gly Val Ser Ala Phe Gly Val Ser Gly Thr Asn Ala His<br>              3045                     3050                     3055 | 9168 |
| gtc atc atc gag cag gcg ccg gtc gag gcg cac gtc atc agt gag ccg<br>Val Ile Ile Glu Gln Ala Pro Val Glu Ala His Val Ile Ser Glu Pro<br>3060                  3065                     3070 | 9216 |
| gta ccg gct gag gcg cac gtc atc gtc gag cag gcg ccg gtc gag gcg<br>Val Pro Ala Glu Ala His Val Ile Val Glu Gln Ala Pro Val Glu Ala<br>              3075                     3080                     3085 | 9264 |
| ccc cac gtg gtc gac gcc acc gga ccg gcg gac ctc acc gag ccg caa<br>Pro His Val Val Asp Ala Thr Gly Pro Ala Asp Leu Thr Glu Pro Gln<br>3090                  3095                     3100 | 9312 |
| gag gag gcg gct gaa ccg gag tgc gtc gct gac gcc gtg acc gag atg<br>Glu Glu Ala Ala Glu Pro Glu Cys Val Ala Asp Ala Val Thr Glu Met<br>3105                  3110                     3115                     3120 | 9360 |
| tcg gct gaa ccg gag tgc gtc gcc gac gcc atg tcc gag atg tcg gct<br>Ser Ala Glu Pro Glu Cys Val Ala Asp Ala Met Ser Glu Met Ser Ala<br>              3125                     3130                     3135 | 9408 |
| gag tgc gtc gcc gag gcc gtg tcc gac aag tcg gct gaa ccg gag tgc<br>Glu Cys Val Ala Glu Ala Val Ser Asp Lys Ser Ala Glu Pro Glu Cys<br>3140                  3145                     3150 | 9456 |
| gtc gcc gac gcc atg tcc gac aag ccg gcc ctc ctg ccc atc ccg tgg<br>Val Ala Asp Ala Met Ser Asp Lys Pro Ala Leu Leu Pro Ile Pro Trp | 9504 |

-continued

```
                    3155                3160                3165
ctg ctc tcc gcc aag tcc gag cga gcg ctg cgg ggc cag gcg cga cgg      9552
Leu Leu Ser Ala Lys Ser Glu Arg Ala Leu Arg Gly Gln Ala Arg Arg
        3170                3175                3180 ttg cgg cag ttc gct gcc agg gca tcc gat gcc cgg ccg gcc gac gtg      9600
Leu Arg Gln Phe Ala Ala Arg Ala Ser Asp Ala Arg Pro Ala Asp Val
3185                3190                3195                3200 gcg cac gcc ctg gcg gca cag cgg tcc gtg ttc gat cac cgg gcc gtc      9648
Ala His Ala Leu Ala Ala Gln Arg Ser Val Phe Asp His Arg Ala Val
                3205                3210                3215 gtc gtg gcc gag gac cgc gac ggc ttc ctt cag gcc ctc gac gcg ctg      9696
Val Val Ala Glu Asp Arg Asp Gly Phe Leu Gln Ala Leu Asp Ala Leu
            3220                3225                3230 gcc gag ggc cgg tcg gcg gac ggc ctg atc gaa ggg tcg gtc ggc ccg      9744
Ala Glu Gly Arg Ser Ala Asp Gly Leu Ile Glu Gly Ser Val Gly Pro
        3235                3240                3245 cgt ggc ggc cac tca ggc cgc cgg cgc gga aag acc gcc atg ctg ttc      9792
Arg Gly Gly His Ser Gly Arg Arg Arg Gly Lys Thr Ala Met Leu Phe
    3250                3255                3260 gcc gga cag ggc acg caa cgc gtg gga atg ggc cgt cag ctg tat gcg      9840
Ala Gly Gln Gly Thr Gln Arg Val Gly Met Gly Arg Gln Leu Tyr Ala
3265                3270                3275                3280 gct cac ccg gcc tac gcg gac gcg ctg gac cag gta ctg gcg gaa ctg      9888
Ala His Pro Ala Tyr Ala Asp Ala Leu Asp Gln Val Leu Ala Glu Leu
                3285                3290                3295 gac ggt cac ctg gac cag ccc ctg cgc ccg ctg atc cac gcc agt gcg      9936
Asp Gly His Leu Asp Gln Pro Leu Arg Pro Leu Ile His Ala Ser Ala
            3300                3305                3310 gat ctt gcg gat gtc gcg gat gcc gcg gat gtt ctg gac cgt acg cgg      9984
Asp Leu Ala Asp Val Ala Asp Ala Ala Asp Val Leu Asp Arg Thr Arg
        3315                3320                3325 tac gcc cag ccg gcg ctg ttc gcc gtc cag gtc gcg ctc ttc cgg cac     10032
Tyr Ala Gln Pro Ala Leu Phe Ala Val Gln Val Ala Leu Phe Arg His
    3330                3335                3340 ctg gaa cgt ctc ggc gtg cgc gcg gac ttc gtg gcc ggg cac tcg atc     10080
Leu Glu Arg Leu Gly Val Arg Ala Asp Phe Val Ala Gly His Ser Ile
3345                3350                3355                3360 ggc gag ctc gcg gcc gcc cac gtc gcc ggg gtg ctt ccc ctg gca gca     10128
Gly Glu Leu Ala Ala Ala His Val Ala Gly Val Leu Pro Leu Ala Ala
                3365                3370                3375 gcc tgc cgc ctg gtg gcg gcc cgc ggg cgc ctg atg gag cag ctc gca     10176
Ala Cys Arg Leu Val Ala Ala Arg Gly Arg Leu Met Glu Gln Leu Ala
            3380                3385                3390 cca ggc ggc gcc atg gtc gcc gta cgg gcg agc gaa gcc gag gcg cga     10224
Pro Gly Gly Ala Met Val Ala Val Arg Ala Ser Glu Ala Glu Ala Arg
        3395                3400                3405 cag gcg ctc gac ggc cgg gaa gcc cgg gtg tcg gtc gcg gcc gtg aac     10272
Gln Ala Leu Asp Gly Arg Glu Ala Arg Val Ser Val Ala Ala Val Asn
    3410                3415                3420 gga ccc gcc tcg gtg gtg ttc tcc ggc gcc gag gac gag gtg ggg aac     10320
Gly Pro Ala Ser Val Val Phe Ser Gly Ala Glu Asp Glu Val Gly Asn
3425                3430                3435                3440 atg gcg gac tgg ttc gcc gag cgc ggg cgg aga gtc aag cgc ctg cga     10368
Met Ala Asp Trp Phe Ala Glu Arg Gly Arg Arg Val Lys Arg Leu Arg
                3445                3450                3455 acc ggg cat gcc ttc cac tca ccg ctg atg gac ccg atg ctg gag gag     10416
Thr Gly His Ala Phe His Ser Pro Leu Met Asp Pro Met Leu Glu Glu
            3460                3465                3470 ttc cag cag gtc gcg gcc tcg ctg acc tac agc gaa cca gcc att ccc     10464
```

```
Phe Gln Gln Val Ala Ala Ser Leu Thr Tyr Ser Glu Pro Ala Ile Pro
    3475                3480                3485 atg gtg tcg acg ctc acc ggc gac atc gtg gcg gcg gga gaa ctg agc    10512
Met Val Ser Thr Leu Thr Gly Asp Ile Val Ala Ala Gly Glu Leu Ser
    3490                3495                3500 gac ccc gag tac tgg gtc cgg cag gta cgg cgg acc gtg cgc ttc ggc    10560
Asp Pro Glu Tyr Trp Val Arg Gln Val Arg Arg Thr Val Arg Phe Gly
3505                3510                3515                3520 gac gcg atc agc cgc ctg cac acc gac gga gtc cgc acc ttc atg gaa    10608
Asp Ala Ile Ser Arg Leu His Thr Asp Gly Val Arg Thr Phe Met Glu
                3525                3530                3535 ctg ggc cca gac ggg acc ctg tcg gca ctg gcc gag gaa tgc cta gag    10656
Leu Gly Pro Asp Gly Thr Leu Ser Ala Leu Ala Glu Glu Cys Leu Glu
        3540                3545                3550 gcc acc gcc gac agc cac ccc gcc gac gac gac acc ggc acc ccg caa    10704
Ala Thr Ala Asp Ser His Pro Ala Asp Asp Asp Thr Gly Thr Pro Gln
    3555                3560                3565 gag aac ctg ctc atc ccg ctc cta cgg ccg gac agc ccg gaa ccc ggc    10752
Glu Asn Leu Leu Ile Pro Leu Leu Arg Pro Asp Ser Pro Glu Pro Gly
    3570                3575                3580 acc ctg ctc acc ggc ttg gcc cgg ctg cat acg cac gga gcg gcg gcg    10800
Thr Leu Leu Thr Gly Leu Ala Arg Leu His Thr His Gly Ala Ala Ala
3585                3590                3595                3600 gtc aac tgg ccc gcc gcc ctg ccc gaa cgc gat cga gcc cgc cac ctc    10848
Val Asn Trp Pro Ala Ala Leu Pro Glu Arg Asp Arg Ala Arg His Leu
                3605                3610                3615 gac ctg ccg acc tac gcc ttc gat cac cac cgc tac tgg gtc gac acc    10896
Asp Leu Pro Thr Tyr Ala Phe Asp His His Arg Tyr Trp Val Asp Thr
        3620                3625                3630 tcg gcc ggc cac ccg ggg gac ctg tcg gca gcg ggg ctc ggc acc gcc    10944
Ser Ala Gly His Pro Gly Asp Leu Ser Ala Ala Gly Leu Gly Thr Ala
    3635                3640                3645 ggg cat ccc ctg ctc ggt tcc gcg gtg gca ctg gcc gag tcg cag gaa    10992
Gly His Pro Leu Leu Gly Ser Ala Val Ala Leu Ala Glu Ser Gln Glu
    3650                3655                3660 ctc ctc ttc acc ggc cgt ctc tcc ctg cgc aca cac ccg tgg ctg gcc    11040
Leu Leu Phe Thr Gly Arg Leu Ser Leu Arg Thr His Pro Trp Leu Ala
3665                3670                3675                3680 gac cac gcc atc ttc ggt acc gtc ctg ctg ccc ggc acg gcc atc ctg    11088
Asp His Ala Ile Phe Gly Thr Val Leu Leu Pro Gly Thr Ala Ile Leu
                3685                3690                3695 gaa ctg gcc gtg cgc gca ggc gac gag gtc gac tgc ggc acc gtc gag    11136
Glu Leu Ala Val Arg Ala Gly Asp Glu Val Asp Cys Gly Thr Val Glu
        3700                3705                3710 gaa ctc acc ctg cgg aca ccg ctc gtc ctt ccc gaa cag ggc tcg gtg    11184
Glu Leu Thr Leu Arg Thr Pro Leu Val Leu Pro Glu Gln Gly Ser Val
    3715                3720                3725 atc ctg caa ctc tcc gtc ggg gca ccc cag ggc ccc cag acg ccc gag    11232
Ile Leu Gln Leu Ser Val Gly Ala Pro Gln Gly Pro Gln Thr Pro Glu
    3730                3735                3740 gag ccc gaa cgg cgc acc ttc gcc ctg tac gcc cgc gaa gac gac gga    11280
Glu Pro Glu Arg Arg Thr Phe Ala Leu Tyr Ala Arg Glu Asp Asp Gly
3745                3750                3755                3760 ctg tcg tcc tcg tcc gcg gcg gcg acc ggc acc gag tgg acc tgc cac    11328
Leu Ser Ser Ser Ser Ala Ala Ala Thr Gly Thr Glu Trp Thr Cys His
                3765                3770                3775 gcc acc ggc gtc ctg acc ggc acc gcc cgg ccc gcg gag gag cac aca    11376
Ala Thr Gly Val Leu Thr Gly Thr Ala Arg Pro Ala Glu Glu His Thr
        3780                3785                3790
```

```
cag gaa ccg tgg ccg ccc gcc gac gca gca ccg gtg gac ctg gac ggc     11424
Gln Glu Pro Trp Pro Pro Ala Asp Ala Ala Pro Val Asp Leu Asp Gly
        3795                3800                3805 tgg tac gag cag ctg gcc ggc gcc ggc ctg gga tac ggg ccg gtg ttc     11472
Trp Tyr Glu Gln Leu Ala Gly Ala Gly Leu Gly Tyr Gly Pro Val Phe
    3810                3815                3820 cag ggg ctg cgc gag gtc tgg cgc ggg gac gag gtg ttc gcc gtc         11520
Gln Gly Leu Arg Glu Val Trp Arg Arg Gly Asp Glu Val Phe Ala Val
3825                3830                3835                3840 gtc acc ctg ccc gag agc acg gag gga cag gcg gcc gac gcc gcc cgg     11568
Val Thr Leu Pro Glu Ser Thr Glu Gly Gln Ala Ala Asp Ala Ala Arg
                3845                3850                3855 tac gcc ctg cac ccg gcc ctg ctg gac gcg gca ctg cac ccg gtc gtt     11616
Tyr Ala Leu His Pro Ala Leu Leu Asp Ala Ala Leu His Pro Val Val
            3860                3865                3870 ctg cgc cac gag ggc gat gcc gcc gcc gac gga cac ggc tgg ctg ccg     11664
Leu Arg His Glu Gly Asp Ala Ala Ala Asp Gly His Gly Trp Leu Pro
        3875                3880                3885 ttc tcc tgg acc ggc gtc acg gtc gcc gcc tcc ggc gcc tcc acc ctg     11712
Phe Ser Trp Thr Gly Val Thr Val Ala Ala Ser Gly Ala Ser Thr Leu
    3890                3895                3900 cac gtc cgt ctc acc gtc cgc acg gac gag gac gcg gtc gga ctg ctg     11760
His Val Arg Leu Thr Val Arg Thr Asp Glu Asp Ala Val Gly Leu Leu
3905                3910                3915                3920 gcc acc gac gca tcg gga cgc atc gtc atc tcc gcg ggg tcc ctc gcc     11808
Ala Thr Asp Ala Ser Gly Arg Ile Val Ile Ser Ala Gly Ser Leu Ala
                3925                3930                3935 ttc cgg ccc gtc tcc gcc gag cag ctc cag gcc gcg cgc acc ggc tac     11856
Phe Arg Pro Val Ser Ala Glu Gln Leu Gln Ala Ala Arg Thr Gly Tyr
            3940                3945                3950 cac gac cac ctc ttc cgc atc gaa tgg cgg ccg ctg cac ctc ccc acc     11904
His Asp His Leu Phe Arg Ile Glu Trp Arg Pro Leu His Leu Pro Thr
        3955                3960                3965 aca ccg gca cgg aca gcc gac tgg gcc cta atc ggc ccc ggt gcc cgg     11952
Thr Pro Ala Arg Thr Ala Asp Trp Ala Leu Ile Gly Pro Gly Ala Arg
    3970                3975                3980 cgg acg gcc gcc gtc ctg gag cgc aac ggc gcc tcc tgg cag gcc tac     12000
Arg Thr Ala Ala Val Leu Glu Arg Asn Gly Ala Ser Trp Gln Ala Tyr
3985                3990                3995                4000 ccg gac ccg gcg gct ctc gca gaa gcc ctg gcg gcc ggc gcc ccg gca     12048
Pro Asp Pro Ala Ala Leu Ala Glu Ala Leu Ala Ala Gly Ala Pro Ala
                4005                4010                4015 ccg ggc atg gtc gtc atc tcg tgc gag ccg gac ggc gca tcc gcc ccc     12096
Pro Gly Met Val Val Ile Ser Cys Glu Pro Asp Gly Ala Ser Ala Pro
            4020                4025                4030 acc gat tcc gcc ctc acc gat tcc gcc ctc acc gat tcc gcc ccg gcc     12144
Thr Asp Ser Ala Leu Thr Asp Ser Ala Leu Thr Asp Ser Ala Pro Ala
        4035                4040                4045 ggc tcg gcc ccg gcc gac tcc acc gcc ctc gcc gac gcc acc cgg caa     12192
Gly Ser Ala Pro Ala Asp Ser Thr Ala Leu Ala Asp Ala Thr Arg Gln
    4050                4055                4060 gcc acc acc cgc gtc ctc gcc ctg ctc cag gaa tgg gtc gcc gac gaa     12240
Ala Thr Thr Arg Val Leu Ala Leu Leu Gln Glu Trp Val Ala Asp Glu
4065                4070                4075                4080 cgg ctc gcg gcc tgc cgc ctg gcc ctc ctc acg cac ggc tcg gtc acc     12288
Arg Leu Ala Ala Cys Arg Leu Ala Leu Leu Thr His Gly Ser Val Thr
                4085                4090                4095 gcg acc ccc gac gag ccc gtg tcc gac ctc gca cac gcc gcc gtc tgg     12336
Ala Thr Pro Asp Glu Pro Val Ser Asp Leu Ala His Ala Ala Val Trp
            4100                4105                4110
```

```
gga ctg gtc cgc tcc gtg cag acc gag aac ccc gac cgg ttc ctg ctg    12384
Gly Leu Val Arg Ser Val Gln Thr Glu Asn Pro Asp Arg Phe Leu Leu
    4115                4120                4125 gcc gac acc gac gac acc gac gcc tcc cgc aac gcc ctt ccc ctg ctg    12432
Ala Asp Thr Asp Asp Thr Asp Ala Ser Arg Asn Ala Leu Pro Leu Leu
4130                4135                4140 gcc ggg gaa ccg cag atc gcc ctg cga aat ggt gcc gtc cgc atc ccg    12480
Ala Gly Glu Pro Gln Ile Ala Leu Arg Asn Gly Ala Val Arg Ile Pro
4145                4150                4155                4160 cgg atg aca cga gtg ccc gtc cgg cag cca cag ccg agc acc acc gac    12528
Arg Met Thr Arg Val Pro Val Arg Gln Pro Gln Pro Ser Thr Thr Asp
        4165                4170                4175 gcc gac tgg gac ccg gag gcc acg gtc ctc atc acg ggc ggt acc ggc    12576
Ala Asp Trp Asp Pro Glu Ala Thr Val Leu Ile Thr Gly Gly Thr Gly
    4180                4185                4190 gtc ctc ggc cgg ctc gtc gcc cgt cat ctc gcc acg gcc cac ggg gta    12624
Val Leu Gly Arg Leu Val Ala Arg His Leu Ala Thr Ala His Gly Val
        4195                4200                4205 cgg cac ctg ctg ctg gcc acc cgc cgc ggc acg gcc gcg gac ggc gcc    12672
Arg His Leu Leu Leu Ala Thr Arg Arg Gly Thr Ala Ala Asp Gly Ala
    4210                4215                4220 gcc gac ctg gtc gcc gaa ctc gcc ggc ctc ggc gcc gag gcc acg gtc    12720
Ala Asp Leu Val Ala Glu Leu Ala Gly Leu Gly Ala Glu Ala Thr Val
4225                4230                4235                4240 gcg gcc tgc gac atc ggg gac cgg gcg gcc gtc gcc gcg ctc ctc gac    12768
Ala Ala Cys Asp Ile Gly Asp Arg Ala Ala Val Ala Ala Leu Leu Asp
            4245                4250                4255 caa gtg ccc gcg cag cac ccc ctg aaa gcc gtg atc cac acg gcc ggt    12816
Gln Val Pro Ala Gln His Pro Leu Lys Ala Val Ile His Thr Ala Gly
    4260                4265                4270 gtg gtc gac gac ggc atc ctc acc tcg ctc act ccg gag cgc atg gag    12864
Val Val Asp Asp Gly Ile Leu Thr Ser Leu Thr Pro Glu Arg Met Glu
        4275                4280                4285 gcc gtc ctg cac gcg aag gcg ttc ggc gcc gcg cac ctg cac gac ctg    12912
Ala Val Leu His Ala Lys Ala Phe Gly Ala Ala His Leu His Asp Leu
    4290                4295                4300 acc cgc gac gcc ggc ctc acc acc ttc acc gtc ttc tcg tcg gcc gcc    12960
Thr Arg Asp Ala Gly Leu Thr Thr Phe Thr Val Phe Ser Ser Ala Ala
4305                4310                4315                4320 gcc tcc ttc ggc agt ccc gga cag ggc aac tac acc gcg gcg aac gcc    13008
Ala Ser Phe Gly Ser Pro Gly Gln Gly Asn Tyr Thr Ala Ala Asn Ala
            4325                4330                4335 ttt ctg gac gcc ctg atg cag cac cgc cac acc cag gca ctg ccg ggc    13056
Phe Leu Asp Ala Leu Met Gln His Arg His Thr Gln Ala Leu Pro Gly
            4340                4345                4350 cgg tcg ctc gcc tgg ggc ctt tgg ggc gag gcc gac ggc atg acc cgc    13104
Arg Ser Leu Ala Trp Gly Leu Trp Gly Glu Ala Asp Gly Met Thr Arg
    4355                4360                4365 aac ctc gcc ggc acc gac ttc gcg cgc atg gcc cgc ggc ggc ctg ctc    13152
Asn Leu Ala Gly Thr Asp Phe Ala Arg Met Ala Arg Gly Gly Leu Leu
    4370                4375                4380 ccc ctg tcc aac gca cag gga ctc gcg ctc ctc gac aca gcg gat cgc    13200
Pro Leu Ser Asn Ala Gln Gly Leu Ala Leu Leu Asp Thr Ala Asp Arg
4385                4390                4395                4400 ctc ggc cct ttc ggt gac ggg ctg ctc ctc gcc acc cgg ctc gac gcg    13248
Leu Gly Pro Phe Gly Asp Gly Leu Leu Leu Ala Thr Arg Leu Asp Ala
            4405                4410                4415 gcc acc ctc cac gca cag gcc acg gcc ggc gcc ctg ccg cgc atc ctg    13296
Ala Thr Leu His Ala Gln Ala Thr Ala Gly Ala Leu Pro Arg Ile Leu
```

-continued

```
            4420            4425            4430
cac ggg ctg atc cgc atc ccg gcc cgg cgg tcc gcc gac cac ggc atc    13344
His Gly Leu Ile Arg Ile Pro Ala Arg Arg Ser Ala Asp His Gly Ile
        4435            4440            4445 gcg acc gac acc ccc gcc acg ctg cgc gag cgc ctg gcc gga ctc acc    13392
Ala Thr Asp Thr Pro Ala Thr Leu Arg Glu Arg Leu Ala Gly Leu Thr
4450            4455            4460 atc ccc gcg cag cgc acc ggt ctc ctg gaa ctc gta cgc acc cat        13440
Ile Pro Ala Gln Arg Thr Gly Leu Leu Glu Leu Val Arg Thr His
4465            4470            4475            4480 gcc gcc gcc gtc ctc ggc cac ccc acc agc gcc gtc aca gcc gcg gac    13488
Ala Ala Ala Val Leu Gly His Pro Thr Ser Ala Val Thr Ala Ala Asp
        4485            4490            4495 ggc gca ctc ccg gac gat ctg gtc ccg gcc gac acc gag ttc cgc gac    13536
Gly Ala Leu Pro Asp Asp Leu Val Pro Ala Asp Thr Glu Phe Arg Asp
            4500            4505            4510 ctc ggc ttc gac tcg ctg acc gcc gtc gaa ctc cgc aac cgg atc aac    13584
Leu Gly Phe Asp Ser Leu Thr Ala Val Glu Leu Arg Asn Arg Ile Asn
        4515            4520            4525 gcc gtc acc ggc ctg cgc ctc ccg gca acg ctc atc ttc gac cag ccc    13632
Ala Val Thr Gly Leu Arg Leu Pro Ala Thr Leu Ile Phe Asp Gln Pro
    4530            4535            4540 agc ccc gcg gca ctc gcc gat cac ctc gcg acc cgc ctg acg gcc gag    13680
Ser Pro Ala Ala Leu Ala Asp His Leu Ala Thr Arg Leu Thr Ala Glu
4545            4550            4555            4560 gcg ggc acg ccg gac gag ccg gcc cct gcc gcc gcg gca gcc ggg gcc    13728
Ala Gly Thr Pro Asp Glu Pro Ala Pro Ala Ala Ala Ala Gly Ala
        4565            4570            4575 ggg agc gca ggg agt gcc gag acc gga cag cag cgc agt acg ggg agc    13776
Gly Ser Ala Gly Ser Ala Glu Thr Gly Gln Gln Arg Ser Thr Gly Ser
    4580            4585            4590 gag aag cag cag acc agg ggc ggc acc tcc acc gaa acc gtc gaa tcc    13824
Glu Lys Gln Gln Thr Arg Gly Gly Thr Ser Thr Glu Thr Val Glu Ser
4595            4600            4605 ctg ttc tgg atc gga cac gac acc cgc cgc atc gag gag tcc atg gcc    13872
Leu Phe Trp Ile Gly His Asp Thr Arg Arg Ile Glu Glu Ser Met Ala
        4610            4615            4620 ctg ctc tcg gcg gcc tcc ttc ttc cgg ccc gcc ttc acg gac ccc tcg    13920
Leu Leu Ser Ala Ala Ser Phe Phe Arg Pro Ala Phe Thr Asp Pro Ser
4625            4630            4635            4640 gac atc ccg gag ccg acg ttc gtc cgg ctc gcc cag ggt gaa gcg cgc    13968
Asp Ile Pro Glu Pro Thr Phe Val Arg Leu Ala Gln Gly Glu Ala Arg
        4645            4650            4655 gcc caa ggt gaa gca ctc gcc cgg ggc gaa aca cgg ccc gcc ctc atc    14016
Ala Gln Gly Glu Ala Leu Ala Arg Gly Glu Thr Arg Pro Ala Leu Ile
        4660            4665            4670 tgc ctg ccc acc gtc gcc gcc gtg tcg agc gtg tac cag tac tca cgt    14064
Cys Leu Pro Thr Val Ala Ala Val Ser Ser Val Tyr Gln Tyr Ser Arg
    4675            4680            4685 ttc gcg gcg gga ctg aac gga cac cga gac gtc tgg tac gtt cct gcg    14112
Phe Ala Ala Gly Leu Asn Gly His Arg Asp Val Trp Tyr Val Pro Ala
        4690            4695            4700 cca ggg ttc ctg gag ggc gaa ccc ctg ccg tcc gga atc ggc gcg gtg    14160
Pro Gly Phe Leu Glu Gly Glu Pro Leu Pro Ser Gly Ile Gly Ala Val
4705            4710            4715            4720 acc cgc atg ttc gcc gac gcg atc gtc cgg ttc acc gac ggc gcg cct    14208
Thr Arg Met Phe Ala Asp Ala Ile Val Arg Phe Thr Asp Gly Ala Pro
        4725            4730            4735 ttt gcg ctc gcc ggg cat tcc gcg ggc gga tgg ttc gtc tac gcg gtg    14256
```

```
                                                    -continued

Phe Ala Leu Ala Gly His Ser Ala Gly Gly Trp Phe Val Tyr Ala Val
            4740                4745                4750 acg agt cat ctg gag cgt cta ggc gtc cgt ccg gaa gcg gtg gtg acc    14304
Thr Ser His Leu Glu Arg Leu Gly Val Arg Pro Glu Ala Val Val Thr
            4755                4760                4765 atg gac gcc tat ctc ccg gac gac ggc atc gca cct gtc gcg tcc gcg    14352
Met Asp Ala Tyr Leu Pro Asp Asp Gly Ile Ala Pro Val Ala Ser Ala
            4770                4775                4780 ctg aca agt gaa atc ttc gac cgc gtc acg cag ttt gtg gac gtg gac    14400
Leu Thr Ser Glu Ile Phe Asp Arg Val Thr Gln Phe Val Asp Val Asp
4785                4790                4795                4800 tac aca cgc ctg gtc gcc atg ggc gga tac ttc cgc atc ttc tcc ggc    14448
Tyr Thr Arg Leu Val Ala Met Gly Gly Tyr Phe Arg Ile Phe Ser Gly
                4805                4810                4815 tgg agt cct ccg gac atc acc aca ccc gcc ctc ttc ctg cgc ggc cgg    14496
Trp Ser Pro Pro Asp Ile Thr Thr Pro Ala Leu Phe Leu Arg Gly Arg
            4820                4825                4830 gac gga gaa cag atg ccg ccg ccg tgg gga gtt ccg cac acc gtt ctg    14544
Asp Gly Glu Gln Met Pro Pro Pro Trp Gly Val Pro His Thr Val Leu
            4835                4840                4845 gac atc cag ggg aat cac ttc acg atg ctg gaa cag ttt gcg gat tcg    14592
Asp Ile Gln Gly Asn His Phe Thr Met Leu Glu Gln Phe Ala Asp Ser
            4850                4855                4860 act gct cgg cat gtc gac gaa tgg ctg aca gaa atc gca tca gtg cgg    14640
Thr Ala Arg His Val Asp Glu Trp Leu Thr Glu Ile Ala Ser Val Arg
4865                4870                4875                4880 cgc tgatcgcgcc tctgatcgcg gtcctgatcg cggccctgat cggcgggtcg         14693
Arg ggcacagccc ggtcggccgg tcggccagtc ggccagtcgg tggtatccgg tcggctccgg    14753
catcgatcag tgctttcccc cttacggcca tacgggcctt tctgagactt cttgaatttg    14813
ggagacagtg atg gac acg tcc agc gaa aag ctc gtc gac gcg ctt agg      14862
           Met Asp Thr Ser Ser Glu Lys Leu Val Asp Ala Leu Arg
                   4885                4890 gcg tct ctg aag gcg aac cag acc ctg cgg gca cgt aat gag caa ctg    14910
Ala Ser Leu Lys Ala Asn Gln Thr Leu Arg Ala Arg Asn Glu Gln Leu
4895                4900                4905                4910 gca gcc gcc atg gag gcg tcc agc gag ccg att gcg att gtg ggg atg    14958
Ala Ala Ala Met Glu Ala Ser Ser Glu Pro Ile Ala Ile Val Gly Met
            4915                4920                4925 gcg tgt cgt ttt ccg ggt ggg gtg tgt tcg ccg gag gag ttg tgg gag    15006
Ala Cys Arg Phe Pro Gly Gly Val Cys Ser Pro Glu Glu Leu Trp Glu
            4930                4935                4940 ctg gtt gcg tcg ggt ggg gat gcg att ggt gaa ttt ccg gcc ggt cgg    15054
Leu Val Ala Ser Gly Gly Asp Ala Ile Gly Glu Phe Pro Ala Gly Arg
            4945                4950                4955 ggg tgg gat ctg gag ggg ttg ttt gat tcg gac cct gac cgg tcg ggg    15102
Gly Trp Asp Leu Glu Gly Leu Phe Asp Ser Asp Pro Asp Arg Ser Gly
            4960                4965                4970 acg tcg tac gcg cgg tat ggc ggg ttt ttg tat gag gcg ggg gag ttc    15150
Thr Ser Tyr Ala Arg Tyr Gly Gly Phe Leu Tyr Glu Ala Gly Glu Phe
4975                4980                4985                4990 gat gcg gac ttc ttc ggg atc agt ccg cgt gag gcg ttg gcg atg gat    15198
Asp Ala Asp Phe Phe Gly Ile Ser Pro Arg Glu Ala Leu Ala Met Asp
                4995                5000                5005 ccg cag cag cgg ttg ttg ctg gag acg tcg tgg gag gcg ttc gag cgg    15246
Pro Gln Gln Arg Leu Leu Leu Glu Thr Ser Trp Glu Ala Phe Glu Arg
            5010                5015                5020 gcg ggt atc gat ccg ctg tcg atg cgt ggc tcc cgt acg ggt gtc ttc    15294
```

```
Ala Gly Ile Asp Pro Leu Ser Met Arg Gly Ser Arg Thr Gly Val Phe
        5025                5030                5035 gcc ggg gtg atg tac cac gac tac gga tcc cgc ctg ggt acc atc ccc        15342
Ala Gly Val Met Tyr His Asp Tyr Gly Ser Arg Leu Gly Thr Ile Pro
    5040                5045                5050 gag gga ttc gag ggc tac atc ggc aac ggt agc ggc ggc gcc gtc gcg        15390
Glu Gly Phe Glu Gly Tyr Ile Gly Asn Gly Ser Gly Gly Ala Val Ala
5055                5060                5065                5070 tcg ggc cgc gtc gcc tac acg ctc ggt ctc gag ggc cct gcc gtc tcg        15438
Ser Gly Arg Val Ala Tyr Thr Leu Gly Leu Glu Gly Pro Ala Val Ser
            5075                5080                5085 gtg gac acg gca tgt tcg tcg tcg ttg gtg gcg ctg cat ctg gcg tgc        15486
Val Asp Thr Ala Cys Ser Ser Ser Leu Val Ala Leu His Leu Ala Cys
        5090                5095                5100 cag tcg ctg cgg tcg ggt gag tgc acg ctc gcg ctg gcc ggc ggt gtg        15534
Gln Ser Leu Arg Ser Gly Glu Cys Thr Leu Ala Leu Ala Gly Gly Val
        5105                5110                5115 acg gtg atg tcg acc ccg cac ctc ttc gtc gag ttc tca cgc cag cgc        15582
Thr Val Met Ser Thr Pro His Leu Phe Val Glu Phe Ser Arg Gln Arg
        5120                5125                5130 gga ctg tcg gtg gac ggc cgc tgc aag tcc ttc gcg ggt gga gcc gac        15630
Gly Leu Ser Val Asp Gly Arg Cys Lys Ser Phe Ala Gly Gly Ala Asp
5135                5140                5145                5150 ggc acc ggc atg ggc gag ggc gtc ggg atg ctg ttg gtg gag cgg ttg        15678
Gly Thr Gly Met Gly Glu Gly Val Gly Met Leu Leu Val Glu Arg Leu
            5155                5160                5165 tcg gat gcg gtg cgg ctg ggg cat cgg gtg ctg gcg gtg ctg cgc ggc        15726
Ser Asp Ala Val Arg Leu Gly His Arg Val Leu Ala Val Leu Arg Gly
        5170                5175                5180 agt gcg gtc aat cag gac ggt gcg tcg aat ggg ttg acg gcg ccg aat        15774
Ser Ala Val Asn Gln Asp Gly Ala Ser Asn Gly Leu Thr Ala Pro Asn
        5185                5190                5195 ggt ccg gct cag gag cgg gtg atc cgg cag gcg ttg gcg aac gcg ggg        15822
Gly Pro Ala Gln Glu Arg Val Ile Arg Gln Ala Leu Ala Asn Ala Gly
        5200                5205                5210 ttg tcc gtg gcg gat gtg gat gtg gtg gag ggg cat ggg acg ggc acg        15870
Leu Ser Val Ala Asp Val Asp Val Val Glu Gly His Gly Thr Gly Thr
5215                5220                5225                5230 acg ctg ggt gat ccg atc gag gcg cag gcg ttg ctc gcc acg tac ggg        15918
Thr Leu Gly Asp Pro Ile Glu Ala Gln Ala Leu Leu Ala Thr Tyr Gly
            5235                5240                5245 cag cgg gcc ggt aac agg ccg ctg tgg ctg gga tcg gtg aag tcg aac        15966
Gln Arg Ala Gly Asn Arg Pro Leu Trp Leu Gly Ser Val Lys Ser Asn
        5250                5255                5260 atc ggc cat gcg cag gct gcc gcg ggt gtg ggt ggg gtc atc aag atg        16014
Ile Gly His Ala Gln Ala Ala Ala Gly Val Gly Gly Val Ile Lys Met
        5265                5270                5275 gtg atg gcg ttg cgg gag ggg gtg ttg ccg cgg acg ttg cat gtg gat        16062
Val Met Ala Leu Arg Glu Gly Val Leu Pro Arg Thr Leu His Val Asp
        5280                5285                5290 gag ccg tcg ccg cag gtg gac tgg tcc gcg ggg gcg gtg cgg ctg ctg        16110
Glu Pro Ser Pro Gln Val Asp Trp Ser Ala Gly Ala Val Arg Leu Leu
5295                5300                5305                5310 acg gag gcg gtg ccg tgg ccg ggg gac gcg gca ggg cgg ttg cgg cgg        16158
Thr Glu Ala Val Pro Trp Pro Gly Asp Ala Ala Gly Arg Leu Arg Arg
            5315                5320                5325 gcg gga gtg tcg tcg ttc ggg gtc agt ggc acg aat gcg cat gtg att        16206
Ala Gly Val Ser Ser Phe Gly Val Ser Gly Thr Asn Ala His Val Ile
        5330                5335                5340
```

```
ttg gag gag gcg ccg gcg gcg ggg ggc tgt gtt gcc ggg ggt ggg gtg     16254
Leu Glu Glu Ala Pro Ala Ala Gly Gly Cys Val Ala Gly Gly Gly Val
            5345                5350                5355 ttg gag ggt gct ccg ggt ctt gcc att tcg gtg gct gag tcg gtg gcc     16302
Leu Glu Gly Ala Pro Gly Leu Ala Ile Ser Val Ala Glu Ser Val Ala
            5360                5365                5370 gct cca gtg gct gtg tct gcg ccg gtg gct gag tcg gtg ccg gtg ccg     16350
Ala Pro Val Ala Val Ser Ala Pro Val Ala Glu Ser Val Pro Val Pro
5375                5380                5385                5390 gtg ccg gtg ccg gtt cct gtg ccg gtg tcg gct agg tct gag gct ggg     16398
Val Pro Val Pro Val Pro Val Pro Val Ser Ala Arg Ser Glu Ala Gly
        5395                5400                5405 ttg cgg gcg cag gcg gag gcg ttg cgt cag tac gtg gca gtc cgg ccg     16446
Leu Arg Ala Gln Ala Glu Ala Leu Arg Gln Tyr Val Ala Val Arg Pro
            5410                5415                5420 gac gtt tcg ctt gcc gat gtg ggt gcg ggt ctg gcc tgt ggg cgg gct     16494
Asp Val Ser Leu Ala Asp Val Gly Ala Gly Leu Ala Cys Gly Arg Ala
            5425                5430                5435 gtg ctg gag cat cgt gcg gtc gtc ctg gcc gcg gac cgt gag gag ctg     16542
Val Leu Glu His Arg Ala Val Val Leu Ala Ala Asp Arg Glu Glu Leu
            5440                5445                5450 gtg caa ggg ttg ggg gcg ctg gcg gcg ggt gag ccg gat cgg cgg gtg     16590
Val Gln Gly Leu Gly Ala Leu Ala Ala Gly Glu Pro Asp Arg Arg Val
5455                5460                5465                5470 acc acg ggt cat gcg ccg ggt ggt gac cgg ggc ggt gtc gtc ttc gtg     16638
Thr Thr Gly His Ala Pro Gly Gly Asp Arg Gly Gly Val Val Phe Val
            5475                5480                5485 ttt ccc gga cag ggt ggg cag tgg gcc ggg atg ggt gtg cgt ctg ctc     16686
Phe Pro Gly Gln Gly Gly Gln Trp Ala Gly Met Gly Val Arg Leu Leu
            5490                5495                5500 gcc tcc tct ccg gtg ttc gcc cgg cgg atg cag gcg tgc gag gag gct     16734
Ala Ser Ser Pro Val Phe Ala Arg Arg Met Gln Ala Cys Glu Glu Ala
            5505                5510                5515 ctg gcg ccg tgg gtg gac tgg tct gtg gtg gac atc ctg cgc cgg gac     16782
Leu Ala Pro Trp Val Asp Trp Ser Val Val Asp Ile Leu Arg Arg Asp
            5520                5525                5530 gcg ggg gat gcg gtg tgg gag cgg gcc gat gtg gtc cag cct gtg ctg     16830
Ala Gly Asp Ala Val Trp Glu Arg Ala Asp Val Val Gln Pro Val Leu
5535                5540                5545                5550 ttc agc gtc atg gtg tct ttg gct gct ctg tgg cgt tcc tac ggt atc     16878
Phe Ser Val Met Val Ser Leu Ala Ala Leu Trp Arg Ser Tyr Gly Ile
            5555                5560                5565 gaa ccc gac gcg gtc ctt ggc cat tcc cag ggc gag atc gcg gcc gcg     16926
Glu Pro Asp Ala Val Leu Gly His Ser Gln Gly Glu Ile Ala Ala Ala
            5570                5575                5580 cat gtg tgt ggg gcg ctg agc ctg aag gac gcg gcg aag act gtt gcg     16974
His Val Cys Gly Ala Leu Ser Leu Lys Asp Ala Ala Lys Thr Val Ala
            5585                5590                5595 ctg cgc agc cgg gcg ctg gcc gct gtg cgg ggc cgg ggc ggc atg gcc     17022
Leu Arg Ser Arg Ala Leu Ala Ala Val Arg Gly Arg Gly Gly Met Ala
5600                5605                5610 tca gtg ccg ctg cct gcc cag gag gtg gag cag ctc att ggt gag cgg     17070
Ser Val Pro Leu Pro Ala Gln Glu Val Glu Gln Leu Ile Gly Glu Arg
5615                5620                5625                5630 tgg gcg ggg cgg ttg tgg gtg gcg gcg gtc aac ggc ccc cgc tcc acc     17118
Trp Ala Gly Arg Leu Trp Val Ala Ala Val Asn Gly Pro Arg Ser Thr
            5635                5640                5645 gcc gtc tcg ggg gat gcc gag gcg gtg gac gag gtg ctg gcg tac tgt     17166
Ala Val Ser Gly Asp Ala Glu Ala Val Asp Glu Val Leu Ala Tyr Cys
            5650                5655                5660
```

-continued

```
gcc ggc acc ggg gtg cgg gcc cgg cgg atc ccg gtc gac tat gcc tcg      17214
Ala Gly Thr Gly Val Arg Ala Arg Arg Ile Pro Val Asp Tyr Ala Ser
        5665            5670                5675 cac tgc ccc cat gtg cag ccc ctg cgg gag gag ttg ctg gag ctg ctg      17262
His Cys Pro His Val Gln Pro Leu Arg Glu Glu Leu Leu Glu Leu Leu
        5680            5685                5690 ggg gac atc agc ccg cag ccg tcc ggc gtg ccg ttc ttc tcc acg gtg      17310
Gly Asp Ile Ser Pro Gln Pro Ser Gly Val Pro Phe Phe Ser Thr Val
5695            5700                5705                5710 gag ggc acc tgg ctg gac acc aca acc ctg gac gcc gcc tac tgg tac      17358
Glu Gly Thr Trp Leu Asp Thr Thr Thr Leu Asp Ala Ala Tyr Trp Tyr
        5715            5720                5725 cgc aac ctg cac cag cct gtc cgt ttc agc gat gcc gtc cag gcc ctg      17406
Arg Asn Leu His Gln Pro Val Arg Phe Ser Asp Ala Val Gln Ala Leu
        5730            5735                5740 gcg gat gac gga cac cgc gtc ttc gtc gaa gtc agc ccc cac ccc acc      17454
Ala Asp Asp Gly His Arg Val Phe Val Glu Val Ser Pro His Pro Thr
        5745            5750                5755 ctc gtc ccc gcc atc gaa gac acc acc gaa gac acc gcc gaa gac gtc      17502
Leu Val Pro Ala Ile Glu Asp Thr Thr Glu Asp Thr Ala Glu Asp Val
        5760            5765                5770 acc gcg atc ggc agc ctc cgc cgc ggc gac aac gac acc cgc cgc ttc      17550
Thr Ala Ile Gly Ser Leu Arg Arg Gly Asp Asn Asp Thr Arg Arg Phe
5775            5780                5785                5790 ctc acc gcc ctc gcc cac acc cac acc acc ggc atc ggc aca ccc acc      17598
Leu Thr Ala Leu Ala His Thr His Thr Thr Gly Ile Gly Thr Pro Thr
        5795            5800                5805 acc tgg cac cac cac tac acc cac cac cac acc cac ccc cac aac cac      17646
Thr Trp His His His Tyr Thr His His His Thr His Pro His Asn His
        5810            5815                5820 cac ctc gac ctc ccc act tat ccc ttc caa cgc cag cac tac tgg ctc      17694
His Leu Asp Leu Pro Thr Tyr Pro Phe Gln Arg Gln His Tyr Trp Leu
        5825            5830                5835 gac gct ccc acg gga gca ggt gac gtc gcc gct gct ggc ttg gag ccg      17742
Asp Ala Pro Thr Gly Ala Gly Asp Val Ala Ala Ala Gly Leu Glu Pro
        5840            5845                5850 gcc gaa cac cct ctg ctc gcg gca aca gtc caa ctc gca gac acg gac      17790
Ala Glu His Pro Leu Leu Ala Ala Thr Val Gln Leu Ala Asp Thr Asp
5855            5860                5865                5870 ggc tgc cta ctg acg ggt cgc ctg tcc ttg cgc tcg cat ccg tgg ctg      17838
Gly Cys Leu Leu Thr Gly Arg Leu Ser Leu Arg Ser His Pro Trp Leu
        5875            5880                5885 ggc gat tac gag gtg ggg ggt gcg gtc ctg ctg tcg ggg tcg gcg ttc      17886
Gly Asp Tyr Glu Val Gly Gly Ala Val Leu Leu Ser Gly Ser Ala Phe
        5890            5895                5900 gtg gag ctg gcg gtc cag gtt ggc gaa cgc gtg ggc tgc acc cga atc      17934
Val Glu Leu Ala Val Gln Val Gly Glu Arg Val Gly Cys Thr Arg Ile
        5905            5910                5915 gag caa ctc act gtg cat gcg ccg ctg gtg gtt cct gtg ggt ggg ggt      17982
Glu Gln Leu Thr Val His Ala Pro Leu Val Val Pro Val Gly Gly Gly
        5920            5925                5930 gtg agt gtg cag gtt ggg gtt gcg gct gcg gat ggg gag ggg cgg cgt      18030
Val Ser Val Gln Val Gly Val Ala Ala Ala Asp Gly Glu Gly Arg Arg
5935            5940                5945                5950 ttg gtg agt gtg tat gcg cgg ggt ggg agt gct tgt ggt ggg ggt ggt      18078
Leu Val Ser Val Tyr Ala Arg Gly Gly Ser Ala Cys Gly Gly Gly Gly
        5955            5960                5965 gcg tcg ggt ggg gtg tgg acg tgt cat gcc tcg ggg gtg ctg gtt gag      18126
Ala Ser Gly Gly Val Trp Thr Cys His Ala Ser Gly Val Leu Val Glu
```

-continued

```
              5970                5975                5980
gct gct gct ggt ggt ggt gtg gtg gtg gat ggt ctg gcg ggg gtg tgg    18174
Ala Ala Ala Gly Gly Gly Val Val Val Asp Gly Leu Ala Gly Val Trp
              5985                5990                5995 ccg ccg cgg ggt gcg gtg gcg gtg gat gtc gat ggt gtc cgt gac cgt    18222
Pro Pro Arg Gly Ala Val Ala Val Asp Val Asp Gly Val Arg Asp Arg
              6000                6005                6010 ttg gct ggg gct ggt tgt gtt ttg ggg ccg gtg ttt tcg ggg ctg cgt    18270
Leu Ala Gly Ala Gly Cys Val Leu Gly Pro Val Phe Ser Gly Leu Arg
              6015                6020                6025                6030 gcg gtg tgg cgt gat ggg ggg gat ttg ctg gct gag gtg tgt ctg ccg    18318
Ala Val Trp Arg Asp Gly Gly Asp Leu Leu Ala Glu Val Cys Leu Pro
                      6035                6040                6045 gag gag gcg tgg ggt gat gcg gct ggt ttt ggg ctg cat ccg gcg ttg    18366
Glu Glu Ala Trp Gly Asp Ala Ala Gly Phe Gly Leu His Pro Ala Leu
              6050                6055                6060 ctg gat ggt gtg gtc cag ccg ttg tcg gtg ttg ctt ccg ggt ggg acg    18414
Leu Asp Gly Val Val Gln Pro Leu Ser Val Leu Leu Pro Gly Gly Thr
              6065                6070                6075 ggg ttt ggg gag ggg gcg ggg ttc ggg gag ggt gtt cgg gtg ccg gct    18462
Gly Phe Gly Glu Gly Ala Gly Phe Gly Glu Gly Val Arg Val Pro Ala
              6080                6085                6090 gtg tgg ggt ggt gtg tcg ctt cac cgg gcg ggt gtg acc ggt gtg cgg    18510
Val Trp Gly Gly Val Ser Leu His Arg Ala Gly Val Thr Gly Val Arg
6095                6100                6105                6110 gtg cgt gtg tgg gct gta ggg cgg ggc ggc ggg cgt gag gcg gtg tcg    18558
Val Arg Val Trp Ala Val Gly Arg Gly Gly Arg Glu Ala Val Ser
              6115                6120                6125 gtc gtg gtc ggg gat gag gcg ggt gtg ccg gtg gcg tcg gtc gat cgt    18606
Val Val Val Gly Asp Glu Ala Gly Val Pro Val Ala Ser Val Asp Arg
              6130                6135                6140 ctt gag ttg cgg cct gtg gat atg ggt cag ttg cgt gct gtc tcg gtt    18654
Leu Glu Leu Arg Pro Val Asp Met Gly Gln Leu Arg Ala Val Ser Val
              6145                6150                6155 tcg gcg ggg cgg cgg ggt tcg ctg tat gcg gtg cag tgg gct gag gtg    18702
Ser Ala Gly Arg Arg Gly Ser Leu Tyr Ala Val Gln Trp Ala Glu Val
              6160                6165                6170 ggt cct gtg ccg gtg tgt ggg cag gcg tgg gcg tgg cac gag gac gtg    18750
Gly Pro Val Pro Val Cys Gly Gln Ala Trp Ala Trp His Glu Asp Val
6175                6180                6185                6190 ggt gag agc ggt ggt ggg cct gtg ccg ggg gtg gtg gtg ttg cgg tgc    18798
Gly Glu Ser Gly Gly Gly Pro Val Pro Gly Val Val Val Leu Arg Cys
              6195                6200                6205 ccg gat gcc ggt gcc ggt ggc ggc ggt ggc ggt ggt gtg ggt gag gtt    18846
Pro Asp Ala Gly Ala Gly Gly Gly Gly Gly Gly Val Gly Glu Val
              6210                6215                6220 gtt ggt ggg gtg ttg ggt gtg gtg cag ggg tgg ctg ggg ctg gag cgg    18894
Val Gly Gly Val Leu Gly Val Val Gln Gly Trp Leu Gly Leu Glu Arg
              6225                6230                6235 ttt gcg ggt tcg cgg ctg gtg gtg gtg acc cgg ggt gcg gtg gtg gcc    18942
Phe Ala Gly Ser Arg Leu Val Val Val Thr Arg Gly Ala Val Val Ala
              6240                6245                6250 ggc caa gaa gac ggc ccg gtg gat gtg gtg ggt gcg gcg gtg tgg ggg    18990
Gly Gln Glu Asp Gly Pro Val Asp Val Val Gly Ala Ala Val Trp Gly
6255                6260                6265                6270 ctg gtg cgg tcg gcg cag gct gag cat ccg gac cgg ttt gtc ctc ctc    19038
Leu Val Arg Ser Ala Gln Ala Glu His Pro Asp Arg Phe Val Leu Leu
              6275                6280                6285 gac ctc gac acc gac acc gac acc ggc acc gac ctc gac acc ggt gct    19086
```

```
                Asp Leu Asp Thr Asp Thr Asp Thr Gly Thr Asp Leu Asp Thr Gly Ala
                            6290                6295                6300 ggt gct ggt gct ggt gct ggt tgg ggc gtg gat ggt ggg cat gtg gcg      19134
Gly Ala Gly Ala Gly Ala Gly Trp Gly Val Asp Gly Gly His Val Ala
            6305                6310                6315 gcg gtg gtg gcg tgt ggt gag ccg cag ttg gcg gtg cgt ggt gag cgg      19182
Ala Val Val Ala Cys Gly Glu Pro Gln Leu Ala Val Arg Gly Glu Arg
            6320                6325                6330 gtg ctg gcc gca cgc ctg acg cga ctt gag tcg tcc gtt gat gta cct      19230
Val Leu Ala Ala Arg Leu Thr Arg Leu Glu Ser Ser Val Asp Val Pro
6335                6340                6345                6350 gct cag cgg tcc ggt gat gtt gct ggt cgg gag gtg ttg ccg tgg ttg      19278
Ala Gln Arg Ser Gly Asp Val Ala Gly Arg Glu Val Leu Pro Trp Leu
            6355                6360                6365 tcg ggt ggg tcg gtg ttg gtg acg ggt ggg acg ggt gtg ctg ggt gcg      19326
Ser Gly Gly Ser Val Leu Val Thr Gly Gly Thr Gly Val Leu Gly Ala
            6370                6375                6380 gcg gtg gcg cgg cat ctg gct ggt gtg tgt ggg gtg cgg gat ctg ctg      19374
Ala Val Ala Arg His Leu Ala Gly Val Cys Gly Val Arg Asp Leu Leu
            6385                6390                6395 ttg gtg agc cgg cgt ggt ccg gat gct ccg ggt gcg gag ggt ttg cgg      19422
Leu Val Ser Arg Arg Gly Pro Asp Ala Pro Gly Ala Glu Gly Leu Arg
            6400                6405                6410 gcg gag ctg gcc gcg ttg ggg gcg gag gtg cgg att gtt gcg tgt gat      19470
Ala Glu Leu Ala Ala Leu Gly Ala Glu Val Arg Ile Val Ala Cys Asp
6415                6420                6425                6430 gtg ggg gag cgg cgg gag gtg gtc cgg ctg ctg gag ggt gtt cct gcc      19518
Val Gly Glu Arg Arg Glu Val Val Arg Leu Leu Glu Gly Val Pro Ala
            6435                6440                6445 ggg tgt ccg ctg acg ggt gtc gtg cat gcg gct ggt gtg ctg gac gat      19566
Gly Cys Pro Leu Thr Gly Val Val His Ala Ala Gly Val Leu Asp Asp
            6450                6455                6460 gcg acg atc gcc tct ctc acg ccc gag cgg ctg ggc acg gtg ttc gcg      19614
Ala Thr Ile Ala Ser Leu Thr Pro Glu Arg Leu Gly Thr Val Phe Ala
            6465                6470                6475 gcc aag gtg gat gcc gct ctt ttg ctg gat gag ctg acg cgg ggt atg      19662
Ala Lys Val Asp Ala Ala Leu Leu Leu Asp Glu Leu Thr Arg Gly Met
            6480                6485                6490 gag ctg tcg gcg ttc gtg ctg ttc tcc tcg gcc gcg ggg atc ctg ggg      19710
Glu Leu Ser Ala Phe Val Leu Phe Ser Ser Ala Ala Gly Ile Leu Gly
6495                6500                6505                6510 tcg gcc ggg cag ggc aac tac gcc gcg gcc aat gcc gct ctg gac gcg      19758
Ser Ala Gly Gln Gly Asn Tyr Ala Ala Ala Asn Ala Ala Leu Asp Ala
            6515                6520                6525 ctg gcg tac cgg cgg cgg gcg gcg ggt ctg ccg ggg gtg tcg ctg gcg      19806
Leu Ala Tyr Arg Arg Arg Ala Ala Gly Leu Pro Gly Val Ser Leu Ala
            6530                6535                6540 tgg ggg ctg tgg gaa gag gcc agc ggg atg acc ggg cac ctg gcc ggc      19854
Trp Gly Leu Trp Glu Glu Ala Ser Gly Met Thr Gly His Leu Ala Gly
            6545                6550                6555 acc gac cac cgg cgc atc atc cgt tcc ggt ctg cat ccc atg tcg acc      19902
Thr Asp His Arg Arg Ile Ile Arg Ser Gly Leu His Pro Met Ser Thr
            6560                6565                6570 ccg gac gca ctg gct ctc ttc gat gcg gcc ctg gct ctg gac cgg ccg      19950
Pro Asp Ala Leu Ala Leu Phe Asp Ala Ala Leu Ala Leu Asp Arg Pro
6575                6580                6585                6590 gtc ctg ctg ccc gcc gac ctg cgt ccc gcc ccg ccc ctg ccg ccc ctg      19998
Val Leu Leu Pro Ala Asp Leu Arg Pro Ala Pro Pro Leu Pro Pro Leu
            6595                6600                6605
```

```
ctg cag gac ctc ctg ccc gcc acc cgc cgc cgc acc acc cgc acc acc       20046
Leu Gln Asp Leu Leu Pro Ala Thr Arg Arg Arg Thr Thr Arg Thr Thr
            6610                6615                6620 act acc ggt ggt gcg gac aac ggc gcc cag ctg cat gcc cgg ctg gcc       20094
Thr Thr Gly Gly Ala Asp Asn Gly Ala Gln Leu His Ala Arg Leu Ala
        6625                6630                6635 ggc cag aca cac gaa caa cag cac acc acc ctc ctc gcc ctg gtc cgc       20142
Gly Gln Thr His Glu Gln Gln His Thr Thr Leu Leu Ala Leu Val Arg
    6640                6645                6650 tcc cac atc gcc acc gtc ctc ggc cac acc acc ccc gac acc atc ccc       20190
Ser His Ile Ala Thr Val Leu Gly His Thr Thr Pro Asp Thr Ile Pro
6655                6660                6665                6670 ccc gac cgc gcg ttc cgc gac ctc ggc ttc gac tcc ctc acc gcc gtc       20238
Pro Asp Arg Ala Phe Arg Asp Leu Gly Phe Asp Ser Leu Thr Ala Val
                6675                6680                6685 gaa cta cgc aac cgg ctc tcc cgc acc acc gga ctc cgc ctc ccc acc       20286
Glu Leu Arg Asn Arg Leu Ser Arg Thr Thr Gly Leu Arg Leu Pro Thr
            6690                6695                6700 acc ctc gcc ttc gac cac ccc aac ccc acc acc ctc acc cac cac ctc       20334
Thr Leu Ala Phe Asp His Pro Asn Pro Thr Thr Leu Thr His His Leu
        6705                6710                6715 cac aca caa ctt ctg ggc tcg gac agc act gcc tcc atc cca gct ccc       20382
His Thr Gln Leu Leu Gly Ser Asp Ser Thr Ala Ser Ile Pro Ala Pro
    6720                6725                6730 cgt gct gcg gct gtg cct gca gac cag gac gag ccc gtc gcg atc att       20430
Arg Ala Ala Ala Val Pro Ala Asp Gln Asp Glu Pro Val Ala Ile Ile
6735                6740                6745                6750 ggc atg gcg tgc cgc tat ccc gga ggc gtc acc tca gcc gag gag ctg       20478
Gly Met Ala Cys Arg Tyr Pro Gly Gly Val Thr Ser Ala Glu Glu Leu
                6755                6760                6765 tgg gaa ctg ctc gca tcg ggg agg gac acg gtc ggc gag ttt ccg acg       20526
Trp Glu Leu Leu Ala Ser Gly Arg Asp Thr Val Gly Glu Phe Pro Thr
            6770                6775                6780 gac cgt ggg tgg gac ctg gaa gca ctg ttc gat ccg gaa ccg ggt cgg       20574
Asp Arg Gly Trp Asp Leu Glu Ala Leu Phe Asp Pro Glu Pro Gly Arg
        6785                6790                6795 ccg ggc acc tcg tac acc cgc tgt ggg agt ttc ctc tac gac gcg ggg       20622
Pro Gly Thr Ser Tyr Thr Arg Cys Gly Ser Phe Leu Tyr Asp Ala Gly
    6800                6805                6810 gag ttc gac gcc ggc ttc ttc ggg atc agt ccg cgt gag gca ctg gcg       20670
Glu Phe Asp Ala Gly Phe Phe Gly Ile Ser Pro Arg Glu Ala Leu Ala
6815                6820                6825                6830 atg gac ccg cag cag cga ttg ctg ctg gag gcc tca tgg gag gcc atg       20718
Met Asp Pro Gln Gln Arg Leu Leu Leu Glu Ala Ser Trp Glu Ala Met
                6835                6840                6845 gag cag gca ggt att gac cct acg acc gta cgc ggg agc cag aca ggc       20766
Glu Gln Ala Gly Ile Asp Pro Thr Thr Val Arg Gly Ser Gln Thr Gly
            6850                6855                6860 gtg ttc gcg ggc ctc att ccg cag gcc tat gga ccc agg ctg cac gaa       20814
Val Phe Ala Gly Leu Ile Pro Gln Ala Tyr Gly Pro Arg Leu His Glu
        6865                6870                6875 aac gcc gca gcc gac acc gag ggc tat gtc ctg acc ggc aca tcc ggg       20862
Asn Ala Ala Ala Asp Thr Glu Gly Tyr Val Leu Thr Gly Thr Ser Gly
    6880                6885                6890 agt gtg gcc tcc ggt cgt atc tcg tac acg ttt ggt ttt gag ggt cct       20910
Ser Val Ala Ser Gly Arg Ile Ser Tyr Thr Phe Gly Phe Glu Gly Pro
6895                6900                6905                6910 gcg gtg tcg gtg gac acg gct tgt tcc tcg tcg ttg gtg gct tta cat       20958
Ala Val Ser Val Asp Thr Ala Cys Ser Ser Ser Leu Val Ala Leu His
                6915                6920                6925
```

| | |
|---|---|
| ctg gcc tgt cag gcg ttg cgt gcg ggt gag tgc tcg atg gcg ctt gcc<br>Leu Ala Cys Gln Ala Leu Arg Ala Gly Glu Cys Ser Met Ala Leu Ala<br>                      6930                        6935                        6940 | 21006 |
| ggg ggt gtg acg gtg atg tcg tct ccg ggt gcc ttc gtg gag ttt tcg<br>Gly Gly Val Thr Val Met Ser Ser Pro Gly Ala Phe Val Glu Phe Ser<br>                      6945                        6950                        6955 | 21054 |
| cgg cag cgg ggt ctg gcc gcg gac ggg cat tgc aag gcg ttc tcg gcg<br>Arg Gln Arg Gly Leu Ala Ala Asp Gly His Cys Lys Ala Phe Ser Ala<br>                      6960                        6965                        6970 | 21102 |
| gcg gcg gac ggg acc ggc tgg ggt gag ggt gtg ggg atg ctg ctg gtg<br>Ala Ala Asp Gly Thr Gly Trp Gly Glu Gly Val Gly Met Leu Leu Val<br>6975                        6980                        6985                        6990 | 21150 |
| gag cgg ctc tcc gac gcc cgt cgc aac ggt cac cgt gtc ctg gcc gtg<br>Glu Arg Leu Ser Asp Ala Arg Arg Asn Gly His Arg Val Leu Ala Val<br>                      6995                        7000                        7005 | 21198 |
| gtg cgt ggc agt gcg gtc aac cag gac ggt gcg agc aac ggg ctg acc<br>Val Arg Gly Ser Ala Val Asn Gln Asp Gly Ala Ser Asn Gly Leu Thr<br>                      7010                        7015                        7020 | 21246 |
| gcg ccc aac ggg ccc tcc cag cag cgt gtc atc cgc cag gcc ctc gcc<br>Ala Pro Asn Gly Pro Ser Gln Gln Arg Val Ile Arg Gln Ala Leu Ala<br>                      7025                        7030                        7035 | 21294 |
| aac gcc ggc ttg tcg gcc ggt gat gtc gat gcg gtg gag gcc cac ggc<br>Asn Ala Gly Leu Ser Ala Gly Asp Val Asp Ala Val Glu Ala His Gly<br>                      7040                        7045                        7050 | 21342 |
| acc ggc acc act ttg ggc gac ccg atc gag gcc cag gcc ctc ctt gcg<br>Thr Gly Thr Thr Leu Gly Asp Pro Ile Glu Ala Gln Ala Leu Leu Ala<br>7055                        7060                        7065                        7070 | 21390 |
| acc tac ggg cag gac cgt gcc ggc gag ggg ccg ctg tgg ctg ggc tcg<br>Thr Tyr Gly Gln Asp Arg Ala Gly Glu Gly Pro Leu Trp Leu Gly Ser<br>                      7075                        7080                        7085 | 21438 |
| gtc aag tcc aat gtc ggt cac aca cag gct gcc gcg ggc gtc gcc ggg<br>Val Lys Ser Asn Val Gly His Thr Gln Ala Ala Ala Gly Val Ala Gly<br>                      7090                        7095                        7100 | 21486 |
| gtg atc aag atg gtg atg gcg ctg cgg aat ggt ctg ctg ccg cgg acg<br>Val Ile Lys Met Val Met Ala Leu Arg Asn Gly Leu Leu Pro Arg Thr<br>                      7105                        7110                        7115 | 21534 |
| ttg cat gtg gat gag ccg tcg ccg cat gtg gac tgg tcc gcg ggt gcg<br>Leu His Val Asp Glu Pro Ser Pro His Val Asp Trp Ser Ala Gly Ala<br>                      7120                        7125                        7130 | 21582 |
| gtg cag ctg ctg acg gag acg gtg ccc tgg ccc ggc ggg gag ggg cgg<br>Val Gln Leu Leu Thr Glu Thr Val Pro Trp Pro Gly Gly Glu Gly Arg<br>7135                        7140                        7145                        7150 | 21630 |
| cta cgg cgg gca gga gtg tca tca ttc ggc gtc agc ggc acc aac gcc<br>Leu Arg Arg Ala Gly Val Ser Ser Phe Gly Val Ser Gly Thr Asn Ala<br>                      7155                        7160                        7165 | 21678 |
| cac gtc atc ctc gaa gaa gca ccc gcc cac aac atc ccg tca gac aca<br>His Val Ile Leu Glu Glu Ala Pro Ala His Asn Ile Pro Ser Asp Thr<br>                      7170                        7175                        7180 | 21726 |
| ccc gcc gac gac gtt ccg ggg gga cca ccc gcc ggc gag gat gcc ggt<br>Pro Ala Asp Asp Val Pro Gly Gly Pro Pro Ala Gly Glu Asp Ala Gly<br>                      7185                        7190                        7195 | 21774 |
| agt ggc gag gag gct gct gcc ggc agt cca ggg gtg tgg ccg tgg ctg<br>Ser Gly Glu Glu Ala Ala Ala Gly Ser Pro Gly Val Trp Pro Trp Leu<br>                      7200                        7205                        7210 | 21822 |
| gtg tcg gcc aag tcg cag ccg gcc ctg cgc gcc cag gcc cag gcc ctg<br>Val Ser Ala Lys Ser Gln Pro Ala Leu Arg Ala Gln Ala Gln Ala Leu<br>7215                        7220                        7225                        7230 | 21870 |
| cac gcc cac ctc acc gac cac ccc ggc ctc gac ctc gcc gac gtc gga<br>His Ala His Leu Thr Asp His Pro Gly Leu Asp Leu Ala Asp Val Gly | 21918 |

```
                    7235            7240            7245
tac acc ctc gcc cac gcc cgc gcc gtg ttc gac cac cgc gcc acc ctc     21966
Tyr Thr Leu Ala His Ala Arg Ala Val Phe Asp His Arg Ala Thr Leu
            7250            7255            7260 atc gcc gcc gac cgc gac acc ttc ctg caa gca ctc cag gca ctc gcc     22014
Ile Ala Ala Asp Arg Asp Thr Phe Leu Gln Ala Leu Gln Ala Leu Ala
            7265            7270            7275 gca ggc gaa ccc cac ccc gcc gtc atc cac agc agc gcc cca ggc ggg     22062
Ala Gly Glu Pro His Pro Ala Val Ile His Ser Ser Ala Pro Gly Gly
            7280            7285            7290 acc ggg acc ggg gag gcc gca gga aag acc gca ttc atc tgc tcc gga     22110
Thr Gly Thr Gly Glu Ala Ala Gly Lys Thr Ala Phe Ile Cys Ser Gly
7295            7300            7305            7310 cag ggc acc caa cgc ccc ggc atg gcc cac ggc ctc tac cac acc cac     22158
Gln Gly Thr Gln Arg Pro Gly Met Ala His Gly Leu Tyr His Thr His
            7315            7320            7325 ccc gtc ttc gcc gcc gca ctc aac gac atc tgc acc cac ctc gac ccc     22206
Pro Val Phe Ala Ala Ala Leu Asn Asp Ile Cys Thr His Leu Asp Pro
            7330            7335            7340 cac ctc gac cac ccc ctc ctc ccc ctc ctc acc cag gac ccc aac acc     22254
His Leu Asp His Pro Leu Leu Pro Leu Leu Thr Gln Asp Pro Asn Thr
            7345            7350            7355 cag gac acc acc acc ctc gaa gaa gcg gcc gca ctg ctc cag cag acc     22302
Gln Asp Thr Thr Thr Leu Glu Glu Ala Ala Ala Leu Leu Gln Gln Thr
            7360            7365            7370 ccg tac gcc cag ccc gcc ctc ttc gcc ttc cag gtc gcc ctc cac cgc     22350
Pro Tyr Ala Gln Pro Ala Leu Phe Ala Phe Gln Val Ala Leu His Arg
7375            7380            7385            7390 ctc ctc acc gac ggc tac cac atc acc ccc cac tac tac gcc gga cac     22398
Leu Leu Thr Asp Gly Tyr His Ile Thr Pro His Tyr Tyr Ala Gly His
            7395            7400            7405 tcc ctc ggc gaa atc acc gcc gcc cac ctc gcc ggc atc ctc acc ctc     22446
Ser Leu Gly Glu Ile Thr Ala Ala His Leu Ala Gly Ile Leu Thr Leu
            7410            7415            7420 acc gac gcc acc acc ctc atc acc caa cgc gcc acc ctc atg caa acc     22494
Thr Asp Ala Thr Thr Leu Ile Thr Gln Arg Ala Thr Leu Met Gln Thr
            7425            7430            7435 atg ccc ccc ggc acc atg acc acc ctc cac acc acc ccc cac cac atc     22542
Met Pro Pro Gly Thr Met Thr Thr Leu His Thr Thr Pro His His Ile
            7440            7445            7450 acc cac cac atc acc gcc cac gaa aac gac ctc gcc atc gcc gcc atc     22590
Thr His His Ile Thr Ala His Glu Asn Asp Leu Ala Ile Ala Ala Ile
7455            7460            7465            7470 aac acc ccc acc tcc ctc gtc atc agc ggc acc ccc cac acc gtc caa     22638
Asn Thr Pro Thr Ser Leu Val Ile Ser Gly Thr Pro His Thr Val Gln
            7475            7480            7485 cac atc acc acc ctc tgc caa caa caa ggc atc aaa acc aaa acc ctc     22686
His Ile Thr Thr Leu Cys Gln Gln Gln Gly Ile Lys Thr Lys Thr Leu
            7490            7495            7500 ccc acc aac cac gcc ttc cac tcc ccc cac acc aac ccc atc ctc aac     22734
Pro Thr Asn His Ala Phe His Ser Pro His Thr Asn Pro Ile Leu Asn
            7505            7510            7515 caa ctc cac cag cac acc caa acc ctc acc tac cac cca ccc cac acc     22782
Gln Leu His Gln His Thr Gln Thr Leu Thr Tyr His Pro Pro His Thr
            7520            7525            7530 ccc ctc atc acc gcc aac acc cca ccc gac caa ctc ctc acc ccc cac     22830
Pro Leu Ile Thr Ala Asn Thr Pro Pro Asp Gln Leu Leu Thr Pro His
7535            7540            7545            7550 tac tgg acc caa caa gcc cgc aac acc gtc gac ata gcc acc acc acc     22878
```

```
                                                                -continued

Tyr Trp Thr Gln Gln Ala Arg Asn Thr Val Asp Ile Ala Thr Thr Thr
            7555                7560                7565 caa acc ctc cac caa cac ggc gtc acc acc tac atc gaa ctc gga ccc      22926
Gln Thr Leu His Gln His Gly Val Thr Thr Tyr Ile Glu Leu Gly Pro
            7570                7575                7580 gac aac acc ctc acc acc ctc acc cac cac aac ctc ccc aac acc ccc      22974
Asp Asn Thr Leu Thr Thr Leu Thr His His Asn Leu Pro Asn Thr Pro
            7585                7590                7595 acc acc acc ctc acc ctc acc cac ccc cac cac cac ccc caa acc cac      23022
Thr Thr Thr Leu Thr Leu Thr His Pro His His His Pro Gln Thr His
            7600                7605            7610 ctc ctc acc aac ctc gcc aaa acc acc acc acc tgg cac ccc cac cac      23070
Leu Leu Thr Asn Leu Ala Lys Thr Thr Thr Thr Trp His Pro His His
7615                7620                7625                7630 tac acc cac cac cac aac caa ccc cac acc cac acc cac ctc gac ctc      23118
Tyr Thr His His His Asn Gln Pro His Thr His Thr His Leu Asp Leu
            7635                7640                7645 ccc acc tac ccc ttc caa cac cac cac tac tgg ctc gaa agc aca cag      23166
Pro Thr Tyr Pro Phe Gln His His His Tyr Trp Leu Glu Ser Thr Gln
            7650                7655                7660 ccc ggt gcc ggc aac gtg tca gca gcc gga ctc gac ccc acc gaa cac      23214
Pro Gly Ala Gly Asn Val Ser Ala Ala Gly Leu Asp Pro Thr Glu His
            7665                7670                7675 ccc cta ctc ggc gcc aca ttg gaa ctg gcc gaa ggg gac ggc tgc cta      23262
Pro Leu Leu Gly Ala Thr Leu Glu Leu Ala Glu Gly Asp Gly Cys Leu
            7680                7685            7690 ctg acg ggg cgc ctc tcg ttg cgc acg cat ccc tgg ctc gcc ggc cat      23310
Leu Thr Gly Arg Leu Ser Leu Arg Thr His Pro Trp Leu Ala Gly His
7695                7700                7705                7710 gcg gta ggc ggt gtc gtg ctg ctg ccg ggt acg gcc ttc gcg gaa ctg      23358
Ala Val Gly Gly Val Val Leu Leu Pro Gly Thr Ala Phe Ala Glu Leu
            7715                7720                7725 gcc ctt cat gcc gga gaa agt gtg ggt tgc gac cac gtg gac gag ctg      23406
Ala Leu His Ala Gly Glu Ser Val Gly Cys Asp His Val Asp Glu Leu
            7730                7735                7740 acg ctc cac aca ccg ttg gtc att cct gag gtc gga gac gtg acc ctt      23454
Thr Leu His Thr Pro Leu Val Ile Pro Glu Val Gly Asp Val Thr Leu
            7745                7750                7755 cag gtt gcc att gcg gcg ccg gac gag tcg ggt cgc cgc atg atg acc      23502
Gln Val Ala Ile Ala Ala Pro Asp Glu Ser Gly Arg Arg Met Met Thr
            7760                7765                7770 atc cac tca cgc ggt gag ggc ggc agt ggt gga gcc gat gcg tcg gcc      23550
Ile His Ser Arg Gly Glu Gly Gly Ser Gly Gly Ala Asp Ala Ser Ala
7775                7780                7785                7790 agt gcg tgg acg cgt cat gcc gcg ggt gtg ctg agc cct gcc aag gac      23598
Ser Ala Trp Thr Arg His Ala Ala Gly Val Leu Ser Pro Ala Lys Asp
            7795                7800                7805 gat gac act gcc tcg tac gag ctg ctt gcg gga ccc tgg cct ccc gtt      23646
Asp Asp Thr Ala Ser Tyr Glu Leu Leu Ala Gly Pro Trp Pro Pro Val
            7810                7815                7820 gga gct acg cct gtc gac ctg aac acg gct tac gat caa atg gcc gac      23694
Gly Ala Thr Pro Val Asp Leu Asn Thr Ala Tyr Asp Gln Met Ala Asp
            7825                7830                7835 gcc ggc ttt gct tat ggc ctg gca ttc caa ggg ttg cgc gcg gcc tgg      23742
Ala Gly Phe Ala Tyr Gly Leu Ala Phe Gln Gly Leu Arg Ala Ala Trp
            7840                7845                7850 cgc tac ggc gac gac atc ctc gtc gag gca cgt ctt ccc gaa gaa gtg      23790
Arg Tyr Gly Asp Asp Ile Leu Val Glu Ala Arg Leu Pro Glu Glu Val
7855                7860                7865                7870
```

| | |
|---|---|
| tcg gga gac gcg gcg gcg tac ggt ctg cac ccg gcc ctg ctc gac gct<br>Ser Gly Asp Ala Ala Ala Tyr Gly Leu His Pro Ala Leu Leu Asp Ala<br>        7875          7880        7885 | 23838 |
| gcc ctt cag ggc acc ggc ctg ctt tct gtg gcg ggt ccg ggg acg ccc<br>Ala Leu Gln Gly Thr Gly Leu Leu Ser Val Ala Gly Pro Gly Thr Pro<br>     7890          7895          7900 | 23886 |
| gtc gtg ccc cat gtg tgg aac ggt ctg cgg ttc cgt acg cat ggt gca<br>Val Val Pro His Val Trp Asn Gly Leu Arg Phe Arg Thr His Gly Ala<br>     7905          7910          7915 | 23934 |
| gtc tcc gtg cgc gcg tgc ctg tcg acg ctt gga gcg aca ggg gcg gcc<br>Val Ser Val Arg Ala Cys Leu Ser Thr Leu Gly Ala Thr Gly Ala Ala<br>     7920          7925          7930 | 23982 |
| gtg tgc gtg cgc atc acc gac gac acc ggg gtg ccg gtg gcg tcg gtc<br>Val Cys Val Arg Ile Thr Asp Asp Thr Gly Val Pro Val Ala Ser Val<br>7935         7940         7945         7950 | 24030 |
| gat cgt ctt gag ttg cgg cct gtg gat atg ggt cag ttg cgt gct gtc<br>Asp Arg Leu Glu Leu Arg Pro Val Asp Met Gly Gln Leu Arg Ala Val<br>         7955         7960         7965 | 24078 |
| tcg gtt tcg gcg ggg cgg cgg ggt tcg ctg tat gcg gtg cag tgg gct<br>Ser Val Ser Ala Gly Arg Arg Gly Ser Leu Tyr Ala Val Gln Trp Ala<br>     7970          7975          7980 | 24126 |
| gag gtg ggt cct gtg ccg gtg tgt ggg cag gcg tgg gcg tgg cac gag<br>Glu Val Gly Pro Val Pro Val Cys Gly Gln Ala Trp Ala Trp His Glu<br>     7985          7990          7995 | 24174 |
| gac gtg ggt gag agc ggt ggt ggg cct gtg ccg ggg gtg gtg gtg ttg<br>Asp Val Gly Glu Ser Gly Gly Gly Pro Val Pro Gly Val Val Val Leu<br>8000         8005         8010 | 24222 |
| cgg tgc ccg gat gcc ggt gcc gat ggc ggt ggc ggt ggt gtg ggt<br>Arg Cys Pro Asp Ala Gly Ala Asp Gly Gly Gly Gly Gly Val Gly<br>8015        8020         8025         8030 | 24270 |
| gag gtt gtt ggt ggg gtg ttg ggt gtg gtg cag ggg tgg ctg ggg ctg<br>Glu Val Val Gly Gly Val Leu Gly Val Val Gln Gly Trp Leu Gly Leu<br>         8035         8040         8045 | 24318 |
| gag cgg ttt gcg ggt tcg cgg ctg gtg gtg gtg acc cgg ggt gcg gtg<br>Glu Arg Phe Ala Gly Ser Arg Leu Val Val Val Thr Arg Gly Ala Val<br>     8050          8055          8060 | 24366 |
| gtg gcc ggc ccg gag gac ggc ccg gtg gat gtg gtg ggt gcg gcg gtg<br>Val Ala Gly Pro Glu Asp Gly Pro Val Asp Val Val Gly Ala Ala Val<br>     8065          8070          8075 | 24414 |
| tgg ggg ctg gtg cgg tcg gcg cag gct gag cat ccg gac cgg ttt gtc<br>Trp Gly Leu Val Arg Ser Ala Gln Ala Glu His Pro Asp Arg Phe Val<br>8080         8085         8090 | 24462 |
| ctc ctc gac ctg gac acc gac ctc gac agc ggc gct gac gcc gat gcc<br>Leu Leu Asp Leu Asp Thr Asp Leu Asp Ser Gly Ala Asp Ala Asp Ala<br>8095         8100         8105         8110 | 24510 |
| ggc aac gag gcc ggt atg ggg tct ggt ctg gat ggt ggg cgt gtg gct<br>Gly Asn Glu Ala Gly Met Gly Ser Gly Leu Asp Gly Gly Arg Val Ala<br>         8115         8120         8125 | 24558 |
| gcg gtg gtg gcg tgt ggt gag ccg cag ttg gcg gtg cgt ggt gag cgg<br>Ala Val Val Ala Cys Gly Glu Pro Gln Leu Ala Val Arg Gly Glu Arg<br>     8130          8135          8140 | 24606 |
| gtg ctg gcc gca cgc ctg aca cga ctt gag tcg ccg gtt gat gta tcg<br>Val Leu Ala Ala Arg Leu Thr Arg Leu Glu Ser Pro Val Asp Val Ser<br>         8145         8150         8155 | 24654 |
| ggt cgg gag gtg ttg ccg tgg ttg tcg ggt ggg tcg gtg ttg gtg acg<br>Gly Arg Glu Val Leu Pro Trp Leu Ser Gly Gly Ser Val Leu Val Thr<br>     8160          8165          8170 | 24702 |
| ggt ggg acg ggt gtg ctg ggt gcg gcg gtg gcg cgg cat ctg gct ggt<br>Gly Gly Thr Gly Val Leu Gly Ala Ala Val Ala Arg His Leu Ala Gly<br>8175         8180         8185         8190 | 24750 |

```
gtg tgt ggg gtg cgg gat ctg ttg ttg gtg agc cgg cgt ggt ccg gat    24798
Val Cys Gly Val Arg Asp Leu Leu Leu Val Ser Arg Arg Gly Pro Asp
        8195                    8200                    8205 gct ccg ggt gcg gag ggt ttg cgg gcg gag ctg gcc gcg ttg ggg gcg    24846
Ala Pro Gly Ala Glu Gly Leu Arg Ala Glu Leu Ala Ala Leu Gly Ala
        8210                    8215                    8220 gag gtg cgg att gtt gcg tgt gat gtg ggg gag cgg cgg gag gtg gtc    24894
Glu Val Arg Ile Val Ala Cys Asp Val Gly Glu Arg Arg Glu Val Val
        8225                    8230                    8235 cgg ctg ctg gag ggt gtt cct gcc ggg tgt ccg ctg acg ggt gtc gtg    24942
Arg Leu Leu Glu Gly Val Pro Ala Gly Cys Pro Leu Thr Gly Val Val
        8240                    8245                    8250 cat gcg gct ggt gtg ctg gac gat gcg acg atc gcc tct ctc acg ccc    24990
His Ala Ala Gly Val Leu Asp Asp Ala Thr Ile Ala Ser Leu Thr Pro
8255                    8260                    8265                    8270 gag cgg ctg ggc acg gtg ttc gcg gcc aag gtg gat gcc gct ctt ttg    25038
Glu Arg Leu Gly Thr Val Phe Ala Ala Lys Val Asp Ala Ala Leu Leu
                8275                    8280                    8285 ctg gat gag ctg acg cgg ggt atg gag ctg tcg gcg ttc gtg ctg ttc    25086
Leu Asp Glu Leu Thr Arg Gly Met Glu Leu Ser Ala Phe Val Leu Phe
        8290                    8295                    8300 tcc tcg gcc gcg ggg atc ctg ggg tcg gcc ggg cag ggc aac tac gcc    25134
Ser Ser Ala Ala Gly Ile Leu Gly Ser Ala Gly Gln Gly Asn Tyr Ala
        8305                    8310                    8315 gcg gcc aat gcc gct ctg gac gcg ctg gcg tac cgg cgg cgg gcg gcg    25182
Ala Ala Asn Ala Ala Leu Asp Ala Leu Ala Tyr Arg Arg Arg Ala Ala
        8320                    8325                    8330 ggt ctg ccg ggg gtg tcg ctg gcg tgg ggg ctg tgg gaa gag gcc agc    25230
Gly Leu Pro Gly Val Ser Leu Ala Trp Gly Leu Trp Glu Glu Ala Ser
8335                    8340                    8345                    8350 ggg atg acc ggg cac ctg gcc ggc acc gac cac cgg cgc atc atc cgt    25278
Gly Met Thr Gly His Leu Ala Gly Thr Asp His Arg Arg Ile Ile Arg
                8355                    8360                    8365 tcc ggt ctg cat ccc atg tcg acc ccg gac gca ctg gct ctc ttc gat    25326
Ser Gly Leu His Pro Met Ser Thr Pro Asp Ala Leu Ala Leu Phe Asp
        8370                    8375                    8380 gcg gcc ctg gct ctg gac cgg ccg gtc ctg ctg ccc gcc gac ctg cgt    25374
Ala Ala Leu Ala Leu Asp Arg Pro Val Leu Leu Pro Ala Asp Leu Arg
        8385                    8390                    8395 ccc gcc ccg ccc ctg ccg ccc ctg ctg cag gac ctc ctg ccc gcc acc    25422
Pro Ala Pro Pro Leu Pro Pro Leu Leu Gln Asp Leu Leu Pro Ala Thr
8400                    8405                    8410 cgc cgc cgc acc acc cgc acc acc act acc ggt ggt gcg gac aac ggc    25470
Arg Arg Arg Thr Thr Arg Thr Thr Thr Thr Gly Gly Ala Asp Asn Gly
8415                    8420                    8425                    8430 gcc cag ctg cat gcc cgg ctg gcc ggc cag aca cac gaa caa cag cac    25518
Ala Gln Leu His Ala Arg Leu Ala Gly Gln Thr His Glu Gln Gln His
        8435                    8440                    8445 acc acc ctc ctc gcc ctg gtc cgc tcc cac atc gcc acc gtc ctc ggc    25566
Thr Thr Leu Leu Ala Leu Val Arg Ser His Ile Ala Thr Val Leu Gly
        8450                    8455                    8460 cac aac gcg ccg gag atg atc ccc gtt gac tcg gcg ttc cgc gac cta    25614
His Asn Ala Pro Glu Met Ile Pro Val Asp Ser Ala Phe Arg Asp Leu
        8465                    8470                    8475 ggc ttc gac tcc ttg aca gcg gtg gaa ctc cgt aac cgc ctg ggt gag    25662
Gly Phe Asp Ser Leu Thr Ala Val Glu Leu Arg Asn Arg Leu Gly Glu
        8480                    8485                    8490 gca acg gga ctg cga ctg ccg acc agt ctg gtc ttc gac cag ccg aat    25710
Ala Thr Gly Leu Arg Leu Pro Thr Ser Leu Val Phe Asp Gln Pro Asn
```

-continued

| | |
|---|---|
| 8495            8500            8505            8510 | |
| gca gcg acc ctg gcg cgt cac cta cgt cgt gag ctg atg ggc gac gac<br>Ala Ala Thr Leu Ala Arg His Leu Arg Arg Glu Leu Met Gly Asp Asp<br>              8515                       8520                    8525 | 25758 |
| gcg gaa ggc gag acg cca tcg cag gtc gca ctt cat cag gtt gcc gcg<br>Ala Glu Gly Glu Thr Pro Ser Gln Val Ala Leu His Gln Val Ala Ala<br>              8530                       8535                    8540 | 25806 |
| gat gag ccg att gcg att gtg ggg atg gcg tgt cgt ttt ccg ggt ggg<br>Asp Glu Pro Ile Ala Ile Val Gly Met Ala Cys Arg Phe Pro Gly Gly<br>              8545                       8550                    8555 | 25854 |
| gtg tgt tcg ccg gag gag ttg tgg gag ctg gtt gcg tcg ggt ggg gat<br>Val Cys Ser Pro Glu Glu Leu Trp Glu Leu Val Ala Ser Gly Gly Asp<br>              8560                       8565                    8570 | 25902 |
| gcg att ggt gaa ttt ccg gcc ggt cgg ggg tgg gat ctg gag ggg ttg<br>Ala Ile Gly Glu Phe Pro Ala Gly Arg Gly Trp Asp Leu Glu Gly Leu<br>              8575                       8580                    8585                    8590 | 25950 |
| ttt gat tcg gac cct gac cgg tcg ggg acg tcg tac gcg cgg tat ggc<br>Phe Asp Ser Asp Pro Asp Arg Ser Gly Thr Ser Tyr Ala Arg Tyr Gly<br>                       8595                       8600                    8605 | 25998 |
| ggg ttt ttg tat gag gcg ggg gag ttc gat gcg gac ttc ttc ggg atc<br>Gly Phe Leu Tyr Glu Ala Gly Glu Phe Asp Ala Asp Phe Phe Gly Ile<br>              8610                       8615                    8620 | 26046 |
| agt ccg cgt gag gcg ttg gcg atg gat ccg cag cag cgg ttg ttg ctg<br>Ser Pro Arg Glu Ala Leu Ala Met Asp Pro Gln Gln Arg Leu Leu Leu<br>              8625                       8630                    8635 | 26094 |
| gag acg tcg tgg gag gcg ttc gag cgg gcg ggt atc gat ccg ctg tcg<br>Glu Thr Ser Trp Glu Ala Phe Glu Arg Ala Gly Ile Asp Pro Leu Ser<br>              8640                       8645                    8650 | 26142 |
| atg cgt ggc tcc cgt acg ggt gtc ttc gcc ggg gtg atg tac cac gac<br>Met Arg Gly Ser Arg Thr Gly Val Phe Ala Gly Val Met Tyr His Asp<br>8655                       8660                       8665                    8670 | 26190 |
| tac gcc gcg cgt ctc cac cat gtc ccc gag ggt ttc gaa ggc ctc atc<br>Tyr Ala Ala Arg Leu His His Val Pro Glu Gly Phe Glu Gly Leu Ile<br>                       8675                       8680                    8685 | 26238 |
| gcc aac ggc agc gca ggc agc gtc gcg acc ggc cgg gtg gcc tac agc<br>Ala Asn Gly Ser Ala Gly Ser Val Ala Thr Gly Arg Val Ala Tyr Ser<br>              8690                       8695                    8700 | 26286 |
| ttt ggc ctt gag ggt ccg gcc gtg acc gtc gat acg gcg tgt tcg tcg<br>Phe Gly Leu Glu Gly Pro Ala Val Thr Val Asp Thr Ala Cys Ser Ser<br>              8705                       8710                    8715 | 26334 |
| tcg ttg gtg gcg ttg cat tgg gcg gcg cag gcg ttg cgt gcg ggt gag<br>Ser Leu Val Ala Leu His Trp Ala Ala Gln Ala Leu Arg Ala Gly Glu<br>              8720                       8725                    8730 | 26382 |
| tgt tcg atg gcg ctt gcc ggg ggt gtg acg gtg atg tcg tct ccg ggt<br>Cys Ser Met Ala Leu Ala Gly Gly Val Thr Val Met Ser Ser Pro Gly<br>8735                       8740                       8745                    8750 | 26430 |
| acg ttt gtg gag ttc tca cgt cag cgg ggt ctg gcc gcg gac ggg cgg<br>Thr Phe Val Glu Phe Ser Arg Gln Arg Gly Leu Ala Ala Asp Gly Arg<br>              8755                       8760                    8765 | 26478 |
| tgc aag gcc tat tcg gcg gct gct gac ggt acc ggc tgg gcc gag ggt<br>Cys Lys Ala Tyr Ser Ala Ala Ala Asp Gly Thr Gly Trp Ala Glu Gly<br>              8770                       8775                    8780 | 26526 |
| gtg ggg atg ctg ctg gtg gag cgg ctc tcc gac gcc gtc gcc aac ggt<br>Val Gly Met Leu Leu Val Glu Arg Leu Ser Asp Ala Arg Arg Asn Gly<br>              8785                       8790                    8795 | 26574 |
| cac cgt gtc ctg gcc gtg gtg cgt ggc agt gcg gtc aac cag gac ggt<br>His Arg Val Leu Ala Val Val Arg Gly Ser Ala Val Asn Gln Asp Gly<br>              8800                       8805                    8810 | 26622 |
| gcg agc aac ggt ctg acc gcg ccc aac ggg ccc tcc cag cag cgt gtc | 26670 |

```
Ala Ser Asn Gly Leu Thr Ala Pro Asn Gly Pro Ser Gln Gln Arg Val
8815            8820            8825            8830 atc cgt cag gcc ctg gcc aat gcg gga ctg acc ccg gcc gat gtc gac    26718
Ile Arg Gln Ala Leu Ala Asn Ala Gly Leu Thr Pro Ala Asp Val Asp
                8835            8840            8845 gca gtg gag ggc cac ggc acc ggg acc act ctg ggg gac ccg atc gag    26766
Ala Val Glu Gly His Gly Thr Gly Thr Thr Leu Gly Asp Pro Ile Glu
        8850            8855            8860 gcc cag gca ctc ctg gcc gcc tac gga caa cac cgc ccc cac cac cgc    26814
Ala Gln Ala Leu Leu Ala Ala Tyr Gly Gln His Arg Pro His His Arg
    8865            8870            8875 ccc ttg tgg ctg gga tcc ctc aaa tcc aac atc ggg cac gca cag gcc    26862
Pro Leu Trp Leu Gly Ser Leu Lys Ser Asn Ile Gly His Ala Gln Ala
8880            8885            8890 gcc gcg ggc gtg ggc gga gtc atc aag atg gtg atg gcc ctg cgc aac    26910
Ala Ala Gly Val Gly Gly Val Ile Lys Met Val Met Ala Leu Arg Asn
8895            8900            8905            8910 ggg ctg ctg cca cag acc ctc cac gtg gac gag ccc acc ccc cag gtc    26958
Gly Leu Leu Pro Gln Thr Leu His Val Asp Glu Pro Thr Pro Gln Val
                8915            8920            8925 gac tgg tcc aca ggc gca gta caa ctc ctg aca caa ccg gtg ccc tgg    27006
Asp Trp Ser Thr Gly Ala Val Gln Leu Leu Thr Gln Pro Val Pro Trp
        8930            8935            8940 ccc gcc gac ccg gcc ggc cgg cca cgc cac gcc ggc gtg tca tca ttc    27054
Pro Ala Asp Pro Ala Gly Arg Pro Arg His Ala Gly Val Ser Ser Phe
    8945            8950            8955 ggc gtc agc ggc acc aac gcc cat gtg att ttg gag gag gcg cct gcg    27102
Gly Val Ser Gly Thr Asn Ala His Val Ile Leu Glu Glu Ala Pro Ala
8960            8965            8970 gcg gcg ggc ggt gct gcc ggt ggt ggg gtg tcg gtg ggt gct ccg aat    27150
Ala Ala Gly Gly Ala Ala Gly Gly Gly Val Ser Val Gly Ala Pro Asn
8975            8980            8985            8990 cca gcc ctt ccg gtg gct gag tct gag ccg gtg ccg gtg ccg gtg ccg    27198
Pro Ala Leu Pro Val Ala Glu Ser Glu Pro Val Pro Val Pro Val Pro
                8995            9000            9005 gtg tcg gcg agg tct gag gcc ggg ttg cgg gcg cag gca cag gcg ttg    27246
Val Ser Ala Arg Ser Glu Ala Gly Leu Arg Ala Gln Ala Gln Ala Leu
        9010            9015            9020 cgc cag tac gtg gca gcc cgc ccg gac atg tca cct gcc gac atc ggt    27294
Arg Gln Tyr Val Ala Ala Arg Pro Asp Met Ser Pro Ala Asp Ile Gly
    9025            9030            9035 gcg ggt ctg gcc cgc ggc cgg gcc gta ctg gaa cac cgc gcc gtc atc    27342
Ala Gly Leu Ala Arg Gly Arg Ala Val Leu Glu His Arg Ala Val Ile
9040            9045            9050 ctg gcc gcg gac cgc gag gaa ctg gcg cag gca ctg aca gcc ctg gca    27390
Leu Ala Ala Asp Arg Glu Glu Leu Ala Gln Ala Leu Thr Ala Leu Ala
9055            9060            9065            9070 gcc ggc gaa ccc cac ccc cac atc acc aca ggc cac acc cgg ggc agt    27438
Ala Gly Glu Pro His Pro His Ile Thr Thr Gly His Thr Arg Gly Ser
                9075            9080            9085 gac cgc ggc ggc gtc gtc ttc gtc ttc ccc gga cag ggc ggc cag tgg    27486
Asp Arg Gly Gly Val Val Phe Val Phe Pro Gly Gln Gly Gly Gln Trp
        9090            9095            9100 gcc ggg atg ggc ctg acc ctg ctc acc tcc tca ccc gtg ttc gcc gaa    27534
Ala Gly Met Gly Leu Thr Leu Leu Thr Ser Ser Pro Val Phe Ala Glu
    9105            9110            9115 cac atc gac gca tgc gag aaa gcc ctc acc ccc tgg gtg ccc tgg tcc    27582
His Ile Asp Ala Cys Glu Lys Ala Leu Thr Pro Trp Val Pro Trp Ser
9120            9125            9130
```

```
ctg acc gac atc ctg cac cgc gac ccc gac gac ccc gca tgg caa caa    27630
Leu Thr Asp Ile Leu His Arg Asp Pro Asp Asp Pro Ala Trp Gln Gln
9135                9140                9145                9150 gcc gac gtg gtc cag ccc gtg ctc ttc agc atc atg gtc tcc ctc gcc    27678
Ala Asp Val Val Gln Pro Val Leu Phe Ser Ile Met Val Ser Leu Ala
                9155                9160                9165 gcc ctg tgg cgc tcc tac ggc atc gaa ccc gac gcg gtc ctc ggc cac    27726
Ala Leu Trp Arg Ser Tyr Gly Ile Glu Pro Asp Ala Val Leu Gly His
                    9170                9175                9180 tcc cag gga gaa atc gcc gcc gcc cac atc tgc ggc gca ctc agc ctg    27774
Ser Gln Gly Glu Ile Ala Ala Ala His Ile Cys Gly Ala Leu Ser Leu
9185                9190                9195 aaa gac gcc gcc aaa acc gtt gca ctg cgc agc cag gca ctg gcc gcc    27822
Lys Asp Ala Ala Lys Thr Val Ala Leu Arg Ser Gln Ala Leu Ala Ala
    9200                9205                9210 gta cga ggc cgg ggc gcc atg gtc tca ctg ccc ctg ccc gcc cag gac    27870
Val Arg Gly Arg Gly Ala Met Val Ser Leu Pro Leu Pro Ala Gln Asp
9215                9220                9225                9230 gtg cag cag ctc att tcc gaa cgg tgg gaa ggg cag ttg tgg gtg gca    27918
Val Gln Gln Leu Ile Ser Glu Arg Trp Glu Gly Gln Leu Trp Val Ala
                9235                9240                9245 gcc ctc aac ggc ccc cac tcc acc acc gtc tcc ggc gac acc acc gca    27966
Ala Leu Asn Gly Pro His Ser Thr Thr Val Ser Gly Asp Thr Thr Ala
                    9250                9255                9260 gta gaa gaa ctc ctc acc cac tgt gcc gac acc ggc cta cgg gcc aaa    28014
Val Glu Glu Leu Leu Thr His Cys Ala Asp Thr Gly Leu Arg Ala Lys
                        9265                9270                9275 cgc atc ccc gtc gac tac gcc tcc cac tgc ccc cac gtc caa ccc ctc    28062
Arg Ile Pro Val Asp Tyr Ala Ser His Cys Pro His Val Gln Pro Leu
    9280                9285                9290 cac gac gaa ctc ctg cac ctg ctg gga gac atc acc ccc cag ccg tcc    28110
His Asp Glu Leu Leu His Leu Leu Gly Asp Ile Thr Pro Gln Pro Ser
9295                9300                9305                9310 acc atg ccg ttc ttc tcc acc gtc gta ggg cac ctg gtc tgg tac acc    28158
Thr Met Pro Phe Phe Ser Thr Val Val Gly His Leu Val Trp Tyr Thr
                9315                9320                9325 aca acc ctg gac gcc gcc tac tgg tac cgc aac ctc cac cag ccc gtc    28206
Thr Thr Leu Asp Ala Ala Tyr Trp Tyr Arg Asn Leu His Gln Pro Val
                    9330                9335                9340 cgc ttc agc cac gcc atc cag acc ctg acc gac gac gga cac cgc ccc    28254
Arg Phe Ser His Ala Ile Gln Thr Leu Thr Asp Asp Gly His Arg Pro
                        9345                9350                9355 ttc atc gaa atc agt ccc cac ccc acc ctc gtc ccc gcc atc gaa gac    28302
Phe Ile Glu Ile Ser Pro His Pro Thr Leu Val Pro Ala Ile Glu Asp
    9360                9365                9370 acc acc gaa aac acc acc gaa aac atc acc gcg acc ggc agc ctc cgc    28350
Thr Thr Glu Asn Thr Thr Glu Asn Ile Thr Ala Thr Gly Ser Leu Arg
9375                9380                9385                9390 cgc ggc gac aac gac acc cac cgc ttc ctc acc gcc ctc gcc cac acc    28398
Arg Gly Asp Asn Asp Thr His Arg Phe Leu Thr Ala Leu Ala His Thr
                9395                9400                9405 cac acc acc ggc att cgg aca ccc acc acc tgg cac cac cac tac acc    28446
His Thr Thr Gly Ile Arg Thr Pro Thr Thr Trp His His His Tyr Thr
                    9410                9415                9420 caa acc cac ccc cac ccc cac aac cac cac ctc gac ctg ccc acc tac    28494
Gln Thr His Pro His Pro His Asn His His Leu Asp Leu Pro Thr Tyr
                        9425                9430                9435 ccc ttc caa cac cag cac tac tgg ctc caa cca ccc acc acg aca acc    28542
Pro Phe Gln His Gln His Tyr Trp Leu Gln Pro Pro Thr Thr Thr Thr
    9440                9445                9450
```

-continued

```
gac ctc acc acc acc ggc ctc acc ccc acc cac cac ccc ctc ctc acc       28590
Asp Leu Thr Thr Thr Gly Leu Thr Pro Thr His His Pro Leu Leu Thr
9455                9460                9465                9470 gca aca ctc acc ctc gcc aac aac aac aca caa cta ctc acc ggc cgc       28638
Ala Thr Leu Thr Leu Ala Asn Asn Asn Thr Gln Leu Leu Thr Gly Arg
            9475                9480                9485 ctc tcc cta cgc acc cac ccc tgg ctc acc gac cac acc gtc gtc ggt       28686
Leu Ser Leu Arg Thr His Pro Trp Leu Thr Asp His Thr Val Val Gly
        9490                9495                9500 acc act ctt gtg cca gga acc gcc ctc ctc gaa ctc gcc ctc caa gca       28734
Thr Thr Leu Val Pro Gly Thr Ala Leu Leu Glu Leu Ala Leu Gln Ala
    9505                9510                9515 acc acg acc gac cac ctc gaa gaa ctc gcc ctc cac acg cct ctc gtc       28782
Thr Thr Thr Asp His Leu Glu Glu Leu Ala Leu His Thr Pro Leu Val
9520                9525                9530 atc ccc cgt gag ggt gcc gtc gac gtt cag gtg cac atc aat cca ccg       28830
Ile Pro Arg Glu Gly Ala Val Asp Val Gln Val His Ile Asn Pro Pro
9535                9540                9545                9550 gac gac acc gac act cgt tca ctg acg atc tac tcg cga agc gag aac       28878
Asp Asp Thr Asp Thr Arg Ser Leu Thr Ile Tyr Ser Arg Ser Glu Asn
            9555                9560                9565 gcc ccc gca gcg gct ccc tgg cgt cat cac gcc acg gcc gtt ctg gga       28926
Ala Pro Ala Ala Ala Pro Trp Arg His His Ala Thr Ala Val Leu Gly
        9570                9575                9580 acc aag acc tcg cgc att gag aca ggc cgt agc cac gat gat ctg tcg       28974
Thr Lys Thr Ser Arg Ile Glu Thr Gly Arg Ser His Asp Asp Leu Ser
    9585                9590                9595 atg tgg ccg cca gcg ggc gca gtt cgc tgt gct gat gag gaa ttg gca       29022
Met Trp Pro Pro Ala Gly Ala Val Arg Cys Ala Asp Glu Glu Leu Ala
9600                9605                9610 gcc ttg tat ggc gac tac gag gca aat ggc ttt gtc tat ggc ccc gca       29070
Ala Leu Tyr Gly Asp Tyr Glu Ala Asn Gly Phe Val Tyr Gly Pro Ala
9615                9620                9625                9630 ttc cgg ggg ctg act gct gcc tgg cgt ctg gga gac gag gtg ttt gcc       29118
Phe Arg Gly Leu Thr Ala Ala Trp Arg Leu Gly Asp Glu Val Phe Ala
            9635                9640                9645 gag gtt cgc ctt cca gaa cag gtg cac ggc gag gca tcc gcg tac aac       29166
Glu Val Arg Leu Pro Glu Gln Val His Gly Glu Ala Ser Ala Tyr Asn
        9650                9655                9660 ctg cac ccg gca ctg ctg gat gct gcc ttg cac gca gcg gcc ttt gcg       29214
Leu His Pro Ala Leu Leu Asp Ala Ala Leu His Ala Ala Ala Phe Ala
    9665                9670                9675 ccg tcg ggc agt ctg ccg cag gga tcc gta ccg ttc tcc ttc acc ggt       29262
Pro Ser Gly Ser Leu Pro Gln Gly Ser Val Pro Phe Ser Phe Thr Gly
9680                9685                9690 gtg acg ctg cac gcc gcc aat gcg tcg tcg ttg cgc gtg cga ctc tcg       29310
Val Thr Leu His Ala Ala Asn Ala Ser Ser Leu Arg Val Arg Leu Ser
9695                9700                9705                9710 ccg gcc gat ccg aac agc ggc cac gcc gca gtt tcc gtg ctg gtc acg       29358
Pro Ala Asp Pro Asn Ser Gly His Ala Ala Val Ser Val Leu Val Thr
            9715                9720                9725 gat gac acc ggt acg ccc gtg gcg tcc gtc gag gcg ttg gcg gtg cgc       29406
Asp Asp Thr Gly Thr Pro Val Ala Ser Val Glu Ala Leu Ala Val Arg
        9730                9735                9740 ccg ttg gcg gcg gac gaa ttg cga gct gcc gag cgc gcc gta cag cgc       29454
Pro Leu Ala Ala Asp Glu Leu Arg Ala Ala Glu Arg Ala Val Gln Arg
    9745                9750                9755 gct gag ctc ttc gac atg aag tgg gtt gag gtg ccc tca gat gta ctg       29502
Ala Glu Leu Phe Asp Met Lys Trp Val Glu Val Pro Ser Asp Val Leu
```

|     |     |
| --- | --- |
| gtg tcg ggc ggg gca tcg gtg gtg gtg ctg gat ggt gcc gac gac ctc<br>Val Ser Gly Gly Ala Ser Val Val Val Leu Asp Gly Ala Asp Asp Leu<br>9775                  9780                  9785                  9790 | 29550 |
| gtt ggt ctg gcg gct gag gag gat ggt gtg ccg ggg gtg gtg gtg ttg<br>Val Gly Leu Ala Ala Glu Glu Asp Gly Val Pro Gly Val Val Val Leu<br>                 9795                  9800                  9805 | 29598 |
| cgg tgc ccg gat gcc ggt gcc gat ggc ggc ggt ggc ggt ggt gtg<br>Arg Cys Pro Asp Ala Gly Ala Asp Gly Gly Gly Gly Gly Gly Val<br>9810                  9815                  9820 | 29646 |
| ggt gag gtt gtt ggt ggg gtg ttg ggt gtg gtg cag ggg tgg ctg ggg<br>Gly Glu Val Val Gly Gly Val Leu Gly Val Val Gln Gly Trp Leu Gly<br>9825                  9830                  9835 | 29694 |
| ctg gag cgg ttt gcg ggt tcg cgg ctg gtg gtg gtg acc cgg ggt gcg<br>Leu Glu Arg Phe Ala Gly Ser Arg Leu Val Val Val Thr Arg Gly Ala<br>        9840                  9845                  9850 | 29742 |
| gtg gtg gcc ggc ccg gag gac ggc ccg gtg gat ggc ccg gtg gat gtg<br>Val Val Ala Gly Pro Glu Asp Gly Pro Val Asp Gly Pro Val Asp Val<br>9855                  9860                  9865                  9870 | 29790 |
| gtg ggt gcg gcg gtg tgg ggg ctg gtg cgg tcg gcg cag gct gag cat<br>Val Gly Ala Ala Val Trp Gly Leu Val Arg Ser Ala Gln Ala Glu His<br>        9875                  9880                  9885 | 29838 |
| ccg gac cgg ttt gtc ctc ctc gac ctg gac acc gac ctc gac agc ggc<br>Pro Asp Arg Phe Val Leu Leu Asp Leu Asp Thr Asp Leu Asp Ser Gly<br>              9890                  9895                  9900 | 29886 |
| gct gac cgc gat gcc ggc aac gag gcc ggt atg ggg tct ggt ctg gat<br>Ala Asp Arg Asp Ala Gly Asn Glu Ala Gly Met Gly Ser Gly Leu Asp<br>9905                  9910                  9915 | 29934 |
| ggt ggg cgt gtg gct gcg gtg gtg gcg tgt ggt gag ccg cag ttg gcg<br>Gly Gly Arg Val Ala Ala Val Val Ala Cys Gly Glu Pro Gln Leu Ala<br>        9920                  9925                  9930 | 29982 |
| gtg cgt ggt gag cgg gtg ctg gcc gca cgc ctg aca cga ctt gag tcg<br>Val Arg Gly Glu Arg Val Leu Ala Ala Arg Leu Thr Arg Leu Glu Ser<br>9935                  9940                  9945                  9950 | 30030 |
| ccg gtt gat gta tcg ggt cgg gag gtg ttg ccg tgg ttg tcg ggt ggg<br>Pro Val Asp Val Ser Gly Arg Glu Val Leu Pro Trp Leu Ser Gly Gly<br>              9955                  9960                  9965 | 30078 |
| tcg gtg ttg gtg acg ggt ggg acg ggt gtg ctg ggt gcg gcg gtg gcg<br>Ser Val Leu Val Thr Gly Gly Thr Gly Val Leu Gly Ala Ala Val Ala<br>        9970                  9975                  9980 | 30126 |
| cgg cat ctg gct ggt gtg tgt ggg gtg cgg gat ctg ttg ttg gtg agc<br>Arg His Leu Ala Gly Val Cys Gly Val Arg Asp Leu Leu Leu Val Ser<br>              9985                  9990                  9995 | 30174 |
| cgg cgt ggt ccg gat gct ccg ggt gcg gag ggt ttg cgg gcg gag ctg<br>Arg Arg Gly Pro Asp Ala Pro Gly Ala Glu Gly Leu Arg Ala Glu Leu<br>10000                10005                10010 | 30222 |
| gcc gcg ttg ggg gcg gag gtg cgg att gtt gcg tgt gat gtg ggg gag<br>Ala Ala Leu Gly Ala Glu Val Arg Ile Val Ala Cys Asp Val Gly Glu<br>10015                10020                10025                10030 | 30270 |
| cgg cgg gag gtg gtc cgg ctg ctg gag ggt gtt cct gcc ggg tgt ccg<br>Arg Arg Glu Val Val Arg Leu Leu Glu Gly Val Pro Ala Gly Cys Pro<br>            10035                10040                10045 | 30318 |
| ctg acg ggt gtc gtg cat gcg gct ggt gtg ctg gac gat gcg acg atc<br>Leu Thr Gly Val Val His Ala Ala Gly Val Leu Asp Asp Ala Thr Ile<br>10050                10055                10060 | 30366 |
| gcc tct ctc acg ccc gag cgg ctg ggc acg gtg ttc gcg gcc aag gtg<br>Ala Ser Leu Thr Pro Glu Arg Leu Gly Thr Val Phe Ala Ala Lys Val<br>            10065                10070                10075 | 30414 |
| gat gcc gct ctt ttg ctg gat gag ctg acg cgg ggt atg gag ctg tcg | 30462 |

```
                Asp Ala Ala Leu Leu Leu Asp Glu Leu Thr Arg Gly Met Glu Leu Ser
                    10080               10085               10090 gcg ttc gtg ctg ttc tcc tcg gcc gcg ggg atc ctg ggg tcg gcc ggg              30510
Ala Phe Val Leu Phe Ser Ser Ala Ala Gly Ile Leu Gly Ser Ala Gly
10095               10100               10105               10110 cag ggc aac tac gcc gcg gcc aat gcc gct ctg gac gcg ctg gcg tac              30558
Gln Gly Asn Tyr Ala Ala Ala Asn Ala Ala Leu Asp Ala Leu Ala Tyr
                10115               10120               10125 cgg cgg cgg gcg gcg ggt ctg ccg ggg gtg tcg ctg gcg tgg ggg ctg              30606
Arg Arg Arg Ala Ala Gly Leu Pro Gly Val Ser Leu Ala Trp Gly Leu
                    10130               10135               10140 tgg gaa gag gcc agc ggg atg acc ggg cat ctg gcc ggc acc gac cac              30654
Trp Glu Glu Ala Ser Gly Met Thr Gly His Leu Ala Gly Thr Asp His
            10145               10150               10155 cgg cgc atc atc cgt tcc ggt ctg cat ccc atg tcg acc ccg gac gca              30702
Arg Arg Ile Ile Arg Ser Gly Leu His Pro Met Ser Thr Pro Asp Ala
                10160               10165               10170 ctg gcc ctc ttc gat gcg gcc ctg gct ctg gac cgg ccg gtc ctg ctg              30750
Leu Ala Leu Phe Asp Ala Ala Leu Ala Leu Asp Arg Pro Val Leu Leu
10175               10180               10185               10190 ccc gcc gac ctg cgt ccc gcc ccg ccc ctg ccg ccc ctg ctg cag gac              30798
Pro Ala Asp Leu Arg Pro Ala Pro Pro Leu Pro Pro Leu Leu Gln Asp
                10195               10200               10205 ctc ctg ccc gcc acc cgc cgc gcc acc acc cgc acc acc act acc ggt              30846
Leu Leu Pro Ala Thr Arg Arg Arg Thr Thr Arg Thr Thr Thr Thr Gly
                10210               10215               10220 ggt gcg gac aac ggc gcc cag ctg cac ggc cgg ctg gcc ggc cag aca              30894
Gly Ala Asp Asn Gly Ala Gln Leu His Gly Arg Leu Ala Gly Gln Thr
                10225               10230               10235 cac gaa caa cag cac acc acc ctc ctc gcc ctg gtc cgc tcc cac atc              30942
His Glu Gln Gln His Thr Thr Leu Leu Ala Leu Val Arg Ser His Ile
        10240               10245               10250 gcc acc gtc ctg ggc cac acc acc ccc gac acc atc ccc ccc gac cgc              30990
Ala Thr Val Leu Gly His Thr Thr Pro Asp Thr Ile Pro Pro Asp Arg
10255               10260               10265               10270 gcg ttc cgc gac ctc ggc ttc gac tcc ctc acc gcc gtc gaa cta cgc              31038
Ala Phe Arg Asp Leu Gly Phe Asp Ser Leu Thr Ala Val Glu Leu Arg
            10275               10280               10285 aac cgg ctc tcc cac acc acc gga ctc cgc ctc ccc acc acc ctc gcc              31086
Asn Arg Leu Ser His Thr Thr Gly Leu Arg Leu Pro Thr Thr Leu Ala
                10290               10295               10300 ttc gac cac ccc aac ccc acc acc ctc acc cac cac ctc cac aca caa              31134
Phe Asp His Pro Asn Pro Thr Thr Leu Thr His His Leu His Thr Gln
            10305               10310               10315 ctc gtc agc aag gga ctc acc gcc gcg gcc gag ccg gac gcc gca acg              31182
Leu Val Ser Lys Gly Leu Thr Ala Ala Ala Glu Pro Asp Ala Ala Thr
                10320               10325               10330 aca ccc ccg ggg ctg ccc tcg ctg ctc tcg gag ctc gag cgg ctg gag              31230
Thr Pro Pro Gly Leu Pro Ser Leu Leu Ser Glu Leu Glu Arg Leu Glu
10335               10340               10345               10350 gcg gta gtg ctc tcc tcc acc aca tcc tcc gct gcc ccg ctg gac gac              31278
Ala Val Val Leu Ser Ser Thr Thr Ser Ser Ala Ala Pro Leu Asp Asp
                10355               10360               10365 ggc gcg cgc acg cgg ctg gcc tcc cga ctg cat tcc ctc gcc cag aag              31326
Gly Ala Arg Thr Arg Leu Ala Ser Arg Leu His Ser Leu Ala Gln Lys
                10370               10375               10380 ttg aac ggc gac gac acc gcc ccc gac ctc gca gag aca tcg gac gag              31374
Leu Asn Gly Asp Asp Thr Ala Pro Asp Leu Ala Glu Thr Ser Asp Glu
                10385               10390               10395
```

-continued

```
gag atg ttc gct ctc atc gac agg gaa gtc gga ttc gaa tct caa tga      31422
Glu Met Phe Ala Leu Ile Asp Arg Glu Val Gly Phe Glu Ser Gln
    10400           10405               10410
```

<210> SEQ ID NO 3
<211> LENGTH: 3972
<212> TYPE: PRT
<213> ORGANISM: Streptomyces avermitilis

<400> SEQUENCE: 3

```
Val Gln Arg Met Asp Gly Gly Glu Pro Arg Pro Ala Ala Gly Glu
 1               5                  10                  15

Val Leu Gly Val Ala Asp Glu Ala Asp Gly Val Val Phe Val Phe
                20                  25                  30

Pro Gly Gln Gly Pro Gln Trp Pro Gly Met Gly Arg Glu Leu Leu Asp
            35                  40                  45

Ala Ser Asp Val Phe Arg Glu Ser Val Arg Ala Cys Glu Ala Ala Phe
        50                  55                  60

Ala Pro Tyr Val Asp Trp Ser Val Glu Gln Val Leu Arg Asp Ser Pro
 65                  70                  75                  80

Asp Ala Pro Gly Leu Asp Arg Val Asp Val Gln Pro Thr Leu Phe
                85                  90                  95

Ala Val Met Ile Ser Leu Ala Ala Leu Trp Arg Ser Gln Gly Val Glu
                100                 105                 110

Pro Cys Ala Val Leu Gly His Ser Leu Gly Glu Ile Ala Ala His
            115                 120                 125

Val Ser Gly Gly Leu Ser Leu Ala Asp Ala Ala Arg Val Val Thr Leu
    130                 135                 140

Trp Ser Gln Ala Gln Thr Thr Leu Ala Gly Thr Gly Ala Leu Val Ser
145                 150                 155                 160

Val Ala Ala Thr Pro Asp Glu Leu Leu Pro Arg Ile Ala Pro Trp Thr
                165                 170                 175

Glu Asp Asn Pro Ala Arg Leu Ala Val Ala Ala Val Asn Gly Pro Arg
            180                 185                 190

Ser Thr Val Val Ser Gly Ala Arg Glu Ala Val Ala Asp Leu Val Ala
        195                 200                 205

Asp Leu Thr Ala Ala Gln Val Arg Thr Arg Met Ile Pro Val Asp Val
    210                 215                 220

Pro Ala His Ser Pro Leu Met Tyr Ala Ile Glu Glu Arg Val Val Ser
225                 230                 235                 240

Gly Leu Leu Pro Ile Thr Pro Arg Pro Ser Arg Ile Pro Phe His Ser
                245                 250                 255

Ser Val Thr Gly Gly Arg Leu Asp Thr Arg Glu Leu Asp Ala Ala Tyr
            260                 265                 270

Trp Tyr Arg Asn Met Ser Ser Thr Val Arg Phe Glu Pro Ala Ala Arg
        275                 280                 285

Leu Leu Leu Gln Gln Gly Pro Lys Thr Phe Val Glu Met Ser Pro His
    290                 295                 300

Pro Val Leu Thr Met Gly Leu Gln Glu Leu Ala Pro Asp Leu Gly Asp
305                 310                 315                 320

Thr Thr Gly Thr Ala Asp Thr Val Ile Met Gly Thr Leu Arg Arg Gly
                325                 330                 335

Gln Gly Thr Leu Asp His Phe Leu Thr Ser Leu Ala Gln Leu Arg Gly
            340                 345                 350

His Gly Glu Thr Ser Ala Thr Thr Val Leu Ser Ala Arg Leu Thr Ala
```

-continued

```
            355                 360                 365
Leu Ser Pro Thr Gln Gln Ser Leu Leu Asp Leu Val Arg Ala
        370                 375                 380
His Thr Met Ala Val Leu Asn Asp Asp Gly Asn Glu Arg Thr Ala Ser
385                 390                 395                 400
Asp Ala Gly Pro Ser Ala Ser Phe Ala His Leu Gly Phe Asp Ser Val
                405                 410                 415
Met Gly Val Glu Leu Arg Asn Arg Leu Ser Lys Ala Thr Gly Leu Arg
                420                 425                 430
Leu Pro Val Thr Leu Ile Phe Asp His Thr Thr Pro Ala Ala Val Ala
                435                 440                 445
Ala Arg Leu Arg Thr Ala Ala Leu Gly His Leu Asp Glu Asp Thr Ala
    450                 455                 460
Pro Val Pro Asp Ser Pro Ser Gly His Gly Gly Thr Ala Ala Ala Asp
465                 470                 475                 480
Asp Pro Ile Ala Ile Ile Gly Met Ala Cys Arg Phe Pro Gly Gly Val
                485                 490                 495
Arg Ser Pro Lys Asp Leu Trp Glu Leu Ala Ala Ser Gly Gly Asp Ala
                500                 505                 510
Ile Gly Pro Phe Pro Thr Asp Arg Gly Trp Pro Thr Glu Gln Arg His
                515                 520                 525
Ala Gln Asp Pro Thr Gln Pro Gly Thr Phe Tyr Pro Gln Gly Gly Gly
                530                 535                 540
Phe Leu His Asp Ala Ala His Phe Asp Ala Gly Phe Phe Gly Ile Ser
545                 550                 555                 560
Pro Arg Glu Ala Leu Ala Met Asp Pro Gln Gln Arg Leu Leu Leu Glu
                565                 570                 575
Thr Ser Trp Glu Ala Phe Glu Arg Ala Gly Ile Asp Pro Leu Ser Val
                580                 585                 590
Arg Gly Ser Arg Thr Gly Val Phe Ala Gly Ala Leu Ser Phe Asp Tyr
                595                 600                 605
Gly Pro Arg Met Asp Thr Ala Ser Ser Glu Gly Ala Ala Asp Val Glu
        610                 615                 620
Gly His Ile Leu Thr Gly Thr Thr Gly Ser Val Leu Ser Gly Arg Ile
625                 630                 635                 640
Ala Tyr Ser Phe Gly Leu Glu Gly Pro Ala Ile Thr Val Asp Thr Gly
                645                 650                 655
Cys Ser Ala Ser Leu Val Thr Leu His Leu Ala Cys Gln Ser Leu Arg
                660                 665                 670
Ser Gly Glu Cys Thr Leu Ala Leu Ala Gly Gly Val Ser Val Met Ser
                675                 680                 685
Thr Leu Gly Met Phe Ile Glu Phe Ser Arg Gln Arg Gly Leu Ser Val
        690                 695                 700
Asp Gly Arg Cys Lys Ala Tyr Ser Ala Ala Ala Asp Gly Thr Gly Trp
705                 710                 715                 720
Gly Glu Gly Val Gly Met Leu Leu Val Glu Arg Leu Ser Asp Ala Val
                725                 730                 735
Arg Leu Gly His Arg Val Leu Ala Val Val Arg Gly Ser Ala Val Asn
                740                 745                 750
Gln Asp Gly Ala Ser Asn Gly Leu Thr Ala Pro Asn Gly Pro Ala Gln
                755                 760                 765
Glu Arg Val Ile Arg Gln Ala Leu Ala Asn Ala Gly Leu Ser Val Ala
        770                 775                 780
```

-continued

```
Asp Val Asp Val Val Glu Gly His Gly Thr Gly Thr Thr Leu Gly Asp
785                 790                 795                 800

Pro Ile Glu Ala Gln Ala Leu Leu Ala Thr Tyr Gly Gln Arg Ala Gly
                805                 810                 815

Asp Arg Pro Leu Trp Leu Gly Ser Leu Lys Ser Asn Ile Gly His Thr
            820                 825                 830

Met Ala Ala Ala Gly Val Gly Gly Val Ile Lys Met Val Met Ala Leu
        835                 840                 845

Arg Glu Gly Val Leu Pro Arg Thr Leu His Val Asp Lys Pro Ser Pro
    850                 855                 860

Gln Val Asp Trp Ser Ala Gly Ala Val Arg Leu Leu Thr Glu Ala Val
865                 870                 875                 880

Pro Trp Pro Gly Asp Ala Ala Gly Arg Leu Arg Ala Gly Val Ser
                885                 890                 895

Ser Phe Gly Ile Gly Gly Thr Asn Ala His Val Ile Leu Glu Glu Ala
                900                 905                 910

Pro Ala Ala Gly Gly Cys Val Ala Gly Gly Gly Val Leu Glu Gly Ala
                915                 920                 925

Pro Gly Leu Ala Ile Ser Val Ala Glu Ser Val Ala Ala Pro Val Ala
            930                 935                 940

Val Ser Ala Pro Val Ala Glu Ser Val Pro Val Pro Val Pro Val Pro
945                 950                 955                 960

Val Pro Val Pro Val Ser Ala Arg Ser Glu Ala Gly Leu Arg Ala Gln
                965                 970                 975

Ala Glu Ala Leu Arg Gln Tyr Val Ala Val Arg Pro Asp Val Ser Leu
            980                 985                 990

Ala Asp Val Gly Ala Gly Leu Ala Cys Gly Arg Ala Val Leu Glu His
                995                1000                1005

Arg Ala Val Val Leu Ala Ala Asp Arg Glu Glu Leu Val Gln Gly Leu
           1010                1015                1020

Gly Ala Leu Ala Ala Gly Glu Pro Asp Arg Arg Val Thr Thr Gly His
1025                1030                1035                1040

Ala Pro Gly Gly Asp Arg Gly Gly Val Val Phe Val Phe Pro Gly Gln
                1045                1050                1055

Gly Gly Gln Trp Ala Gly Met Gly Val Arg Leu Leu Ala Ser Ser Pro
            1060                1065                1070

Val Phe Ala Arg Arg Met Gln Ala Cys Glu Glu Ala Leu Ala Pro Trp
            1075                1080                1085

Val Asp Trp Ser Val Val Asp Ile Leu Arg Arg Asp Ala Gly Asp Ala
            1090                1095                1100

Val Trp Glu Arg Ala Asp Val Val Gln Pro Val Leu Phe Ser Val Met
1105                1110                1115                1120

Val Ser Leu Ala Ala Leu Trp Arg Ser Tyr Gly Ile Glu Pro Asp Ala
                1125                1130                1135

Val Leu Gly His Ser Gln Gly Glu Ile Ala Ala Ala His Val Cys Gly
            1140                1145                1150

Ala Leu Ser Leu Lys Asp Ala Ala Lys Thr Val Ala Leu Arg Ser Arg
            1155                1160                1165

Ala Leu Ala Ala Val Arg Gly Arg Gly Gly Met Ala Ser Val Pro Leu
            1170                1175                1180

Pro Ala Gln Glu Val Glu Gln Leu Ile Gly Glu Arg Trp Ala Gly Arg
1185                1190                1195                1200
```

```
Leu Trp Val Ala Ala Val Asn Gly Pro Arg Ser Thr Ala Val Ser Gly
            1205                1210                1215

Asp Ala Glu Ala Val Asp Glu Val Leu Ala Tyr Cys Ala Gly Thr Gly
            1220                1225                1230

Val Arg Ala Arg Arg Ile Pro Val Asp Tyr Ala Ser His Cys Pro His
        1235                1240                1245

Val Gln Pro Leu Arg Glu Glu Leu Leu Glu Leu Leu Gly Asp Ile Ser
    1250                1255                1260

Pro Gln Pro Ser Gly Val Pro Phe Phe Ser Thr Val Glu Gly Thr Trp
1265                1270                1275                1280

Leu Asp Thr Thr Thr Leu Asp Ala Ala Tyr Trp Tyr Arg Asn Leu His
                1285                1290                1295

Gln Pro Val Arg Phe Ser Asp Ala Val Gln Ala Leu Ala Asp Asp Gly
            1300                1305                1310

His Arg Val Phe Val Glu Val Ser Pro His Pro Thr Leu Val Pro Ala
        1315                1320                1325

Ile Glu Asp Thr Thr Glu Asp Thr Ala Glu Asp Val Thr Ala Ile Gly
    1330                1335                1340

Ser Leu Arg Arg Gly Asp Asn Asp Thr Arg Arg Phe Leu Thr Ala Leu
1345                1350                1355                1360

Ala His Thr His Thr Thr Gly Ile Gly Thr Pro Thr Thr Trp His His
                1365                1370                1375

His Tyr Thr His His His Thr His Pro His Pro His Thr His Leu Asp
            1380                1385                1390

Leu Pro Thr Tyr Pro Phe Gln His Gln His Tyr Trp Leu Glu Ser Ser
        1395                1400                1405

Gln Pro Gly Ala Gly Ser Gly Ser Gly Ala Gly Ala Gly Ser Gly Ala
    1410                1415                1420

Gly Ser Gly Arg Ala Gly Thr Ala Gly Gly Thr Ala Glu Val Glu Ser
1425                1430                1435                1440

Arg Phe Trp Asp Ala Val Ala Arg Gln Asp Leu Glu Thr Val Ala Thr
                1445                1450                1455

Thr Leu Ala Val Pro Pro Ser Ala Gly Leu Asp Thr Val Val Pro Ala
            1460                1465                1470

Leu Ser Ala Trp His Arg His Gln His Asp Gln Ala Arg Ile Asn Thr
        1475                1480                1485

Trp Thr Tyr Gln Glu Thr Trp Lys Pro Leu Thr Leu Pro Thr Thr His
    1490                1495                1500

Gln Pro His Gln Thr Trp Leu Ile Ala Ile Pro Glu Thr Gln Thr His
1505                1510                1515                1520

His Pro His Ile Thr Asn Ile Leu Thr Asn Leu His His His Gly Ile
                1525                1530                1535

Thr Pro Ile Pro Leu Thr Leu Asn His Thr His Thr Asn Pro Gln His
            1540                1545                1550

Leu His His Thr Leu His His Thr Arg Gln Gln Ala Gln Asn His Thr
        1555                1560                1565

Thr Gly Ala Ile Thr Gly Leu Leu Ser Leu Leu Ala Leu Asp Glu Thr
    1570                1575                1580

Pro His Pro His His Pro His Thr Pro Thr Gly Thr Leu Leu Asn Leu
1585                1590                1595                1600

Thr Leu Thr Gln Thr His Thr Gln Thr His Pro Pro Thr Pro Leu Trp
                1605                1610                1615

Tyr Ala Thr Thr Asn Ala Thr Thr Thr His Pro Asn Asp Pro Leu Thr
```

-continued

```
                1620                1625                1630
His Pro Thr Gln Ala Gln Thr Trp Gly Leu Ala Arg Thr Thr Leu Leu
                1635                1640                1645
Glu His Pro Thr His Thr Ala Gly Ile Ile Asp Leu Pro Thr Thr Pro
                1650                1655                1660
Thr Pro His Thr Leu Gln His Leu Thr Gln Thr Leu Thr Gln Pro His
1665                1670                1675                1680
His Gln Thr Gln Leu Ala Ile Arg Thr Thr Gly Thr His Thr Arg Arg
                1685                1690                1695
Leu Thr Pro Thr Thr Leu Thr Pro Thr His Gln Pro Pro Thr Pro Thr
                1700                1705                1710
Pro His Gly Thr Thr Leu Ile Thr Gly Gly Thr Gly Ala Leu Ala Thr
                1715                1720                1725
His Leu Thr His His Leu Thr Thr His Gln Pro Thr Gln His Leu Leu
                1730                1735                1740
Leu Thr Ser Arg Thr Gly Pro His Thr Pro His Ala Gln His Leu Thr
1745                1750                1755                1760
Thr Gln Leu Gln Gln Lys Gly Ile His Leu Thr Ile Thr Thr Cys Asp
                1765                1770                1775
Thr Ser Asn Pro Asp Gln Leu Gln Gln Leu Leu Asn Thr Ile Pro Pro
                1780                1785                1790
Gln His Pro Leu Thr Thr Val Ile His Thr Ala Gly Ile Leu Asp Asp
                1795                1800                1805
Ala Thr Leu Thr Asn Leu Thr Pro Thr Gln Leu Asn Asn Val Leu Arg
                1810                1815                1820
Ala Lys Ala His Ser Ala His Leu Leu His Gln Leu Thr Gln His Thr
1825                1830                1835                1840
Pro Leu Thr Ala Phe Val Leu Tyr Ser Ser Ala Ala Ala Thr Phe Gly
                1845                1850                1855
Ala Pro Gly Gln Ala Asn Tyr Ala Ala Ala Asn Ala Tyr Leu Asp Ala
                1860                1865                1870
Leu Ala His His Arg His Thr His His Leu Pro Ala Thr Ser Ile Ala
                1875                1880                1885
Trp Gly Thr Trp Gln Gly Asn Gly Leu Ala Asp Ser Asp Lys Ala Arg
                1890                1895                1900
Ala Tyr Leu Asp Arg Arg Gly Phe Arg Pro Met Ser Pro Glu Leu Ala
1905                1910                1915                1920
Thr Ala Ala Val Thr Gln Ala Ile Ala Asp Thr Glu Arg Pro Tyr Val
                1925                1930                1935
Val Ile Ala Asp Ile Asp Trp Ser Lys Ile Glu His Thr Ser Gln Thr
                1940                1945                1950
Ser Asp Leu Val Ser Ala Ala Arg Glu Arg Glu Pro Ala Val Gln Arg
                1955                1960                1965
Pro Thr Pro Pro Ala Glu Leu His Lys Thr Leu Ala His Gln Thr Ser
                1970                1975                1980
Ala Asp Gln Arg Ala Ala Leu Leu Glu Leu Val Arg Asp His Val Ala
1985                1990                1995                2000
Ala Val Leu Arg His Ala Asp Pro Lys Ala Ile Ala Pro Asp Gln Ser
                2005                2010                2015
Phe Arg Ala Leu Gly Phe Asp Ser Leu Thr Ala Val Glu Phe Arg Asn
                2020                2025                2030
Leu Leu Ile Lys Ala Thr Gly Leu Arg Leu Pro Val Ser Leu Val Phe
                2035                2040                2045
```

-continued

Asp His Pro Thr Pro Ala Lys Leu Ala Val His Leu Gln Asn Gln Leu
    2050                2055                2060

Arg Gly Thr Ala Ala Glu Ser Ala Pro Ser Ala Ala Val Thr Ala
2065            2070                2075                2080

Glu Ala Ser Val Thr Glu Pro Ile Ala Ile Val Gly Met Ala Cys Arg
                2085                2090                2095

Phe Pro Gly Gly Val Thr Ser Ala Asp Asp Phe Trp Asp Leu Ile Ser
            2100                2105                2110

Ser Glu Gln Asp Ala Ile Gly Gly Phe Pro Thr Asp Arg Gly Trp Asp
        2115                2120                2125

Leu Asp Thr Leu Tyr Asp Pro Asp Pro Asp His Pro Gly Thr Cys Tyr
    2130                2135                2140

Thr Arg Asn Gly Gly Phe Leu Tyr Asp Ala Gly His Phe Asp Ala Glu
2145            2150                2155                2160

Phe Phe Gly Ile Ser Pro Arg Glu Ala Leu Ala Met Asp Pro Gln Gln
                2165                2170                2175

Arg Leu Leu Leu Glu Thr Ala Trp Glu Thr Ile Glu His Ala Gly Ile
            2180                2185                2190

Asn Pro His Thr Leu His Gly Thr Pro Thr Gly Val Phe Thr Gly Thr
        2195                2200                2205

Asn Gly Gln Asp Tyr Ala Leu Arg Val His Asn Ala Gly Gln Ser Thr
    2210                2215                2220

Asp Gly Phe Ala Leu Thr Gly Thr Ala Gly Ser Val Ile Ser Gly Arg
2225            2230                2235                2240

Ile Ser Tyr Thr Phe Gly Phe Glu Gly Pro Ala Val Ser Val Asp Thr
                2245                2250                2255

Ala Cys Ser Ser Ser Leu Val Ala Leu His Leu Ala Cys Gln Ala Leu
            2260                2265                2270

Arg Ala Gly Glu Cys Ser Met Ala Leu Ala Gly Gly Val Thr Val Met
        2275                2280                2285

Ser Ser Pro Gly Ala Phe Val Glu Phe Ser Arg Gln Arg Gly Leu Ala
    2290                2295                2300

Ala Asp Gly His Cys Lys Ala Phe Ser Ala Ala Ala Asp Gly Thr Gly
2305            2310                2315                2320

Trp Gly Glu Gly Val Gly Met Leu Leu Val Glu Arg Leu Ser Asp Ala
                2325                2330                2335

His Arg Asn Gly His Arg Val Leu Ala Val Val Arg Gly Ser Ala Val
            2340                2345                2350

Asn Gln Asp Gly Ala Ser Asn Gly Leu Thr Ala Pro Asn Gly Pro Ser
        2355                2360                2365

Gln Gln Arg Val Ile Arg Gln Ala Leu Ala Asn Ala Gly Leu Ser Ala
    2370                2375                2380

Gly Asp Val Asp Ala Val Glu Ala His Gly Thr Gly Thr Thr Leu Gly
2385            2390                2395                2400

Asp Pro Ile Glu Ala Gln Ala Leu Leu Ala Thr Tyr Gly Gln Asp Arg
                2405                2410                2415

Ala Gly Glu Gly Pro Leu Trp Leu Gly Ser Val Lys Ser Asn Val Gly
            2420                2425                2430

His Thr Gln Ala Ala Ala Gly Val Ala Gly Val Ile Lys Met Val Met
        2435                2440                2445

Ala Leu Arg His Gly Leu Leu Pro Arg Thr Leu His Val Asp Glu Pro
    2450                2455                2460

```
Ser Pro His Val Asp Trp Ser Ala Gly Ala Val Gln Leu Leu Thr Glu
2465                2470                2475                2480

Thr Val Pro Trp Pro Gly Glu Gly Arg Leu Arg Arg Ala Gly Val
            2485                2490                2495

Ser Ser Phe Gly Val Ser Gly Thr Asn Ala His Val Ile Leu Glu Glu
                2500                2505                2510

Ala Pro Ala Asp Asp Val Pro Gly Gly Pro Ala Gly Glu Gly Asp
            2515                2520                2525

Ala Gly Ser Asp Asp Glu Ala Ala Gly Ser Pro Gly Val Trp Pro
            2530                2535                2540

Trp Leu Val Ser Ala Lys Ser Gln Pro Ala Leu Arg Ala Gln Ala Gln
2545                2550                2555                2560

Ala Leu His Ala His Leu Thr Asp His Pro Gly Leu Asp Leu Ala Asp
                2565                2570                2575

Val Gly Tyr Thr Leu Ala His Ala Arg Ala Val Phe Asp His Arg Ala
                2580                2585                2590

Thr Leu Ile Ala Ala Asp Arg Asp Thr Phe Leu Gln Ala Leu Gln Ala
                2595                2600                2605

Leu Ala Ala Gly Glu Pro His Pro Ala Val Ile His Ser Ser Ala Pro
2610                2615                2620

Gly Gly Thr Gly Thr Gly Glu Ala Ala Gly Lys Thr Ala Phe Ile Cys
2625                2630                2635                2640

Ser Gly Gln Gly Thr Gln Arg Pro Gly Met Ala His Gly Leu Tyr His
                2645                2650                2655

Thr His Pro Val Phe Ala Ala Leu Asn Asp Ile Cys Thr His Leu
            2660                2665                2670

Asp Pro His Leu Asp His Pro Leu Leu Pro Leu Leu Thr Gln Asn Asp
            2675                2680                2685

Asn Asp Asn Glu Asp Ala Ala Ala Leu Leu Gln Gln Thr Arg Tyr Ala
            2690                2695                2700

Gln Pro Ala Leu Phe Ala Phe Gln Val Ala Leu His Arg Leu Leu Thr
2705                2710                2715                2720

Asp Gly Tyr His Ile Thr Pro His Tyr Tyr Ala Gly His Ser Leu Gly
                2725                2730                2735

Glu Ile Thr Ala Ala His Leu Ala Gly Ile Leu Thr Leu Thr Asp Ala
                2740                2745                2750

Thr Thr Leu Ile Thr Gln Arg Ala Thr Leu Met Gln Thr Met Pro Pro
            2755                2760                2765

Gly Thr Met Thr Thr Leu His Thr Thr Pro His His Ile Thr His His
    2770                2775                2780

Leu Thr Ala His Glu Asn Asp Leu Ala Ile Ala Ala Ile Asn Thr Pro
2785                2790                2795                2800

Thr Ser Leu Val Ile Ser Gly Thr Pro His Thr Val Gln His Ile Thr
                2805                2810                2815

Thr Leu Cys Gln Gln Gln Gly Ile Lys Thr Lys Thr Leu Pro Thr Asn
                2820                2825                2830

His Ala Phe His Ser Pro His Thr Asn Pro Ile Leu Asn Gln Leu His
            2835                2840                2845

Gln His Thr Gln Thr Leu Thr Tyr His Pro His Thr Pro Leu Ile
    2850                2855                2860

Thr Ala Asn Thr Pro Pro Asp Gln Leu Leu Thr Pro His Tyr Trp Thr
2865                2870                2875                2880

Gln Gln Ala Arg Asn Thr Val Asp Tyr Ala Thr Thr Thr Gln Thr Leu
```

-continued

```
                2885                2890                2895
His Gln His Gly Val Thr Thr Tyr Ile Glu Leu Gly Pro Asp Asn Thr
                2900                2905                2910

Leu Thr Thr Leu Thr His His Asn Leu Pro Asn Pro Pro Thr Thr Thr
                2915                2920                2925

Leu Thr Leu Thr His Pro His His Pro Gln Thr His Leu Leu Thr
                2930                2935            2940

Asn Leu Ala Lys Thr Thr Thr Thr Trp His Pro His His Tyr Thr His
2945                2950                2955                2960

His Asp Asn Gln Pro His Thr His Thr His Leu Asp Leu Pro Thr Tyr
                2965                2970                2975

Pro Phe Gln His His His Tyr Trp Leu Glu Ser Thr Gln Pro Gly Ala
                2980                2985            2990

Gly Asn Val Ser Ala Ala Gly Leu Asp Pro Thr Glu His Pro Leu Leu
                2995            3000                3005

Gly Ala Thr Leu Glu Leu Ala Thr Asp Gly Gly Ala Leu Leu Ala Gly
            3010                3015                3020

Arg Leu Ser Leu Arg Ser His Pro Trp Leu Ala Asp His Ala Val Gly
3025                3030                3035                3040

Gly Thr Val Leu Leu Ser Gly Ala Thr Phe Leu Glu Leu Ala Leu His
                3045                3050                3055

Ala Gly Thr Tyr Val Gly Cys Asp Arg Val Asp Glu Leu Thr Leu His
                3060                3065                3070

Ala Pro Leu Val Val Pro Val Asp Gly Gly Val Ser Val Gln Val Gly
            3075                3080                3085

Val Ala Ala Ala Asp Gly Glu Gly Arg Arg Leu Val Ser Val Tyr Ala
            3090                3095                3100

Arg Gly Gly Ser Ala Cys Gly Gly Gly Gly Ala Ser Gly Gly Val Trp
3105                3110                3115                3120

Thr Cys His Ala Ser Gly Val Leu Val Glu Ala Ala Gly Gly Val
            3125                3130                3135

Val Val Asp Gly Leu Ala Gly Val Trp Pro Pro Arg Gly Ala Val Ala
            3140                3145                3150

Val Asp Val Asp Gly Val Arg Asp Arg Leu Ala Gly Ala Gly Cys Val
            3155                3160                3165

Leu Gly Pro Val Phe Ser Gly Leu Arg Ala Val Trp Arg Asp Gly Gly
            3170                3175            3180

Asp Leu Leu Ala Glu Val Cys Leu Pro Glu Glu Ala Trp Gly Asp Ala
3185                3190                3195                3200

Ala Gly Phe Gly Leu His Pro Ala Leu Leu Asp Gly Val Val Gln Pro
                3205                3210                3215

Leu Ser Val Leu Leu Pro Gly Gly Thr Gly Phe Gly Glu Gly Ala Gly
                3220                3225            3230

Phe Gly Glu Gly Val Arg Val Pro Ala Val Trp Gly Val Ser Leu
                3235                3240                3245

His Arg Ala Gly Val Thr Gly Val Arg Val Ser Ala Val Gly
            3250                3255            3260

Arg Gly Gly Gly Arg Glu Ala Val Ser Val Val Gly Asp Glu Ala
3265                3270                3275                3280

Gly Val Pro Val Ala Ser Val Asp Arg Leu Glu Leu Arg Pro Val Asp
                3285                3290                3295

Met Gly Gln Leu Arg Ala Val Ser Val Ser Ala Gly Arg Arg Gly Ser
            3300                3305                3310
```

```
Leu Tyr Ala Val Gln Trp Ala Glu Val Gly Pro Val Pro Val Cys Gly
         3315                3320                3325

Gln Ala Trp Ala Trp His Glu Asp Val Gly Glu Ser Gly Gly Gly Pro
     3330                3335                3340

Val Pro Gly Val Val Leu Arg Cys Pro Asp Ala Gly Ala Gly Gly
3345                3350                3355                3360

Gly Gly Gly Gly Gly Gly Gly Gly Val Gly Glu Val Val Gly Gly
             3365                3370                3375

Val Leu Gly Val Val Gln Gly Trp Leu Gly Leu Glu Arg Phe Ala Gly
         3380                3385                3390

Ser Arg Leu Val Val Val Thr Arg Gly Ala Val Ala Gly Pro Glu
         3395                3400                3405

Asp Gly Pro Val Asp Val Val Gly Ala Ser Val Trp Gly Leu Val Arg
     3410                3415                3420

Ser Ala Gln Ala Glu His Pro Asp Arg Phe Val Leu Leu Asp Leu Asp
3425                3430                3435                3440

Thr Asp Thr Gly Thr Asp Leu Asp Thr Gly Ala Gly Ala Gly Trp Gly
             3445                3450                3455

Val Asp Gly Gly Arg Val Ala Ala Val Val Ala Cys Gly Glu Pro Gln
         3460                3465                3470

Leu Ala Val Arg Gly Glu Arg Leu Leu Ala Ala Arg Leu Lys Arg Leu
         3475                3480                3485

Glu Ser Ser Gly Asp Val Pro Ala Gln Arg Ser Gly Asp Thr Arg Ala
     3490                3495                3500

Arg Arg Ser Asp Val Pro Ala Gln Arg Ser Gly Val Pro Ala Arg
3505                3510                3515                3520

Arg Ser Val Asp Val Ser Gly Arg Glu Val Leu Pro Trp Leu Ser Gly
             3525                3530                3535

Gly Ser Val Leu Val Thr Gly Thr Gly Val Leu Gly Ala Ala Val
         3540                3545                3550

Ala Arg His Leu Ala Gly Val Cys Gly Val Arg Asp Leu Leu Leu Val
         3555                3560                3565

Ser Arg Arg Gly Pro Asp Ala Pro Gly Ala Glu Gly Leu Arg Ala Glu
     3570                3575                3580

Leu Ala Ala Leu Gly Ala Glu Val Arg Ile Val Ala Cys Asp Val Gly
3585                3590                3595                3600

Glu Arg Arg Glu Val Val Arg Leu Leu Glu Gly Val Pro Ala Gly Cys
             3605                3610                3615

Pro Leu Thr Gly Val Val His Ala Ala Gly Val Leu Asp Asp Ala Thr
         3620                3625                3630

Ile Ala Ser Leu Thr Pro Glu Arg Leu Gly Thr Val Phe Ala Ala Lys
         3635                3640                3645

Val Asp Ala Ala Leu Leu Leu Asp Glu Leu Thr Arg Gly Met Glu Leu
     3650                3655                3660

Ser Ala Phe Val Leu Phe Ser Ser Ala Ala Gly Ile Leu Gly Ser Ala
3665                3670                3675                3680

Gly Gln Gly Asn Tyr Ala Ala Ala Asn Ala Ala Leu Asp Ala Leu Ala
             3685                3690                3695

Tyr Arg Arg Arg Ala Ala Gly Leu Pro Gly Val Ser Leu Ala Trp Gly
         3700                3705                3710

Leu Trp Glu Glu Ala Ser Gly Met Thr Gly His Leu Ala Gly Thr Asp
         3715                3720                3725
```

-continued

```
His Arg Arg Ile Ile Arg Ser Gly Leu His Pro Met Ser Thr Pro Asp
    3730                3735                3740

Ala Leu Ala Leu Phe Asp Ala Ala Leu Ala Leu Asp Arg Pro Val Leu
3745            3750                3755                3760

Leu Pro Ala Asp Leu Arg Pro Ala Pro Pro Leu Pro Pro Leu Leu Gln
        3765                3770                3775

Asp Leu Leu Pro Ala Thr Arg Arg Thr Thr Arg Thr Thr Thr Thr Thr
            3780                3785                3790

Gly Gly Ala Asp Asn Gly Ala Gln Leu His Ala Arg Leu Ala Gly Gln
        3795                3800                3805

Thr His Glu Gln Gln His Thr Thr Leu Leu Ala Leu Val Arg Ser His
    3810                3815                3820

Ile Ala Thr Val Leu Gly His Thr Thr Pro Asp Thr Ile Pro Pro Asp
3825            3830                3835                3840

Arg Ala Phe Arg Asp Leu Gly Phe Asp Ser Leu Thr Ala Val Glu Leu
            3845                3850                3855

Arg Asn Arg Leu Ser Arg Thr Thr Gly Leu Arg Leu Pro Thr Thr Leu
        3860                3865                3870

Ala Phe Asp His Pro Asn Pro Thr Thr Leu Thr His His Leu His Thr
        3875                3880                3885

Gln Leu Gln Pro Gln Pro Asp Asn Ala Val Ala Pro Val Leu Ala Glu
    3890                3895                3900

Leu Asp Lys Leu Glu Ser Ala Leu Ser Ala Leu Asp Lys Thr Asp Ser
3905            3910                3915                3920

Ala Ser Glu Arg Val Thr Leu Arg Leu Lys Ser Leu Met Leu Arg Trp
            3925                3930                3935

Asn Ala Pro Gln His Pro Thr Ala Glu Ser Ala Asp Asp Glu Lys
        3940                3945                3950

Phe Thr Ser Ala Thr Glu Ala Glu Ile Phe Lys Phe Ile Asp Asn Asp
        3955                3960                3965

Leu Gly Leu Ser
    3970

<210> SEQ ID NO 4
<211> LENGTH: 6239
<212> TYPE: PRT
<213> ORGANISM: Streptomyces avermitilis

<400> SEQUENCE: 4

Met Gln Leu Ala Asn Glu Ala Lys Leu Leu Glu Tyr Leu Lys Arg Val
 1               5                  10                  15

Thr Ala Asp Leu Asp Arg Thr Arg Arg Arg Leu Tyr Glu Val Val Glu
            20                  25                  30

Arg Glu Gln Glu Pro Ile Ala Ile Val Gly Met Ala Cys Arg Tyr Pro
        35                  40                  45

Gly Gly Ala Thr Ser Pro Thr Arg Leu Trp His Leu Val Lys Ser Gln
    50                  55                  60

Thr Asp Ala Ile Gly Glu Phe Pro Thr Asp Arg Gly Trp Asn Leu Glu
65                  70                  75                  80

Gln Leu Tyr Asp Pro Asp Pro Asp Arg Ser Gly Thr Ser Tyr Thr Arg
                85                  90                  95

Ser Gly Gly Phe Leu Tyr Asp Ala Gly Asp Phe Asp Ala Ala Phe Phe
            100                 105                 110

Glu Leu Ser Pro Arg Glu Ala Leu Ala Met Asp Pro Gln Gln Arg Leu
        115                 120                 125
```

```
Leu Leu Glu Thr Thr Trp Glu Thr Phe Glu Gln Gly Gly Ile Asp Pro
    130                 135                 140

Arg Ser Met Arg Gly Ser Arg Thr Gly Val Phe Val Gly Ile Asn Pro
145                 150                 155                 160

Glu Asp Tyr Thr Thr Gly Tyr Thr His Gln Pro Ser Asn Ala Val Glu
                165                 170                 175

Gly Tyr Leu Leu Thr Gly Ser Ala Ala Ser Ile Ala Ser Gly Arg Ile
            180                 185                 190

Ser Tyr Asn Phe Gly Leu Glu Gly Pro Ala Ile Thr Ile Asp Thr Ala
        195                 200                 205

Cys Ser Ser Ser Leu Val Ala Leu His Leu Ala Cys Gln Ala Leu Arg
    210                 215                 220

Ser Gly Glu Cys Thr Met Ala Leu Ala Gly Gly Ala Ser Val Met Ala
225                 230                 235                 240

Thr Pro Phe Val Phe Thr Glu Phe Ser Arg Gln Arg Gly Leu Ala Ala
                245                 250                 255

Asp Gly Arg Cys Lys Ala Phe Ser Ala Ala Asp Gly Thr Gly Trp
            260                 265                 270

Ser Glu Gly Val Gly Met Leu Leu Val Glu Arg Leu Ser Asp Ala Arg
            275                 280                 285

Arg Asn Gly His Arg Val Leu Ala Val Val Arg Gly Ser Ala Val Asn
        290                 295                 300

Gln Asp Gly Ala Ser Asn Gly Leu Thr Ala Pro Asn Gly Arg Ser Gln
305                 310                 315                 320

Val Lys Val Ile Arg Gln Ala Leu Ala Asn Ala His Leu Ser Pro Ala
                325                 330                 335

Asp Val Asp Ala Val Glu Ala His Gly Thr Gly Thr Thr Leu Gly Asp
            340                 345                 350

Pro Ile Glu Ala Gln Ala Leu Val Glu Ala Tyr Gly Gln Asp Arg Pro
        355                 360                 365

Asn Gly Arg Pro Leu Trp Leu Gly Thr Leu Lys Ser Asn Ile Gly His
    370                 375                 380

Ser Met Ala Ala Ala Gly Val Gly Gly Val Ile Lys Met Val Met Ala
385                 390                 395                 400

Leu Arg Asn Gly Leu Leu Pro Arg Thr Leu His Val Asp Glu Pro Ser
                405                 410                 415

Pro His Val Asp Trp Ser Ala Gly Ala Val Gln Leu Leu Thr Glu Thr
            420                 425                 430

Val Pro Trp Pro Gly Gly Glu Gly Arg Leu Arg Arg Ala Gly Val Ser
        435                 440                 445

Ser Phe Gly Val Ser Gly Thr Asn Ala His Val Ile Leu Glu Glu Ala
    450                 455                 460

Pro Ala His Asn Ile Pro Ser Asp Thr Pro Ala Asp Val Pro Gly
465                 470                 475                 480

Glu Ser Ala Ala Asp Glu Asp Ala Gly Ser Gly Asp Glu Ala Ala Ala
                485                 490                 495

Gly Ser Pro Gly Val Trp Pro Trp Leu Val Ser Ala Lys Ser Gln Pro
            500                 505                 510

Ala Leu Arg Ala Gln Ala Gln Ala Leu His Ala His Leu Thr Asp His
        515                 520                 525

Pro Gly Leu Asp Leu Ala Asp Val Gly Tyr Thr Leu Ala His Ala Arg
    530                 535                 540
```

-continued

```
Ala Val Phe Asp His Arg Ala Thr Leu Ile Ala Ala Asp Arg Asp Thr
545                 550                 555                 560

Phe Leu Gln Ala Leu Gln Ala Leu Ala Ala Gly Glu Pro His Pro Ala
            565                 570                 575

Val Ile His Ser Ser Ala Pro Gly Gly Thr Gly Thr Gly Glu Ala Ala
            580                 585                 590

Gly Lys Thr Ala Phe Ile Cys Ser Gly Gln Gly Thr Gln Arg Pro Gly
            595                 600                 605

Met Ala His Gly Leu Tyr His Thr His Pro Val Phe Ala Ala Ala Leu
610                 615                 620

Asn Asp Ile Cys Thr His Leu Asp Pro His Leu Asp His Pro Leu Leu
625                 630                 635                 640

Pro Leu Leu Thr Gln Asp Pro Asn Thr Gln Asp Thr Thr Thr Leu Glu
            645                 650                 655

Glu Ala Ala Ala Leu Leu Gln Gln Thr Arg Tyr Ala Gln Pro Ala Leu
            660                 665                 670

Phe Ala Phe Gln Val Ala Leu His Arg Leu Leu Thr Asp Gly Tyr His
            675                 680                 685

Ile Thr Pro His Tyr Tyr Ala Gly His Ser Leu Gly Glu Ile Thr Ala
            690                 695                 700

Ala His Leu Ala Gly Ile Leu Thr Leu Thr Asp Ala Thr Thr Leu Ile
705                 710                 715                 720

Thr Gln Arg Ala Thr Leu Met Gln Thr Met Pro Pro Gly Thr Met Thr
            725                 730                 735

Thr Leu His Thr Thr Pro His His Ile Thr His His Leu Thr Ala His
            740                 745                 750

Glu Asn Asp Leu Ala Ile Ala Ala Ile Asn Thr Pro Thr Ser Leu Val
            755                 760                 765

Ile Ser Gly Thr Pro His Thr Val Gln His Ile Thr Thr Leu Cys Gln
770                 775                 780

Gln Gln Gly Ile Lys Thr Lys Thr Leu Pro Thr Asn His Ala Phe His
785                 790                 795                 800

Ser Pro His Thr Asn Pro Ile Leu Asn Gln Leu His Gln His Thr Gln
            805                 810                 815

Thr Leu Thr Tyr His Pro Pro Thr Pro Leu Ile Thr Ala Asn Thr
            820                 825                 830

Pro Pro Asp Gln Leu Leu Thr Pro His Tyr Trp Thr Gln Gln Ala Arg
            835                 840                 845

Asn Thr Val Asp Tyr Ala Thr Thr Gln Thr Leu His Gln His Gly
850                 855                 860

Val Thr Thr Tyr Ile Glu Leu Gly Pro Asp Asn Thr Leu Thr Thr Leu
865                 870                 875                 880

Thr His Asp Asn Leu Pro Asn Thr Pro Thr Thr Leu Thr Leu Thr
            885                 890                 895

His Pro His His His Pro Gln Thr His Leu Leu Thr Asn Leu Ala Lys
            900                 905                 910

Thr Thr Thr Thr Trp His Pro His Tyr Thr His His Asn Gln
            915                 920                 925

Pro His Thr His Thr His Leu Asp Leu Pro Thr Tyr Pro Phe Gln His
            930                 935                 940

His His Tyr Trp Leu Gln Pro Pro Gly Lys Pro Ser Asp Ser Pro
945                 950                 955                 960

Ser Glu Gly Arg Glu Gln Ala Thr Thr Pro Ser Thr Pro Leu Arg Asp
```

-continued

```
                965                 970                 975
Val Leu Val Gly Lys Ser Pro Gln Glu Arg Asp Glu Leu Leu Arg
                980                 985                 990
Leu Val Arg Thr His Ala Ala Val Leu Gly His Ala Thr Pro Glu
                995                1000                1005
Val Ile Val Pro Asn Lys Ala Phe Lys Glu Leu Gly Phe Asp Ser Leu
           1010                1015                1020
Ala Ala Ile Gln Leu Arg Asn Arg Leu Leu Ala Asp Val Asp Leu Pro
1025                1030                1035                1040
Leu Pro Ala Thr Leu Ile Phe Asp Tyr Pro Thr Pro Met Ala Leu Cys
                1045                1050                1055
Gln Phe Leu Arg Ala Ala Ile Val Gly Ala Asp Thr Gly Thr Thr Thr
                1060                1065                1070
Arg Leu Pro Leu Thr Ala Val Pro Ala Asp Glu Pro Ile Ala Ile Val
                1075                1080                1085
Gly Met Ala Cys Arg Tyr Pro Gly Asp Val Arg Thr Val Asp Asp Leu
                1090                1095                1100
Trp Gln Val Val Ser Gly Gly His Asp Ala Ile Gly Gly Phe Pro Thr
1105                1110                1115                1120
Asn Arg Gly Trp Asp Leu Asp Thr Leu Tyr Asn Pro Asp Pro Asp His
                1125                1130                1135
His Gly Thr Ser Tyr Thr Arg Ser Gly Gly Phe Leu Tyr Asp Ala Gly
                1140                1145                1150
Asn Phe Asp Pro Asp Phe Phe Gly Ile Ser Pro Arg Glu Ala Leu Ala
                1155                1160                1165
Met Asp Pro Gln Gln Arg Leu Leu Leu Glu Thr Ala Trp Glu Ser Ile
           1170                1175                1180
Glu His Ala Cys Ile Asn Pro Asp Ser Leu Arg Gly Thr Pro Thr Gly
1185                1190                1195                1200
Val Phe Ala Gly Leu Thr Tyr His Asp Tyr Ala Ala Arg Phe Pro Thr
                1205                1210                1215
Ala Pro Ala Gly Phe Glu Gly Tyr Leu Gly His Gly Ser Ala Gly Ser
                1220                1225                1230
Ile Ala Ser Gly Arg Val Ala Tyr Ala Leu Gly Leu Glu Gly Pro Ala
                1235                1240                1245
Leu Thr Val Asp Thr Ala Cys Ser Ser Ser Leu Val Ala Leu His Leu
           1250                1255                1260
Ala Cys Gln Ala Leu Arg Ser Gly Glu Cys Ser Met Ala Leu Ala Gly
1265                1270                1275                1280
Gly Val Thr Val Met Ser Thr Pro Ala Gly Phe Val Glu Phe Ser Arg
                1285                1290                1295
Gln Arg Gly Leu Ala Val Asp Gly Arg Cys Lys Ala Phe Ser Ala Ala
                1300                1305                1310
Ala Asp Gly Thr Gly Trp Gly Glu Gly Val Gly Met Leu Leu Val Glu
                1315                1320                1325
Arg Leu Ser Asp Ala Arg Arg Leu Gly His Arg Ile Leu Ala Val Val
                1330                1335                1340
Arg Gly Ser Ala Val Asn Gln Asp Gly Ala Ser Asn Gly Leu Thr Ala
1345                1350                1355                1360
Pro Asn Gly Pro Ser Gln Glu Arg Val Ile Arg Leu Ala Leu Ala Asn
                1365                1370                1375
Ala Asp Leu Thr Pro Ala Asp Val Asp Ala Val Glu Ala His Gly Thr
                1380                1385                1390
```

-continued

Gly Thr Thr Leu Gly Asp Pro Ile Glu Ala Gln Ala Leu Leu Ala Thr
             1395                1400                1405
Tyr Gly Gln Asp Arg Pro Gly Asn Glu Pro Leu Trp Leu Gly Ser Met
    1410                1415                1420
Lys Ser Asn Ile Gly His Ala Gln Ala Ala Gly Val Gly Gly Val
1425                1430                1435                1440
Ile Lys Met Val Met Ala Leu Arg Asn Gly Leu Leu Pro Arg Thr Leu
                1445                1450                1455
His Val Asp Glu Pro Ser Pro His Val Asp Trp Ser Ala Gly Ala Val
                1460                1465                1470
Gln Leu Leu Thr Glu Thr Val Pro Trp Pro Gly Gly Glu Gly Arg Leu
            1475                1480                1485
Arg Arg Ala Gly Val Ser Ser Phe Gly Val Ser Gly Thr Asn Ala His
            1490                1495                1500
Val Ile Leu Glu Glu Ala Pro Ala His Asn Ile Pro Ser Asp Thr Pro
1505                1510                1515                1520
Ala Asp Asp Ala Pro Gly Glu Ala Ala Ala Asp Val Pro Gly Glu
                1525                1530                1535
Ala Ala Gly Asp Asp Ala Gly Thr Gly Gly Glu Ala Thr Gly Pro Ala
            1540                1545                1550
Ala Gly Ser Pro Gly Val Trp Pro Trp Leu Val Ser Ala Lys Ser Gln
            1555                1560                1565
Pro Ala Leu Arg Ala Gln Ala Gln Ala Leu His Ala His Leu Thr Asp
    1570                1575                1580
His Pro Gly Leu Asp Leu Ala Asp Val Gly Tyr Thr Leu Ala His Ala
1585                1590                1595                1600
Arg Ala Val Phe Asp His Arg Ala Thr Leu Ile Ala Ala Asp Arg Asp
                1605                1610                1615
Thr Phe Leu Gln Ala Leu Gln Ala Leu Ala Ala Gly Glu Pro His Pro
            1620                1625                1630
Ala Val Ile His Ser Ser Ala Pro Gly Gly Thr Gly Thr Gly Glu Ala
            1635                1640                1645
Ala Gly Lys Thr Ala Phe Ile Cys Ser Gly Gln Gly Thr Gln Arg Pro
    1650                1655                1660
Gly Met Ala His Gly Leu Tyr His Thr His Pro Val Phe Ala Ala Ala
1665                1670                1675                1680
Leu Asn Asp Ile Cys Thr His Leu Asp Pro His Leu Asp His Pro Leu
                1685                1690                1695
Leu Pro Leu Leu Thr Gln Asp Pro Asn Thr Gln Asp Thr Thr Thr Leu
            1700                1705                1710
Glu Glu Ala Ala Ala Leu Leu Gln Gln Thr Pro Tyr Ala Gln Pro Ala
        1715                1720                1725
Leu Phe Ala Phe Gln Val Ala Leu His Arg Leu Thr Asp Gly Tyr
    1730                1735                1740
His Ile Thr Pro His Tyr Tyr Ala Gly His Ser Leu Gly Glu Ile Thr
1745                1750                1755                1760
Ala Ala His Leu Ala Gly Ile Leu Thr Leu Thr Asp Ala Thr Thr Leu
                1765                1770                1775
Ile Thr Gln Arg Ala Thr Leu Met Gln Thr Met Pro Pro Gly Thr Met
            1780                1785                1790
Thr Thr Leu His Thr Thr Pro His His Ile Thr His His Leu Thr Ala
        1795                1800                1805

```
His Glu Asn Asp Leu Ala Ile Ala Ala Ile Asn Thr Pro Thr Ser Leu
    1810                1815                1820

Val Ile Ser Gly Thr Pro His Thr Val Gln His Ile Thr Thr Leu Cys
1825                1830                1835                1840

Gln Gln Gln Gly Ile Lys Thr Lys Thr Leu Pro Thr Lys Asn Ala Phe
            1845                1850                1855

His Ser Pro His Thr Asn Pro Ile Leu Asn Gln Leu His Gln His Thr
            1860                1865                1870

Gln Thr Leu Thr Tyr His Pro Pro His Thr Pro Leu Ile Thr Ala Asn
            1875                1880                1885

Thr Pro Pro Asp Gln Leu Leu Thr Pro His Tyr Trp Thr Gln Gln Ala
            1890                1895                1900

Arg Asn Thr Val Asp Tyr Ala Thr Thr Thr Gln Thr Leu His Gln His
1905                1910                1915                1920

Gly Val Thr Thr Tyr Ile Glu Leu Gly Pro Asp Asn Thr Leu Thr Thr
            1925                1930                1935

Leu Thr His His Asn Leu Pro Asn Thr Pro Thr Thr Leu Thr Leu
            1940                1945                1950

Thr His Pro His His His Pro Gln Thr His Leu Leu Thr Asn Leu Ala
            1955                1960                1965

Lys Thr Thr Thr Thr Trp His Pro His His Tyr Thr His His His Asn
            1970                1975                1980

Gln Pro His Thr His Thr His Leu Asp Leu Pro Thr Tyr Pro Phe Gln
1985                1990                1995                2000

His Gln His Tyr Trp Leu Glu Ser Thr Gln Pro Gly Ala Gly Ser Gly
            2005                2010                2015

Ser Gly Ser Gly Ser Gly Arg Ala Gly Thr Ala Gly Gly Thr Ala Glu
            2020                2025                2030

Val Glu Ser Arg Phe Trp Asp Ala Val Ala Arg Gln Asp Leu Glu Thr
            2035                2040                2045

Val Ala Thr Thr Leu Ala Val Pro Pro Ser Ala Gly Leu Asp Thr Val
            2050                2055                2060

Val Pro Ala Leu Ser Ala Trp His Arg His Gln His Asp Gln Ala Arg
2065                2070                2075                2080

Ile Asn Thr Trp Thr Tyr Gln Glu Thr Trp Lys Pro Leu Thr Leu Pro
            2085                2090                2095

Thr Thr His Gln Pro His Gln Thr Trp Leu Ile Ala Ile Pro Glu Thr
            2100                2105                2110

Gln Thr His His Pro His Ile Thr Asn Ile Leu Thr Asn Leu His His
            2115                2120                2125

His Gly Ile Thr Pro Ile Pro Leu Thr Leu Asn His Thr His Thr Asn
            2130                2135                2140

Pro Gln His Leu His His Thr Arg Gln Gln Ala Gln Asn His Thr Thr
2145                2150                2155                2160

Gly Pro Ile Thr Gly Leu Leu Ser Leu Leu Ala Leu Asp Glu Thr Pro
            2165                2170                2175

His Pro His His Pro His Thr Pro Thr Gly Thr Leu Leu Asn Leu Thr
            2180                2185                2190

Leu Thr Gln Thr His Thr Gln Thr His Pro Pro Thr Pro Leu Trp Tyr
            2195                2200                2205

Ala Thr Thr Asn Ala Thr Thr Thr His Pro Asn Asp Pro Leu Thr His
            2210                2215                2220

Pro Thr Gln Ala Gln Thr Trp Gly Leu Ala Arg Thr Thr Leu Leu Glu
```

-continued

```
         2225                2230                2235                2240
His Pro Thr His Thr Ala Gly Ile Ile Asp Leu Pro Thr Thr Pro Thr
                 2245                2250                2255
Pro His Thr Leu His His Leu Thr Gln Thr Leu Thr Gln Pro His His
                 2260                2265                2270
Gln Thr Gln Leu Ala Ile Arg Thr Thr Gly Thr His Thr Arg Arg Leu
                 2275                2280                2285
Thr Pro Thr Thr Leu Thr Pro Thr His Gln Pro Pro Thr Pro Thr Pro
                 2290                2295                2300
His Gly Thr Thr Leu Ile Thr Gly Gly Thr Gly Ala Leu Ala Thr His
2305                2310                2315                2320
Leu Thr His His Leu Thr Thr His Gln Pro Thr Gln His Leu Leu Leu
                 2325                2330                2335
Thr Ser Arg Thr Gly Pro His Thr Pro His Ala Gln His Leu Thr Thr
                 2340                2345                2350
Gln Leu Gln Gln Lys Gly Ile His Leu Thr Ile Thr Thr Cys Asp Thr
                 2355                2360                2365
Ser Asn Pro Asp Gln Leu Gln Gln Leu Leu Asn Thr Ile Pro Pro Gln
                 2370                2375                2380
His Pro Leu Thr Thr Val Ile His Thr Ala Gly Ile Leu Asp Asp Ala
2385                2390                2395                2400
Thr Leu Thr Asn Leu Thr Pro Thr Gln Leu Asn Asn Val Leu Arg Ala
                 2405                2410                2415
Lys Ala His Ser Ala His Leu Leu His Gln Leu Thr Gln His Thr Pro
                 2420                2425                2430
Leu Asn Ala Phe Val Leu Tyr Ser Ser Ala Ala Ala Thr Phe Gly Ala
                 2435                2440                2445
Pro Gly Gln Ala Asn Tyr Ala Ala Ala Asn Ala Tyr Leu Asp Ala Leu
                 2450                2455                2460
Ala His His Arg His Thr His His Leu Pro Ala Thr Ser Ile Ala Trp
2465                2470                2475                2480
Gly Thr Trp Gln Gly Asn Gly Leu Ala Thr Gly Gln Val Ser Glu His
                 2485                2490                2495
Leu Arg Arg Arg Gly Met Phe Ala Met Pro Pro Glu Leu Ala Val Thr
                 2500                2505                2510
Ala Val Asp Gly Ala Ile Ala Ser Gly Arg Pro Ser Leu Leu Val Ala
                 2515                2520                2525
Asp Ile Asp Trp Lys Lys Leu Gly Pro Val Leu Ser Ser Lys Ser Ser
                 2530                2535                2540
Val Leu Leu Glu Asp Leu Pro Gln Ala Gln Gly Thr Glu Glu Ala Arg
2545                2550                2555                2560
Ser Thr Val Glu Gln Thr Glu Ser Thr Asn Leu Arg Gln Leu Leu Met
                 2565                2570                2575
Gly Arg Ser Arg Ser Glu Gln Glu Glu Leu Leu Ser Leu Val Arg
                 2580                2585                2590
Ile His Ser Ala Ala Val Leu Gly Arg Asp Asp Ser Glu Ala Ile Pro
                 2595                2600                2605
Pro Gly Arg Leu Phe Arg Asp Leu Gly Phe Asp Ser Leu Ala Ala Val
                 2610                2615                2620
Glu Leu Arg Asn His Leu Ala Ala Gln Thr Glu Leu Ala Leu Pro Thr
2625                2630                2635                2640
Thr Leu Val Phe Asp Tyr Pro Ser Pro Thr Lys Leu Ala Gln Phe Leu
                 2645                2650                2655
```

```
Leu Ser Glu Ile Ala Glu Phe Gln Pro Asp Asn Ser Thr Pro Leu Pro
            2660                2665                2670

Arg Pro Arg Ala Glu Leu Asp Glu Pro Ile Ala Ile Val Gly Met Ala
        2675                2680                2685

Cys Arg Phe Pro Gly Gly Val Thr Ser Ala Asp Asp Phe Trp Asp Leu
    2690                2695                2700

Ile Ser Ser Glu Gln Asp Ala Ile Gly Gly Phe Pro Thr Asp Arg Gly
2705                2710                2715                2720

Trp Asp Leu Asp Thr Leu Tyr Asp Pro Asp Pro Asp His Pro Gly Thr
                2725                2730                2735

Cys Tyr Thr Arg Asn Gly Gly Phe Leu Tyr Asp Ala Gly His Phe Asp
            2740                2745                2750

Ala Glu Phe Phe Gly Ile Ser Pro Arg Glu Ala Leu Ala Met Asp Pro
        2755                2760                2765

Gln Gln Arg Leu Leu Leu Glu Thr Ala Trp Glu Thr Ile Glu His Ala
    2770                2775                2780

Gly Ile Asn Pro His Thr Leu His Gly Thr Pro Thr Gly Val Phe Thr
2785                2790                2795                2800

Gly Thr Asn Gly Gln Asp His Ala Ala His Ile Arg Gln Ala Pro Ser
                2805                2810                2815

Gly Thr Glu Gly Phe Val Leu Thr Gly Ala Ala Thr Ser Ile Ala Ser
            2820                2825                2830

Gly Arg Ile Ser Tyr Ile Leu Gly Leu Glu Gly Pro Ala Val Thr Leu
        2835                2840                2845

Asp Thr Ala Cys Ser Ser Ser Leu Val Ala Leu His Leu Ala Cys Gln
    2850                2855                2860

Ser Leu Arg Ser Gly Glu Cys Thr Met Ala Leu Ala Gly Gly Ala Thr
2865                2870                2875                2880

Val Met Thr Thr Pro Ile Thr Phe Thr Glu Phe Ala Arg Gln Arg Gly
                2885                2890                2895

Leu Ala Pro Asp Gly Arg Cys Lys Ala Phe Ser Ala Ala Ala Asp Gly
            2900                2905                2910

Thr Gly Trp Gly Glu Gly Val Gly Met Leu Leu Val Glu Arg Leu Ser
        2915                2920                2925

Asp Ala Arg Arg Asn Gly His Arg Val Leu Ala Val Val Arg Gly Ser
    2930                2935                2940

Ala Val Asn Gln Asp Gly Ala Ser Asn Gly Leu Thr Ala Pro Asn Gly
2945                2950                2955                2960

Pro Ser Gln Gln Arg Val Ile Arg Gln Ala Leu Ala Asn Ala Asp Leu
                2965                2970                2975

Thr Pro Ala Asp Val Asp Ala Val Glu Ala His Gly Thr Gly Thr Thr
            2980                2985                2990

Leu Gly Asp Pro Ile Glu Ala Gln Ala Ile Leu Ala Thr Tyr Gly Gln
        2995                3000                3005

Asp Arg Pro Gly Asn Gly Pro Leu Trp Leu Gly Ser Val Lys Ser Asn
    3010                3015                3020

Val Gly His Thr Gln Ala Ala Ala Gly Val Ala Gly Val Ile Lys Met
3025                3030                3035                3040

Val Met Ala Leu Arg His Arg Thr Leu Pro Pro Thr Leu His Ala Asp
                3045                3050                3055

Glu Pro Ser Pro His Val Asp Trp Ser Ala Gly Ala Val Gln Leu Leu
            3060                3065                3070
```

-continued

```
Thr Glu Thr Val Pro Trp Pro Gly Glu Gly Arg Pro Arg Arg Ala
            3075                3080                3085
Gly Val Ser Ser Phe Gly Val Ser Gly Thr Asn Ala His Val Ile Leu
        3090                3095                3100
Glu Glu Ala Pro Ala Asp Asp Val Pro Gly Gly Pro Pro Ala Asp Glu
3105                3110                3115                3120
Asp Ala Gly Ser Gly Glu Glu Ala Ala Ala Gly Ser Pro Gly Val Trp
            3125                3130                3135
Pro Trp Leu Val Ser Ala Lys Ser Gln Pro Ala Leu Arg Ala Gln Ala
            3140                3145                3150
Gln Ala Leu His Ala His Leu Thr Asp His Pro Gly Leu Asp Leu Ala
            3155                3160                3165
Asp Val Gly Tyr Thr Leu Ala His Ala Arg Ala Val Phe Asp His Arg
            3170                3175                3180
Ala Thr Leu Ile Ala Ala Asp Arg Asp Thr Phe Leu Gln Ala Leu Gln
3185                3190                3195                3200
Ala Leu Ala Ala Gly Glu Pro His Pro Ala Val Ile His Ser Ser Ala
            3205                3210                3215
Pro Gly Gly Thr Gly Thr Gly Glu Ala Ala Gly Lys Thr Ala Phe Ile
            3220                3225                3230
Cys Ser Gly Gln Gly Thr Gln Arg Pro Gly Met Ala His Gly Leu Tyr
            3235                3240                3245
His Thr His Pro Val Phe Ala Ala Ala Leu Asn Asp Ile Cys Thr His
            3250                3255                3260
Leu Asp Pro His Leu Asp His Pro Leu Leu Pro Leu Leu Thr Gln Asn
3265                3270                3275                3280
Asp Asn Asp Asn Asp Asn Glu Asp Ala Ala Ala Leu Leu Gln Gln Thr
            3285                3290                3295
Pro Tyr Ala Gln Pro Ala Leu Phe Ala Phe Gln Val Ala Leu His Arg
            3300                3305                3310
Leu Leu Thr Asp Gly Tyr His Ile Thr Pro His Tyr Tyr Ala Gly His
            3315                3320                3325
Ser Leu Gly Glu Ile Thr Ala Ala His Leu Ala Gly Ile Leu Thr Leu
            3330                3335                3340
Thr Asp Ala Thr Thr Leu Ile Thr Gln Arg Ala Thr Leu Met Gln Thr
3345                3350                3355                3360
Met Pro Pro Gly Thr Met Thr Thr Leu His Thr Thr Pro His His Ile
            3365                3370                3375
Thr His His Leu Thr Ala His Glu Asn Asp Leu Ala Ile Ala Ala Ile
            3380                3385                3390
Asn Thr Pro Thr Ser Leu Val Ile Ser Gly Thr Pro His Thr Val Gln
            3395                3400                3405
His Ile Thr Thr Leu Cys Gln Gln Gln Gly Ile Lys Thr Lys Thr Leu
            3410                3415                3420
Pro Thr Asn His Ala Phe His Ser Pro His Thr Asn Pro Ile Leu Asn
3425                3430                3435                3440
Gln Leu His Gln His Thr Gln Thr Leu Thr Tyr His Pro Pro His Thr
            3445                3450                3455
Pro Leu Ile Thr Ala Asn Thr Pro Pro Asp Gln Leu Leu Thr Pro His
            3460                3465                3470
Tyr Trp Thr Gln Gln Ala Arg Asn Thr Val Asp Tyr Ala Thr Thr Thr
            3475                3480                3485
Gln Thr Leu His Gln His Gly Val Thr Thr Tyr Ile Glu Leu Gly Pro
```

```
                3490            3495            3500
Asp Asn Thr Leu Thr Thr Leu Thr His His Asn Leu Pro Asn Thr Pro
3505                3510            3515                3520

Thr Thr Thr Leu Thr Leu Thr His Pro His His His Pro Gln Thr His
                3525            3530            3535

Leu Leu Thr Asn Leu Ala Lys Thr Thr Thr Thr Trp His Pro His His
                3540            3545            3550

Tyr Thr His His His Asn Gln Pro His Thr His Thr His Leu Asp Leu
                3555            3560            3565

Pro Thr Tyr Pro Phe Gln His His His Tyr Trp Leu Glu Leu Pro Ser
3570            3575            3580

Ala Gln Thr Ser Pro Gly Gln Arg Arg Ser Arg Arg Ser Ala Pro Asp
3585            3590            3595            3600

Thr Ala Glu Ser Glu Phe Trp Asp Ala Val Asn Glu Glu Asp Leu Gln
                3605            3610            3615

Ser Leu Ala Glu Thr Leu Asp Ile Asp Ala Ser Ala Leu Asp Thr Val
                3620            3625            3630

Val Pro Ala Leu Ser Ala Trp His Arg His Gln His Asp Gln Ala Arg
                3635            3640            3645

Ile Asn Thr Trp Thr Tyr Gln Glu Thr Trp Lys Pro Leu Thr Leu Pro
                3650            3655            3660

Thr Thr His Gln Pro His Gln Thr Trp Leu Ile Ala Ile Pro Glu Thr
3665            3670            3675            3680

Gln Thr His His Pro His Ile Thr Asn Ile Leu Thr Asn Leu His His
                3685            3690            3695

His Gly Ile Thr Pro Ile Pro Leu Thr Val Asn His Thr His Thr Asn
                3700            3705            3710

Pro Gln His Leu His His Thr Leu His His Thr Arg Gln Gln Ala Gln
                3715            3720            3725

Asn His Thr Thr Gly Pro Ile Thr Gly Leu Leu Ser Leu Leu Ala Leu
                3730            3735            3740

Asp Glu Thr Pro His Pro His His Pro His Thr Pro Thr Gly Thr Leu
3745            3750            3755            3760

Leu Asn Leu Thr Leu Pro Gln Thr His Thr Gln Thr His Pro Pro Thr
                3765            3770            3775

Pro Leu Trp Tyr Ala Thr Thr Asn Ala Thr Thr His Pro Asn Asp
                3780            3785            3790

Pro Leu Thr His Pro Thr Gln Ala Gln Thr Trp Gly Leu Ala Arg Thr
                3795            3800            3805

Thr Leu Leu Glu His Pro Thr His Thr Ala Gly Ile Ile Asp Leu Pro
                3810            3815            3820

Thr Thr Pro Thr Pro His Thr Leu His His Leu Thr Gln Thr Leu Thr
3825            3830            3835            3840

Gln Pro His His Gln Thr Gln Leu Ala Ile Arg Thr Thr Gly Thr His
                3845            3850            3855

Thr Arg Arg Leu Thr Pro Thr Thr Leu Thr Pro Thr His Gln Pro Pro
                3860            3865            3870

Thr Pro Thr Pro His Gly Thr Thr Leu Ile Thr Gly Gly Thr Gly Ala
                3875            3880            3885

Leu Ala Thr His Leu Thr His His Leu Thr Thr His Gln Pro Thr Gln
                3890            3895            3900

His Leu Leu Leu Thr Ser Arg Thr Gly Pro His Thr Pro His Ala Gln
3905            3910            3915            3920
```

```
His Leu Thr Thr Gln Leu Gln Gln Lys Gly Ile His Leu Thr Ile Thr
                3925                3930                3935

Thr Cys Asp Thr Ser Asn Pro Asp Gln Leu Gln Gln Leu Leu Asn Thr
                3940                3945            3950

Ile Pro Pro Gln His Pro Leu Thr Thr Val Ile His Thr Ala Gly Val
                3955                3960            3965

Asn Leu Phe Ala Pro Val Ser Glu Thr Asp Ala Glu Ser Phe Ser Ser
                3970                3975            3980

Val Thr Ala Ala Lys Ala Thr Gly Ala Ala Ile Leu His Glu Leu Leu
3985                3990                3995                4000

Leu Asp His Glu Thr Leu Glu His Phe Ile Leu Phe Ser Ser Gly Ala
                4005                4010            4015

Gly Ala Trp Gly Ser Gly Asn Gln Cys Ala Tyr Ser Ala Ala Asn Ala
                4020                4025            4030

Tyr Leu Asp Ala Leu Ala Thr His Arg Gln Thr His Gly Leu Pro Gly
                4035                4040            4045

Ala Ser Ile Ala Trp Gly Pro Trp Ala Gly Lys Gly Met Ser Ala Gly
                4050                4055            4060

Asp Ala Ala His Gly Tyr Leu Glu Lys Arg Gly Ile Leu Pro Met Glu
4065                4070                4075                4080

Pro Arg Met Ala Leu Ala Ala Phe His Arg Ala Arg Ala Gln Arg Pro
                4085                4090            4095

Asn Ser Asn Leu Ile Ile Ala Asp Ile Asp Trp Glu Arg Phe Val Pro
                4100                4105            4110

Ala Phe Thr Ala Arg Arg His Ser Pro Leu Ile Glu Asp Ile Pro Glu
                4115                4120            4125

Val Arg Gln Ala Ala Gln Glu Leu Glu Ala Ala Ala Ser Thr Ala Lys
                4130                4135            4140

Thr Thr Thr Ala Gln Pro Ile Ala Thr Ser Leu Arg Glu Arg Leu Ala
4145                4150                4155                4160

Arg Leu Thr Ser Ser Lys Gln Asn Gln Val Leu Leu Gly Leu Ile Arg
                4165                4170            4175

Thr Gly Ile Cys Thr Val Leu Gly Leu Arg Asn Pro Glu Gly Ile Glu
                4180                4185            4190

Asp Gln Arg Ala Phe Arg Asp Leu Gly Phe Asp Ser Leu Thr Ser Ala
                4195                4200            4205

Gln Phe Ser Lys Glu Leu Ala Lys Glu Thr Gly Leu Pro Leu Pro Pro
                4210                4215            4220

Ser Leu Val Phe Asp Tyr Pro Thr Pro Gln Glu Cys Ala Ala His Leu
4225                4230                4235                4240

Arg Thr Gln Leu Val Asp Leu Asp Asp Glu Glu Asp Ala Ala Leu Ser
                4245                4250            4255

Asn Ala Leu Pro Gln Val Ala His Arg Thr Val Glu Asp Glu Pro
                4260                4265            4270

Ile Ala Ile Ile Gly Met Ala Cys Arg Phe Pro Gly Gly Val Arg Ser
                4275                4280            4285

Ala Asp Asp Leu Trp Glu Leu Leu Ala Ser Gly Lys Asp Ala Ile Gly
                4290                4295            4300

Val Phe Pro Thr Asp Arg Gly Trp Asp Leu Asp Thr Leu Tyr Asp Pro
4305                4310                4315                4320

Asp Pro Asp His Pro Gly Thr Cys Tyr Thr Arg Asn Gly Gly Phe Leu
                4325                4330            4335
```

-continued

Tyr Gly Ala Gly His Phe Asp Ala Glu Phe Gly Ile Ser Pro Arg
            4340                4345                4350

Glu Ala Leu Ala Met Asp Pro Gln Gln Arg Leu Leu Leu Glu Thr Ala
            4355                4360                4365

Trp Glu Thr Ile Glu His Ala Gly Ile Asn Pro His Thr Leu His Gly
        4370                4375                4380

Thr Pro Thr Gly Val Phe Ala Gly Ile Asn Ala Gln Asp His Ala Ala
4385                4390                4395                4400

His Ile Arg Gln Ser Arg Asp Val Glu Thr Ile Glu Gly Tyr Ala Leu
                4405                4410                4415

Thr Gly Ser Ser Gly Ser Val Ala Ser Gly Arg Val Ala Tyr Thr Leu
                4420                4425                4430

Gly Leu Glu Gly Pro Ala Val Ser Val Asp Thr Ala Cys Ser Ser Ser
            4435                4440                4445

Leu Val Ala Leu His Trp Ala Ala Gln Ala Leu Arg Ala Gly Glu Cys
        4450                4455                4460

Ser Met Ala Leu Ala Gly Gly Val Thr Val Met Ser Ser Pro Gly Thr
4465                4470                4475                4480

Phe Val Glu Phe Ser Arg Gln Arg Gly Leu Ala Ala Asp Gly Arg Cys
            4485                4490                4495

Lys Ala Tyr Ser Ala Ala Ala Asp Gly Thr Gly Trp Ala Glu Gly Val
            4500                4505                4510

Gly Met Leu Leu Val Glu Arg Leu Ser Asp Ala Arg Arg Asn Gly His
            4515                4520                4525

Arg Val Leu Ala Val Val Arg Gly Ser Ala Val Asn Gln Asp Gly Ala
            4530                4535                4540

Ser Asn Gly Leu Thr Ala Pro Asn Gly Pro Ser Gln Gln Arg Val Ile
4545                4550                4555                4560

Arg Gln Ala Leu Ala Asn Ala Gly Leu Thr Pro Ala Asp Val Asp Ala
            4565                4570                4575

Val Glu Gly His Gly Thr Gly Thr Thr Leu Gly Asp Pro Ile Glu Ala
            4580                4585                4590

Gln Ala Leu Leu Ala Ala Tyr Gly Gln His Arg Pro His His Arg Pro
        4595                4600                4605

Leu Trp Leu Gly Ser Leu Lys Ser Asn Ile Gly His Ala Gln Ala Ala
            4610                4615                4620

Ala Gly Val Gly Gly Val Ile Lys Met Val Met Ala Leu Arg Asn Gly
4625                4630                4635                4640

Leu Leu Pro Gln Thr Leu His Val Asp Glu Pro Thr Pro Gln Val Asp
                4645                4650                4655

Trp Ser Thr Gly Ala Val Gln Leu Leu Thr Gln Pro Val Pro Trp Pro
            4660                4665                4670

Ala Asp Pro Ala Gly Arg Pro Arg His Ala Gly Val Ser Ser Phe Gly
        4675                4680                4685

Val Ser Gly Thr Asn Ala His Ile Ile Leu Glu Glu Ala Pro Thr Pro
        4690                4695                4700

Gln Asp Ser Asp Thr Asp Glu Pro Pro Ala Asn Ala Pro Ala Leu
4705                4710                4715                4720

Pro His Pro Leu Pro Leu Pro Val Pro Val Ser Ala Arg Ser Glu Ala
                4725                4730                4735

Gly Leu Arg Ala Gln Ala Gln Ala Leu Arg Gln Tyr Val Ala Ala Arg
            4740                4745                4750

Pro Asp Met Ser Pro Ala Asp Ile Gly Ala Gly Leu Ala Arg Gly Arg

-continued

```
                 4755                4760                4765
Ala Val Leu Glu His Arg Ala Val Ile Leu Ala Ala Asp Arg Glu Glu
            4770                4775                4780
Leu Ala Gln Ala Leu Thr Ala Leu Ala Ala Gly Glu Pro His Pro His
4785                4790                4795                4800
Ile Thr Thr Gly His Thr Arg Gly Gly Asp Arg Gly Gly Val Val Phe
                4805                4810                4815
Val Phe Pro Gly Gln Gly Gly Gln Trp Ala Gly Met Gly Leu Thr Leu
                    4820                4825                4830
Leu Thr Ser Ser Pro Val Phe Ala Glu His Ile Asp Ala Cys Glu Lys
            4835                4840                4845
Ala Leu Thr Pro Trp Val Pro Trp Ser Leu Thr Asp Ile Leu His Arg
            4850                4855                4860
Asp Pro Asp Asp Pro Ala Trp Gln Ala Asp Val Val Gln Pro Val
4865                4870                4875                4880
Leu Phe Ser Ile Met Val Ser Leu Ala Ala Leu Trp Arg Ser Tyr Gly
                4885                4890                4895
Ile Glu Pro Asp Ala Val Leu Gly His Ser Gln Gly Glu Ile Ala Ala
                    4900                4905                4910
Ala His Ile Cys Gly Ala Leu Ser Leu Lys Asp Ala Ala Lys Thr Val
                    4915                4920                4925
Ala Leu Arg Ser Arg Ala Leu Ala Ala Val Arg Gly Arg Gly Ala Met
                    4930                4935                4940
Ala Ser Leu Pro Leu Pro Ala Gln Asp Val Gln Gln Leu Ile Ser Glu
4945                4950                4955                4960
Arg Trp Glu Gly Gln Leu Trp Val Ala Ala Leu Asn Gly Pro His Ser
                4965                4970                4975
Thr Thr Val Ser Gly Asp Thr Lys Ala Val Asp Glu Val Leu Ala His
                    4980                4985                4990
Cys Thr Asp Thr Gly Leu Arg Ala Lys Arg Ile Pro Val Asp Tyr Ala
            4995                5000                5005
Ser His Cys Pro His Val Gln Pro Leu His Asp Glu Leu Leu His Leu
        5010                5015                5020
Leu Gly Asp Ile Thr Pro Gln Pro Ser Thr Val Pro Phe Phe Ser Thr
5025                5030                5035                5040
Val Glu Gly Thr Trp Leu Asp Thr Thr Thr Leu Asp Ala Ala Tyr Trp
                    5045                5050                5055
Tyr Arg Asn Leu His Gln Pro Val Arg Phe Ser His Ala Ile Gln Thr
                5060                5065                5070
Leu Thr Asp Asp Gly His Arg Ala Phe Ile Glu Ile Ser Pro His Pro
            5075                5080                5085
Thr Leu Val Pro Ala Ile Glu Asp Thr Thr Glu Asn Thr Thr Glu Asn
        5090                5095                5100
Ile Thr Ala Thr Gly Ser Leu Arg Arg Gly Asp Asn Asp Thr His Arg
5105                5110                5115                5120
Phe Leu Thr Ala Leu Ala His Thr His Thr Thr Gly Ile Gly Thr Pro
                    5125                5130                5135
Thr Thr Trp His His His Tyr Thr Gln Thr His Pro His Pro Asn Pro
            5140                5145                5150
His Thr His Leu Asp Leu Pro Thr Tyr Pro Phe Gln His Gln His Tyr
            5155                5160                5165
Trp Leu Gln Pro Pro Thr Thr Thr Thr Asp Leu Thr Thr Thr Gly Leu
        5170                5175                5180
```

```
Thr Pro Thr His His Pro Leu Leu Thr Ala Thr Leu Thr Leu Ala Asp
5185                5190                5195                5200

Asn Asn Thr Gln Leu Leu Thr Gly Arg Leu Ser Leu Arg Thr His Pro
                5205                5210                5215

Trp Leu Thr Asp His Thr Val Ala Gly Met Val Leu Leu Pro Gly Thr
            5220                5225                5230

Ala Leu Leu Glu Leu Ala Leu Gln Ala Gly Glu Arg Val Asp Cys Pro
        5235                5240                5245

Arg Val Glu Glu Leu Thr Leu His Ala Pro Leu Val Ile Pro His Thr
    5250                5255                5260

Glu Asp Val Thr Leu Gln Val Thr Val Arg Ala Ala Asp Glu Ser Gly
5265                5270                5275                5280

His Arg Ala Leu Ala Ile His Ser Tyr Ser Gly Thr Ala Ser Ser Ala
                5285                5290                5295

Asp Arg Glu Trp Thr Arg His Ala Thr Gly Leu Leu Thr His His Ala
            5300                5305                5310

Asp Thr Asp His Arg Ala Asp Thr His Thr Asp Ala Cys Leu Gly Gly
        5315                5320                5325

Ser Trp Pro Pro Pro Gly Ala Gln Pro Ile Glu Leu Gly Asp Val Tyr
    5330                5335                5340

Gly Arg Met Ala Ala Asp Ser Asp Ile Ala Tyr Gly Pro Val Phe Gln
5345                5350                5355                5360

Gly Leu His Ala Ala Trp Arg Phe Gly Asp Asp Val Leu Ala Glu Val
                5365                5370                5375

Arg Leu Pro Glu Glu Ala Leu Arg Asp Ala Pro Ala Ala Phe Gly
            5380                5385                5390

Val His Pro Ala Leu Leu Asp Ala Ala Leu His Ala Thr Ala Leu Thr
        5395                5400                5405

Pro Gln Asn Gly Asp Gly Ser Thr Glu Asn Val Ala Gln Glu Ser Met
    5410                5415                5420

Pro Asp Arg Ala Ala His Gln Ala Arg Leu Pro Phe Ser Trp Ser Gly
5425                5430                5435                5440

Val Ser Leu His Thr Ala Gly Ser Ser Val Leu Arg Val Arg Leu Ser
                5445                5450                5455

Arg Ser Pro Gln His Gly Asn Ala Val Ala Leu Thr Ala Ala Asp Glu
            5460                5465                5470

Asp Gly Arg Pro Val Val Thr Ile Glu Ser Leu Ala Leu Arg Pro Val
        5475                5480                5485

Ser Thr Glu Glu Leu Arg Ala Ala Ala Asp Arg Thr Pro Glu His Glu
    5490                5495                5500

Ser Leu Phe Arg Leu Asp Trp Val Ser Val Pro Val Pro Ala Asn Ala
5505                5510                5515                5520

Pro Ser Pro Thr Ala Asp Arg Pro Trp Ala Val Ile Gly Ala Gly Leu
                5525                5530                5535

Pro His Leu Pro Gly Leu Thr Glu His Glu His Val Thr Ala Tyr Asp
            5540                5545                5550

Glu Pro Ala Asp Leu Leu Leu Ala Leu Asp Arg Gly Ala Pro Pro Pro
        5555                5560                5565

Gly Val Leu Val Val Gly Gly Val Ala His Thr Glu Ala Arg Glu Tyr
    5570                5575                5580

Ser Ala Glu Ala Pro Gly Glu Arg Gly Thr Glu Ala Cys Glu Ala Arg
5585                5590                5595                5600
```

```
Pro Asp Val Val His Val Gly Val His Thr Ala Ala Val His Ala
            5605                5610                5615

Ala Ala Ala Gln Met Leu Ala Arg Leu Gln Ala Trp Leu Gly Asp Glu
            5620                5625                5630

Arg Leu Ala Asp Ser Arg Leu Leu Val Leu Thr Cys Gly Ala Val Ala
            5635                5640                5645

Arg Ala Ser Gly Asp Asp Ala Thr Asp Leu Pro Gly Ala Ala Val Trp
            5650                5655                5660

Gly Leu Val Arg Ser Ala Gln Ser Glu His Pro Asp Arg Ile Thr Leu
5665                5670                5675                5680

Leu Asp Phe Glu Arg Gly Thr Glu Ala Glu Pro Gly Gln Leu Ala Thr
            5685                5690                5695

Ala Leu Asn Cys Gly Glu Arg Gln Leu Ala Val Arg Pro Gly Gly Leu
            5700                5705                5710

Phe Thr Pro Arg Leu Val Arg Ala Pro Arg Val Ala Asp Ala Val Pro
            5715                5720                5725

Ala Val Pro Ala Val Ala Val Pro Ser Ala Gly His Ala Ala Val Pro
            5730                5735                5740

Ala Ala Gly Pro Phe Leu Pro Gly Gly Thr Val Leu Ile Thr Gly Gly
5745                5750                5755                5760

Thr Gly Val Leu Gly Arg Leu Val Ala Arg His Leu Val Glu Ala His
            5765                5770                5775

Gly Val Arg His Leu Leu Leu Ala Gly Arg Arg Gly Pro Asp Ala Glu
            5780                5785                5790

Gly Ala Pro Glu Leu Arg Ala Glu Leu Gly Gly Leu Gly Ala Thr Val
            5795                5800                5805

Glu Val Val Ala Cys Asp Ala Ala Asp Arg Gln Gln Leu Ala Asp Leu
            5810                5815                5820

Leu Thr Arg Ile Pro Asp Asp Arg Pro Leu Thr Gly Val Val His Ser
5825                5830                5835                5840

Ala Gly Ile Leu Asp Asp Gly Val Ile Thr Ser Leu Ser Pro Glu Arg
            5845                5850                5855

Leu Gly Ala Val Leu Arg Ala Lys Ala Asp Ala Ala Leu Leu Leu Asp
            5860                5865                5870

Glu Leu Thr Arg Gly Ala Glu Leu Ser Ala Phe Val Met Phe Ser Ser
            5875                5880                5885

Ala Ser Ala Val Val Gly Ser Pro Gly Gln Gly Asn Tyr Ala Ala Ala
            5890                5895                5900

Asn Ala Val Leu Asp Phe Leu Ala His Arg Arg Ala Glu Gly Leu
5905                5910                5915                5920

Pro Ala Val Ser Leu Ala Trp Gly Leu Trp Glu Glu Gly Thr Gly Met
            5925                5930                5935

Thr Gly His Leu Asp Val Asp Asp His Ala Arg Ile Ser Arg Ala Gly
            5940                5945                5950

Met Arg Pro Leu Pro Thr Ala Glu Ala Leu Ala Leu Phe Asp Ala Ala
            5955                5960                5965

Leu Ala Asp Gly Glu Pro Phe Leu Met Pro Ala Arg Leu Asp Leu Thr
            5970                5975                5980

Ala Val Arg Ser Gly Ala Ala Ser Ala Pro Val Pro Pro Leu Leu Gln
5985                5990                5995                6000

Gly Leu Leu Gln Leu Pro Arg Ser Arg Ser Ala Ala Ala Pro Gly
            6005                6010                6015

His Gly Ala Pro Ala Ala Asp Glu Ala Ala Ala Trp Arg Glu Arg Leu
```

```
                   6020              6025              6030
Ala Arg Gln Ser Ala Gly Glu Arg Arg Gln Ala Leu Leu Arg Leu Val
        6035              6040              6045

Arg Ser His Val Ala Ala Val Leu Gly His Ser Gly Ala Asp Gly Ile
        6050              6055              6060

Asp Ala Ser Arg Ala Phe Arg Glu Leu Gly Phe Asp Ser Leu Thr Ala
6065              6070              6075              6080

Val Glu Leu Arg Asn Arg Leu Thr Ala Thr Gly Leu Arg Leu Arg
                6085              6090              6095

Ala Thr Leu Ala Phe Asp Phe Pro Thr Pro Ala Leu Ala Glu His
        6100              6105              6110

Leu Gly Glu Arg Leu Leu Pro Asp Gln Glu Ala Thr Gly Glu Gln Ala
        6115              6120              6125

Gly Asp Gln Leu Ser Gly Gly Ser Glu Glu Asp Val Arg Ser Leu Leu
6130              6135              6140

Thr Ser Ile Pro Ile Gly Arg Leu Arg Asp Ala Gly Leu Leu Gly Pro
6145              6150              6155              6160

Leu Leu Thr Leu Ala Asp Thr Gly Arg Gly Ala Ser Gly Ala Ala Ala
                6165              6170              6175

Gly Pro Glu Asp Ala Pro Pro Ser Gly Gln Asp Thr Pro Ala Pro Val
                6180              6185              6190

Ser Ile Asp Glu Met Asp Ile Asp Asp Leu Met Asp Leu Ala His Gly
        6195              6200              6205

His Gly Thr Ala Pro Ala Arg Glu Pro Ala Asp Ala Glu Asp Ser Ser
        6210              6215              6220

Ser Ser Arg Asn Arg Thr His His Thr His Glu Gly Glu Thr Ala
6225              6230              6235

<210> SEQ ID NO 5
<211> LENGTH: 4881
<212> TYPE: PRT
<213> ORGANISM: Streptomyces avermitilis

<400> SEQUENCE: 5

Met Ala Asn Glu Glu Lys Leu Arg Asp Tyr Leu Lys Arg Val Thr Ala
1               5                   10                  15

Asp Leu Leu Asn Val Arg Arg Leu Gln Gln Ile Glu Ser Gly Glu
                20                  25                  30

Gln Glu Pro Ile Ala Ile Val Gly Met Ala Cys Arg Phe Pro Gly Gly
        35                  40                  45

Val Glu Ser Ala Glu Asp Phe Trp Glu Leu Ile Ala Ser Gly Arg Asp
    50                  55                  60

Ala Val Gly Glu Phe Pro Val Asp Arg Gly Trp Asp Val Glu Ala Phe
65                  70                  75                  80

Tyr Asp Pro Glu Pro Gly Arg Ala Gly Ser Ser Tyr Thr Arg Arg Gly
                85                  90                  95

Gly Phe Leu Glu Gly Ala Ala Glu Phe Asp Ala Gly Phe Phe Gly Ile
            100                 105                 110

Ser Pro Arg Glu Ala Leu Ala Met Asp Pro Gln Gln Arg Leu Met Leu
        115                 120                 125

Glu Val Ser Trp Glu Ala Leu Glu Arg Ala Gly Ile Asp Pro Ala Thr
    130                 135                 140

Leu Arg Gly Ser Arg Thr Gly Val Phe Ala Gly Leu Met Ser Gln Asp
145                 150                 155                 160
```

```
Tyr Ala Thr Arg Leu Leu Ser Val Pro Asp Asp Leu Ala Gly Tyr Leu
                165                 170                 175
Gly Asn Gly Asn Ala Gly Ser Ile Leu Ser Gly Arg Val Ala Tyr Thr
                180                 185                 190
Phe Gly Phe Glu Gly Pro Ala Val Thr Val Asp Thr Ala Cys Ser Ser
                195                 200                 205
Ser Leu Val Ala Leu His Leu Ala Cys Gln Ser Leu Arg Thr Gly Glu
            210                 215                 220
Ser Ser Phe Ala Leu Ala Gly Gly Val Thr Val Met Ser Thr Pro Gly
225                 230                 235                 240
Met Phe Val Glu Phe Ser Arg Gln Arg Gly Leu Ser Pro Asp Gly Arg
                245                 250                 255
Cys Lys Ala Tyr Ala Ser Ala Ala Asp Gly Thr Gly Met Ser Glu Gly
                260                 265                 270
Val Gly Ile Leu Leu Leu Glu Arg Leu Ser Glu Ala Glu Arg Arg Gly
                275                 280                 285
His Arg Val Leu Ala Val Val Arg Gly Ser Ala Val Asn Gln Asp Gly
                290                 295                 300
Ala Ser Asn Gly Leu Thr Ala Pro Asn Gly Pro Ser Gln Gln Arg Val
305                 310                 315                 320
Ile Arg Gln Ala Leu Ala Cys Ala Gly Leu Ser Val Ala Asp Val Asp
                325                 330                 335
Val Val Glu Gly His Gly Thr Gly Thr Thr Leu Gly Asp Pro Ile Glu
                340                 345                 350
Ala Gln Ala Leu Leu Ala Thr Tyr Gly Gln Arg Ala Gly Asp Thr Pro
                355                 360                 365
Val Trp Leu Gly Ser Val Lys Ser Asn Ile Gly His Ala Gln Ala Ala
                370                 375                 380
Ala Gly Val Ala Gly Val Ile Lys Met Val Met Ala Leu Arg Ala Gly
385                 390                 395                 400
Val Leu Pro Arg Thr Leu His Val Asp Glu Pro Ser Ser Gln Val Asp
                405                 410                 415
Trp Ser Ser Gly Ser Val Arg Val Leu Ala Asp Glu Val Glu Trp Pro
                420                 425                 430
Gly Val Glu Gly Arg Leu Arg Arg Ala Gly Val Ser Ala Phe Gly Val
                435                 440                 445
Ser Gly Thr Asn Ala His Val Ile Leu Glu Glu Ala Ser Gly Gly Ala
                450                 455                 460
Gly Gly Gly Ala Gly Arg Leu Gln Glu Leu Gly Pro Gly Val Val Ser
465                 470                 475                 480
Gly Ser Gly Val Val Pro Trp Val Val Ser Ala Arg Ser Glu Leu Ala
                485                 490                 495
Leu Arg Gly Gln Ala Arg Arg Leu Arg Gly Val Val Ala Val Gly Gly
                500                 505                 510
Gly Ala Asp Gly Val Gly Val Ser Pro Ala Gly Val Gly Arg Ala Leu
                515                 520                 525
Val Ser Glu Arg Ser Val Phe Glu His Arg Ala Val Val Ala Glu
                530                 535                 540
Asp Arg Asp Glu Phe Leu His Ala Leu Asp Ala Leu Ala Gly Gly Arg
545                 550                 555                 560
Pro Val Pro Gly Val Val Glu Gly Arg Thr Thr Ser Gly Glu Leu Ala
                565                 570                 575
Val Leu Phe Ala Gly Gln Gly Thr Gln Arg Ala Gly Met Gly Arg Glu
```

-continued

```
                580                 585                 590
Leu Tyr Glu Ala Tyr Pro Val Phe Ala Gln Ala Ile Asp Glu Ile Cys
            595                 600                 605

Ala Glu Ala Asp Thr Ala Arg Thr Asp Pro Gly Ala Pro Gly Leu Arg
            610                 615                 620

Asp Val Leu Phe Ala Pro Gln Asp Ser Pro Glu Gly Arg Leu Ile Glu
625                 630                 635                 640

Asp Thr Gly Phe Ala Gln Pro Ala Leu Phe Ala Phe Glu Val Ala Leu
                645                 650                 655

Phe Arg Leu Leu Glu Thr Trp Gly Leu Thr Pro Asp Tyr Val Leu Gly
            660                 665                 670

His Ser Val Gly Glu Leu Ala Ala Ala His Val Ala Gly Met Leu Cys
            675                 680                 685

Leu Ala Asp Ala Val Ala Leu Val Ala Arg Gly Arg Leu Met Gln
            690                 695                 700

Gly Leu Pro Ser Gly Gly Ala Met Val Ala Ile Glu Ala Ser Glu Asp
705                 710                 715                 720

Glu Ile Leu Pro Leu Pro Asp Glu Tyr Ala Ser Arg Val Ala His Ala
                725                 730                 735

Ala Val Asn Gly Pro Arg Ser Ile Val Leu Ser Gly Asp Glu Asp Ala
            740                 745                 750

Val Leu Asp Leu Ala Gln Gln Trp Ala Ala Arg Gly Arg Arg Thr Arg
            755                 760                 765

Arg Leu Arg Thr Ser His Ala Phe His Ser Pro His Met Asp Ala Met
            770                 775                 780

Leu Gly Asp Phe Arg Arg Ala Ala Glu Gln Val Thr Phe Ser Ala Pro
785                 790                 795                 800

Arg Ile Pro Val Val Ser Asn Val Thr Gly Ala Pro Leu Pro Ala Glu
                805                 810                 815

Thr Met Cys Thr Pro Asp Tyr Trp Val Glu His Ala Arg Ser Thr Val
                820                 825                 830

Arg Phe Ala Asp Gly Ile Ser Trp Leu Gln Glu Gln Gly Val Thr Thr
            835                 840                 845

Cys Leu Glu Ile Gly Pro Asp Gly Thr Leu Ser Ala Leu Ala Gln Asp
850                 855                 860

Ser Leu Ser Ala Pro Ala Arg Ala Ile Pro Ala Leu Arg Pro Asp Gln
865                 870                 875                 880

Pro Glu Ala Arg Ser Val Met Thr Ala Leu Ala Glu Leu Phe Val Ala
                885                 890                 895

Gly Thr Ala Val Glu Trp Ala Gly Val Phe Glu Gly Thr Ala Arg Glu
            900                 905                 910

Val Gly Asp Gly Cys Gly Val Glu Leu Pro Thr Tyr Ala Phe Glu Arg
            915                 920                 925

Glu Arg Phe Trp Leu Asp Val Glu Glu Gly Ser Ala Gly Gly Ser Gly
            930                 935                 940

Val Ser Gly Met Trp Gly Gly Pro Leu Trp Glu Ala Val Glu Cys Gly
945                 950                 955                 960

Asp Ala Gly Val Val Ala Ser Leu Leu Gly Val Asp Glu Gly Ala Ser
                965                 970                 975

Leu Gly Ala Val Val Ser Ala Leu Gly Glu Trp Gly Arg Val Arg His
            980                 985                 990

Glu Arg Glu Val Val Asp Gly Trp Arg Tyr Arg Glu Val Trp Arg Pro
            995                 1000                1005
```

-continued

```
Val Ser Gly Gly Gly Val Gly Gly Leu Ser Gly Ala Trp Leu Val Val
        1010                1015                1020

Ser Glu Gly Glu Ala Gly Pro Val Asp Val Val Ala Glu Gly Leu Glu
1025            1030                1035                1040

Arg Cys Gly Ala Arg Val Arg Val Glu Val Ala Gly Cys Val
                1045            1050            1055

Ser Arg Glu Val Leu Ala Gly His Leu Arg Glu Ala Val Asp Gly Glu
        1060                1065                1070

Ala Val Gly Gly Val Val Ser Leu Val Gly Trp Gly Ser Gly Val Val
        1075                1080                1085

Gln Ala Gly Val Ala Ser Val Gly Leu Val Gln Ala Leu Gly Asp Val
        1090                1095                1100

Gly Val Gly Ala Arg Leu Trp Cys Val Thr Gly Ala Val Ser Val
1105            1110            1115                1120

Gly Gly Arg Asp Ala Val Trp Gly Pro Ala Ser Gly Val Val Trp Gly
                1125                1130                1135

Leu Gly Arg Val Val Gly Ala Glu Ala Pro Asp Arg Trp Gly Gly Leu
        1140                1145                1150

Val Asp Val Pro Glu Leu Val Asp Glu Arg Val Val Asp Gly Leu Val
        1155                1160                1165

Gly Val Leu Ala Gly Val Gly Gly Gly Glu Ser Glu Phe Ala Val
        1170                1175                1180

Arg Ser Ser Gly Ala Phe Val Arg Arg Leu Val Arg Ala Pro Leu Glu
1185            1190                1195                1200

Glu Ala Val Ala Glu Arg Glu Trp Arg Pro Arg Gly Thr Val Leu Val
                1205                1210                1215

Thr Gly Gly Thr Gly Glu Leu Gly Ala His Val Ala Arg Trp Met Ala
                1220                1225                1230

Arg Arg Gly Ala Glu His Leu Leu Leu Val Ser Arg Arg Gly Glu Ser
                1235                1240                1245

Ala Gln Gly Val Glu Glu Leu Arg Ala Asp Leu Met Gly Leu Gly Ala
        1250                1255                1260

Arg Val Ser Val Val Ala Cys Asp Ala Ala Asp Arg Glu Ala Leu Ala
1265            1270                1275                1280

Glu Val Leu Arg Ser Ala Val Pro Ala Glu Cys Pro Leu Gly Val Val
                1285                1290                1295

Val His Ala Ala Gly Val Asp Asp Gly Val Leu Glu Gly Leu Ser
        1300                1305                1310

Ser Glu Arg Val Thr Gly Val Leu Arg Ala Lys Ala Leu Ala Ala Trp
        1315                1320                1325

Asn Leu His Glu Leu Thr Arg Gly Ala Asp Leu Ser Gly Phe Val Val
        1330                1335                1340

Phe Ser Ser Ala Ala Ala Thr Phe Gly Pro Ala Gly Gln Gly Ser Tyr
1345            1350            1355                1360

Ala Ala Ala Asn Ala Tyr Val Glu Ala Ile Val Arg His Arg Gly
                1365                1370                1375

Glu Gly Leu Pro Gly Leu Ala Val Ala Trp Gly Pro Trp Ala Gly Gly
                1380                1385                1390

Gly Met Ala Glu Gly Ala Val Gly Gln Met Arg Arg Gly Leu Ala
                1395                1400                1405

Ala Met Thr Pro Glu Thr Ala Leu Val Ala Leu Gly Gln Ala Leu Asp
        1410                1415                1420
```

-continued

His Asp Glu Thr Cys Val Thr Val Ala Asp Ile Asp Trp Asp Arg Phe
1425                1430                1435                1440

Thr Ala Asn Ser Leu Pro Gly Ser Arg Leu Ser Pro Leu Ile Ser Asp
            1445                1450                1455

Ile Pro Glu Ala Arg Leu Ala Arg Glu Thr Thr Gly Leu Asp Thr Ala
        1460                1465                1470

Thr Ala Ser Pro Asp Ser Phe Ser Ala Arg Leu Lys Ala Met Asp Thr
    1475                1480                1485

Ala Glu Gln Glu Arg Ala Leu Leu Asp Leu Val Arg Thr Tyr Ala Ala
1490                1495                1500

Thr Val Leu Gly His Ser Thr Pro Thr Ala Val Arg Pro Glu Arg Ala
1505                1510                1515                1520

Phe Arg Asp Leu Gly Phe Val Ser Val Ser Ala Val Glu Leu Arg Asn
            1525                1530                1535

Arg Leu Asn Ala Val Thr Gly Leu Leu Leu Pro Thr Thr Leu Ile Phe
            1540                1545                1550

Asp Tyr Pro Thr Pro Ser Ala Leu Ala Gly Tyr Leu Lys Glu Gln Leu
        1555                1560                1565

Glu Glu Gly Ala Gly Gly Gln Arg Asp Ile Ala Pro Pro Val Pro Ala
    1570                1575                1580

Ser Arg Val Asp Val Asp Glu Pro Ile Ala Ile Val Gly Met Ala Cys
1585                1590                1595                1600

Arg Phe Pro Gly Gly Val Glu Ser Ala Glu Asp Leu Trp Glu Leu Val
            1605                1610                1615

Ala Ser Gly Arg Asp Ala Val Gly Glu Phe Pro Val Asp Arg Gly Trp
            1620                1625                1630

Asp Val Glu Ala Phe Tyr Asp Pro Glu Pro Gly Arg Ala Gly Ser Ser
        1635                1640                1645

Tyr Thr Arg Arg Gly Gly Phe Leu Glu Gly Ala Ala Glu Phe Asp Ala
    1650                1655                1660

Gly Phe Phe Gly Ile Ser Pro Arg Glu Ala Leu Ala Met Asp Pro Gln
1665                1670                1675                1680

Gln Arg Leu Met Leu Glu Val Ser Trp Glu Ala Leu Glu Arg Ala Gly
            1685                1690                1695

Ile Asp Pro Ala Thr Leu Arg Gly Ser Thr Thr Gly Val Phe Ala Gly
        1700                1705                1710

Met Cys Ser Gln Asp Tyr Ala Asp Leu Val Arg Arg Ala Thr Glu Asp
        1715                1720                1725

Leu Glu Gly Tyr Ala Met Thr Gly Leu Ser Ser Ser Val Thr Ser Gly
    1730                1735                1740

Arg Val Ala Tyr Thr Leu Gly Leu Glu Gly Pro Ala Val Thr Val Asp
1745                1750                1755                1760

Thr Ala Cys Ser Ser Ser Leu Val Ala Leu His Leu Ala Cys Gln Ala
            1765                1770                1775

Leu Arg Ser Gly Glu Cys Ser Leu Ala Leu Ala Gly Gly Val Thr Val
            1780                1785                1790

Met Ser Thr Pro Gly Ala Phe Val Glu Phe Ser Arg Gln Arg Gly Leu
        1795                1800                1805

Ser Pro Asp Gly Arg Cys Lys Ala Tyr Gly Ser Gly Ala Asp Gly Val
        1810                1815                1820

Gly Trp Ala Glu Gly Val Gly Val Leu Leu Val Glu Arg Leu Ser Glu
    1825                1830                1835                1840

Ala Glu Arg Arg Gly His Arg Val Leu Ala Val Val Arg Gly Ser Ala

-continued

```
              1845                1850                1855
Val Asn Gln Asp Gly Ala Ser Asn Gly Leu Thr Ala Pro Asn Gly Pro
              1860                1865                1870
Ser Gln Gln Arg Val Ile Arg Gln Ala Leu Ala Cys Ala Gly Leu Ser
              1875                1880                1885
Val Ala Asp Val Asp Val Val Glu Gly His Gly Thr Gly Thr Thr Leu
              1890                1895                1900
Gly Asp Pro Ile Glu Ala Gln Ala Leu Leu Ala Thr Tyr Gly Gln Gly
1905                1910                1915                1920
Arg Ser Gly Glu Arg Pro Val Trp Leu Gly Ser Val Lys Ser Asn Ile
              1925                1930                1935
Gly His Ala Gln Ala Ala Ala Gly Val Ala Gly Val Ile Lys Met Val
              1940                1945                1950
Met Ala Leu Arg Ala Gly Val Leu Pro Arg Thr Leu His Val Asp Glu
              1955                1960                1965
Pro Ser Ser Gln Val Asp Trp Ser Ser Gly Ser Val Arg Val Leu Ala
              1970                1975                1980
Asp Glu Val Glu Trp Pro Gly Val Gly Arg Leu Arg Arg Ala Gly
1985                1990                1995                2000
Val Ser Ala Phe Gly Val Ser Gly Thr Asn Ala His Val Ile Leu Glu
              2005                2010                2015
Glu Ala Ser Gly Gly Ala Asp Gly Gly Ala Gly Arg Leu Gln Glu Leu
              2020                2025                2030
Gly Pro Gly Val Val Ser Gly Ser Gly Val Val Pro Trp Val Val Ser
              2035                2040                2045
Ala Arg Ser Glu Leu Ala Leu Arg Gly Gln Ala Arg Arg Leu Arg Gly
              2050                2055                2060
Val Val Ala Val Gly Gly Gly Ala Asp Gly Val Gly Val Ser Pro Ala
2065                2070                2075                2080
Gly Val Gly Arg Ala Leu Val Ser Glu Arg Ser Val Phe Glu His Arg
              2085                2090                2095
Ala Val Val Val Ala Glu Asp Arg Asp Glu Phe Leu His Ala Leu Asp
              2100                2105                2110
Ala Leu Ala Glu Gly Ala Pro Thr Ala Gly Val Val Gln Gly Val Ala
              2115                2120                2125
Gly Pro Ala Ala Asp Gly Lys Ile Ala Met Leu Phe Gly Gly Gln Gly
              2130                2135                2140
Thr His Trp Glu Gly Met Ala Gln Glu Leu Leu Gly Ser Ser Pro Val
2145                2150                2155                2160
Phe Ala Gln Gln Met Ser Asp Cys Ala Gln Ala Leu Glu Pro Tyr Leu
              2165                2170                2175
Asp Trp Ser Leu Leu Asp Val Leu Arg Gly Ala Pro Asp Ala Pro Pro
              2180                2185                2190
Leu Gln Arg Val Asp Val Val Gln Pro Val Leu Phe Ala Val Met Val
              2195                2200                2205
Ser Leu Ala Ala Leu Trp Arg Ser Tyr Gly Val His Pro Asp Ala Val
              2210                2215                2220
Ala Gly His Ser Gln Gly Glu Ile Ala Ala Ala Tyr Val Ala Gly Ala
2225                2230                2235                2240
Leu Ser Leu Asp Asp Ala Ala Arg Val Thr Ala Leu Arg Ser Gln Ala
              2245                2250                2255
Leu Ala Ala Leu Ala Gly Gln Gly Ala Met Ala Ser Val Gly Leu Pro
              2260                2265                2270
```

```
Val Glu Lys Leu Glu Pro Arg Leu Ala Thr Trp Gly Asp Arg Leu Val
        2275                2280                2285

Ile Ala Ala Val Asn Gly Ala Arg Ser Ala Val Val Ser Gly Glu Pro
        2290                2295                2300

Glu Ala Val Asp Ala Leu Val Glu Glu Leu Ser His Glu Asp Val Pro
2305                2310                2315                2320

Ala Arg Arg Leu Met Val Asp Trp Ala Ser His Ser Pro Gln Val Glu
                2325                2330                2335

Ala Ile Gln Gly Arg Leu Leu Glu Leu Leu Ala Pro Ile Arg Ala Arg
        2340                2345                2350

Thr Gly Asp Val Pro Phe Tyr Ser Thr Val Thr Gly Glu Arg Ile Asp
        2355                2360                2365

Gly Thr Glu Leu Asp Ala Asp Tyr Trp Tyr Arg Asn Leu Arg Gln Val
        2370                2375                2380

Val Arg Phe Arg Asp Ala Thr Gln Ala Leu Val Arg Ala Gly His Thr
2385                2390                2395                2400

Val Phe Ile Glu Ala Cys Pro His Pro Ala Val Ala Val Gly Val Gln
                2405                2410                2415

Glu Thr Leu Asp Glu Met Gly Asp Leu Asp Ser Leu Val Val Gly Ser
        2420                2425                2430

Leu Arg Arg Gly Glu Gly Gly Leu Arg Arg Phe Leu Met Ser Val Ala
        2435                2440                2445

Glu Leu Phe Val Gly Gly Val Ala Val Glu Trp Ser Gly Val Phe Gly
        2450                2455                2460

Ser Val Gly Arg Gly Val Ala Gly Gly Cys Gly Val Glu Leu Pro Thr
2465                2470                2475                2480

Tyr Ala Phe Glu Arg Glu Arg Phe Trp Leu Asp Val Glu Gly Ala Pro
                2485                2490                2495

Arg Gly Ser Gly Val Ser Gly Gln Trp Gly Gly Gln Leu Ser Glu Ala
        2500                2505                2510

Val Asp Thr Val Arg Gly Gly Met Leu Arg Asp Cys Leu Ala Gly Leu
        2515                2520                2525

Asp Pro Ala Ala Gln Ala Glu Thr Val Leu Asp Leu Val Leu Thr His
        2530                2535                2540

Ala Ala Ala Val Leu Gly His Gly Thr Ala Asp Ala Val Val Pro Glu
2545                2550                2555                2560

Arg Ala Phe Arg Asp Leu Gly Phe Asp Ser Leu Thr Ala Val Glu Leu
                2565                2570                2575

Arg Asn Arg Leu Asn Thr Ala Thr Gly Leu Arg Phe Pro Arg Thr Leu
        2580                2585                2590

Val Phe Asp His Pro Arg Pro Val Ala Leu Ala Ala His Ile His Glu
        2595                2600                2605

Gln Leu Ser Gly Gly Ser Pro Thr Thr Gly Thr Ala Leu Ala Leu Ala
        2610                2615                2620

Leu Arg Ala Pro Ala Pro Arg Val Asp Val Asp Glu Pro Ile Ala Ile
2625                2630                2635                2640

Val Gly Met Ala Cys Arg Phe Pro Gly Gly Val Glu Ser Ala Glu Asp
                2645                2650                2655

Phe Trp Glu Leu Ile Ala Ser Gly Arg Asp Ala Val Gly Glu Phe Pro
        2660                2665                2670

Val Asp Arg Gly Trp Asp Val Glu Ala Phe Tyr Asp Pro Glu Pro Gly
        2675                2680                2685
```

-continued

```
Arg Ala Gly Thr Ser Tyr Thr Arg Cys Gly Gly Phe Leu Gln Gly Ala
    2690                2695                2700
Ala Glu Phe Asp Ala Gly Phe Phe Gly Ile Ser Pro Arg Glu Ala Leu
2705                2710                2715                2720
Ala Met Asp Pro Gln Gln Arg Leu Met Leu Glu Val Ser Trp Glu Ala
                2725                2730                2735
Leu Glu Arg Ala Gly Ile Asp Pro Ala Thr Leu His Gly Ser Thr Thr
                2740                2745                2750
Gly Val Phe Ala Gly Val Ser Gln Gln Asp Tyr Ala Glu Leu Leu Arg
                2755                2760                2765
Arg Gly Thr Gln Asp His Glu Gly Tyr Ala Leu Thr Gly Val Ser Asn
                2770                2775                2780
Ser Val Val Ser Gly Arg Leu Ser Tyr Thr Phe Gly Phe Glu Gly Pro
2785                2790                2795                2800
Ala Val Thr Val Asp Thr Ala Cys Ser Ser Leu Val Ala Leu His
                2805                2810                2815
Leu Ala Cys Gln Ala Leu Arg Ser Gly Glu Cys Ser Leu Ala Leu Ala
                2820                2825                2830
Gly Gly Val Thr Val Met Ser Thr Pro Gly Ala Phe Val Glu Phe Ser
                2835                2840                2845
Arg Gln Arg Gly Leu Ser Pro Asp Gly Arg Cys Lys Ala Tyr Gly Ser
                2850                2855                2860
Gly Ala Asp Gly Val Gly Trp Ala Glu Gly Val Gly Val Leu Leu Val
2865                2870                2875                2880
Glu Arg Leu Ser Glu Ala Glu Arg Arg Gly His Arg Val Leu Ala Val
                2885                2890                2895
Val Arg Gly Ser Ala Val Asn Gln Asp Gly Ala Ser Asn Gly Leu Thr
                2900                2905                2910
Ala Pro Asn Gly Pro Ser Gln Gln Arg Val Ile Arg Gln Ala Leu Ala
                2915                2920                2925
Cys Ala Gly Leu Ser Val Ala Asp Val Asp Val Val Glu Gly His Gly
                2930                2935                2940
Thr Gly Thr Thr Leu Gly Asp Pro Ile Glu Ala Gln Ala Leu Leu Ala
2945                2950                2955                2960
Thr Tyr Gly Gln Gly Arg Ser Gly Glu Arg Pro Val Trp Leu Gly Ser
                2965                2970                2975
Val Lys Ser Asn Ile Gly His Ala Gln Ala Ala Gly Val Ala Gly
                2980                2985                2990
Val Ile Lys Met Val Met Ala Leu Asn His Glu Leu Leu Pro Thr Ser
                2995                3000                3005
Leu His Ile Asp Glu Pro Ser Pro His Ile Asp Trp Ser Ser Gly Gly
                3010                3015                3020
Val Arg Leu Leu Thr Glu Pro Val Pro Trp Gln Gln Asn Gly Arg Pro
3025                3030                3035                3040
Arg Arg Ala Gly Val Ser Ala Phe Gly Val Ser Gly Thr Asn Ala His
                3045                3050                3055
Val Ile Ile Glu Gln Ala Pro Val Glu Ala His Val Ile Ser Glu Pro
                3060                3065                3070
Val Pro Ala Glu Ala His Val Ile Val Glu Gln Ala Pro Val Glu Ala
                3075                3080                3085
Pro His Val Val Asp Ala Thr Gly Pro Ala Asp Leu Thr Glu Pro Gln
                3090                3095                3100
Glu Glu Ala Ala Glu Pro Glu Cys Val Ala Asp Ala Val Thr Glu Met
```

-continued

```
        3105             3110             3115             3120
Ser Ala Glu Pro Glu Cys Val Ala Asp Ala Met Ser Glu Met Ser Ala
            3125             3130             3135
Glu Cys Val Ala Glu Ala Val Ser Asp Lys Ser Ala Glu Pro Glu Cys
            3140             3145             3150
Val Ala Asp Ala Met Ser Asp Lys Pro Ala Leu Leu Pro Ile Pro Trp
            3155             3160             3165
Leu Leu Ser Ala Lys Ser Glu Arg Ala Leu Arg Gly Gln Ala Arg Arg
    3170             3175             3180
Leu Arg Gln Phe Ala Ala Arg Ala Ser Asp Ala Arg Pro Ala Asp Val
3185             3190             3195             3200
Ala His Ala Leu Ala Ala Gln Arg Ser Val Phe Asp His Arg Ala Val
            3205             3210             3215
Val Val Ala Glu Asp Arg Asp Gly Phe Leu Gln Ala Leu Asp Ala Leu
            3220             3225             3230
Ala Glu Gly Arg Ser Ala Asp Gly Leu Ile Glu Gly Ser Val Gly Pro
            3235             3240             3245
Arg Gly Gly His Ser Gly Arg Arg Gly Lys Thr Ala Met Leu Phe
            3250             3255             3260
Ala Gly Gln Gly Thr Gln Arg Val Gly Met Gly Arg Gln Leu Tyr Ala
3265             3270             3275             3280
Ala His Pro Ala Tyr Ala Asp Ala Leu Asp Gln Val Leu Ala Glu Leu
            3285             3290             3295
Asp Gly His Leu Asp Gln Pro Leu Arg Pro Leu Ile His Ala Ser Ala
            3300             3305             3310
Asp Leu Ala Asp Val Ala Asp Ala Ala Asp Val Leu Asp Arg Thr Arg
            3315             3320             3325
Tyr Ala Gln Pro Ala Leu Phe Ala Val Gln Val Ala Leu Phe Arg His
            3330             3335             3340
Leu Glu Arg Leu Gly Val Arg Ala Asp Phe Val Ala Gly His Ser Ile
3345             3350             3355             3360
Gly Glu Leu Ala Ala Ala His Val Ala Gly Val Leu Pro Leu Ala Ala
            3365             3370             3375
Ala Cys Arg Leu Val Ala Ala Arg Gly Arg Leu Met Glu Gln Leu Ala
            3380             3385             3390
Pro Gly Gly Ala Met Val Ala Val Arg Ala Ser Glu Ala Glu Ala Arg
            3395             3400             3405
Gln Ala Leu Asp Gly Arg Glu Ala Arg Val Ser Val Ala Ala Val Asn
            3410             3415             3420
Gly Pro Ala Ser Val Val Phe Ser Gly Ala Glu Asp Glu Val Gly Asn
3425             3430             3435             3440
Met Ala Asp Trp Phe Ala Glu Arg Gly Arg Arg Val Lys Arg Leu Arg
            3445             3450             3455
Thr Gly His Ala Phe His Ser Pro Leu Met Asp Pro Met Leu Glu Glu
            3460             3465             3470
Phe Gln Gln Val Ala Ala Ser Leu Thr Tyr Ser Glu Pro Ala Ile Pro
            3475             3480             3485
Met Val Ser Thr Leu Thr Gly Asp Ile Val Ala Gly Glu Leu Ser
            3490             3495             3500
Asp Pro Glu Tyr Trp Val Arg Gln Val Arg Arg Thr Val Arg Phe Gly
3505             3510             3515             3520
Asp Ala Ile Ser Arg Leu His Thr Asp Gly Val Arg Thr Phe Met Glu
            3525             3530             3535
```

```
Leu Gly Pro Asp Gly Thr Leu Ser Ala Leu Ala Glu Glu Cys Leu Glu
            3540                3545                3550

Ala Thr Ala Asp Ser His Pro Ala Asp Asp Thr Gly Thr Pro Gln
        3555                3560                3565

Glu Asn Leu Leu Ile Pro Leu Leu Arg Pro Asp Ser Pro Glu Pro Gly
    3570                3575                3580

Thr Leu Leu Thr Gly Leu Ala Arg Leu His Thr His Gly Ala Ala Ala
3585                3590                3595                3600

Val Asn Trp Pro Ala Ala Leu Pro Glu Arg Asp Arg Ala Arg His Leu
            3605                3610                3615

Asp Leu Pro Thr Tyr Ala Phe Asp His His Arg Tyr Trp Val Asp Thr
        3620                3625                3630

Ser Ala Gly His Pro Gly Asp Leu Ser Ala Ala Gly Leu Gly Thr Ala
    3635                3640                3645

Gly His Pro Leu Leu Gly Ser Ala Val Ala Leu Ala Glu Ser Gln Glu
3650                3655                3660

Leu Leu Phe Thr Gly Arg Leu Ser Leu Arg Thr His Pro Trp Leu Ala
3665                3670                3675                3680

Asp His Ala Ile Phe Gly Thr Val Leu Leu Pro Gly Thr Ala Ile Leu
        3685                3690                3695

Glu Leu Ala Val Arg Ala Gly Asp Glu Val Asp Cys Gly Thr Val Glu
    3700                3705                3710

Glu Leu Thr Leu Arg Thr Pro Leu Val Leu Pro Glu Gln Gly Ser Val
        3715                3720                3725

Ile Leu Gln Leu Ser Val Gly Ala Pro Gln Gly Pro Gln Thr Pro Glu
    3730                3735                3740

Glu Pro Glu Arg Arg Thr Phe Ala Leu Tyr Ala Arg Glu Asp Asp Gly
3745                3750                3755                3760

Leu Ser Ser Ser Ala Ala Thr Gly Thr Glu Trp Thr Cys His
            3765                3770                3775

Ala Thr Gly Val Leu Thr Gly Thr Ala Arg Pro Ala Glu Glu His Thr
        3780                3785                3790

Gln Glu Pro Trp Pro Ala Asp Ala Ala Pro Val Asp Leu Asp Gly
    3795                3800                3805

Trp Tyr Glu Gln Leu Ala Gly Ala Gly Leu Gly Tyr Gly Pro Val Phe
    3810                3815                3820

Gln Gly Leu Arg Glu Val Trp Arg Arg Gly Asp Glu Val Phe Ala Val
3825                3830                3835                3840

Val Thr Leu Pro Glu Ser Thr Glu Gly Gln Ala Ala Asp Ala Ala Arg
            3845                3850                3855

Tyr Ala Leu His Pro Ala Leu Leu Asp Ala Ala Leu His Pro Val Val
        3860                3865                3870

Leu Arg His Glu Gly Asp Ala Ala Ala Asp Gly His Gly Trp Leu Pro
    3875                3880                3885

Phe Ser Trp Thr Gly Val Thr Val Ala Ala Ser Gly Ala Ser Thr Leu
    3890                3895                3900

His Val Arg Leu Thr Val Arg Thr Asp Glu Asp Ala Val Gly Leu Leu
3905                3910                3915                3920

Ala Thr Asp Ala Ser Gly Arg Ile Val Ile Ser Ala Gly Ser Leu Ala
            3925                3930                3935

Phe Arg Pro Val Ser Ala Glu Gln Leu Gln Ala Ala Arg Thr Gly Tyr
        3940                3945                3950
```

```
His Asp His Leu Phe Arg Ile Glu Trp Arg Pro Leu His Leu Pro Thr
        3955                3960                3965

Thr Pro Ala Arg Thr Ala Asp Trp Ala Leu Ile Gly Pro Gly Ala Arg
        3970                3975                3980

Arg Thr Ala Ala Val Leu Glu Arg Asn Gly Ala Ser Trp Gln Ala Tyr
3985                3990                3995                4000

Pro Asp Pro Ala Ala Leu Ala Glu Ala Leu Ala Ala Gly Ala Pro Ala
        4005                4010                4015

Pro Gly Met Val Val Ile Ser Cys Glu Pro Asp Gly Ala Ser Ala Pro
        4020                4025                4030

Thr Asp Ser Ala Leu Thr Asp Ser Ala Leu Thr Asp Ser Ala Pro Ala
        4035                4040                4045

Gly Ser Ala Pro Ala Asp Ser Thr Ala Leu Ala Asp Ala Thr Arg Gln
        4050                4055                4060

Ala Thr Thr Arg Val Leu Ala Leu Leu Gln Glu Trp Val Ala Asp Glu
4065                4070                4075                4080

Arg Leu Ala Ala Cys Arg Leu Ala Leu Leu Thr His Gly Ser Val Thr
        4085                4090                4095

Ala Thr Pro Asp Glu Pro Val Ser Asp Leu Ala His Ala Ala Val Trp
        4100                4105                4110

Gly Leu Val Arg Ser Val Gln Thr Glu Asn Pro Asp Arg Phe Leu Leu
        4115                4120                4125

Ala Asp Thr Asp Asp Thr Asp Ala Ser Arg Asn Ala Leu Pro Leu Leu
4130                4135                4140

Ala Gly Glu Pro Gln Ile Ala Leu Arg Asn Gly Ala Val Arg Ile Pro
4145                4150                4155                4160

Arg Met Thr Arg Val Pro Val Arg Gln Pro Gln Pro Ser Thr Thr Asp
        4165                4170                4175

Ala Asp Trp Asp Pro Glu Ala Thr Val Leu Ile Thr Gly Gly Thr Gly
        4180                4185                4190

Val Leu Gly Arg Leu Val Ala Arg His Leu Ala Thr Ala His Gly Val
        4195                4200                4205

Arg His Leu Leu Leu Ala Thr Arg Arg Gly Thr Ala Ala Asp Gly Ala
        4210                4215                4220

Ala Asp Leu Val Ala Glu Leu Ala Gly Leu Gly Ala Glu Ala Thr Val
4225                4230                4235                4240

Ala Ala Cys Asp Ile Gly Asp Arg Ala Ala Val Ala Ala Leu Leu Asp
                4245                4250                4255

Gln Val Pro Ala Gln His Pro Leu Lys Ala Val Ile His Thr Ala Gly
        4260                4265                4270

Val Val Asp Asp Gly Ile Leu Thr Ser Leu Thr Pro Glu Arg Met Glu
        4275                4280                4285

Ala Val Leu His Ala Lys Ala Phe Gly Ala Ala His Leu His Asp Leu
        4290                4295                4300

Thr Arg Asp Ala Gly Leu Thr Thr Phe Thr Val Phe Ser Ser Ala Ala
4305                4310                4315                4320

Ala Ser Phe Gly Ser Pro Gly Gln Gly Asn Tyr Thr Ala Ala Asn Ala
                4325                4330                4335

Phe Leu Asp Ala Leu Met Gln His Arg His Thr Gln Ala Leu Pro Gly
                4340                4345                4350

Arg Ser Leu Ala Trp Gly Leu Trp Gly Glu Ala Asp Gly Met Thr Arg
        4355                4360                4365

Asn Leu Ala Gly Thr Asp Phe Ala Arg Met Ala Arg Gly Gly Leu Leu
```

-continued

```
            4370                4375                4380

Pro Leu Ser Asn Ala Gln Gly Leu Ala Leu Leu Asp Thr Ala Asp Arg
4385                4390                4395                4400

Leu Gly Pro Phe Gly Asp Gly Leu Leu Leu Ala Thr Arg Leu Asp Ala
            4405                4410                4415

Ala Thr Leu His Ala Gln Ala Thr Ala Gly Ala Leu Pro Arg Ile Leu
            4420                4425                4430

His Gly Leu Ile Arg Ile Pro Ala Arg Arg Ser Ala Asp His Gly Ile
            4435                4440                4445

Ala Thr Asp Thr Pro Ala Thr Leu Arg Glu Arg Leu Ala Gly Leu Thr
4450                4455                4460

Ile Pro Ala Gln Arg Thr Gly Leu Leu Glu Leu Val Arg Thr His
4465                4470                4475                4480

Ala Ala Ala Val Leu Gly His Pro Thr Ser Ala Val Thr Ala Ala Asp
            4485                4490                4495

Gly Ala Leu Pro Asp Asp Leu Val Pro Ala Asp Thr Glu Phe Arg Asp
            4500                4505                4510

Leu Gly Phe Asp Ser Leu Thr Ala Val Glu Leu Arg Asn Arg Ile Asn
            4515                4520                4525

Ala Val Thr Gly Leu Arg Leu Pro Ala Thr Leu Ile Phe Asp Gln Pro
            4530                4535                4540

Ser Pro Ala Ala Leu Ala Asp His Leu Ala Thr Arg Leu Thr Ala Glu
4545                4550                4555                4560

Ala Gly Thr Pro Asp Glu Pro Ala Pro Ala Ala Ala Ala Gly Ala
            4565                4570                4575

Gly Ser Ala Gly Ser Ala Glu Thr Gly Gln Gln Arg Ser Thr Gly Ser
            4580                4585                4590

Glu Lys Gln Gln Thr Arg Gly Gly Thr Ser Thr Glu Thr Val Glu Ser
            4595                4600                4605

Leu Phe Trp Ile Gly His Asp Thr Arg Arg Ile Glu Glu Ser Met Ala
            4610                4615                4620

Leu Leu Ser Ala Ala Ser Phe Phe Arg Pro Ala Phe Thr Asp Pro Ser
4625                4630                4635                4640

Asp Ile Pro Glu Pro Thr Phe Val Arg Leu Ala Gln Gly Glu Ala Arg
            4645                4650                4655

Ala Gln Gly Glu Ala Leu Ala Arg Gly Glu Thr Arg Pro Ala Leu Ile
            4660                4665                4670

Cys Leu Pro Thr Val Ala Ala Val Ser Ser Val Tyr Gln Tyr Ser Arg
            4675                4680                4685

Phe Ala Ala Gly Leu Asn Gly His Arg Asp Val Trp Tyr Val Pro Ala
            4690                4695                4700

Pro Gly Phe Leu Glu Gly Glu Pro Leu Pro Ser Gly Ile Gly Ala Val
4705                4710                4715                4720

Thr Arg Met Phe Ala Asp Ala Ile Val Arg Phe Thr Asp Gly Ala Pro
            4725                4730                4735

Phe Ala Leu Ala Gly His Ser Ala Gly Gly Trp Phe Val Tyr Ala Val
            4740                4745                4750

Thr Ser His Leu Glu Arg Leu Gly Val Arg Pro Glu Ala Val Val Thr
            4755                4760                4765

Met Asp Ala Tyr Leu Pro Asp Asp Gly Ile Ala Pro Val Ala Ser Ala
            4770                4775                4780

Leu Thr Ser Glu Ile Phe Asp Arg Val Thr Gln Phe Val Asp Val Asp
4785                4790                4795                4800
```

```
Tyr Thr Arg Leu Val Ala Met Gly Gly Tyr Phe Arg Ile Phe Ser Gly
                    4805                4810                4815

Trp Ser Pro Pro Asp Ile Thr Thr Pro Ala Leu Phe Leu Arg Gly Arg
                4820                4825                4830

Asp Gly Glu Gln Met Pro Pro Trp Gly Val Pro His Thr Val Leu
            4835                4840                4845

Asp Ile Gln Gly Asn His Phe Thr Met Leu Gln Phe Ala Asp Ser
        4850                4855                4860

Thr Ala Arg His Val Asp Glu Trp Leu Thr Glu Ile Ala Ser Val Arg
4865                4870                4875                4880

Arg

<210> SEQ ID NO 6
<211> LENGTH: 5532
<212> TYPE: PRT
<213> ORGANISM: Streptomyces avermitilis

<400> SEQUENCE: 6

Met Asp Thr Ser Ser Glu Lys Leu Val Asp Ala Leu Arg Ala Ser Leu
  1               5                  10                  15

Lys Ala Asn Gln Thr Leu Arg Ala Arg Asn Glu Gln Leu Ala Ala Ala
                 20                  25                  30

Met Glu Ala Ser Ser Glu Pro Ile Ala Ile Val Gly Met Ala Cys Arg
             35                  40                  45

Phe Pro Gly Gly Val Cys Ser Pro Glu Glu Leu Trp Glu Leu Val Ala
 50                  55                  60

Ser Gly Gly Asp Ala Ile Gly Glu Phe Pro Ala Gly Arg Gly Trp Asp
 65                  70                  75                  80

Leu Glu Gly Leu Phe Asp Ser Asp Pro Asp Arg Ser Gly Thr Ser Tyr
                 85                  90                  95

Ala Arg Tyr Gly Gly Phe Leu Tyr Glu Ala Gly Glu Phe Asp Ala Asp
            100                 105                 110

Phe Phe Gly Ile Ser Pro Arg Glu Ala Leu Ala Met Asp Pro Gln Gln
        115                 120                 125

Arg Leu Leu Leu Glu Thr Ser Trp Glu Ala Phe Glu Arg Ala Gly Ile
130                 135                 140

Asp Pro Leu Ser Met Arg Gly Ser Arg Thr Gly Val Phe Ala Gly Val
145                 150                 155                 160

Met Tyr His Asp Tyr Gly Ser Arg Leu Gly Thr Ile Pro Glu Gly Phe
                165                 170                 175

Glu Gly Tyr Ile Gly Asn Gly Ser Gly Gly Ala Val Ala Ser Gly Arg
            180                 185                 190

Val Ala Tyr Thr Leu Gly Leu Glu Gly Pro Ala Val Ser Val Asp Thr
        195                 200                 205

Ala Cys Ser Ser Ser Leu Val Ala Leu His Leu Ala Cys Gln Ser Leu
    210                 215                 220

Arg Ser Gly Glu Cys Thr Leu Ala Leu Ala Gly Gly Val Thr Val Met
225                 230                 235                 240

Ser Thr Pro His Leu Phe Val Glu Phe Ser Arg Gln Arg Gly Leu Ser
                245                 250                 255

Val Asp Gly Arg Cys Lys Ser Phe Ala Gly Ala Asp Gly Thr Gly
            260                 265                 270

Met Gly Glu Gly Val Gly Met Leu Leu Val Glu Arg Leu Ser Asp Ala
        275                 280                 285
```

```
Val Arg Leu Gly His Arg Val Leu Ala Val Leu Arg Gly Ser Ala Val
    290                 295                 300

Asn Gln Asp Gly Ala Ser Asn Gly Leu Thr Ala Pro Asn Gly Pro Ala
305                 310                 315                 320

Gln Glu Arg Val Ile Arg Gln Ala Leu Ala Asn Ala Gly Leu Ser Val
                325                 330                 335

Ala Asp Val Asp Val Val Glu Gly His Gly Thr Gly Thr Thr Leu Gly
                340                 345                 350

Asp Pro Ile Glu Ala Gln Ala Leu Leu Ala Thr Tyr Gly Gln Arg Ala
                355                 360                 365

Gly Asn Arg Pro Leu Trp Leu Gly Ser Val Lys Ser Asn Ile Gly His
    370                 375                 380

Ala Gln Ala Ala Ala Gly Val Gly Gly Val Ile Lys Met Val Met Ala
385                 390                 395                 400

Leu Arg Glu Gly Val Leu Pro Arg Thr Leu His Val Asp Glu Pro Ser
                405                 410                 415

Pro Gln Val Asp Trp Ser Ala Gly Ala Val Arg Leu Leu Thr Glu Ala
                420                 425                 430

Val Pro Trp Pro Gly Asp Ala Ala Gly Arg Leu Arg Arg Ala Gly Val
                435                 440                 445

Ser Ser Phe Gly Val Ser Gly Thr Asn Ala His Val Ile Leu Glu Glu
    450                 455                 460

Ala Pro Ala Ala Gly Gly Cys Val Ala Gly Gly Val Leu Glu Gly
465                 470                 475                 480

Ala Pro Gly Leu Ala Ile Ser Val Ala Glu Ser Val Ala Ala Pro Val
                485                 490                 495

Ala Val Ser Ala Pro Val Ala Glu Ser Val Pro Val Pro Val Pro Val
                500                 505                 510

Pro Val Pro Val Pro Val Ser Ala Arg Ser Glu Ala Gly Leu Arg Ala
                515                 520                 525

Gln Ala Glu Ala Leu Arg Gln Tyr Val Ala Val Arg Pro Asp Val Ser
    530                 535                 540

Leu Ala Asp Val Gly Ala Gly Leu Ala Cys Gly Arg Ala Val Leu Glu
545                 550                 555                 560

His Arg Ala Val Val Leu Ala Ala Asp Arg Glu Glu Leu Val Gln Gly
                565                 570                 575

Leu Gly Ala Leu Ala Ala Gly Glu Pro Asp Arg Arg Val Thr Thr Gly
                580                 585                 590

His Ala Pro Gly Gly Asp Arg Gly Val Val Phe Val Phe Pro Gly
                595                 600                 605

Gln Gly Gly Gln Trp Ala Gly Met Gly Val Arg Leu Leu Ala Ser Ser
    610                 615                 620

Pro Val Phe Ala Arg Arg Met Gln Ala Cys Glu Glu Ala Leu Ala Pro
625                 630                 635                 640

Trp Val Asp Trp Ser Val Val Asp Ile Leu Arg Arg Asp Ala Gly Asp
                645                 650                 655

Ala Val Trp Glu Arg Ala Asp Val Val Gln Pro Val Leu Phe Ser Val
                660                 665                 670

Met Val Ser Leu Ala Ala Leu Trp Arg Ser Tyr Gly Ile Glu Pro Asp
                675                 680                 685

Ala Val Leu Gly His Ser Gln Gly Glu Ile Ala Ala His Val Cys
    690                 695                 700
```

```
Gly Ala Leu Ser Leu Lys Asp Ala Ala Lys Thr Val Ala Leu Arg Ser
705                 710                 715                 720

Arg Ala Leu Ala Ala Val Arg Gly Arg Gly Gly Met Ala Ser Val Pro
            725                 730                 735

Leu Pro Ala Gln Glu Val Glu Gln Leu Ile Gly Glu Arg Trp Ala Gly
            740                 745                 750

Arg Leu Trp Val Ala Ala Val Asn Gly Pro Arg Ser Thr Ala Val Ser
            755                 760                 765

Gly Asp Ala Glu Ala Val Asp Glu Val Leu Ala Tyr Cys Ala Gly Thr
770                 775                 780

Gly Val Arg Ala Arg Arg Ile Pro Val Asp Tyr Ala Ser His Cys Pro
785                 790                 795                 800

His Val Gln Pro Leu Arg Glu Glu Leu Leu Glu Leu Leu Gly Asp Ile
            805                 810                 815

Ser Pro Gln Pro Ser Gly Val Pro Phe Phe Ser Thr Val Glu Gly Thr
            820                 825                 830

Trp Leu Asp Thr Thr Thr Leu Asp Ala Ala Tyr Trp Tyr Arg Asn Leu
            835                 840                 845

His Gln Pro Val Arg Phe Ser Asp Ala Val Gln Ala Leu Ala Asp Asp
850                 855                 860

Gly His Arg Val Phe Val Glu Val Ser Pro His Pro Thr Leu Val Pro
865                 870                 875                 880

Ala Ile Glu Asp Thr Thr Glu Asp Thr Ala Glu Asp Val Thr Ala Ile
            885                 890                 895

Gly Ser Leu Arg Arg Gly Asp Asn Asp Thr Arg Arg Phe Leu Thr Ala
            900                 905                 910

Leu Ala His Thr His Thr Thr Gly Ile Gly Thr Pro Thr Thr Trp His
            915                 920                 925

His His Tyr Thr His His His Thr His Pro His Asn His His Leu Asp
930                 935                 940

Leu Pro Thr Tyr Pro Phe Gln Arg Gln His Tyr Trp Leu Asp Ala Pro
945                 950                 955                 960

Thr Gly Ala Gly Asp Val Ala Ala Ala Gly Leu Glu Pro Ala Glu His
            965                 970                 975

Pro Leu Leu Ala Ala Thr Val Gln Leu Ala Asp Thr Asp Gly Cys Leu
            980                 985                 990

Leu Thr Gly Arg Leu Ser Leu Arg Ser His Pro Trp Leu Gly Asp Tyr
            995                 1000                1005

Glu Val Gly Gly Ala Val Leu Leu Ser Gly Ser Ala Phe Val Glu Leu
    1010                1015                1020

Ala Val Gln Val Gly Glu Arg Val Gly Cys Thr Arg Ile Glu Gln Leu
1025                1030                1035                1040

Thr Val His Ala Pro Leu Val Val Pro Val Gly Gly Val Ser Val
    1045                1050                1055

Gln Val Gly Val Ala Ala Ala Asp Gly Glu Gly Arg Arg Leu Val Ser
            1060                1065                1070

Val Tyr Ala Arg Gly Gly Ser Ala Cys Gly Gly Gly Ala Ser Gly
            1075                1080                1085

Gly Val Trp Thr Cys His Ala Ser Gly Val Leu Val Glu Ala Ala Ala
    1090                1095                1100

Gly Gly Gly Val Val Asp Gly Leu Ala Gly Val Trp Pro Pro Arg
1105                1110                1115                1120

Gly Ala Val Ala Val Asp Val Asp Gly Val Arg Asp Arg Leu Ala Gly
```

-continued

```
                1125                1130                1135
Ala Gly Cys Val Leu Gly Pro Val Phe Ser Gly Leu Arg Ala Val Trp
            1140                1145                1150

Arg Asp Gly Gly Asp Leu Leu Ala Glu Val Cys Leu Pro Glu Glu Ala
            1155                1160                1165

Trp Gly Asp Ala Ala Gly Phe Gly Leu His Pro Ala Leu Leu Asp Gly
            1170                1175                1180

Val Val Gln Pro Leu Ser Val Leu Leu Pro Gly Thr Gly Phe Gly
1185                1190                1195                1200

Glu Gly Ala Gly Phe Gly Glu Gly Val Arg Val Pro Ala Val Trp Gly
            1205                1210                1215

Gly Val Ser Leu His Arg Ala Gly Val Thr Gly Val Arg Val Arg Val
            1220                1225                1230

Trp Ala Val Gly Arg Gly Gly Arg Glu Ala Val Ser Val Val Val
            1235                1240                1245

Gly Asp Glu Ala Gly Val Pro Val Ala Ser Val Asp Arg Leu Glu Leu
            1250                1255                1260

Arg Pro Val Asp Met Gly Gln Leu Arg Ala Val Ser Val Ser Ala Gly
1265                1270                1275                1280

Arg Arg Gly Ser Leu Tyr Ala Val Gln Trp Ala Glu Val Gly Pro Val
            1285                1290                1295

Pro Val Cys Gly Gln Ala Trp Ala Trp His Glu Asp Val Gly Glu Ser
            1300                1305                1310

Gly Gly Gly Pro Val Pro Gly Val Val Leu Arg Cys Pro Asp Ala
            1315                1320                1325

Gly Ala Gly Gly Gly Gly Gly Val Gly Glu Val Val Gly Gly
            1330                1335                1340

Val Leu Gly Val Val Gln Gly Trp Leu Gly Leu Glu Arg Phe Ala Gly
1345                1350                1355                1360

Ser Arg Leu Val Val Val Thr Arg Gly Ala Val Val Ala Gly Gln Glu
            1365                1370                1375

Asp Gly Pro Val Asp Val Val Gly Ala Ala Val Trp Gly Leu Val Arg
            1380                1385                1390

Ser Ala Gln Ala Glu His Pro Asp Arg Phe Val Leu Leu Asp Leu Asp
            1395                1400                1405

Thr Asp Thr Asp Thr Gly Thr Asp Leu Asp Thr Gly Ala Gly Ala Gly
            1410                1415                1420

Ala Gly Ala Gly Trp Gly Val Asp Gly Gly His Val Ala Ala Val Val
1425                1430                1435                1440

Ala Cys Gly Glu Pro Gln Leu Ala Val Arg Gly Glu Arg Val Leu Ala
            1445                1450                1455

Ala Arg Leu Thr Arg Leu Glu Ser Ser Val Asp Val Pro Ala Gln Arg
            1460                1465                1470

Ser Gly Asp Val Ala Gly Arg Glu Val Leu Pro Trp Leu Ser Gly Gly
            1475                1480                1485

Ser Val Leu Val Thr Gly Gly Thr Gly Val Leu Gly Ala Ala Val Ala
            1490                1495                1500

Arg His Leu Ala Gly Val Cys Gly Val Arg Asp Leu Leu Val Ser
1505                1510                1515                1520

Arg Arg Gly Pro Asp Ala Pro Gly Ala Glu Gly Leu Arg Ala Glu Leu
            1525                1530                1535

Ala Ala Leu Gly Ala Glu Val Arg Ile Val Ala Cys Asp Val Gly Glu
            1540                1545                1550
```

```
Arg Arg Glu Val Val Arg Leu Leu Glu Gly Val Pro Ala Gly Cys Pro
        1555                1560                1565

Leu Thr Gly Val Val His Ala Ala Gly Val Leu Asp Asp Ala Thr Ile
    1570                1575                1580

Ala Ser Leu Thr Pro Glu Arg Leu Gly Thr Val Phe Ala Ala Lys Val
1585                1590                1595                1600

Asp Ala Ala Leu Leu Leu Asp Glu Leu Thr Arg Gly Met Glu Leu Ser
                1605                1610                1615

Ala Phe Val Leu Phe Ser Ser Ala Ala Gly Ile Leu Gly Ser Ala Gly
            1620                1625                1630

Gln Gly Asn Tyr Ala Ala Asn Ala Ala Leu Asp Ala Leu Ala Tyr
        1635                1640                1645

Arg Arg Arg Ala Ala Gly Leu Pro Gly Val Ser Leu Ala Trp Gly Leu
        1650                1655                1660

Trp Glu Glu Ala Ser Gly Met Thr Gly His Leu Ala Gly Thr Asp His
1665                1670                1675                1680

Arg Arg Ile Ile Arg Ser Gly Leu His Pro Met Ser Thr Pro Asp Ala
            1685                1690                1695

Leu Ala Leu Phe Asp Ala Ala Leu Ala Leu Asp Arg Pro Val Leu Leu
            1700                1705                1710

Pro Ala Asp Leu Arg Pro Ala Pro Pro Leu Pro Leu Leu Gln Asp
        1715                1720                1725

Leu Leu Pro Ala Thr Arg Arg Thr Thr Arg Thr Thr Thr Thr Gly
        1730                1735                1740

Gly Ala Asp Asn Gly Ala Gln Leu His Ala Arg Leu Ala Gly Gln Thr
1745                1750                1755                1760

His Glu Gln Gln His Thr Thr Leu Leu Ala Leu Val Arg Ser His Ile
            1765                1770                1775

Ala Thr Val Leu Gly His Thr Thr Pro Asp Thr Ile Pro Pro Asp Arg
            1780                1785                1790

Ala Phe Arg Asp Leu Gly Phe Asp Ser Leu Thr Ala Val Glu Leu Arg
        1795                1800                1805

Asn Arg Leu Ser Arg Thr Thr Gly Leu Arg Leu Pro Thr Thr Leu Ala
    1810                1815                1820

Phe Asp His Pro Asn Pro Thr Thr Leu Thr His Leu His Thr Gln
1825                1830                1835                1840

Leu Leu Gly Ser Asp Ser Thr Ala Ser Ile Pro Ala Pro Arg Ala Ala
                1845                1850                1855

Ala Val Pro Ala Asp Gln Asp Glu Pro Val Ala Ile Ile Gly Met Ala
                1860                1865                1870

Cys Arg Tyr Pro Gly Gly Val Thr Ser Ala Glu Glu Leu Trp Glu Leu
        1875                1880                1885

Leu Ala Ser Gly Arg Asp Thr Val Gly Glu Phe Pro Thr Asp Arg Gly
        1890                1895                1900

Trp Asp Leu Glu Ala Leu Phe Asp Pro Glu Pro Gly Arg Pro Gly Thr
1905                1910                1915                1920

Ser Tyr Thr Arg Cys Gly Ser Phe Leu Tyr Asp Ala Gly Glu Phe Asp
            1925                1930                1935

Ala Gly Phe Phe Gly Ile Ser Pro Arg Glu Ala Leu Ala Met Asp Pro
            1940                1945                1950

Gln Gln Arg Leu Leu Leu Glu Ala Ser Trp Glu Ala Met Glu Gln Ala
        1955                1960                1965
```

-continued

```
Gly Ile Asp Pro Thr Thr Val Arg Gly Ser Gln Thr Gly Val Phe Ala
    1970                1975                1980
Gly Leu Ile Pro Gln Ala Tyr Gly Pro Arg Leu His Glu Asn Ala Ala
1985                1990                1995                2000
Ala Asp Thr Glu Gly Tyr Val Leu Thr Gly Thr Ser Gly Ser Val Ala
        2005                2010                2015
Ser Gly Arg Ile Ser Tyr Thr Phe Gly Phe Glu Gly Pro Ala Val Ser
        2020                2025                2030
Val Asp Thr Ala Cys Ser Ser Leu Val Ala Leu His Leu Ala Cys
            2035                2040                2045
Gln Ala Leu Arg Ala Gly Glu Cys Ser Met Ala Leu Ala Gly Gly Val
    2050                2055                2060
Thr Val Met Ser Ser Pro Gly Ala Phe Val Glu Phe Ser Arg Gln Arg
2065                2070                2075                2080
Gly Leu Ala Ala Asp Gly His Cys Lys Ala Phe Ser Ala Ala Ala Asp
                2085                2090                2095
Gly Thr Gly Trp Gly Glu Gly Val Gly Met Leu Leu Val Glu Arg Leu
            2100                2105                2110
Ser Asp Ala Arg Arg Asn Gly His Arg Val Leu Ala Val Val Arg Gly
            2115                2120                2125
Ser Ala Val Asn Gln Asp Gly Ala Ser Asn Gly Leu Thr Ala Pro Asn
            2130                2135                2140
Gly Pro Ser Gln Gln Arg Val Ile Arg Gln Ala Leu Ala Asn Ala Gly
2145                2150                2155                2160
Leu Ser Ala Gly Asp Val Asp Ala Val Glu Ala His Gly Thr Gly Thr
                2165                2170                2175
Thr Leu Gly Asp Pro Ile Glu Ala Gln Ala Leu Leu Ala Thr Tyr Gly
            2180                2185                2190
Gln Asp Arg Ala Gly Glu Gly Pro Leu Trp Leu Gly Ser Val Lys Ser
            2195                2200                2205
Asn Val Gly His Thr Gln Ala Ala Ala Gly Val Ala Gly Val Ile Lys
    2210                2215                2220
Met Val Met Ala Leu Arg Asn Gly Leu Leu Pro Arg Thr Leu His Val
2225                2230                2235                2240
Asp Glu Pro Ser Pro His Val Asp Trp Ser Ala Gly Ala Val Gln Leu
                2245                2250                2255
Leu Thr Glu Thr Val Pro Trp Pro Gly Gly Glu Gly Arg Leu Arg Arg
                2260                2265                2270
Ala Gly Val Ser Ser Phe Gly Val Ser Gly Thr Asn Ala His Val Ile
            2275                2280                2285
Leu Glu Glu Ala Pro Ala His Asn Ile Pro Ser Asp Thr Pro Ala Asp
    2290                2295                2300
Asp Val Pro Gly Gly Pro Pro Ala Gly Glu Asp Ala Gly Ser Gly Glu
2305                2310                2315                2320
Glu Ala Ala Ala Gly Ser Pro Gly Val Trp Pro Trp Leu Val Ser Ala
                2325                2330                2335
Lys Ser Gln Pro Ala Leu Arg Ala Ala Gln Ala Leu His Ala His
            2340                2345                2350
Leu Thr Asp His Pro Gly Leu Asp Leu Ala Asp Val Gly Tyr Thr Leu
            2355                2360                2365
Ala His Ala Arg Ala Val Phe Asp His Arg Ala Thr Leu Ile Ala Ala
    2370                2375                2380
Asp Arg Asp Thr Phe Leu Gln Ala Leu Gln Ala Leu Ala Ala Gly Glu
```

-continued

```
              2385                2390                2395                2400
Pro His Pro Ala Val Ile His Ser Ser Ala Pro Gly Gly Thr Gly Thr
              2405                2410                2415
Gly Glu Ala Ala Gly Lys Thr Ala Phe Ile Cys Ser Gly Gln Gly Thr
              2420                2425                2430
Gln Arg Pro Gly Met Ala His Gly Leu Tyr His Thr His Pro Val Phe
              2435                2440                2445
Ala Ala Ala Leu Asn Asp Ile Cys Thr His Leu Asp Pro His Leu Asp
              2450                2455                2460
His Pro Leu Leu Pro Leu Leu Thr Gln Asp Pro Asn Thr Gln Asp Thr
 2465                2470                2475                2480
Thr Thr Leu Glu Glu Ala Ala Ala Leu Leu Gln Gln Thr Pro Tyr Ala
              2485                2490                2495
Gln Pro Ala Leu Phe Ala Phe Gln Val Ala Leu His Arg Leu Leu Thr
              2500                2505                2510
Asp Gly Tyr His Ile Thr Pro His Tyr Ala Gly His Ser Leu Gly
              2515                2520                2525
Glu Ile Thr Ala Ala His Leu Ala Gly Ile Leu Thr Leu Thr Asp Ala
              2530                2535                2540
Thr Thr Leu Ile Thr Gln Arg Ala Thr Leu Met Gln Thr Met Pro Pro
 2545                2550                2555                2560
Gly Thr Met Thr Thr Leu His Thr Thr Pro His His Ile Thr His His
              2565                2570                2575
Ile Thr Ala His Glu Asn Asp Leu Ala Ile Ala Ala Ile Asn Thr Pro
              2580                2585                2590
Thr Ser Leu Val Ile Ser Gly Thr Pro His Thr Val Gln His Ile Thr
              2595                2600                2605
Thr Leu Cys Gln Gln Gln Gly Ile Lys Thr Lys Thr Leu Pro Thr Asn
              2610                2615                2620
His Ala Phe His Ser Pro His Thr Asn Pro Ile Leu Asn Gln Leu His
 2625                2630                2635                2640
Gln His Thr Gln Thr Leu Thr Tyr His Pro Pro His Thr Pro Leu Ile
              2645                2650                2655
Thr Ala Asn Thr Pro Pro Asp Gln Leu Leu Thr Pro His Tyr Trp Thr
              2660                2665                2670
Gln Gln Ala Arg Asn Thr Val Asp Ile Ala Thr Thr Gln Thr Leu
              2675                2680                2685
His Gln His Gly Val Thr Thr Tyr Ile Glu Leu Gly Pro Asp Asn Thr
              2690                2695                2700
Leu Thr Thr Leu Thr His His Asn Leu Pro Asn Thr Pro Thr Thr Thr
 2705                2710                2715                2720
Leu Thr Leu Thr His Pro His His Pro Gln Thr His Leu Leu Thr
              2725                2730                2735
Asn Leu Ala Lys Thr Thr Thr Thr Trp His Pro His His Tyr Thr His
              2740                2745                2750
His His Asn Gln Pro His Thr His Thr His Leu Asp Leu Pro Thr Tyr
              2755                2760                2765
Pro Phe Gln His His His Tyr Trp Leu Glu Ser Thr Gln Pro Gly Ala
              2770                2775                2780
Gly Asn Val Ser Ala Ala Gly Leu Asp Pro Thr Glu His Pro Leu Leu
 2785                2790                2795                2800
Gly Ala Thr Leu Glu Leu Ala Glu Gly Asp Gly Cys Leu Leu Thr Gly
              2805                2810                2815
```

-continued

```
Arg Leu Ser Leu Arg Thr His Pro Trp Leu Ala Gly His Ala Val Gly
            2820                2825                2830
Gly Val Val Leu Leu Pro Gly Thr Ala Phe Ala Glu Leu Ala Leu His
        2835                2840                2845
Ala Gly Glu Ser Val Gly Cys Asp His Val Asp Glu Leu Thr Leu His
    2850                2855                2860
Thr Pro Leu Val Ile Pro Glu Val Gly Asp Val Thr Leu Gln Val Ala
2865                2870                2875                2880
Ile Ala Ala Pro Asp Glu Ser Gly Arg Arg Met Met Thr Ile His Ser
            2885                2890                2895
Arg Gly Glu Gly Gly Ser Gly Gly Ala Asp Ala Ser Ala Ser Ala Trp
        2900                2905                2910
Thr Arg His Ala Ala Gly Val Leu Ser Pro Ala Lys Asp Asp Asp Thr
    2915                2920                2925
Ala Ser Tyr Glu Leu Leu Ala Gly Pro Trp Pro Pro Val Gly Ala Thr
    2930                2935                2940
Pro Val Asp Leu Asn Thr Ala Tyr Asp Gln Met Ala Asp Ala Gly Phe
2945                2950                2955                2960
Ala Tyr Gly Leu Ala Phe Gln Gly Leu Arg Ala Ala Trp Arg Tyr Gly
            2965                2970                2975
Asp Asp Ile Leu Val Glu Ala Arg Leu Pro Glu Glu Val Ser Gly Asp
        2980                2985                2990
Ala Ala Ala Tyr Gly Leu His Pro Ala Leu Leu Asp Ala Ala Leu Gln
    2995                3000                3005
Gly Thr Gly Leu Leu Ser Val Ala Gly Pro Gly Thr Pro Val Val Pro
    3010                3015                3020
His Val Trp Asn Gly Leu Arg Phe Arg Thr His Gly Ala Val Ser Val
3025                3030                3035                3040
Arg Ala Cys Leu Ser Thr Leu Gly Ala Thr Gly Ala Ala Val Cys Val
            3045                3050                3055
Arg Ile Thr Asp Asp Thr Gly Val Pro Val Ala Ser Val Asp Arg Leu
        3060                3065                3070
Glu Leu Arg Pro Val Asp Met Gly Gln Leu Arg Ala Val Ser Val Ser
    3075                3080                3085
Ala Gly Arg Arg Gly Ser Leu Tyr Ala Val Gln Trp Ala Glu Val Gly
    3090                3095                3100
Pro Val Pro Val Cys Gly Gln Ala Trp Ala Trp His Glu Asp Val Gly
3105                3110                3115                3120
Glu Ser Gly Gly Gly Pro Val Pro Gly Val Val Leu Arg Cys Pro
            3125                3130                3135
Asp Ala Gly Ala Asp Gly Gly Gly Gly Gly Val Gly Glu Val Val
        3140                3145                3150
Gly Gly Val Leu Gly Val Val Gln Gly Trp Leu Gly Leu Glu Arg Phe
    3155                3160                3165
Ala Gly Ser Arg Leu Val Val Thr Arg Gly Ala Val Val Ala Gly
    3170                3175                3180
Pro Glu Asp Gly Pro Val Asp Val Val Gly Ala Ala Val Trp Gly Leu
3185                3190                3195                3200
Val Arg Ser Ala Gln Ala Glu His Pro Asp Arg Phe Val Leu Leu Asp
            3205                3210                3215
Leu Asp Thr Asp Leu Asp Ser Gly Ala Asp Ala Asp Ala Gly Asn Glu
        3220                3225                3230
```

-continued

```
Ala Gly Met Gly Ser Gly Leu Asp Gly Gly Arg Val Ala Ala Val Val
        3235                3240                3245
Ala Cys Gly Glu Pro Gln Leu Ala Val Arg Gly Glu Arg Val Leu Ala
        3250                3255                3260
Ala Arg Leu Thr Arg Leu Glu Ser Pro Val Asp Val Ser Gly Arg Glu
3265                3270                3275                3280
Val Leu Pro Trp Leu Ser Gly Gly Ser Val Leu Val Thr Gly Gly Thr
                3285                3290                3295
Gly Val Leu Gly Ala Ala Val Ala Arg His Leu Ala Gly Val Cys Gly
        3300                3305                3310
Val Arg Asp Leu Leu Val Ser Arg Arg Gly Pro Asp Ala Pro Gly
        3315                3320                3325
Ala Glu Gly Leu Arg Ala Glu Leu Ala Ala Leu Gly Ala Glu Val Arg
        3330                3335                3340
Ile Val Ala Cys Asp Val Gly Glu Arg Arg Glu Val Val Arg Leu Leu
3345                3350                3355                3360
Glu Gly Val Pro Ala Gly Cys Pro Leu Thr Gly Val Val His Ala Ala
                3365                3370                3375
Gly Val Leu Asp Asp Ala Thr Ile Ala Ser Leu Thr Pro Glu Arg Leu
        3380                3385                3390
Gly Thr Val Phe Ala Ala Lys Val Asp Ala Ala Leu Leu Leu Asp Glu
        3395                3400                3405
Leu Thr Arg Gly Met Glu Leu Ser Ala Phe Val Leu Phe Ser Ser Ala
        3410                3415                3420
Ala Gly Ile Leu Gly Ser Ala Gly Gln Gly Asn Tyr Ala Ala Ala Asn
3425                3430                3435                3440
Ala Ala Leu Asp Ala Leu Ala Tyr Arg Arg Ala Ala Gly Leu Pro
        3445                3450                3455
Gly Val Ser Leu Ala Trp Gly Leu Trp Glu Glu Ala Ser Gly Met Thr
        3460                3465                3470
Gly His Leu Ala Gly Thr Asp His Arg Arg Ile Ile Arg Ser Gly Leu
        3475                3480                3485
His Pro Met Ser Thr Pro Asp Ala Leu Ala Leu Phe Asp Ala Ala Leu
        3490                3495                3500
Ala Leu Asp Arg Pro Val Leu Leu Pro Ala Asp Leu Arg Pro Ala Pro
3505                3510                3515                3520
Pro Leu Pro Pro Leu Leu Gln Asp Leu Leu Pro Ala Thr Arg Arg Arg
                3525                3530                3535
Thr Thr Arg Thr Thr Thr Gly Gly Ala Asp Asn Gly Ala Gln Leu
        3540                3545                3550
His Ala Arg Leu Ala Gly Gln Thr His Glu Gln His Thr Thr Leu
        3555                3560                3565
Leu Ala Leu Val Arg Ser His Ile Ala Thr Val Leu Gly His Asn Ala
        3570                3575                3580
Pro Glu Met Ile Pro Val Asp Ser Ala Phe Arg Asp Leu Gly Phe Asp
        3585                3590                3595                3600
Ser Leu Thr Ala Val Glu Leu Arg Asn Arg Leu Gly Glu Ala Thr Gly
                3605                3610                3615
Leu Arg Leu Pro Thr Ser Leu Val Phe Asp Gln Pro Asn Ala Ala Thr
        3620                3625                3630
Leu Ala Arg His Leu Arg Arg Glu Leu Met Gly Asp Asp Ala Glu Gly
        3635                3640                3645
Glu Thr Pro Ser Gln Val Ala Leu His Gln Val Ala Ala Asp Glu Pro
```

```
                3650                3655                3660
Ile Ala Ile Val Gly Met Ala Cys Arg Phe Pro Gly Gly Val Cys Ser
3665                3670                3675                3680

Pro Glu Glu Leu Trp Glu Leu Val Ala Ser Gly Gly Asp Ala Ile Gly
                3685                3690                3695

Glu Phe Pro Ala Gly Arg Gly Trp Asp Leu Glu Gly Leu Phe Asp Ser
                3700                3705                3710

Asp Pro Asp Arg Ser Gly Thr Ser Tyr Ala Arg Tyr Gly Gly Phe Leu
                3715                3720                3725

Tyr Glu Ala Gly Glu Phe Asp Ala Asp Phe Phe Gly Ile Ser Pro Arg
                3730                3735                3740

Glu Ala Leu Ala Met Asp Pro Gln Gln Arg Leu Leu Leu Glu Thr Ser
3745                3750                3755                3760

Trp Glu Ala Phe Glu Arg Ala Gly Ile Asp Pro Leu Ser Met Arg Gly
                3765                3770                3775

Ser Arg Thr Gly Val Phe Ala Gly Val Met Tyr His Asp Tyr Ala Ala
                3780                3785                3790

Arg Leu His His Val Pro Glu Gly Phe Glu Gly Leu Ile Ala Asn Gly
                3795                3800                3805

Ser Ala Gly Ser Val Ala Thr Gly Arg Val Ala Tyr Ser Phe Gly Leu
                3810                3815                3820

Glu Gly Pro Ala Val Thr Val Asp Thr Ala Cys Ser Ser Ser Leu Val
3825                3830                3835                3840

Ala Leu His Trp Ala Ala Gln Ala Leu Arg Ala Gly Glu Cys Ser Met
                3845                3850                3855

Ala Leu Ala Gly Gly Val Thr Val Met Ser Ser Pro Gly Thr Phe Val
                3860                3865                3870

Glu Phe Ser Arg Gln Arg Gly Leu Ala Ala Asp Gly Arg Cys Lys Ala
                3875                3880                3885

Tyr Ser Ala Ala Ala Asp Gly Thr Gly Trp Ala Glu Gly Val Gly Met
                3890                3895                3900

Leu Leu Val Glu Arg Leu Ser Asp Ala Arg Arg Asn Gly His Arg Val
3905                3910                3915                3920

Leu Ala Val Val Arg Gly Ser Ala Val Asn Gln Asp Gly Ala Ser Asn
                3925                3930                3935

Gly Leu Thr Ala Pro Asn Gly Pro Ser Gln Gln Arg Val Ile Arg Gln
                3940                3945                3950

Ala Leu Ala Asn Ala Gly Leu Thr Pro Ala Asp Val Asp Ala Val Glu
                3955                3960                3965

Gly His Gly Thr Gly Thr Thr Leu Gly Asp Pro Ile Glu Ala Gln Ala
                3970                3975                3980

Leu Leu Ala Ala Tyr Gly Gln His Arg Pro His His Arg Pro Leu Trp
3985                3990                3995                4000

Leu Gly Ser Leu Lys Ser Asn Ile Gly His Ala Gln Ala Ala Ala Gly
                4005                4010                4015

Val Gly Gly Val Ile Lys Met Val Met Ala Leu Arg Asn Gly Leu Leu
                4020                4025                4030

Pro Gln Thr Leu His Val Asp Glu Pro Thr Pro Gln Val Asp Trp Ser
                4035                4040                4045

Thr Gly Ala Val Gln Leu Leu Thr Gln Pro Val Pro Trp Pro Ala Asp
                4050                4055                4060

Pro Ala Gly Arg Pro Arg His Ala Gly Val Ser Ser Phe Gly Val Ser
4065                4070                4075                4080
```

-continued

```
Gly Thr Asn Ala His Val Ile Leu Glu Glu Ala Pro Ala Ala Gly
                4085                4090                4095

Gly Ala Ala Gly Gly Gly Val Ser Val Gly Ala Pro Asn Pro Ala Leu
        4100                4105                4110

Pro Val Ala Glu Ser Glu Pro Val Pro Val Pro Val Pro Val Ser Ala
        4115                4120                4125

Arg Ser Glu Ala Gly Leu Arg Ala Gln Ala Gln Ala Leu Arg Gln Tyr
        4130                4135                4140

Val Ala Ala Arg Pro Asp Met Ser Pro Ala Asp Ile Gly Ala Gly Leu
4145                4150                4155                4160

Ala Arg Gly Arg Ala Val Leu Glu His Arg Ala Val Ile Leu Ala Ala
                4165                4170                4175

Asp Arg Glu Glu Leu Ala Gln Ala Leu Thr Ala Leu Ala Ala Gly Glu
                4180                4185                4190

Pro His Pro His Ile Thr Thr Gly His Thr Arg Gly Ser Asp Arg Gly
                4195                4200                4205

Gly Val Val Phe Val Phe Pro Gly Gln Gly Gly Gln Trp Ala Gly Met
        4210                4215                4220

Gly Leu Thr Leu Leu Thr Ser Ser Pro Val Phe Ala Glu His Ile Asp
4225                4230                4235                4240

Ala Cys Glu Lys Ala Leu Thr Pro Trp Val Pro Trp Ser Leu Thr Asp
                4245                4250                4255

Ile Leu His Arg Asp Pro Asp Pro Ala Trp Gln Gln Ala Asp Val
                4260                4265                4270

Val Gln Pro Val Leu Phe Ser Ile Met Val Ser Leu Ala Ala Leu Trp
        4275                4280                4285

Arg Ser Tyr Gly Ile Glu Pro Asp Ala Val Leu Gly His Ser Gln Gly
        4290                4295                4300

Glu Ile Ala Ala Ala His Ile Cys Gly Ala Leu Ser Leu Lys Asp Ala
4305                4310                4315                4320

Ala Lys Thr Val Ala Leu Arg Ser Gln Ala Leu Ala Ala Val Arg Gly
                4325                4330                4335

Arg Gly Ala Met Val Ser Leu Pro Leu Pro Ala Gln Asp Val Gln Gln
                4340                4345                4350

Leu Ile Ser Glu Arg Trp Glu Gly Gln Leu Trp Val Ala Ala Leu Asn
        4355                4360                4365

Gly Pro His Ser Thr Thr Val Ser Gly Asp Thr Thr Ala Val Glu Glu
        4370                4375                4380

Leu Leu Thr His Cys Ala Asp Thr Gly Leu Arg Ala Lys Arg Ile Pro
4385                4390                4395                4400

Val Asp Tyr Ala Ser His Cys Pro His Val Gln Pro Leu His Asp Glu
                4405                4410                4415

Leu Leu His Leu Leu Gly Asp Ile Thr Pro Gln Pro Ser Thr Met Pro
                4420                4425                4430

Phe Phe Ser Thr Val Val Gly His Leu Val Trp Tyr Thr Thr Thr Leu
        4435                4440                4445

Asp Ala Ala Tyr Trp Tyr Arg Asn Leu His Gln Pro Val Arg Phe Ser
        4450                4455                4460

His Ala Ile Gln Thr Leu Thr Asp Asp Gly His Arg Pro Phe Ile Glu
4465                4470                4475                4480

Ile Ser Pro His Pro Thr Leu Val Pro Ala Ile Glu Asp Thr Thr Glu
                4485                4490                4495
```

-continued

```
Asn Thr Thr Glu Asn Ile Thr Ala Thr Gly Ser Leu Arg Arg Gly Asp
            4500                4505                4510

Asn Asp Thr His Arg Phe Leu Thr Ala Leu Ala His Thr His Thr Thr
            4515                4520                4525

Gly Ile Arg Thr Pro Thr Thr Trp His His His Tyr Thr Gln Thr His
            4530                4535                4540

Pro His Pro His Asn His His Leu Asp Leu Pro Thr Tyr Pro Phe Gln
4545                4550                4555                4560

His Gln His Tyr Trp Leu Gln Pro Pro Thr Thr Thr Thr Asp Leu Thr
            4565                4570                4575

Thr Thr Gly Leu Thr Pro Thr His His Pro Leu Leu Thr Ala Thr Leu
            4580                4585                4590

Thr Leu Ala Asn Asn Asn Thr Gln Leu Leu Thr Gly Arg Leu Ser Leu
            4595                4600                4605

Arg Thr His Pro Trp Leu Thr Asp His Thr Val Val Gly Thr Thr Leu
            4610                4615                4620

Val Pro Gly Thr Ala Leu Leu Glu Leu Ala Leu Gln Ala Thr Thr Thr
4625                4630                4635                4640

Asp His Leu Glu Glu Leu Ala Leu His Thr Pro Leu Val Ile Pro Arg
            4645                4650                4655

Glu Gly Ala Val Asp Val Gln Val His Ile Asn Pro Pro Asp Asp Thr
            4660                4665                4670

Asp Thr Arg Ser Leu Thr Ile Tyr Ser Arg Ser Glu Asn Ala Pro Ala
            4675                4680                4685

Ala Ala Pro Trp Arg His His Ala Thr Ala Val Leu Gly Thr Lys Thr
            4690                4695                4700

Ser Arg Ile Glu Thr Gly Arg Ser His Asp Asp Leu Ser Met Trp Pro
4705                4710                4715                4720

Pro Ala Gly Ala Val Arg Cys Ala Asp Glu Glu Leu Ala Ala Leu Tyr
            4725                4730                4735

Gly Asp Tyr Glu Ala Asn Gly Phe Val Tyr Gly Pro Ala Phe Arg Gly
            4740                4745                4750

Leu Thr Ala Ala Trp Arg Leu Gly Asp Glu Val Phe Ala Glu Val Arg
            4755                4760                4765

Leu Pro Glu Gln Val His Gly Glu Ala Ser Ala Tyr Asn Leu His Pro
            4770                4775                4780

Ala Leu Leu Asp Ala Ala Leu His Ala Ala Phe Ala Pro Ser Gly
4785                4790                4795                4800

Ser Leu Pro Gln Gly Ser Val Pro Phe Ser Phe Thr Gly Val Thr Leu
            4805                4810                4815

His Ala Ala Asn Ala Ser Ser Leu Arg Val Arg Leu Ser Pro Ala Asp
            4820                4825                4830

Pro Asn Ser Gly His Ala Ala Val Ser Val Leu Val Thr Asp Asp Thr
            4835                4840                4845

Gly Thr Pro Val Ala Ser Val Glu Ala Leu Ala Val Arg Pro Leu Ala
            4850                4855                4860

Ala Asp Glu Leu Arg Ala Ala Glu Arg Ala Val Gln Arg Ala Glu Leu
4865                4870                4875                4880

Phe Asp Met Lys Trp Val Glu Val Pro Ser Asp Val Leu Val Ser Gly
            4885                4890                4895

Gly Ala Ser Val Val Val Leu Asp Gly Ala Asp Asp Leu Val Gly Leu
            4900                4905                4910

Ala Ala Glu Glu Asp Gly Val Pro Gly Val Val Val Leu Arg Cys Pro
```

-continued

```
                4915                4920                4925
Asp Ala Gly Ala Asp Gly Gly Gly Gly Gly Val Gly Glu Val
            4930            4935            4940
Val Gly Gly Val Leu Gly Val Val Gln Gly Trp Leu Gly Leu Glu Arg
4945            4950            4955            4960
Phe Ala Gly Ser Arg Leu Val Val Val Thr Arg Gly Ala Val Val Ala
            4965            4970            4975
Gly Pro Glu Asp Gly Pro Val Asp Gly Pro Val Asp Val Val Gly Ala
            4980            4985            4990
Ala Val Trp Gly Leu Val Arg Ser Ala Gln Ala Glu His Pro Asp Arg
            4995            5000            5005
Phe Val Leu Leu Asp Leu Asp Thr Asp Leu Asp Ser Gly Ala Asp Arg
        5010            5015            5020
Asp Ala Gly Asn Glu Ala Gly Met Gly Ser Gly Leu Asp Gly Gly Arg
5025            5030            5035            5040
Val Ala Ala Val Val Ala Cys Gly Glu Pro Gln Leu Ala Val Arg Gly
            5045            5050            5055
Glu Arg Val Leu Ala Ala Arg Leu Thr Arg Leu Glu Ser Pro Val Asp
        5060            5065            5070
Val Ser Gly Arg Glu Val Leu Pro Trp Leu Ser Gly Gly Ser Val Leu
        5075            5080            5085
Val Thr Gly Gly Thr Gly Val Leu Gly Ala Ala Val Ala Arg His Leu
        5090            5095            5100
Ala Gly Val Cys Gly Val Arg Asp Leu Leu Val Ser Arg Arg Gly
5105            5110            5115            5120
Pro Asp Ala Pro Gly Ala Glu Gly Leu Arg Ala Glu Leu Ala Ala Leu
            5125            5130            5135
Gly Ala Glu Val Arg Ile Val Ala Cys Asp Val Gly Glu Arg Arg Glu
            5140            5145            5150
Val Val Arg Leu Leu Glu Gly Val Pro Ala Gly Cys Pro Leu Thr Gly
        5155            5160            5165
Val Val His Ala Ala Gly Val Leu Asp Asp Ala Thr Ile Ala Ser Leu
        5170            5175            5180
Thr Pro Glu Arg Leu Gly Thr Val Phe Ala Ala Lys Val Asp Ala Ala
5185            5190            5195            5200
Leu Leu Leu Asp Glu Leu Thr Arg Gly Met Glu Leu Ser Ala Phe Val
            5205            5210            5215
Leu Phe Ser Ser Ala Ala Gly Ile Leu Gly Ser Ala Gly Gln Gly Asn
            5220            5225            5230
Tyr Ala Ala Ala Asn Ala Ala Leu Asp Ala Leu Ala Tyr Arg Arg Arg
            5235            5240            5245
Ala Ala Gly Leu Pro Gly Val Ser Leu Ala Trp Gly Leu Trp Glu Glu
            5250            5255            5260
Ala Ser Gly Met Thr Gly His Leu Ala Gly Thr Asp His Arg Arg Ile
5265            5270            5275            5280
Ile Arg Ser Gly Leu His Pro Met Ser Thr Pro Asp Ala Leu Ala Leu
            5285            5290            5295
Phe Asp Ala Ala Leu Ala Leu Asp Arg Pro Val Leu Leu Pro Ala Asp
            5300            5305            5310
Leu Arg Pro Ala Pro Pro Leu Pro Pro Leu Leu Gln Asp Leu Leu Pro
            5315            5320            5325
Ala Thr Arg Arg Arg Thr Thr Arg Thr Thr Thr Gly Gly Ala Asp
            5330            5335            5340
```

Asn Gly Ala Gln Leu His Gly Arg Leu Ala Gly Gln Thr His Glu Gln
5345                5350                5355                5360

Gln His Thr Thr Leu Leu Ala Leu Val Arg Ser His Ile Ala Thr Val
            5365                5370                5375

Leu Gly His Thr Thr Pro Asp Thr Ile Pro Pro Asp Arg Ala Phe Arg
        5380                5385                5390

Asp Leu Gly Phe Asp Ser Leu Thr Ala Val Glu Leu Arg Asn Arg Leu
    5395                5400                5405

Ser His Thr Thr Gly Leu Arg Leu Pro Thr Thr Leu Ala Phe Asp His
    5410                5415                5420

Pro Asn Pro Thr Thr Leu Thr His His Leu His Thr Gln Leu Val Ser
5425                5430                5435                5440

Lys Gly Leu Thr Ala Ala Ala Glu Pro Asp Ala Ala Thr Thr Pro Pro
                5445                5450                5455

Gly Leu Pro Ser Leu Leu Ser Glu Leu Glu Arg Leu Glu Ala Val Val
            5460                5465                5470

Leu Ser Ser Thr Thr Ser Ser Ala Ala Pro Leu Asp Asp Gly Ala Arg
        5475                5480                5485

Thr Arg Leu Ala Ser Arg Leu His Ser Leu Ala Gln Lys Leu Asn Gly
    5490                5495                5500

Asp Asp Thr Ala Pro Asp Leu Ala Glu Thr Ser Asp Glu Glu Met Phe
5505                5510                5515                5520

Ala Leu Ile Asp Arg Glu Val Gly Phe Glu Ser Gln
                5525                5530

<210> SEQ ID NO 7
<211> LENGTH: 438
<212> TYPE: DNA
<213> ORGANISM: Streptomyces avermitilis
<220> FEATURE:
<221> NAME/KEY: CDS
<222> LOCATION: (1)..(438)

<400> SEQUENCE: 7 tac tgg ctc gaa agc aca cag ccc ggt gcc ggc aac gtg tca gca gcc      48
Tyr Trp Leu Glu Ser Thr Gln Pro Gly Ala Gly Asn Val Ser Ala Ala
 1               5                  10                  15 gga ctc gac ccc acc gaa cac ccc cta ctc ggc gcc aca ttg gaa ctg      96
Gly Leu Asp Pro Thr Glu His Pro Leu Leu Gly Ala Thr Leu Glu Leu
             20                  25                  30 gcg act gac ggt gga gcg ctt ctt gca ggg cgc ttg tct ttg agg tcg     144
Ala Thr Asp Gly Gly Ala Leu Leu Ala Gly Arg Leu Ser Leu Arg Ser
         35                  40                  45 cat ccg tgg ctg gct gac tac gag gtc ggc ggc acg gtg ctg ctg tcg     192
His Pro Trp Leu Ala Asp Tyr Glu Val Gly Gly Thr Val Leu Leu Ser
     50                  55                  60 ggc gcc acc ttc ctc gaa ctc gcc ctt cat gcg ggc aca tac gtg ggc     240
Gly Ala Thr Phe Leu Glu Leu Ala Leu His Ala Gly Thr Tyr Val Gly
 65                  70                  75                  80 tgc gac cga gtg gat gag ctg acg ctg cat gcg ccg ctg gtg gtt cct     288
Cys Asp Arg Val Asp Glu Leu Thr Leu His Ala Pro Leu Val Val Pro
                 85                  90                  95 gtg gat ggg ggt gtg agt gtg cag gtt ggg gtt gcg gct gcg gat ggg     336
Val Asp Gly Gly Val Ser Val Gln Val Gly Val Ala Ala Ala Asp Gly
            100                 105                 110 gag ggg cgg cgt ttg gtg agt gtg tat gcg cgg ggt ggg agt gct tgt     384
Glu Gly Arg Arg Leu Val Ser Val Tyr Ala Arg Gly Gly Ser Ala Cys
        115                 120                 125

```
ggt ggg ggt ggt gcg tcg ggt ggg gtg tgg acg tgt cat gcc tcg ggg      432
Gly Gly Gly Gly Ala Ser Gly Gly Val Trp Thr Cys His Ala Ser Gly
    130                 135                 140 gtg ctg                                                               438
Val Leu
145

<210> SEQ ID NO 8
<211> LENGTH: 146
<212> TYPE: PRT
<213> ORGANISM: Streptomyces avermitilis

<400> SEQUENCE: 8

Tyr Trp Leu Glu Ser Thr Gln Pro Gly Ala Gly Asn Val Ser Ala Ala
 1               5                  10                  15

Gly Leu Asp Pro Thr Glu His Pro Leu Leu Gly Ala Thr Leu Glu Leu
            20                  25                  30

Ala Thr Asp Gly Gly Ala Leu Leu Ala Gly Arg Leu Ser Leu Arg Ser
        35                  40                  45

His Pro Trp Leu Ala Asp Tyr Glu Val Gly Gly Thr Val Leu Leu Ser
    50                  55                  60

Gly Ala Thr Phe Leu Glu Leu Ala Leu His Ala Gly Thr Tyr Val Gly
 65                  70                  75                  80

Cys Asp Arg Val Asp Glu Leu Thr Leu His Ala Pro Leu Val Val Pro
                85                  90                  95

Val Asp Gly Gly Val Ser Val Gln Val Gly Val Ala Ala Ala Asp Gly
            100                 105                 110

Glu Gly Arg Arg Leu Val Ser Val Tyr Ala Arg Gly Gly Ser Ala Cys
        115                 120                 125

Gly Gly Gly Gly Ala Ser Gly Gly Val Trp Thr Cys His Ala Ser Gly
    130                 135                 140

Val Leu
145

<210> SEQ ID NO 9
<211> LENGTH: 30
<212> TYPE: DNA
<213> ORGANISM: Artificial Sequence
<220> FEATURE:
<223> OTHER INFORMATION: Primer from the sequence between 9098 and 9127
      of SEQ ID NO:1

<400> SEQUENCE: 9
ggctggctga ctacgaggtc ggcggcacgg                                      30

<210> SEQ ID NO 10
<211> LENGTH: 30
<212> TYPE: DNA
<213> ORGANISM: Artificial Sequence
<220> FEATURE:
<223> OTHER INFORMATION: Antisense primer from the sequence between 9193
      and 9222 of SEQ ID NO:1

<400> SEQUENCE: 10
cggcgcatgc agcgtcagct catccactcg                                      30

<210> SEQ ID NO 11
<211> LENGTH: 30
<212> TYPE: DNA
<213> ORGANISM: Artificial Sequence
<220> FEATURE:
```

```
<223> OTHER INFORMATION: Antisense primer from the sequence between 9098
      and 9127 of SEQ ID NO:1

<400> SEQUENCE: 11
ccgtgccgcc gacctcgtag tcagccagcc                                          30

<210> SEQ ID NO 12
<211> LENGTH: 30
<212> TYPE: DNA
<213> ORGANISM: Artificial Sequence
<220> FEATURE:
<223> OTHER INFORMATION: Primer from the sequence between 8948 and 8977
      of SEQ ID NO:1

<400> SEQUENCE: 12
actggctcga agcacacag cccggtgccg                                           30

<210> SEQ ID NO 13
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 13

His Xaa Xaa Xaa Gly Xaa Xaa Xaa Xaa Pro
 1               5                  10

<210> SEQ ID NO 14
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 14

His Xaa Xaa Xaa Gly Xaa Xaa Xaa Xaa Ser
 1               5                  10

<210> SEQ ID NO 15
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 15

Tyr Xaa Xaa Xaa Gly Xaa Xaa Xaa Xaa Ser
 1               5                  10

<210> SEQ ID NO 16
<211> LENGTH: 10
<212> TYPE: PRT
<213> ORGANISM: Streptomyces avermitilis

<400> SEQUENCE: 16

His Ala Val Gly Gly Thr Val Leu Leu Ser
 1               5                  10
```

AVERMECTIN AGLYCON SYNTHASE GENES

This application is a continuation of U.S. application Ser. No. 09/914,286, filed Aug. 24, 2001, now U.S. Pat. No. 6,864,073; which is a national stage application filed under 35 U.S.C. 371 of Int'l Appln. No. PCT/JP00/01041, filed Feb. 23, 2000; the contents of which is incorporated herein by reference.

TECHNICAL FIELD

The present invention relates to DNAs encoding multifunctional enzyme involved in the biosynthesis of an avermectin compound which is a polyketide; polypeptides encoded by the DNAs; vectors containing the DNAs; host cells transformed with the DNAs or the vectors; and a process for producing avermectin.

BACKGROUND ART

A polyketide is a group of compounds containing a number of natural substances which vary in their structures and functions. Polyketides are known to include compounds having a variety of bioactivities such as antibacterial agents, antimyotic agents, antiparasitic agents, anti-insect agents, antitumor agents, and immunosuppressant agents, and aromatic compounds which are produced by bacteria, fungi and plants.

The above-mentioned various polyketide compounds are synthesized by the same biosynthetic mechanism which is very similar to the biosynthesis of fatty acids. That is, a polyketide compound is biosynthesized by the steps of continuous condensation of lower fatty acids including acetic acids and propionic acids, and subsequent reactions such as reduction of ketone, dehydration and enoyl reduction of each carbonyl group at $\beta$ position of the extended acyl group which is similar to fatty acid synthesis. These various repetitive synthetic processes of many polyketide compounds are carried out a macromolecule, multifunctional enzyme complex, which has specific active sites (domains) required for each catalytic activity. A general reaction manner of polyketide biosynthesis is outlined, for example in Ann. Rev. Gen., 24, 37 (1990), and Ann. Rev. Microbiol., 47, 875 (1993).

It has been shown that a DNA sequence encoding polyketide synthase usually encodes all the required activities for the synthesis of a polyketide backbone. The DNA sequence encoding polyketide synthase is composed of modules, that is, repeating units involving condensation steps and modification steps following condensation. Each catalytic activity is involved in specificity to a specific carboxylic acid component of each condensation step, or in a different site which specifies a modification function following a specific condensation step to be achieved. For example, International Publication WO93/13663 describes the constitution of a gene encoding polyketide synthase of *Saccharopolyspora erythaea*. This gene consists of 6 modules, each of which is responsible for one condensation step. That is, a correct sequence of acyl side chain elongation and modification of an elongating chain are determined by genetic information present in each module.

Regarding the biosynthetic mechanism of avermectin aglycon, it has been reported that like other polyketide compounds, synthesis units of avermectin aglycon are lower fatty acids, such as acetic acid and propionic acid as its components [J. Antibiot., 39, 541-549 (1986)], and as in *Saccharopolyspora erythaea*, polyketide synthase consisting of modules is present in avermectin-producing bacteria [Gene, 115, 119-125 (1992), Ann. New York Acad. of Sci., 721, 123-132 (1994)].

Japanese Published Unexamined Patent Application No. 15391/91 describes a DNA fragment involved in avermectin biosynthesis, but shows no nucleotide sequence of the DNA fragment. This publication merely assumes the presence of polyketide synthase, which is involved in the synthesis of avermectin aglycon and the presence of partial modules. Therefore, the entire structure of polyketide synthase of avermectin cannot be predicted.

Similarly, MacNeil et al have reported a domain structure of partial modules [Ann. New York Acad. of Sci., 721, 123-132 (1994)]. However, they have not revealed the nucleotide sequence that should be evidence for polyketide synthase of avermectin.

Alteration of polyketide synthase would be a very useful breeding technique upon breeding of bacterial strains which can be used for a novel process for producing a novel avermectin useful as veterinary drugs and agricultural chemicals, and can produce a more effective avermectin derivative. Steps required to carry out such alteration include determination of the entire nucleotide sequence of a gene encoding polyketide synthase, accurate determination of a domain structure of each module based on the sequence, and introduction of a desired mutation. However, as described above, it was very difficult to carry out such improved-breeding, since the polyketide synthase gene of avermectin aglycon had not been specified and the nucleotide sequence of the gene was unknown.

The present inventors have studied approaches for producing a component different from that produced by the wild type strain by engineering DNA involved in polyketide synthesis with various methods. To apply this methodology, first we had to isolate a DNA molecule involved in the biosynthesis of a polyketide compound.

Hence, an object of the present invention is to provide a DNA encoding a multifunctional enzyme involved in biosynthesis of avermectin aglycon, and a process for producing avermectin aglycon, altered avermectin aglycon, avermectin, and altered avermectin using the DNA.

DISCLOSURE OF THE INVENTION

The present inventors made an intensive investigation to attain the object. As a result, the inventors have succeeded in isolating DNAs encoding a multifunctional enzyme involved in biosynthesis of avermectin aglycon. The present invention has been completed on the basis of this result.

The present invention relates to the following (1) to (43).

(1) A DNA encoding avermectin aglycon synthase (hereinafter, also referred to as an avermectin aglycon synthase gene).

In an embodiment of the present invention, the DNA is derived from a wild-type avermectin-producing strain or a mutant strain thereof, such as one belonging to the genus *Streptomyces*, specifically *Streptomyces avermitilis*.

(2) A DNA comprising a nucleotide sequence selected from the group consisting of nucleotide Nos. 1-11916 and 11971-30688 of SEQ ID NO: 1, and nucleotide Nos. 1-14643 and 14824-31419 of SEQ ID NO: 2; or a DNA which hybridizes with this DNA under stringent conditions and which encodes a polypeptide having avermectin aglycon synthase activity.

The above term "a DNA which hybridizes with this DNA under stringent conditions" refers to a DNA which is obtained by colony hybridization, plaque hybridization or Southern hybridization or the like using the DNA having a nucleotide sequence of SEQ ID NO. 1 or 2. For example, such a DNA can be identified by carrying out hybridization at 65° C. in the presence of 0.7 to 1.0 mol/l sodium chloride using a filter on which DNAs derived from colonies or plaques have been immobilized, followed by washing the filter at 65° C. using 0.1 to 2-fold concentrated SSC solution (1-fold concentrated SSC solution consists of 150 mmol/l sodium chloride, 15 mmol/l sodium citrate).

Hybridization can be carried out according to a method described in experimental protocols, such as Molecular Cloning, A Laboratory Manual, Second Edition, Cold Spring Harbor Laboratory Press, 1989 (hereinafter abbreviated as Molecular Cloning $2^{nd}$ Edition), Current Protocols in Molecular Biology, John Wiley & Sons, 1987-1997 (hereinafter abbreviated as Current Protocols in Molecular Biology), DNA Cloning 1; Core Techniques, A Practical Approach, Second Edition, Oxford University, 1995. Specific examples of the DNA which can be hybridized include a DNA having at least homology of 80% or more, preferably 95% or more with a nucleotide sequence selected from the group consisting of nucleotide Nos. 1-11916 and 11971-30688 of SEQ ID NO: 1, and nucleotide Nos. 1-14643 and 14824-31419 of SEQ ID NO: 2.

The following term "a DNA which hybridizes with this DNA (or said DNA) under stringent conditions" can also be defined in the same manner as described above.

(3) The DNA according to the above (1) or (2) wherein the DNA comprises DNAs encoding avermectin aglycon synthase domains.

(4) The DNA according to the above (3) wherein the DNA encoding avermectin aglycon synthase domains is selected from the group consisting of:

a DNA encoding a polypeptide having acyltransferase activity and acyl carrier protein activity;

a DNA encoding a polypeptide having β-ketoacyl-ACP synthase activity, acyltransferase activity, β-ketoacyl-ACP reductase activity and acyl carrier protein activity;

a DNA encoding a polypeptide having β-ketoacyl-ACP synthase activity, acyltransferase activity, dehydratase activity, β-ketoacyl-ACP reductase activity and acyl carrier protein activity;

a DNA encoding a polypeptide having β-ketoacyl-ACP synthase activity, acyltransferase activity, and acyl carrier protein activity; and a DNA encoding a polypeptide having β-ketoacyl-ACP synthase activity, acyltransferase activity, dehydratase activity, β-ketoacyl-ACP reductase activity, acyl carrier protein activity, and thioesterase activity.

(5) The DNA according to the above (4) wherein the DNA encoding a polypeptide having acyltransferase activity and acyl carrier protein activity is a DNA comprising the nucleotide sequence of nucleotide Nos. 85-1353 of SEQ ID NO: 1; or a DNA which hybridizes with this DNA under stringent conditions and which encodes a polypeptide having acyltransferase activity and acyl carrier protein activity.

(6) The DNA according to the above (4) wherein the DNA encoding a polypeptide having β-ketoacyl-ACP synthase activity, acyltransferase activity, β-ketoacyl-ACP reductase activity, and acyl carrier protein activity is:

a DNA comprising the nucleotide sequence selected from the group consisting of nucleotide Nos. 1441-6180, 15217-19938 and 20008-24690 of SEQ ID NO: 1, and nucleotide Nos. 100-4692 and 14935-20334 of SEQ ID NO: 2; or a DNA which hybridizes with this DNA under stringent conditions and which encodes a polypeptide having β-ketoacyl-ACP synthase activity, acyltransferase activity, β-ketoacyl-ACP reductase activity, and acyl carrier protein activity.

(7) The DNA according to the above (4) wherein the DNA encoding a polypeptide having β-ketoacyl-ACP synthase activity, acyltransferase activity, dehydratase activity, β-ketoacyl-ACP reductase activity, and acyl carrier protein activity is:

a DNA comprising the nucleotide sequence selected from the group consisting of nucleotide Nos. 6256-11658 and 24781-30309 of SEQ ID NO: 1, and nucleotide Nos. 20413-25734 and 25810-31125 of SEQ ID NO: 2; or a DNA which hybridizes with this DNA under stringent conditions and which encodes polypeptides having β-ketoacyl-ACP synthase activity, acyltransferase activity, dehydratase activity, β-ketoacyl-ACP reductase activity, and acyl carrier protein activity.

(8) The DNA according to the above (4) wherein the DNA encoding a polypeptide having β3-ketoacyl-ACP synthase activity, acyltransferase activity, and acyl carrier protein activity is:

a DNA comprising the nucleotide sequence of nucleotide No. 12076-15147 of SEQ ID NO: 1, or nucleotide No. 4771-7818 of SEQ ID NO: 2;

or a DNA which hybridizes with this DNA under stringent conditions and which encodes a polypeptide having β-ketoacyl-ACP synthase activity, acyltransferase activity, and acyl carrier protein activity.

(9) The DNA according to the above (4) wherein the DNA encoding a polypeptide having β-ketoacyl-ACP synthase activity, acyltransferase activity, dehydratase activity, β-ketoacyl-ACP reductase activity, acyl carrier protein activity, and thioesterase activity is:

a DNA comprising the nucleotide sequence of nucleotide Nos. 7906-14619 of SEQ ID NO: 2; or a DNA which hybridizes with this DNA under stringent conditions and which encodes a polypeptide having β-ketoacyl-ACP synthase activity, acyltransferase activity, dehydratase activity, β-ketoacyl-ACP reductase activity, acyl carrier protein activity, and thioesterase activity.

(10) The DNA according to the above (4) wherein the DNA encoding a polypeptide having acyltransferase activity is:

a DNA comprising the nucleotide sequence selected from the group consisting of nucleotide Nos. 85-1032, 7906-8829, 13756-14694, 16917-17862, 21658-22584, and 26413-27336 of SEQ ID NO: 1, and nucleotide Nos. 1648-2673, 6322-7344, 9676-10773, 16543-17565, 21991-23019 and 27367-28392 of SEQ ID NO: 2; or a DNA which hybridizes with this DNA under stringent conditions and which encodes a polypeptide having acyltransferase activity.

(11) The DNA according to the above (4) wherein the DNA encoding a polypeptide having acyl carrier protein activity is:

a DNA comprising the nucleotide sequence selected from the group consisting of nucleotide Nos. 1096-1353, 5935-6180, 11413-11658, 14902-15147, 19693-19938, 24445-24690 and 30064-30309 of SEQ ID NO: 1, and nucleotide Nos. 4447-4692, 7573-7818, 13378-13659, 20089-20334, 25489-25734 and 30880-31125 of SEQ ID NO: 2; or a DNA which hybridizes with this DNA under stringent conditions and which encodes a polypeptide having acyl carrier protein activity.

(12) The DNA according to the above (4) wherein the DNA encoding a polypeptide having β-ketoacyl-ACP synthase activity is:
a DNA comprising the nucleotide sequence selected from the group consisting of nucleotide Nos. 1441-2742, 6256-7545, 12076-13368, 15217-16506, 20008-21297 and 24781-26079 of SEQ ID NO: 1, and nucleotide Nos. 100-1383, 4771-6060, 7906-9258, 14935-16224, 20413-21705 and 25810-27102 of SEQ ID NO: 2; or
a DNA which hybridizes with this DNA under stringent conditions and which encodes a polypeptide having β-ketoacyl-ACP synthase activity.

(13) The DNA according to the above (4) wherein the DNA encoding a polypeptide having β-ketoacyl-ACP reductase activity is:
a DNA comprising the nucleotide sequence selected from the group consisting of nucleotide Nos. 5143-5676, 10609-11142, 18886-19419, 23602-24138 and 29227-29760 of SEQ ID NO: 1, and nucleotide Nos. 3634-4188, 12547-13104, 19285-19842, 24685-25242 and 30076-30633 of SEQ ID NO: 2; or
a DNA which hybridizes with this DNA under stringent conditions and which encodes a polypeptide having β-ketoacyl-ACP reductase activity.

(14) The DNA according to the above (4) wherein the DNA encoding a polypeptide having dehydratase activity is:
a DNA comprising the nucleotide sequence selected from the group consisting of nucleotide Nos. 8947-9384 and 27475-27894 of SEQ ID NO: 1, and nucleotide Nos. 10885-11289, 23149-23529 and 28516-28878 of SEQ ID NO: 2; or
a DNA which hybridizes with this DNA under stringent conditions and which encodes a polypeptide having dehydratase activity.

(15) The DNA according to the above (4) wherein the DNA encoding a polypeptide having thioesterase activity is:
a DNA having the nucleotide sequence of nucleotide No. 13879-14619 of SEQ ID NO: 2; or
a DNA which hybridizes with this DNA under stringent conditions and which encodes a polypeptide having thioesterase activity.

(16) The DNA according to the above (3) or (4) wherein the DNA encoding an avermectin aglycon synthase domain is a mutated DNA encoding a polypeptide having enhanced or diminished activity of the domain.

(17) The DNA according to the above (16) wherein the DNA encoding a polypeptide having diminished activity of avermectin aglycon synthase domain is the DNA comprising a nucleotide sequence of SEQ ID NO: 7.

(18) A DNA encoding an avermectin aglycon synthase domain which comprises a nucleotide sequence selected from the group consisting of nucleotide Nos. 85-1032, 1096-1353, 1441-2742, 3148-4068, 5143-5676, 5935-6180, 6256-7545, 7906-8829, 8947-9384, 10609-11142, 11413-11658, 12076-13368, 13756-14694, 14902-15147, 15217-16506, 16917-17862, 18886-19419, 19693-19938, 20008-21297, 21658-22584, 23602-24138, 24445-24690, 24781-26079, 26413-27336, 27475-27894, 29227-29760 and 30064-30309 of SEQ ID NO: 1, and nucleotide Nos. 100-1383, 1648-2673, 36344188, 4447-4692, 4771-6060, 6322-7344, 7573-7818, 7906-9258, 9676-10773, 10885-11289, 12547-13104, 13378-13659, 13879-14619, 14935-16224, 16543-17565, 17689-18066, 19285-19842, 20089-20334, 20413-21705, 21991-23019, 23149-23529, 24685-25242, 25489-25734, 25810-27102, 27367-28392, 28516-28878, 30076-30633, and 30880-31125 of SEQ ID NO: 2; or
a DNA which hybridizes with this DNA under stringent conditions and which encodes a polypeptide having avermectin aglycon synthase domain activity.

(19) A DNA comprising the nucleotide sequence of nucleotide No. 85-1353 of SEQ ID NO: 1; or
a DNA which hybridizes with this DNA under stringent conditions and which encodes a polypeptide having acyltransferase activity and acyl carrier protein activity.

(20) A DNA comprising the nucleotide sequence selected from the group consisting of nucleotide Nos. 1441-6180, 15217-19938 and 20008-24690 of SEQ ID NO: 1, and nucleotide Nos. 100-4692 of SEQ ID NO: 2; or
a DNA which hybridizes with this DNA under stringent conditions and which encodes a polypeptide having β-ketoacyl-ACP synthase activity, acyltransferase activity, β-ketoacyl-ACP reductase activity and acyl carrier protein activity.

(21) A DNA comprising the nucleotide sequence selected from the group consisting of nucleotide Nos. 6256-11658 and 24781-30309 of SEQ ID NO: 1, and nucleotide Nos. 14935-20334, 20413-25734 and 25810-31125 of SEQ ID NO: 2; or
a DNA which hybridizes with this DNA under stringent conditions and which encodes a polypeptide having β-ketoacyl-ACP synthase activity, acyltransferase activity, dehydratase activity, β-ketoacyl-ACP reductase activity and acyl carrier protein activity.

(22) A DNA comprising the nucleotide sequence of nucleotide No. 12076-15147 of SEQ ID NO: 1, or the nucleotide sequence of nucleotide No. 4771-7818 of SEQ ID NO: 2; or
a DNA which hybridizes with this DNA under stringent conditions and which encodes a polypeptide having β-ketoacyl-ACP synthase activity, acyltransferase activity, and acyl carrier protein activity.

(23) A DNA comprising the nucleotide sequence of nucleotide No. 7906-14619 of SEQ ID NO: 2; or
a DNA which hybridizes with this DNA under stringent conditions and which encodes a polypeptide having β-ketoacyl-ACP synthase activity, acyltransferase activity, dehydratase activity, β-ketoacyl-ACP reductase activity, acyl carrier protein activity, and thioesterase activity.

(24) A DNA comprising the nucleotide sequence selected from the group consisting of nucleotide Nos. 85-1032, 7906-8829, 13756-14694, 16917-17862, 21658-22584 and 26413-27336 of SEQ ID NO: 1, and nucleotide Nos. 1648-2673, 6322-7344, 9676-10773, 16543-17565, 21991-23019 and 27367-28392 of SEQ ID NO: 2; or
a DNA which hybridizes with this DNA under stringent conditions and which encodes a polypeptide having acyltransferase activity.

(25) A DNA comprising the nucleotide sequence selected from the group consisting of nucleotide Nos. 1096-1353, 5935-6180, 11413-11658, 14902-15147, 19693-19938, 24445-24690, and 30064-30309 of SEQ ID NO: 1, and nucleotide Nos. 44474692, 7573-7818, 13378-13659, 20089-20334, 25489-25734 and 30880-31125 of SEQ ID NO: 2; or
a DNA which hybridizes with this DNA under stringent conditions and which encodes a polypeptide having acyl carrier protein activity.

(26) A DNA comprising the nucleotide sequence selected from the group consisting of nucleotide Nos. 1441-2742, 6256-7545, 12076-13368, 15217-16506, 20008-21297 and 24781-26079 of SEQ ID NO: 1, and nucleotide Nos. 100-1383, 4771-6060, 7906-9258, 14935-16224, 20413-21705, and 25810-27102 of SEQ ID NO: 2; or a DNA which hybridizes with this DNA under stringent conditions and which encodes a polypeptide having β-ketoacyl-ACP synthase activity.

(27) A DNA comprising the nucleotide sequence selected from the group consisting of nucleotide Nos. 5143-5676, 10609-11142, 18886-19419, 23602-24138, and 29227-29760 of SEQ ID NO: 1, and nucleotide Nos. 3634-4188, 12547-13104, 19285-19842, 24685-25242 and 30076-30633 of SEQ ID NO: 2; or a DNA which hybridizes with this DNA under stringent conditions and which encodes a polypeptide having β ketoacyl ACP reductase activity.

(28) A DNA comprising the nucleotide sequence selected from the group consisting of nucleotide Nos. 8947-9384 and 27475-27894 of SEQ ID NO: 1, and nucleotide Nos. 10885-11289, 17689-18066, 23149-23529 and 28516-28878 of SEQ ID NO: 2; or a DNA which hybridizes with this DNA under stringent conditions and which encodes a polypeptide having dehydratase activity.

(29) A DNA comprising the nucleotide sequence of nucleotide Nos. 13879-14619 of SEQ ID NO: 2; or a DNA which hybridizes with this DNA under stringent conditions and which encodes a polypeptide having thioesterase activity.

(30) A DNA comprising the nucleotide sequence shown in SEQ ID NO: 7.

(31) A polypeptide encoded by the DNA according to any one of the above (1) to (29).

(32) A polypeptide comprising the amino acid sequence according to any one of SEQ ID NOS: 3 to 6; or a polypeptide comprising an amino acid sequence wherein one or more amino acids are deleted, replaced or added in the amino acid sequence according to any one of SEQ ID NOS: 3 to 6, and having avermectin aglycon synthase activity.

The above "polypeptide comprising an amino acid sequence wherein one or more amino acids are deleted, replaced or added, and having avermectin aglycon synthase activity" can be prepared according to site-directed mutagenesis as described in Molecular Cloning, $2^{nd}$ Edition, Current Protocols in Molecular Biology, Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985) and the like. The number of amino acids which are deleted, replaced or added is not specifically limited, but is a number of amino acids which can be deleted, replaced, or added by known methods, such as the above site-directed mutagenesis, and within the range from 1 to several tens of amino acids, preferably 1 to 20, more preferably 1 to 10, and even more preferably 1 to 5 amino acids.

(33) A polypeptide comprising the amino acid sequence selected from the group consisting of amino acid Nos. 29-344, 366-451, 481-914, 1050-1356, 1715-1892, 1979-2060, 2086-2515, 2983-3128, 3537-3714 and 3805-3886 of SEQ ID NO: 3, amino acid Nos. 36-466, 596-908, 978-1059, 1083-1512, 1653-1964, 2306-2483, 2575-2656, 2680-3109, 3230-3538, 38784056, 4159-4240, 42714703, 4815-5122, 5168-5307, 5753-5930 and 6032-6113 of SEQ ID NO: 4, amino acid Nos. 34-461, 550-891, 1212-1396, 1483-1564, 1591-2020, 2108-2448, 2525-2606, 2636-3086, 3226-3591, 3629-3763, 4183-4363, 44604553 and 4627-4873 of SEQ ID NO: 5, amino acid Nos. 38-467, 574-914, 956-1081, 1488-1673, 1756-1837, 1864-2294, 2390-2732, 2776-2902, 3288-3473, 3556-3637, 3663-4093, 41824523, 4565-4685, 5085-5270 and 5353-5434 of SEQ ID NO: 6; or a polypeptide comprising an amino acid sequence wherein one or more amino acids are deleted, replaced or added in the amino acid sequence selected above, and having avermectin aglycon synthase domain activity.

The above "polypeptide comprising an amino acid sequence wherein one or more amino acids are deleted, replaced or added in the amino acid sequence selected above, and having avermectin aglycon synthase domain activity" can be obtained according to the method described in the above (32).

(34) A recombinant vector comprising the DNA according to any one of the above (1) to (30).

(35) A transformant which is obtained by introducing the DNA according to any one of the above (1) to (30) or the recombinant vector of the above (34) into a host cell.

(36) The transformant according to the above (35) wherein the host cell is an avermectin-producing bacterial strain.

(37) The transformant according to the above (35) or (36) wherein the host cell is *Streptomyces avermitilis* K2038 (FERM BP-2775).

(38) A process for producing avermectin aglycon synthase or an avermectin aglycon synthase domain polypeptide comprising:

culturing the transformant according to any one of the above (35) to (37) in a medium to form and accumulate the enzyme or the domain polypeptide in the culture, and recovering the enzyme or the domain polypeptide from the culture.

(39) A process for producing avermectin aglycon or an altered avermectin aglycon comprising:

culturing the transformant according to any one of the above (35) to (37) in a medium to form and accumulate the avermectin aglycon or the altered avermectin aglycon in the culture, and recovering the avermectin aglycon or the altered avermectin aglycon from the culture.

(40) A process for producing avermectin or altered avermectin comprising:

culturing the transformant according to any one of the above (35) to (37) in a medium to form and accumulate avermectin aglycon or altered avermectin aglycon in the culture, glycosylating the avermectin aglycon or altered avermectin glycon, and recovering avermectin or altered avermectin.

(41) The method according to the above (40) wherein altered avermectin is an avermectin which has been altered from avermectin B1a to avermectin B2a.

(42) An altered avermectin obtainable by the process according to the above (40).

(43) An oligonucleotide having a sequence corresponding to 5 to 60 continuous nucleotides in the nucleotide sequence of the DNA according to the above (1) or (2); or an oligonucleotide having a sequence complementary to the oligonucleotide.

BRIEF DESCRIPTION OF THE DRAWINGS

FIG. 1 is a restriction enzyme map showing BamHI, BglII, ClaI, EcoRI, KpnI, MluI, PstI, StuI and XhoI sites of avermectin aglycon synthase genes, aveAI and aveAII, of *Streptomyces avermitilis*. Each arrow indicates the predicted transcriptional direction of each gene.

DETAILED DESCRIPTION OF THE INVENTION

Figure 2B:
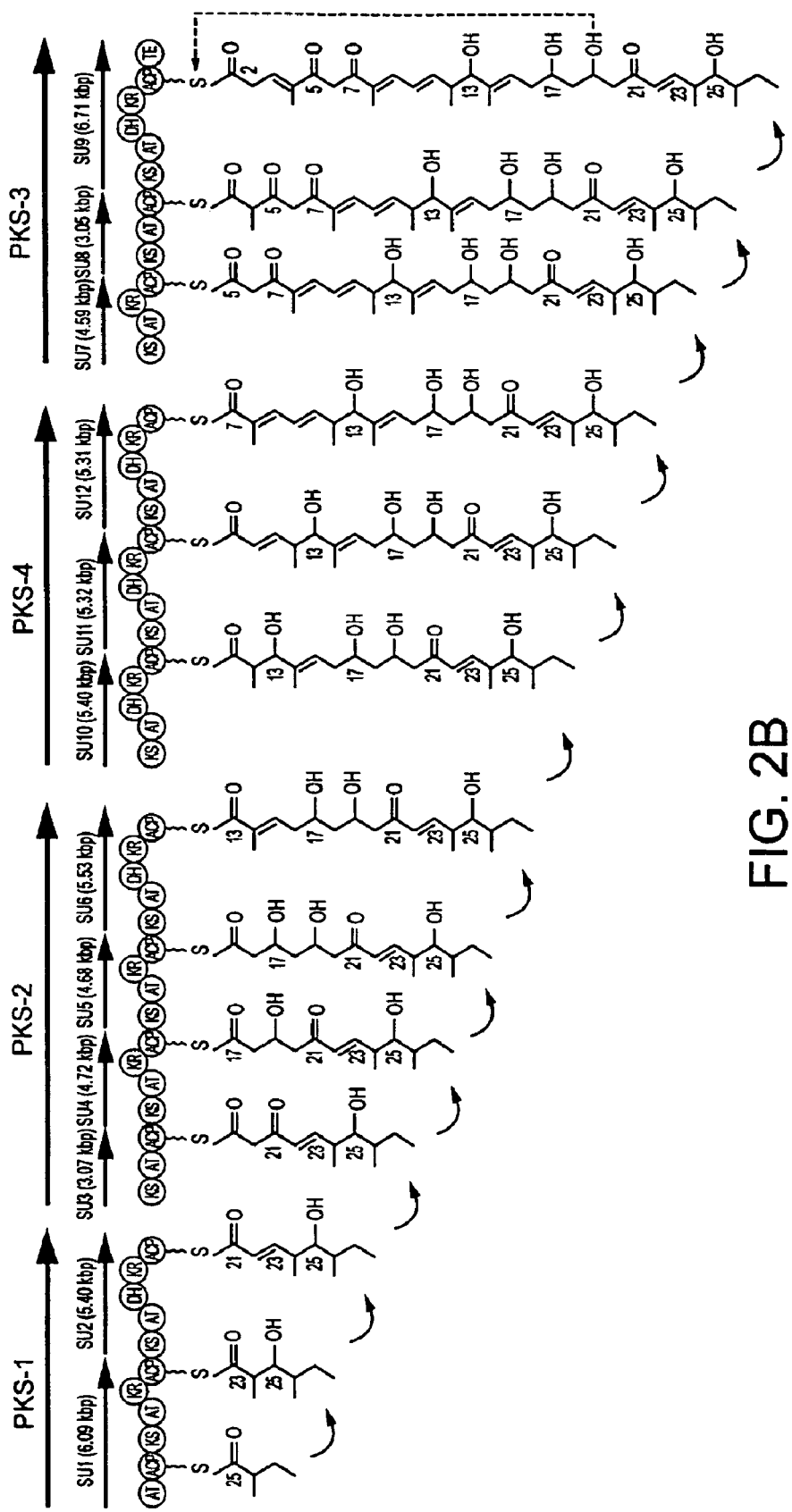
FIG. 2 shows (FIG. 2A) the chromosomal positions of avermectin aglycon synthase genes and the domain sequences of synthase units, (FIG. 2B) the estimated steps of synthesizing avermectin aglycon, and (FIG. 2C) the structure of 6,8a-seco-6,8a-deoxy-5-oxoAvermectin aglycon synthesized with polyketide synthases, which are the gene products of avermectin aglycon synthase genes aveAI and aveAII, and the positions of lower fatty acids which are incorporated into the skeleton of the compound. In this figure, SU indicates synthase unit, ACP indicates acyl carrier protein, AT indicates an acyltransferase, DH indicates dehydratase, DH* indicates a dehydratase-like domain which is estimated to be inactive, KR indicates β-ketoacyl-ACP reductase, KR* indicates a β-ketoacyl-ACP reductase-like domain which is estimated to be active but is not reflected in the polyketide synthetic reaction, KS indicates β-ketoacyl-ACP synthase, and TE indicates thioesterase.

The present invention will be described in detail below.

The present invention relates to DNA sequences of genes encoding avermectin aglycon synthase, and a process for producing avermectin aglycon, a basic constitutional unit of avermectin. According to the present invention, it becomes possible to produce a novel avermectin-associated compound or a specific component of avermectins by modification of the DNA to make a change to the type and number of carboxylic acids to be taken in, modification reaction after condensation, or any combination thereof.

1. Preparation of the DNA of the Present Invention

A DNA encoding avermectin aglycon synthase (an avermectin aglycon synthase gene) can be isolated from bacteria belonging to the genus *Streptomyces*, e.g. *Streptomyces avermitilis*.

Examples of a method for isolating an avermectin aglycon synthase gene include the method described in Japanese Published Unexamined Patent Application No. 15391/91, colony hybridization described in *Molecular Cloning*, Second Edition, etc.

Specific examples include a method which comprises: ligating the partially digested chromosomal DNA of *Streptomyces avermitilis* with appropriate restriction enzyme such as Sau3AI, to a cosmid vector capable of replicating in *E. coli* cleaved at a unique restriction enzyme site, e.g. the vector digested with BamHI; transforming *E. coli* with the obtained recombinant DNA; and selecting a transformant having the avermectin aglycon synthase gene from the obtained transformant by colony hybridization.

Examples of DNAs obtained by the above method include DNAs having the nucleotide sequences shown in SEQ ID NOS: 1 and 2.

The DNA having the nucleotide sequence of SEQ ID NO: 1 or 2 was found by chance to be a DNA fragment encoding a portion of polyketide synthase, when a gene encoding avermectin B5-O-methyl transferase (aveD) was isolated (*Gene*, 206, 175-180 (1998)), and was obtained by the above method.

Modules, domains and ORFs, which are relevant to the avermectin aglycon synthase genes of the present invention, can be determined by comparing similarity with the sequences of 3 types of polyketide synthase domains of erythromycin (*Nature*, 348, 176-178 (1990), *Science*, 252, 675-679 (1991), or *Eur. J. Biochem.*, 204, 39-49 (1992)).

FIG. 1 shows a restriction map of the avermectin aglycon synthase gene regions (aveAI and aveAII) of genomic DNA (~65 kbp) of *Streptomyces avermitilis* together with predicted transcription units (arrow).

Polyketide compounds are natural organic compounds having a variety of structures and functions, and the common characteristics of these compounds are that their synthesis is carried out with a multifunctional enzyme called polyketide synthase.

One polyketide synthase has substrate specificity, and catalyzes the extention of a lower fatty acid constitutional unit (which is used in the form of CoA ester of dicarboxylic acid in reactions other than intial reaction), i.e., condensation to make a polyketide carbon chain, and has a catalytic activity and a controlling activity which modify a β-carbonyl group generated from such a reaction.

The condensation reaction, which is a basic reaction in the synthesis of polyketide, needs various catalytic activities including an acyl carrier protein (ACP) activity, a β-ketoacyl-ACP synthase (KS) activity and an acyltransferase (AT) activity.

In many cases, β-carbonyl groups generated by the condensation reaction are modified. However, depending on a module, some β-carbonyl groups may not be modified and may be used for the next condensation reaction.

Catalytic activities associated with the modification of a β-carbonyl group after the condensation reaction include a β-ketoacyl-ACP reductase (KR) activity, a dehydratase (DH) activity and an enoyl reductase (ER) activity. The biosynthesis of a polyketide chain is terminated by cleaving out the polyketide chain from polyketide synthase by action of thioesterase (TE) activity.

All or several of these modification activities act in each condensation process, thereby determining the structure of a final product.

The avermectin aglycon synthase genes (aveAI and aveAII) of *Streptomyces avermitilis* are characterized in that the genes have several open reading frames each of which comprises one or more repeating units called a module, just as with other known polyketide biosynthetic genes. A module is defined as a gene fragment which encodes activities for a one-time synthesis, i.e., a one-time condensation reaction, and the subsequent various modification reactions of the β-carbonyl group. Each module encodes ACP, KS and AT associated with the condensation reaction in polyketide synthesis, and all or several of KR, DH and ER associated with the modification reaction of the β-carbonyl group. Furthermore, there is also a module which does not have any domain for a modification reaction. A polypeptide encoding such a module is referred to as synthase unit (SU).

FIG. 2 shows a biosynthetic pathway of 6,8a-seco-6,8a-deoxy-5-oxo-avermectin aglycon synthesized with avermectin aglycon synthases of *Streptomyces avermitilis*.

It is clear that PKS-1 is associated with initiation reaction, since an initiation module (SUs), differing from other modules, has acyltransferase (AT) activity on the N-terminal side. It is clear that PKS-3 is associated with the final reaction of polyketide, since module 9 (SU9) has a thioesterase (TE) domain.

The determined DNA sequences comprising avermectin aglycon synthase genes derived from *Streptomyces avermitilis* are shown in SEQ ID NOS: 1 and 2. The DNA of the present invention comprises open reading frames (ORFs) encoding respective multifunctional enzymes, and these ORFs are ORFs corresponding to nucleotide Nos. 11 to 11916 and nucleotide Nos. 211971 to 30688 of SEQ ID NO: 1 and nucleotide Nos. 31 to 14643 and nucleotide Nos. 414824 to 31419 of SEQ ID NO: 2. The amino acid sequences of various peptides encoded by these sequences are shown in SEQ ID NOS: 3,4,5 and 6.

Each of the above DNAs comprises a module encoding a synthesis unit having all catalytic activities necessary for a one-time carbon chain extension reaction. These modules are represented as the following nucleotides in SEQ ID NOS: 1 and 2. That is to say, the modules are represented in SEQ ID NO: 1 as,
Initiation Module: 85 to 1353,
Module 1: 1441 to 6180,
Module 2: 6256 to 11658,
Module 3: 12076 to 15147,
Module 4: 15217 to 19938,
Module 5: 20008 to 24690,
Module 6: 24781 to 30309, and, are represented in SEQ ID NO: 2 as,
Module 7: 100 to 4692,
Module 8: 4771 to 7818,
Module 9: 7906 to 14619,
Module 10: 14935 to 20334,
Module 11: 20413 to 25734,
Module 12: 25810 to 31125.

The amino acid sequences of various synthase units (SU) encoded by these modules are represented as the following amino acids. That is to say, the sequences are represented in SEQ ID NO: 3 as,
Initiation SU: 29 to 451,
SU1: 481 to 2060,
SU2: 2086 to 3886;

in SEQ ID NO: 4 as,
SU3: 36 to 1059,
SU4: 1083 to 2656,
SU5: 2680 to 4240,
SU6: 4271 to 6113;

in SEQ ID NO: 5 as,
SU7: 34 to 1564,
SU8: 1591 to 2606,
SU9: 2636 to 4873; and, in SEQ ID NO: 6 as,
SU10: 38 to 1837,
SU11: 1864 to 3637,
SU12: 3663 to 5434.

DNAs encoding Avermectin aglycon synthase domains (submodules) are represented as the following nucleotides. That is to say, the DNAs are represented in SEQ ID NO: 1 as, in Initiation Module,
ATs: 85 to 1032,
ACPs: 1096 to 1353;

in Module 1,
KS1: 1441 to 2742,
AT1: 3148 to 4068,
KR1: 5143 to 5676,
ACP1: 5935 to 6180;

in Module 2,
KS2: 6256 to 7545,
AT2: 7906 to 8829,
DH2: 8947 to 9384,
KR2: 10609 to 11142,
ACP2: 11413 to 11658;

in Module 3,
KS3: 12076 to 13368,
AT3: 13756 to 14694,
ACP3: 14902 to 15147;

in Module 4,
KS4: 15217 to 16506,
AT4: 16917 to 17862,
KR4: 18886 to 19419,
ACP4: 19693 to 19938;

in Module 5,
KS5: 20008 to 21297,
AT5: 21658 to 22584,
KR5: 23602 to 24138,
ACP5: 24445 to 24690;

in Module 6,
KS6: 24781 to 26079,
AT6: 26413 to 27336,
DH6: 27475 to 27894,
KR6: 29227 to 29760,
ACP6: 30064 to 30309; and, are also represented in SEQ ID NO: 2 as, in Module 7,
KS7: 100 to 1383,
AT7: 1648 to 2673,
KR7: 3634 to 4188,
ACP7: 4447 to 4692;

in Module 8,
KS8: 4771 to 6060,
AT8: 6322 to 7344,
ACP8: 7573 to 7818;

in Module 9,
KS9: 7906 to 9258,
AT9: 9676 to 10773,
DH9: 10885 to 11289,
KR9: 12547 to 13104,
ACP9: 13378 to 13659,
TE9: 13879 to 14619;

in Module 10,
KS10: 14935 to 16224,
AT10: 16543 to 17565,
DH10: 17689 to 18066,
KR10: 19285 to 19842,
ACP10: 20089 to 20334;

in Module 11,
KS11: 20413 to 21705,
AT11: 21991 to 23019,
DH11: 23149 to 23529,
KR11: 24685 to 25242,
ACP11: 25489 to 25734;

in Module 12,
KS12: 25810 to 27102,
AT12: 27367 to 28392,
DH12: 28516 to 28878,
KR12: 30076 to 30633,
ACP12: 30880 to 31125.

The deduced amino acid sequences of various domains encoded by these submodules are represented as:

in SEQ ID NO: 3,
ATs: 29 to 344,
ACPs: 366 to 451,
KS1: 481 to 914,
AT1: 1050 to 1356,
KR1: 1715 to 1892,
ACP1: 1979 to 2060,
KS2: 2086 to 2515,
DH2: 2983 to 3128,

KR2: 3537 to 3714,
ACP2: 3805 to 3886;

in SEQ ID NO: 4,
KS3: 36 to 466,
AT3: 596 to 968,
ACP3: 978 to 1059,
KS4: 1083 to 1512,
AT4: 1653 to 1964,
KR4: 2306 to 2483,
ACP4: 2575 to 2656,
KS5: 2680 to 3109,
AT5: 3230 to 3538,
KR5: 3878 to 4056,
ACP5: 4159 to 4240,
KS6: 4271 to 4703,
AT6: 4815 to 5122,
DH6: 5168 to 5307,
KR6: 5753 to 5930,
ACP6: 6032 to 6113;

in SEQ ID NO: 5,
KS7: 34 to 461,
AT7: 550 to 891,
KR7: 1212 to 1396,
ACP7: 1483 to 1564,
KS8: 1591 to 2020,
AT8: 2108 to 2448,
ACP8: 2525 to 2606,
KS9: 2636 to 3086,
AT9: 3226 to 3591,
DH9: 3629 to 3763,
KR9: 4183 to 4363,
ACP9: 4460 to 4553,
TE9: 4627 to 4873; and, in SEQ ID NO: 6,
KS10: 38 to 467,
AT10: 574 to 914,
DH10: 956 to 1081,
KR10: 1488 to 1673,
ACP10: 1756 to 1837,
KS11: 1864 to 2294,
AT11: 2390 to 2732,
DH11: 2776 to 2902,
KR11: 3288 to 3473,
ACP11: 3556 to 3637,
KS12: 3663 to 4093,
AT12: 4182 to 4523,
DH12: 4565 to 4685,
KR12: 5085 to 5270,
ACP12: 5353 to 5434.

From a comparison of sequence information regarding the known polyketide synthase genes, it was found that a similarity of sequences exists between domains having identical functions. By using such similarity, it becomes possible to predict the domain of a novel polyketide synthase gene.

In other words, based on the above module, domain and ORF information obtained from DNAs having nucleotide sequences of SEQ ID NO: 1 and 2 derived from *Streptomyces avermitilis*, modules, domains and ORFs, which are relevant to the Avermectin aglycon synthase genes derived from other bacteria capable of producing avermectin, can be determined.

Using a DNA having the nucleotide sequence of SEQ ID NO: 1 or 2, an avermectin aglycon synthase gene can be obtained by the following method.

A DNA having the nucleotide sequence of SEQ ID NO: 1 or 2 is digested with appropriate restriction enzymes, the DNA fragment was separated and recovered by the method described in *Molecular Cloning*, Second Edition, and an oligonucleotide consisting of the DNA fragment is used as a probe or primer.

As a probe, the DNA fragment labeled with digoxigenin etc. is preferably used. The DIG labeling & detection kit, which can be purchased from Roche Diagnostic Corp., can be used for labeling with digoxigenin.

A library is prepared from bacteria producing avermectin by genome cloning or cDNA cloning described in *Molecular Cloning*, Second Edition etc.

A clone (or a colony) which is to be cross-hybridized with the probe obtained above is selected from the library, then a plasmid is extracted from the clone by the method described in *Molecular Cloning*, Second Edition, and finally an avermectin aglycon synthase gene can be obtained from the plasmid. In addition, DNAs (i.e. submodules) and modules which encode an avermectin aglycon synthase gene domain can be obtained by the same method.

Otherwise, an avermectin aglycon synthase gene, a submodule and a module can also be obtained by direct PCR amplification, using the above library and primers prepared as above.

In a case where the only partial DNA fragment encoding an avermectin aglycon synthase exists in the plasmid extracted as above, according to standard techniques, a restriction map of the plasmid is prepared by digesting the extracted plasmid with appropriate restriction enzymes such as BamHI.

A restriction enzyme map of a DNA comprising the DNA encoding the entire avermectin polyketide synthase can be prepared by finding restriction enzyme fragments which commonly exist in several clones and binding up the cloned fragments at overlapping portions, so that the DNA encoding avermectin polyketide synthase can be obtained.

The nucleotide sequence of a DNA encoding avermectin polyketide synthase can be determined by commonly applied nucleotide sequencing analysis, e.g. the dideoxy method (*Proc. Natl. Acad. Sci.* USA, 74, 5463 (1977)), or by the analysis with a DNA sequencing analyzer such as 373A DNA sequencer (Perkin Elmer Corp.).

Specifically, a DNA sequence can be determined by directly using double-stranded plasmid DNA as a template for a cycle sequence reaction, wherein oligonucleotide primers specific for various sequences are used. Alternatively, a DNA sequence can also be determined by: cleaving a DNA fragment into its small fragments; introducing the resulting fragments into bacteria phage M13 at random; preparing an overlapping library, which comprises DNA fragments deleted successively from the termini thereof, using a library or plasmid vector comprising partially overlapping fragments; and subjecting each recombinant DNA fragment to the DNA sequencing using oligonucleotide primers specific to the vector sequence. The fluorescently labeled reactant obtained by the cycle sequence reaction can be analyzed with a DNA sequencer (e.g. Model 4000L, LiCor).

Moreover, based on the nucleotide sequence of the determined DNA, a desired DNA can also be prepared by the chemical synthesis, using a DNA synthesizer (Model 8905, Perceptive BioSystems) etc.

The obtained nucleotide sequence data can be arranged, edited and analyzed using existing software, for example, Genetyx™ (Software Development).

Using the DNAs and DNA fragments of the present invention obtained by the above method, oligonucleotides such as an antisense oligonucleotide and a sense oligonucleotide, which have a portion of the DNA sequence of the present invention, or oligonucleotides comprising an RNA can be prepared according to standard techniques. Alternatively, based on the DNA sequence information obtained as above, these oligonucleotides can also be synthesized with the above-mentioned DNA synthesizer.

Examples of the thus obtained oligonucleotides include a DNA having a sequence corresponding to 5 to 60 continuous nucleotides in the nucleotide sequence of the DNA obtained by the above-mentioned method, or a DNA having a sequence complementary to this DNA. Furthermore, the oligonucleotides of the present invention also include an RNA having a sequence complementary to these DNAs.

Examples of the thus obtained oligonucleotides include a DNA having a sequence corresponding to 5 to 60 continuous nucleotides in the nucleotide sequence of SEQ ID NO: 1 or 2, or a DNA having a sequence complementary to this DNA. Where the oligonucletides are used as sense and antisense primers, from among the above oligonucleotides, it is preferable to apply oligonucleotides wherein melting temperature (Tm) and the number of bases do not significantly differ between both oligonucleotides.

Examples of the thus obtained oligonucleotides include ones having the nucleotide sequences shown in SEQ ID NOS: 9 to 14.

Moreover, the derivatives of these oligonucleotides (hereinafter, also referred to as oligonucleotide derivatives) can also be used as the oligonucleotides of the present invention.

Examples of the oligonucleotide derivatives include: an oligonucleotide derivative obtained by conversion of a phosphodiester phosphate bond into a phosphorothioate bond in the above-described oligonucleotide; an oligonucleotide derivative obtained by conversion of a phosphodiester bond into a N3'-P5' phosphoamidate bond in the above-described oligonucleotide; an oligonucleotide derivative obtained by conversion of a ribose and a phosphodiester phosphate bond into a peptide nucleic acid bond in the above-described oligonucleotide; an oligonucleotide derivative obtained by substitution of uracil by C-5 propynyl uracil in the above-described oligonucleotide; an oligonucleotide derivative obtained by substitution of uracil by C-5 thiazole uracil in the above-described oligonucleotide; an oligonucleotide derivative obtained by substitution of cytosine by C-5 propynyl cytosine in the above-described oligonucleotide; an oligonucleotide derivative obtained by substitution of cytosine by phenoxazine-modified cytosine in the above-described oligonucleotide; an oligonucleotide derivative obtained by substitution of ribose by 2'-O-propyl ribose in the above-described oligonucleotide; and an oligonucleotide derivative obtained by substitution of ribose by 2'-methoxyethoxy ribose in the above-described oligonucleotide etc. (*Cell Engineering* (Saibo Kogaku) 16, 1463 (1997)).

2. Preparation of the Polypeptide of the Present Invention

The polypeptide of the present invention can be produced by using a method described in Molecular Cloning, Second Edition or Current Protocols in Molecular Biology. For example, it can be produced by expressing the DNA of the present invention obtained as described in the above Section 1 in a host cell, according to the following procedure.

Based on the DNA of the present invention, a DNA fragment of an appropriate length containing a region encoding the polypeptide of the present invention can be prepared, if necessary. Further, DNA useful for improving the production efficiency of the polypeptide can be prepared by replacing a nucleotide in the nucleotide sequence of the region encoding the polypeptide so as to make a codon most suitable for expression in a host cell.

The DNA fragment is inserted at a site downstream of a promoter in an appropriate expression vector to construct a recombinant vector.

The recombinant vector is introduced into a host cell suitable for the expression vector, whereby a transformant producing the polypeptide of the present invention can be obtained.

As a host cell, any bacterial cells, yeast cells, animal cells, insect cells, plant cells etc, that are capable of expressing the desired gene can be used.

As an expression vector, it is possible to use any vector that can autonomously replicate in the above host cells or can be integrated into chromosomes thereof and that contains a promoter at a position appropriate for the transcription of the DNA of the present invention.

When a prokaryote (e.g., a bacterial cell) is used as a host cell, a preferred expression vector for the polypeptide of the present invention may be a recombinant DNA construct that is autonomously replicative in prokaryotes and that comprises a promoter, a ribosome-binding sequence, the DNA of the present invention and a terminator. The vector may further comprise a gene regulating the promoter.

Examples of expression vectors include pBTrp2, pBTac1, pBTac2 (each of which is manufactured by Boehringer Mannheim), pKK233-2 (manufactured by Pharmacia), pGEX (manufactured by Pharmacia), pSE280 (manufactured by Invitrogen), pGEMEX-1 (manufactured by Promega), pQE-8 (manufactured by QIAGEN), pQE-9 (manufactured by QIAGEN), pQE-70 (manufactured by QIAGEN), pQE-60 (manufactured by QIAGEN), pET-3 (manufactured by Novagen), pET-11a (manufactured by Novagen), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci;, USA, 82, 4306 (1985)], pBluescript II SK+ (manufactured by Stratagene), pBluescript II SK(−) (manufactured by Stratagene), pTrS30 [prepared from *E. coli* JM109/pTrS30 (FERM BP-5407)], pTrS32 [prepared from *E. coli* JM109/pTrS32 (FERM BP-5408)], pUC19 [Gene, 33, 103 (1985)], pSTV28 (manufactured by Takara Shuzo Co., Ltd.), pUC118 (manufactured by Takara Shuzo Co., Ltd.), pPA1 (Japanese Published Unexamined Patent Application No. 233798/88), pKC30 (Rosenberg et al., 1983, in "Methods in Enzymology," Vol. 101, pp. 123-138, Academic Press, San Diego), pKK223-3 (manufactured by Pharmacia), pDR540 (manufactured by Pharmacia), pRIT2T (manufactured by Pharmacia), and ptrc99a [Gene, 69, 301 (1988)].

As a promoter, any promoter capable of expressing in host cells, such as *E. coli*, can be used, including promoters derived from *E. coli* or a phage such as trp promoter (Ptrp), lac promoter (Plac), $P_L$ promoter, $P_R$ promoter and $P_{SE}$ promoter, SPO1 promoter, SPO2 promoter, and penP promoter. An artificially designed, modified promoter may also be used, including a promoter obtained by binding two Ptrp promoters in tandem (Ptrp×2), tac promoter, lac T7 promoter, and let I promoter.

It is preferable to use a plasmid having an appropriate distance (e.g., 6-18 bases) between Shine-Dalgarno sequence (i.e., ribosome-binding sequence) and an initiation codon.

A terminator is not necessarily required for expression of the recombinant DNA construct of the present invention, but it is desirably located immediately downstream of a structural gene.

A prokaryote includes a microorganism belonging to *Escherichia, Serratia, Bacillus, Brevibacterium, Corynebacterium, Microbacterium, Pseudomonas*, and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, and *Pseudomonas* sp. D-0110.

Introduction of the recombinant DNA can be carried out by any method for introducing DNA into these host cells: for example, the calcium ion method [Proc. Natl. Acad. Sci. USA, 69, 2110 (1972)], the protoplast method (Japanese Published Unexamined Patent Application No. 248394/88) and electroporation [Nucleic Acids Research., 16, 6127 (1988)].

When a yeast cell is used as a host cell, an expression vector which can be used includes YEp13 (ATCC37115), YEp24 (ATCC37051), YCp50 (ATCC37419), pHS19, pHS15, pG-1, pXT1 (manufactured by Stratagene), pSG5 (manufactured by Stragtagene), pSVK3 (manufactured by Pharmacia), pBPV, pMSG (manufactured by Pharmacia), and pSVL SV40 (manufactured by Pharmacia).

As a promoter, any promoter capable of expressing in yeast cells may be used, including PHO5 promoter, PGK promoter, GAP promoter, ADH promoter, GPD promoter, AOX1 promoter, gal 1 promoter, gal 10 promoter, heat shock polypeptide promoter, MF α 1 promoter, and CUP 1 promoter.

Examples of the host cell include yeast strains belonging to the genus *Saccharomyces, Schizosaccharomyces, Kluyveromyces, Trichosporon, Schwanniomyces, Pichia* and the like. Specific examples include *Saccharomyces cerevisiae, Schizosaccharomyces pombe, Kluyveromyces lactis, Trichosporon pullulans, Schwanniomyces alluvius,* or *Pichia pastoris*.

Introduction of the recombinant DNA can be carried out by any method for introducing DNA into yeast cells: for example, electroporation [Methods in Enzymol., 194, 182 (1990)], the spheroplast method [Proc. Natl. Acad. Sci. USA, 81, 4889 (1984)], the lithium acetate method [J. Bacteriol., 153, 163 (1983)] and the method described in Proc. Natl. Acad. Sci. USA, 75, 1929 (1978).

When an animal cell is used as a host cell, an expression vector which can be used includes pcDNAI, pcDM8 (commercially available from Funakoshi), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (manufactured by Invitrogen), pREP4 (manufactured by Invitrogen), pAGE103 [J. Biochem, 101, 1307 (1987)], pAGE210, pAMo, and pAMoA.

As a promoter, any promoter capable of expressing in animal cells can be used, including a promoter for immediate early (1E) gene of Cytomegalovirus (CMV), SV40 early promoter or metallothionein promoter, retroviral promoter, heat shock promoter, and SRα promoter. An enhancer for IE gene of Human CMV may also be used together with such a promoter.

Host cells include mouse myeloma cells, rat myeloma cells, mouse hybridoma cells, human Namalwa or Namalwa KJM-1 cells, human fetal kidney cells, human leukemia cells, African green monkey kidney cells, chinese hamster CHO cells, or HBT5637 (Japanese Published Unexamined Patent Application No. 299/88).

Specific examples include SP2/O, NSO and the like for mouse myeloma cells, YB2/O and the like for rat myeloma cells, HEK293 (ATCC: CRL-1573), and the like for human fetal kidney cells, BALL-1 and the like for human leukemia cells, and COS-1, COS-7 and the like for African green monkey kidney cells.

Introduction of the recombinant DNA can be carried out by any method for introducing DNA into animal cells: for example, electroporation [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)] and the method described in Virology, 52, 456 (1973).

When an insect cell is used as a host cell, a polypeptide can be expressed by a method described in Baculovirus Expression Vectors, A Laboratory Manual, W. H. Freeman and Company, New York (1992); Current Protocols in Molecular Biology; Molecular Biology, A Laboratory Manual; or Bio/Technology, 6, 47 (1988).

More specifically, a recombinant gene transfer vector and a baculovirus may be co-introduced into insect cells to obtain a recombinant virus in the supernatant from the cultured insect cells. Thereafter, insect cells may further be infected with the resulting recombinant virus to express the polypeptide.

Examples of the gene transfer vector used in the above procedure includes pVL1392, pVL1393, pBlueBacIII (commercially available from Invitrogen, respectively) and the like.

Examples of the baculovirus include *Autographa californica* nuclear polyhedrosis virus, which infects Noctuidae insects, and the like.

Examples of insect cells include *Spodoptera frugiperda* ovarian cells, *Trichoplusia ni* ovarian cells, cultured cells derived from silk worm ovary, and the like.

Specific examples are Sf9 and Sf21 (Baculovirus Expression Vectors, A Laboratory Manual) for *Spodoptera frugiperda* ovarian cells, High 5 and BTI-TN-5B 1-4 (manufactured by Invitrogen) for *Trichoplusia ni* ovarian cells, *Bombyx mori* N4 for cultured cells derived from silk worm ovary, and the like.

Co-introduction of the recombinant gene transfer vector and the baculovirus into insect cells for recombinant virus production can be carried out by the calcium phosphate method (Japanese Published Unexamined Patent Application No. 227075/90) or the lipofection method [Proc. Natl. Acad. Sci. USA, 84, 7413 (1987)].

When a plant cell is used as a host cell, examples of an expression vector include Ti plasmid, tobacco mosaic virus vector, and the like.

As a promoter, any promoter capable of expressing in plant cells can be used, including cauliflower mosaic virus (CaMV) 35S promoter, rice actin 1 promoter, and the like.

Host cells include plant cells such as tobacco, potato, tomato, carrot, soy bean, Brassica, alfalfa, rice, wheat, barley, and the like.

Introduction of the recombinant vector can be carried out by any method for introducing DNA into plant cells: for example, the *Agrobacterium* method (Japanese Published Unexamined Patent Application No. 140885/84, Japanese Published Unexamined Patent Application No. 70080/85, WO94/00977), electroporation (Japanese Published Unexamined Patent Application No. 251887/85), and the particle gun method (Japanese Patent No. 2606856, Japanese Patent No. 2517813).

The gene can be either expressed directly, or expressed as a secreted polypeptide or a fusion polypeptide according to the method as described in Molecular Cloning, Second Edition. Expression in yeast, animal, insect or plant cells can provide a polypeptide with sugar or sugar chain attached thereto.

The polypeptide of the present invention can be produced by culturing the thus obtained transformant in a medium to produce and accumulate the polypeptide of the present invention in the culture, and recovering the polypeptide from the culture.

The transformant of the present invention can be cultured in a medium according to a conventional method used for culturing host cells.

A medium for culturing a transformant derived from a prokaryote host (e.g., *E. coli*) or a eukaryote host (e.g., yeast) may be a natural or synthetic medium insofar as the medium contains a carbon source, a nitrogen source, an inorganic salt etc., which can be assimilated by the organism, and enables the efficient culture of the transformant.

Any carbon source assimilated by the organisms can be used as a carbon source. Illustrative examples include carbohydrates such as glucose, fructose, sucrose, molasses containing them, starch or starch hydrolysate; organic acids such as acetic acid, propionic acid; alcohols such as ethanol, propanol, and the like.

Examples of the nitrogen source which can be used include ammonium salts of various inorganic or organic acids, such as ammonia, ammonium chloride, ammonium sulfate, ammonium acetate, and ammonium phosphate; other nitrogen-containing compounds; and peptone, meat extracts, yeast extracts, corn steep liquor, casein hydrolysate, soy bean meal, soy bean meal hydrolysate, various fermented cells and hydrolysates thereof and the like.

Inorganic salts which can be used include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

Culture is carried out under aerobic conditions by shaking culture, submerged spinner culture under aeration, and the like. The culture temperature is preferably from 15 to 40° C., and culturing time is usually from 5 hours to 7 days. During the culture, pH is maintained at 3.0 to 9.0. The pH can be adjusted using an inorganic or organic acid, an alkaline solution, urea, calcium carbonate, ammonia and the like.

Also, if necessary, antibiotics such as ampicillin and tetracycline can be added to a medium during the culturing.

In a case where a microorganism is transformed with an expression vector containing an inducible promoter, the transformant can be cultured in a medium supplemented with an inducer, if necessary. For example, when an expression vector containing lac promoter is used for transformation, the transformant may be cultured in a medium supplemented with isopropyl-β-D-thiogalactopyranoside or the like; when an expression vector containing trp promoter is used for transformation, the transformant can be cultured in a medium supplemented with indole acrylic acid or the like.

A medium for culturing a transformant obtained using an animal cell as the host includes generally-used media such as RPMI 1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] as well as other media to which fetal calf serum or the like has been added to the above media and the like.

Culturing is generally carried out at pH 6 to 8, at a temperature of 25 to 40° C. for a period of 1 to 7 days in the presence of 5% $CO_2$.

Also, if necessary, antibiotics such as kanamycin, penicillin and streptomycin may be added to a medium during the culturing.

A medium for culturing a transformant obtained using an insect cell as the host includes generally-used media such as TNM-FH medium (manufactured by PharMingen), Sf-900 II SFM medium (manufactured by Life Technologies), ExCell 400 and ExCell 405 [both being products of JRH Biosciences], Grace's Insect Medium [Nature, 195, 788 (1962)] or the like.

Culturing is generally carried out at pH 6 to 7, at a temperature of 25 to 30° C. for a period of 1 to 5 days.

Also, if necessary, antibiotics such as gentamycin can be added to a medium during the culture.

The transformant obtained using a plant cell as the host can be cultured as a cell or can be allowed to differentiate into plant cell or organ before culture. Examples of the medium for culturing the transformant include a generally used medium such as Murashige and Skoog (MS) medium, White medium, or any one of these media further supplemented with a plant hormone such as auxin or cytokinin.

Culturing is carried out usually at pH 5 to 9, at a temperature of 20 to 40° C. for a period of 3 to 60 days.

Also, if necessary, antibiotics such as kanamycin and hygromycin can be added to a medium during the culturing.

As described above, the polypeptide of the present invention can be produced by culturing a microorganism-, animal cell-, or plant cell-derived transformant carrying a recombinant vector in which a DNA encoding the polypeptide of the present invention has been inserted according to a general manner to produce and accumulate the polypeptide, and then recovering the polypeptide from the culture.

A method for producing the polypeptide of the present invention includes intracellular production in host cells, extracellular secretion by host cells or production on outer membranes of host cells, and the method can be selected depending on the type of host cells to be used and/or the structure of polypeptide to be produced.

If the polypeptide of the present invention is produced in host cells or on outer membranes of host cells, the polypeptide can be efficiently secreted to extracellularly from the host cells by using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)] or methods as described in Japanese Published Unexamined Patent Application No. 336963/93 and PCT WO94/23021.

More specifically, the polypeptide of the present invention can be efficiently secreted from host cells by expressing it in a form with signal peptide using genetic recombination techniques, the signal peptide being added upstream of a portion containing the active site of the polypeptide of the present invention.

Furthermore, the amount of the production can be increased using a gene amplification system using a dihydrofolate reductase gene or the like according to the method described in Japanese Published Unexamined Patent Application No. 227075/90.

Further, animal or plant cells introduced with a gene may be re-differentiated to create an animal individual carrying a transgene (transgenic non-human animal) or a plant individual carrying a transgene (transgenic plant), which may be used for producing the polypeptide of the present invention.

When the transformant is an animal or plant individual, the polypeptide may be obtained by feeding or cultivating the individual in a general manner to produce and accumulate the polypeptide, and then recovering the polypeptide from the animal or plant individual.

The methods for producing the polypeptide of the present invention using an animal individual include a method using an animal obtained by introducing a gene in accordance with known manners as described in American Journal of Clinical Nutrition, 63, 639S (1996); American Journal of Clinical Nutrition, 63, 627S (1996); and Bio/Technology, 9, 830 (1991).

In the case of an animal individual, for example, the polypeptide of the present invention may be obtained by feeding a transgenic non-human animal introduced with a DNA insert encoding the polypeptide of the present invention to produce and accumulate therein the polypeptide, and then recovering the polypeptide from the animal. The polypeptide can be produced and accumulated in the animal's milk (Japanese Published Unexamined Patent Application No. 309192/88), egg, and the like. As a promoter used for this purpose, any promoter can be used so long as it can be expressed in the animal, for example, mammary gland cell-specific promoters such as an α-casein promoter, a β-casein promoter, a β-lactoglobulin promoter and a whey acidic protein promoter being preferred.

The methods for producing the polypeptide of the present invention using a plant individual include a method cultivating a transgenic plant obtained by introducing a gen encoding the polypeptide of the present invention to produce and accumulate therein the polypeptide in a known manner as described in Tissue Culture (Soshiki Baiyo), 20 (1994); Tissue Culture, 21 (1995); and Trends in Biotechnology, 15, 45 (1997), and then the polypeptide can be recovered from the plant.

For isolation and purification of the polypeptide produced by the transformant of the present invention, conventional methods for the isolation and purification of enzymes can be used.

For example, if the polypeptide of the present invention is expressed in a soluble form in cells, after completion of culturing, the cells are recovered by centrifugation, and suspended in an aqueous buffer and then disrupted with ultrasonic disrupter, French Press, Manton-Gaulin homogenizer, Dynomill or the like, to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose; phenyl sepharose or the like, gel filtration using a molecular sieve, affinity chromatography, chromatofocusing, or electrophoresis, such as isoelectronic focusing or the like, alone or in combination thereof.

When the protein is expressed as an inclusion body in the host cells, the cells are collected in the same manner, disrupted and centrifuged to recover the inclusion body of the protein as the precipitate fraction. Next, the inclusion body of the protein is solubilized with a protein-denaturing agent.

The solubilized protein solution is diluted with or dialyzed against a solution containing no protein-denaturing agent or such a dilute solution containing the protein-denaturing agent at a lower concentration that denaturation of the protein is not caused. Thus, the normal tertiary structure of the protein is reconstituted. After the procedure, a purified product of the protein can be obtained by a purification and isolation method similar to the above.

When the protein of the present invention or its glycosylated-derivative is secreted out of cells, the protein or its derivative can be collected from the culture supernatant.

Namely, the culture supernatant is obtained by treating the culture in a similar manner to the above-mentioned centrifugation or the like. Then, a purified product can be obtained from the supernatant using a purification and isolation method similar to the above.

Examples of the thus obtained protein include a protein comprising the amino acid sequences represented by SEQ ID NOS: 3, 4, 5 and 6.

Furthermore, a fusion protein of the protein of the present invention and other protein may be produced, and purified by affinity chromatography using a substance having affinity to the fusion protein. For example, the protein of the present invention may be produced as a fusion protein with protein A according to the method of Lowe et al. (*Proc. Natl. Acad. Sci. USA*, 86: 8227 (1989); *Genes Develop.*, 4: 1288 (1990)), or the method described in Japanese Published Unexamined Patent Application No. 336963/93 or WO 94/23021, and purified by affinity chromatography using immunoglobulin G.

Moreover, the protein of the present invention may be produced as a fusion protein with Flag peptide, and the fusion protein can be purified by affinity chromatography using an anti-Flag antibody (*Proc. Natl. Acad. Sci., USA*, 86: 8227 (1989), *Genes Develop.*, 4: 1288 (1990)). Further purification can be carried out by affinity chromatography using the antibody against the protein per se.

Also, based on the information of the thus obtained protein, the protein of the present invention can be produced by the chemical synthesis method, such as Fmoc (fluorenylmethyloxycarbonyl) method, tBoc (t-butyloxycarbonyl) method, or the like. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

3. Production of Avermectin Aglycon or Avermectin

Avermectin aglycon can be produced by culturing the transformant prepared in the above Section 2, which carries the avermectin aglycon synthase gene or a module or submodule thereof, in a medium to produce and accumulate avermectin aglycon in the culture, and then recovering avermectin aglycon from the culture.

When a host used for preparation of a transformant can produce avermectin, avermectin aglycon or avermectin can be efficiently produced in any one of the transformants obtained by introducing the avermectin aglycon synthase gene or a module or submodule thereof into the host. The transformant thus obtained can produce avermectin aglycon or avermectin with higher efficiency than that of the host.

When a host used for preparation of a transformant cannot produce avermectin, the avermectin aglycon synthase gene may be introduced into the host to obtain a transformant capable of producing avermectin aglycon.

In the production of avermectin or avermectin aglycon, the above transformant can be cultured according to a culture procedure as described in the above Section 2.

A known avermectin is a macrocyclic lactone having a 16-membered ring with two sugar residues attached thereto via glycosidic linkage. Avermectin aglycon can be converted into avermectin in a manner well known in the art, for example, by glycosylating avermectin aglycon as described in J. Bacteriol., 175, 2552-2563 (1993).

4. Production of Modified Avermectin Aglycon or Avermectin

Avermectin aglycon is formed through extension of lower-fatty acid units (used in the form of CoA ester of dicarboxylic acid in reactions other than the initial reaction) by avermectin aglycon synthase, i.e., condensation to give a polyketide carbon chain, and modification of β-carbonyl groups generated during the condensation.

As described above, the avermectin aglycon synthase gene is composed of modules, each module comprising DNA encoding avermectin aglycon synthase domains (submodule).

A submodule encodes ACP, KS and AT involved in condensation during polyketide synthesis, as well as KR, DH or ER involved in modification of β-carbonyl groups.

Accordingly, the carbon chain length of the aglycon part and the type of functional group on β-carbon in the condensation process can be altered by modifying a submodule, based on nucleotide sequence information of the Avermectin aglycon synthase gene determined in the above Section 1.

Further, selective inactivation of a submodule can result in production of a predictable novel avermectin or a particular component thereof alone.

By way of example, a strain producing avermectin B1a and B2a, Streptomyces avermitilis K2038, can be converted into a strain producing only avermectin B2a by replacing or converting a submodule DH2 region of the avermectin aglycon synthase gene by or into its inactivated form without dehydratase activity.

The submodule DH2 region can be replaced by or converted into its inactivated form, for example, by homologous recombination on submodule DH2 of the above strain to give the nucleotide sequence shown in SEQ ID NO: 7 in a general manner as described in Molecular Cloning, Second Edition.

The strain thus obtained, which becomes capable of producing a modified (or altered) avermectin aglycon, can be used to produce and obtain the modified avermectin aglycon or modified avermectin according to the general process for producing avermectin.

BEST MODES FOR CARRYING OUT THE INVENTION

The following examples are provided for illustrative purposes only, and are not intended to limit the scope of the invention clearly defined above.

EXAMPLE 1

Determination of the Nucleotide Sequence of the Avermectin Aglycon Synthase Gene of Streptomyces avermitilis A nucleotide sequence of the DNA encoding avermectin aglycon synthase derived from Streptomyces avermitilis K2033 (U.S. Pat. No. 5,206,155, FERM BP-2773) was determined as follows.

Continuous or overlapping DNA fragments within the avermectin aglycon synthase gene were subcloned from plasmids containing a fragment of the avermectin aglycon synthase genes (aveAI and aveAII) co-isolated with a gene encoding avermectin B5-O-transmethylase (aveD; Gene, 206, 175-180 (1998)). Nucleotide sequences of the inserted DNA fragments in these subclones were then determined.

More specifically, the entire nucleotide sequences of aveAI and aveAII were determined by subcloning BamHI-treated fragments of 3.4 kbp, 2.0 kbp, 0.5 kbp, 6.8 kbp, 7.0 kbp, 7.8 kbp, 3.7 kbp, 4.8 kbp, 1.3 kbp, 2.4 kbp, 0.7 kbp, 1.0 kbp, 5.4 kbp, 2.5 kbp, 1.9 kbp, 0.1 kbp, 7.0 kbp, 3.1 kbp, 4.7 kbp and 1.3 kbp found in the BamHI-restriction map of aveAI and aveAII shown in FIG. 1; treating the inserted DNA fragments in these subclones with exonuclease III and S1 nuclease to prepare a series of deletion fragments; and then carrying out a cycle-sequencing reaction using fluorescently-labeled primers to determine a nucleotide sequence of each deletion fragment. The genes aveAI and aveAII had the nucleotide sequences shown in SEQ ID NO: 1 and SEQ ID NO: 2, respectively.

EXAMPLE 2

Production of Avermectin B2a Alone by Nucleotide Modification of Dehydratase Domain in Module 2

Streptomyces avermitilis K2038 (FERM BP-2775) produces avermectin B1a and B2a.

Figure 2C:
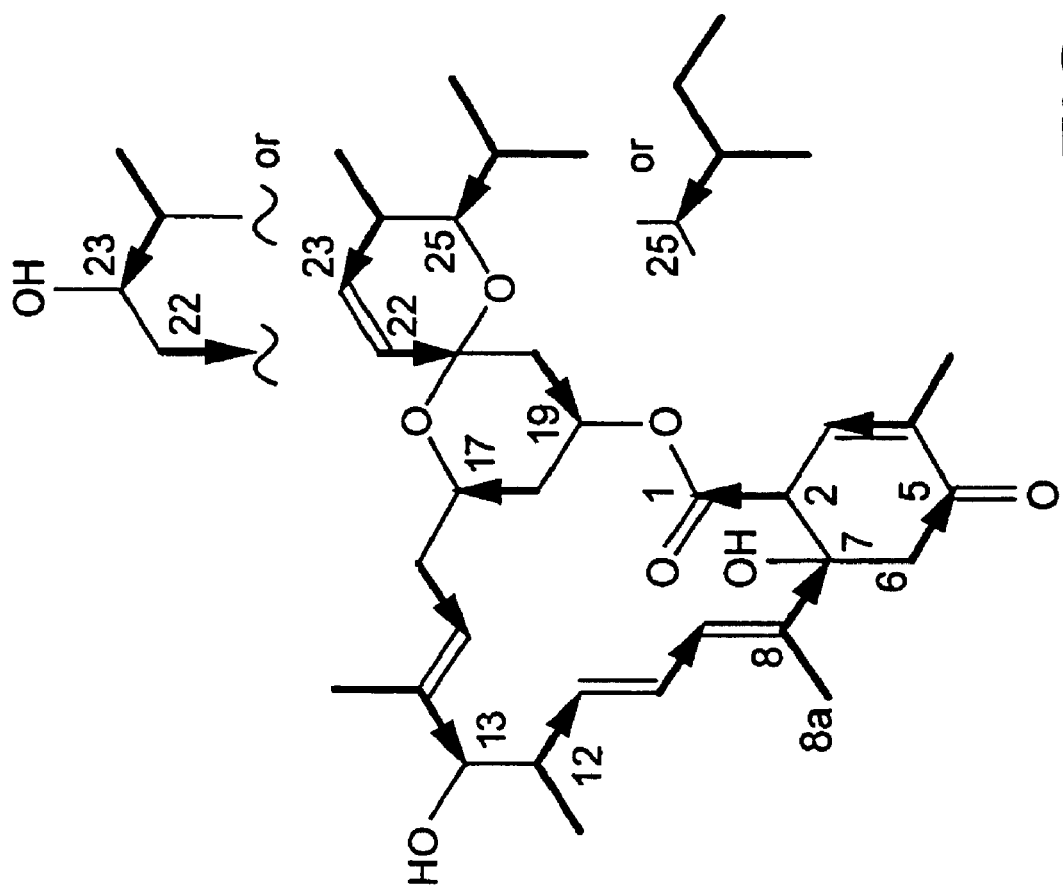

The information of avermectin aglycon synthase genes (SEQ ID NOS: 1 and 2) derived from the avermectin-producing strain, which were obtained and sequenced in Example 1, indicated that avermectin was biosynthesized through the biosynthetic pathway shown in FIGS. 2A-2C.

Avermectin B1a differs from avermectin B2a only in that avermectin B1a has a double bond between 22- and 23-positions in its aglycon part, while avermectin B2a has a single bond between 22- and 23-positions and a hydroxyl group at 23-position in its aglycon part.

The biosynthetic pathway for avermectin found above indicated that avermectin aglycon synthase domain DH of SU2 (DH2) is responsible for the formation of a double bond between 22- and 23-positions in the aglycon part of avermectin B1a and that avermectin aglycon synthase domain DH of SU10 (DH10) has no dehydratase activity.

Based on the idea that a strain producing only avermectin B2a could be obtained by converting DH2 into a domain without dehydratase activity like DH10, DH2 without dehydratase activity was prepared as follows.

The Avermectin aglycon synthase genes obtained in Example 1 had six DH domains: DH2, DH6, DH9, DH10, DH11 and DH12. Comparisons of nucleotide sequences of these domains showed that DH10 clearly differed from other DH domains in a consensus sequence common to dehydratase.

More specifically, amino acid sequences of DH2, DH6, DH9, DH11 and DH12, which were directly involved in the avermectin aglycon formation, were shown to include a consensus sequence of HXaaXaaXaaGXaaXaaXaaXaaP (SEQ ID NO: 13) or HXaaXaaXaaGXaaXaaXaaXaaS (SEQ ID NO: 14), wherein H, G, P, S and Xaa represent histidine, glycine, proline, serine and any amino acid, respectively; whereas the corresponding sequence of DH10 was YXaaXaaXaaGXaaXaaXaaXaaS (SEQ ID NO: 15), wherein Y represents tyrosine, and Xaa, G and S are as defined above.

Thus, replacement of an N-terminal H (His) by Y (Tyr) was thought to provide dehydratase without its activity.

A DNA was constructed, which had a nucleotide sequence encoding the sequence for replacement of the N-terminal amino acid sequence -His-Ala- in the consensus sequence of DH2 [-His-Ala-Val-Gly-Gly-Thr-Val-Leu-Leu-Ser- (SEQ ID NO: 16), amino acids 3037-3046 in SEQ ID NO: 3] by the corresponding sequence of DH10: -Tyr-Glu- (amino acids 1008-1017 in SEQ ID NO: 6). That is, the DNA sequence of DH2 domain: 5'-CAT GCC-3' (nucleotides 9109-9114 in SEQ ID NO: 1) was replaced by the sequence: 5'-TAC GAG-3' as follows.

A DNA fragment of the aveAI region containing DH2 domain was digested with restriction enzyme SmaI, and the 2327 bp SmaI fragment corresponding to nucleotides 7869-10196 in SEQ ID NO: 1 was cloned into the SmaI site of vector plasmid pUC19.

Taq DNA polymerase buffer, dATP, dGTP, dCTP, dTTp and Taq DNA polymerase were added to the resulting recombinant plasmid, which was then divided into two aliquots.

To one of these two aliquots, a primer having the nucleotide sequence shown in SEQ ID NO: 9 (corresponding to nucleotides 9098-9127 in SEQ ID NO: 1) and an antisense primer having the nucleotide sequence shown in SEQ ID NO: 10 (corresponding to an antisense of nucleotides 9193-9222 in SEQ ID NO: 1) were added.

To the other aliquot, an antisense primer having the nucleotide sequence shown in SEQ ID NO: 11 (corresponding to an antisense of nucleotides 9098-9127 in SEQ ID NO: 1) and a primer having the nucleotide sequence shown in SEQ ID NO: 12(corresponding to nucleotides 8948-8977 in SEQ ID NO: 1) were added.

After the addition, each aliquot was treated at 96 C for 5 minutes, and the reaction was repeated for 5 to 10 cycles under the following conditions: at 98° C. for 15 seconds and 68° C. for 30 seconds per cycle.

After the reaction, exonuclease I and alkaline phosphatase were added to each aliquot, incubated at 37 C for 15 minutes, and then treated at 80 C for 10 minutes to inactivate both the enzymes.

After the inactivation of both the enzymes, Taq DNA polymerase buffer, dATP, dGTP, dCTP, dTTp, a primer having the nucleotide sequence of SEQ ID NO: 12 (corresponding to nucleotides 8948-8977 in SEQ ID NO: 1), an antisense primer having the nucleotide sequence of SEQ ID NO: 10 (corresponding to an antisense of nucleotides 9193-9222 in SEQ ID NO: 1) and Taq DNA polymerase were added to each reaction solution. Each reaction solution was then treated at 96 C for 5 minutes, and the reaction was repeated for 25 cycles under the following conditions: at 98 C for 15 seconds and 68 C for 30 seconds per cycle.

After the reaction, exonuclease I and alkaline phosphatase were added to each reaction solution, incubated at 37 C for 15 minutes, and then treated at 80 C for 10 minutes to inactivate the enzymes.

After the inactivation of the enzymes, restriction enzymes XcmI and BsaAI were added to each reaction solution to obtain a XcmI-BsaAI treated DNA fragment.

Restriction enzymes XcmI and BsaAI were added to the recombinant plasmid prepared above, which carried the inserted 2327 bp SmaI fragment, to obtain a XcmI-BsaAI treated vector fragment. The XcmI-BsaAI treated vector fragment, T4 DNA ligase buffer, ATP and T4 DNA ligase were added to the XcmI-BsaAI treated DNA fragment; and then incubated overnight at 22° C. to ligate these fragments together, thereby obtaining a plasmid carrying the inserted XcmI-BsaAI treated DNA fragment.

After the transformation of E. coli cells with the plasmid, the recombinant plasmids were extracted from individual colonies, and each DNA fragment inserted into the vector was then confirmed for its nucleotide sequence, thereby selecting a clone carrying a fragment introduced with the intended nucleotide replacement.

The inserted DNA fragment was taken from the selected clone, and then carried out recombination with DH2 region on the chromosome of *Streptomyces avermitilis* K2038 by homologous recombination according to a method as described in Japanese Published Examined Patent Application No. 344605/92.

The resulting recombinant *Streptomyces avermitilis* K2210 was cultured under the conditions for general avermectin production, and then the resulting cells were extracted with methanol.

The resulting extract was analyzed using two procedures presented below.

(1) Procedure using Thin-layer Chromatography on Silica Gel

Chromatography condition: silica gel, Merck Silica Gel plate F254 (Merck Corp.)

Development solution: n-hexane/iso-propyl alcohol=85/15

Detection: UV (2) Procedure using High Performance Liquid Chromatography

Chromatography condition: column, ODS-Hypersil-3 (Elmer Corp.)

Mobile phase: acetonitrile/methanol/water=60/14/26

Flow rate: 0.6 ml/min

Detection: 246 nm

Temperature: room temperature

In both analytical procedures, only the same peak as that of avermectin B2a was observed. Further, the culture extract was purified by chromatographies on Sephadex LH-20 and silica gel to give the purified product. The purified product was analyzed by NMR and mass spectrometry, indicating that the above recombinant strain produced only avermectin B2a.

Namely, avermectin B2a alone could be produced and obtained according to the method as described above.

INDUSTRIAL APPLICABILITY

The present invention can provide the DNAs encoding a multifunctional enzyme involved in the biosynthesis of avermectin compound useful as a pharmaceutical agent, a veterinary agent and a agricultural chemical; polypeptides encoded by the DNAs; vectors comprising the DNAs; a host cell transformed with the DNA or vector; and a process for producing avermectin or modified avermectin.

Sequence Listing Free Text

SEQ ID NO: 9 represents a primer based on the sequence between nucleotides 9098 and 9127 in SEQ ID NO: 1

SEQ ID NO: 10 represents an antisense primer based on the sequence between nucleotides 9193 and 9222 in SEQ ID NO: 1

SEQ ID NO: 11 represents an antisense primer based on the sequence between nucleotides 9098 and 9127 in SEQ ID NO: 1

SEQ ID NO: 12 represents a primer based on the sequence between nucleotides 8948 and 8977 in SEQ ID NO: 1

The scope of the present invention will be defined by the appended claims, and it will be appreciated that other numerous variations and modifications may be made without departing from the spirit or scope of the invention. The above examples are therefore to be construed in all respects as illustrative and not restrictive. Further, equivalents of the claims will also fall within the scope of the present invention.

All of patents, patent applications and other publications cited in this specification and the contents as disclosed in the specification and/or drawings of Japanese Patent Application No. 046961/99, which is a priority document of the present application, are incorporated herein by reference in their entirety.

What is claimed is:

1. An isolated DNA comprising the nucleotide sequence of nucleotide No. 11971-30688 of SEQ ID NO: 1.

2. The DNA according to claim 1 which further comprises the nucleotide sequence of nucleotide No. 85-1353 of SEQ ID NO: 1.

3. The DNA according to claim 1 which further comprises the nucleotide sequence selected from the group consisting of nucleotide No. 1441-6180 of SEQ ID NO: 1 and nucleotide No. 100-4692 of SEQ ID NO: 2.

4. The DNA according to claim 1 which further comprises the nucleotide sequence selected from the group consisting of nucleotide No. 6256-11658 of SEQ ID NO: 1 and nucleotide Nos. 14935-20334, 20413-25734 and 25810-31125 of SEQ ID NO: 2.

5. The DNA according to claim 1 which further comprises or the nucleotide sequence of nucleotide No. 4771-7818 of SEQ ID NO: 2.

6. The DNA according to claim 1 which further comprises the nucleotide sequence of nucleotide No. 7906-14619 of SEQ ID NO: 2.

7. The DNA according to claim 1 which further comprises the nucleotide sequence selected from the group consisting of nucleotide No. 85-1032 and 7906-8829 of SEQ ID NO: 1 and nucleotide Nos. 1648-2673, 6322-7344, 9676-10773, 16543-17565, 21991-23019 and 27367-28392 of SEQ ID NO: 2.

8. The DNA according to claim 1 which further comprises the nucleotide sequence selected from the group consisting of nucleotide Nos. 1096-1353, 5935-6180, and 11413-11658 of SEQ ID NO: 1 and nucleotide Nos. 4447-4692, 7573-7818, 13378-13659, 20089-20334, 25489-25734 and 30880-31125 of SEQ ID NO: 2.

9. The DNA according to claim 1 which further comprises the nucleotide sequence selected from the group consisting of nucleotide Nos. 1441-2742 and 6256-7545 of SEQ ID NO: 1 and nucleotide Nos. 100-1383, 4771-6060, 7906-9258, 14935-16224, 20413-21705 and 25810-27102 of SEQ ID NO: 2.

10. The DNA according to claim 1 which further comprises the nucleotide sequence selected from the group consisting of nucleotide Nos. 5143-5676 and 10609-11142 of SEQ ID NO: 1 and nucleotide Nos. 3634-4188, 12547-131 04, 19285-19842, 24685-25242 and 30076-30633 of SEQ ID NO: 2.

11. The DNA according to claim 1 which further comprises the nucleotide sequence selected from the group consisting of nucleotide No. 8947-9384 of SEQ ID NO: 1 and nucleotide Nos. 10885-11289, 17689-18066, 23149-23529 and 2851 6-28878 of SEQ ID NO: 2.

12. The DNA according to claim 1 which further comprises the nucleotide sequence of nucleotide No. 13879-14619 of SEQ ID NO: 2.

13. A host cell obtainable by introducing the DNA according to claim 1 or a recombinant vector comprising the DNA into a host cell.

14. The host cell according to claim 13 wherein the host cell is an avermectin-producing bacterial strain.

15. The host cell according to claim 13 wherein the host cell is *Streptomyces avermitilis* K2038 (FERM BP-2775).

16. A process for producing a polyketide synthase polypeptide comprising: culturing a host cell transformed with a DNA encoding the amino acid sequence of SEQ ID NO: 4 or a recombinant vector comprising said DNA in a medium to produce and accumulate the polypeptide in the culture, and recovering the polypeptide from the culture.

* * * * *